US010220092B2

(12) United States Patent
Deisseroth et al.

(10) Patent No.: US 10,220,092 B2
(45) Date of Patent: Mar. 5, 2019

(54) DEVICES, SYSTEMS AND METHODS FOR OPTOGENETIC MODULATION OF ACTION POTENTIALS IN TARGET CELLS

(71) Applicants: The Board of Trustees of the Leland Stanford Junior University, Stanford, CA (US); Humboldt-Universitat Zu Berlin, Berlin (DE)

(72) Inventors: Karl A. Deisseroth, Palo Alto, CA (US); Emily Anne Ferenczi, Stanford, CA (US); Peter Hegemann, Falkensee (DE)

(73) Assignees: The Board of Trustees of The Leland Stanford Junior University, Stanford, CA (US); HUMBOLDT-UNIVERSITAT ZU BERLIN, Berlin (DE)

( * ) Notice: Subject to any disclaimer, the term of this patent is extended or adjusted under 35 U.S.C. 154(b) by 0 days.

(21) Appl. No.: 14/782,201

(22) PCT Filed: Apr. 29, 2014

(86) PCT No.: PCT/US2014/035900
§ 371 (c)(1),
(2) Date: Mar. 4, 2016

(87) PCT Pub. No.: WO2014/179331
PCT Pub. Date: Nov. 6, 2014

(65) Prior Publication Data
US 2016/0045599 A1 Feb. 18, 2016

Related U.S. Application Data

(60) Provisional application No. 61/817,221, filed on Apr. 29, 2013.

(51) Int. Cl.
*A61K 41/00* (2006.01)
*A61N 5/06* (2006.01)
*C12N 5/10* (2006.01)
*C12N 15/85* (2006.01)
*C07K 14/00* (2006.01)
*A01K 67/027* (2006.01)
*C07K 14/705* (2006.01)

(52) U.S. Cl.
CPC ...... *A61K 41/0057* (2013.01); *A01K 67/0275* (2013.01); *A61N 5/0613* (2013.01); *C07K 14/00* (2013.01); *C07K 14/705* (2013.01); *C12N 15/85* (2013.01); *A01K 2207/05* (2013.01); *A01K 2227/105* (2013.01); *A01K 2267/0393* (2013.01); *A61N 2005/0662* (2013.01); *C07K 2319/33* (2013.01); *C12N 2750/14143* (2013.01); *C12N 2830/002* (2013.01); *C12N 2830/15* (2013.01)

(58) Field of Classification Search
None
See application file for complete search history.

(56) References Cited

U.S. PATENT DOCUMENTS

| 2,968,302 | A | 1/1961 | Fry et al. |
|---|---|---|---|
| 3,131,690 | A | 5/1964 | Innis et al. |
| 3,499,437 | A | 3/1970 | Balamuth et al. |
| 3,567,847 | A | 3/1971 | Price |
| 4,343,301 | A | 8/1982 | Indech |
| 4,559,951 | A | 12/1985 | Dahl et al. |
| 4,616,231 | A | 10/1986 | Autrey et al. |
| 4,865,042 | A | 9/1989 | Umemura et al. |
| 4,879,284 | A | 11/1989 | Lang et al. |
| 5,032,123 | A | 7/1991 | Katz et al. |
| 5,041,224 | A | 8/1991 | Ohyama et al. |
| 5,082,670 | A | 1/1992 | Gage et al. |
| 5,249,575 | A | 10/1993 | Di Mino et al. |
| 5,267,152 | A | 11/1993 | Yang et al. |
| 5,290,280 | A | 3/1994 | Daikuzono et al. |
| 5,330,515 | A | 7/1994 | Rutecki et al. |
| 5,382,516 | A | 1/1995 | Bush |
| 5,411,540 | A | 5/1995 | Edell et al. |

(Continued)

FOREIGN PATENT DOCUMENTS

| CN | 1079464 A | 12/1993 |
|---|---|---|
| CN | 1558222 A | 12/2004 |

(Continued)

OTHER PUBLICATIONS

Caro et al, Engineering of an Artificial Light-Modulated Potassium Channel, PLOS ONE, 2012, pp. 1-9.*

(Continued)

*Primary Examiner* — Maria Marvich
(74) *Attorney, Agent, or Firm* — Bozicevic, Field & Francis LLP; Paula A. Borden

(57) ABSTRACT

Aspects of the disclosure include devices, systems and methods for optogenetic modulation of action potentials in target cells. The subject devices include light-generating devices, control devices, and delivery devices for delivering vectors to target cells. The subject systems include light-activated proteins, response proteins, nucleic acids comprising nucleotide sequences encoding these proteins, as well as expression systems that facilitate expression of these proteins in target cells. Also provided are methods of using the subject devices and systems to optogenetically inhibit and intercept action potentials in target cells, e.g., to treat a neurological or psychiatric condition in a human or non-human animal subject.

18 Claims, 70 Drawing Sheets
Specification includes a Sequence Listing.

(56) References Cited

U.S. PATENT DOCUMENTS

| | | |
|---|---|---|
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 8,956,363 B2 | 2/2015 | Deisseroth et al. |
| 8,962,589 B2 | 2/2015 | Deisseroth et al. |
| 9,057,734 B2 | 6/2015 | Cohen |
| 9,079,940 B2 | 7/2015 | Deisseroth et al. |
| 9,084,885 B2 | 7/2015 | Deisseroth et al. |
| 9,101,690 B2 | 8/2015 | Deisseroth et al. |
| 9,101,759 B2 | 8/2015 | Deisseroth et al. |
| 9,175,095 B2 | 11/2015 | Deisseroth et al. |
| 9,187,745 B2 | 11/2015 | Deisseroth et al. |
| 9,238,150 B2 | 1/2016 | Deisseroth et al. |
| 9,249,200 B2 | 2/2016 | Deisseroth et al. |
| 9,249,234 B2 | 2/2016 | Deisseroth et al. |
| 9,271,674 B2 | 3/2016 | Deisseroth et al. |
| 9,274,099 B2 | 3/2016 | Deisseroth et al. |
| 9,278,159 B2 | 3/2016 | Deisseroth et al. |
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |
| 9,421,258 B2 | 8/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 9,636,380 B2 | 5/2017 | Deisseroth et al. |
| 9,850,290 B2 | 12/2017 | Deisseroth et al. |
| 9,968,652 B2 | 5/2018 | Deisseroth et al. |
| 10,064,912 B2 | 9/2018 | Deisseroth et al. |
| 10,071,132 B2 | 9/2018 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0103949 A1 | 6/2003 | Carpenter et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |

(56) References Cited

U.S. PATENT DOCUMENTS

| | | |
|---|---|---|
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0209352 A1 | 8/2010 | Hultman et al. |
| 2010/0234273 A1 | 9/2010 | Deisseroth et al. |
| 2011/0221970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1* | 7/2011 | Boyden ............... A61K 38/164 435/455 |
| 2011/0166632 A1 | 7/2011 | Delp et al. |
| 2011/0233046 A1 | 9/2011 | Nikolenko et al. |
| 2011/0301529 A1 | 12/2011 | Deisseroth et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0089503 A1 | 4/2013 | Deisseroth et al. |
| 2013/0144359 A1 | 6/2013 | Kishawi et al. |
| 2013/0284920 A1 | 10/2013 | Deisseroth et al. |
| 2013/0286181 A1 | 10/2013 | Betzig et al. |
| 2013/0288365 A1 | 10/2013 | Deisseroth et al. |
| 2013/0289669 A1 | 10/2013 | Deisseroth et al. |
| 2013/0289675 A1 | 10/2013 | Deisseroth et al. |
| 2013/0296406 A1 | 11/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0148880 A1 | 5/2014 | Deisseroth et al. |
| 2014/0235826 A1 | 8/2014 | Deisseroth et al. |
| 2014/0271479 A1 | 9/2014 | Lammel et al. |
| 2014/0324133 A1 | 10/2014 | Deisseroth et al. |
| 2015/0040249 A1 | 2/2015 | Deisseroth et al. |
| 2015/0072394 A1 | 3/2015 | Deisseroth et al. |
| 2015/0112411 A1 | 4/2015 | Beckman et al. |
| 2015/0165227 A1 | 6/2015 | Deisseroth et al. |
| 2015/0174244 A1 | 6/2015 | Deisseroth et al. |
| 2015/0217128 A1 | 8/2015 | Deisseroth et al. |
| 2015/0218547 A1 | 8/2015 | Deisseroth et al. |
| 2015/0297719 A1 | 10/2015 | Deisseroth et al. |
| 2016/0002302 A1 | 1/2016 | Deisseroth et al. |

(56) References Cited

U.S. PATENT DOCUMENTS

| | | |
|---|---|---|
| 2016/0015996 A1 | 1/2016 | Deisseroth et al. |
| 2016/0038764 A1 | 2/2016 | Deisseroth et al. |
| 2016/0045599 A1 | 2/2016 | Deisseroth et al. |

FOREIGN PATENT DOCUMENTS

| | | |
|---|---|---|
| CN | 102076866 A | 5/2011 |
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |
| EP | 1873566 | 1/2008 |
| JP | 6295350 | 10/1994 |
| JP | H 09505771 A | 6/1997 |
| JP | 2004534508 | 11/2004 |
| JP | 2005034073 A | 2/2005 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001/025466 | 4/2001 |
| WO | WO 2003/016486 | 2/2003 |
| WO | WO 2003/040323 | 5/2003 |
| WO | WO 2003/046141 | 6/2003 |
| WO | WO 2003/084994 | 10/2003 |
| WO | WO 2003/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/016486 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2016/019075 | 2/2016 |

OTHER PUBLICATIONS

Kleinlogel et al, A gene-fusion strategy for stoichiometric and co-localized expression of light-gated membrane proteins, Nature Methods, 2011, pp. 1083-1088 plus supplemental methods pp. 1-3.*
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation], abstract only.
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Jones, et al.; "Animal Models of Schizophrenia"; British Journal of Pharmacology; vol. 164, pp. 1162-1194 (2011).
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Davidson, et al.; "Viral Vectors for Gene Delivery to the Nervous System"; Nature Reviews Neuroscience; vol. 4, pp. 353-364 (May 2003).

(56) References Cited

OTHER PUBLICATIONS

Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Definition of integral. Merriam-Webster Dictionary, retrieved on Mar. 20, 2017; Retrieved from the internet: <http://www.merriam-webster.com/dictionary/integral>.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Ahmad, et al. "The *Drosophila rhodopsin* cytoplasmic tail domain is required for maintenance of rhabdomere structure." The FASEB Journal, 2007, vol. 21, p. 449-455.
Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Arenkiel, et al. "In vivo light-induced activation of neural circuitry in transgenic mice expressing Channelrhodopsin-2", Neuron, 2007, 54:205-218.
Argos, et al. "The integrase family of site-specific recombinases: regional similarities and global diversity", The EMBO Journal, 1986, vol. 5, No. 2, pp. 433-440.
Asano, et al.; "Optically Controlled Contraction of Photosensitive Skeletal Muscle Cells"; Biotechnology & Bioengineering; vol. 109, No. 1, pp. 199-204 (Jan. 2012).
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Babin et al., "Zebrafish Models of Human Motor Neuron Diseases: Advantages and Limitations", Progress in Neurobiology (2014), 118:36-58.
Balint et al., "The Nitrate Transporting Photochemical Reaction Cycle of the Pharanois Halorhodopsin", Biophysical Journal, 2004, 86:1655-1663.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Basil et al.; "Is There Evidence for Effectiveness of Transcranial Magnetic Stimulation in the Treatment of Psychiatric Disorders?"; Psychiatry; vol. 1, No. 11, pp. 64-69 (Nov. 2005).
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.
Berridge et al., "The Versatility and Universality of Calcium Signaling", Nature Reviews: Molecular Cell Biology, 2000, vol. 1: pp. 11-21.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga *Volvox carteri*", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascu-

(56) References Cited

OTHER PUBLICATIONS lar smooth muscle cells in vitro and in vivo"; European Heart Journal; vol. 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cardin, et al. "Driving Fast spiking Cells Induces Gamma Rhythm and Controls Sensory Responses", 2009, Nature, vol. 459, vol. 7247, pp. 663-667.
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chow et al., "Optogenetics and translation medicine", Sci Transl Med., 2013, 5(177):177.
Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Crouse, et al. "Expression and amplification of engineered mouse dihydrofolate reductase minigenes" Mol. Cell. Biol. 1983, vol. 3(2): pp. 257-266.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cui, et al., "Electrochemical deposition and characterization of conducting polymer polypyrrole/PSS on multichannel neural probes," Sensors and Actuators, 2001, vol. 93(1): pp. 8-18.
Dalva, et al. "Rearrangements of Synaptic Connections in Visual Cortex Revealed by Laser Photostimulation", Science, 1994,vol. 265, pp. 255-258.
Date, et al. "Grafting of Encapsulated Dopamine-Secreting Cells in Parkinson's Disease: Long-Term Primate Study", Cell Transplant, 2000, vol. 9, pp. 705-709.
Davis; "The many faces of epidermal growth factor repeats," The New Biologist; vol. 2, No. 5, pp. 410-419 (1990).
Day, et al.; "The Nucleus Accumbens and Pavlovian Reward Learning"; Neuroscientist; vol. 13, No. 2, pp. 148-159 (Apr. 2007).
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).

Dederen, et al. "Retrograde neuronal tracing with cholera toxin B subunit: comparison of three different visualization methods", Histochemical Journal, 1994, vol. 26, pp. 856-862.
Definition of Psychosis (2015).
Deisseroth "Next-generation optical technologies for illuminating genetically targeted brain circuits," The Journal of Neuroscience, 2006, vol. 26, No. 41, pp. 10380-10386.
Deisseroth et al., "Excitation-neurogenesis Coupling in Adult Neural Stem/Progenitor Cells", 2004, Neuron, vol. 42, pp. 535-552.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Signaling from Synapse to Nucleus: the logic Behind the Mechanisms", Currrent Opinion in Neurobiology, 2003, vol. 13, pp. 354-365.
Deisseroth et al., "Translocation of Calmodulin to the Nucleus Supports CREB Phosphorylation in Hippocampal Neurons", Nature, 1998, vol. 392, pp. 198-202.
Deisseroth, et al., "Controlling the Brain with Light", Scientific American, 2010, vol. 303, pp. 48-55.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 10I, No. 52, pp. 18206-18211.
Do Carmo, et al.; "Modeling Alzheimer's disease in transgenic rats"; Molecular Neurodegeneration; vol. 8, No. 37, 11 pages (2013).
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Ebert et al., "A Moloney MLV-rat somatotropin fusion gene produces biologically active somatotropin in a transgenic pig", Mol. Endocrinology, 1988, vol. 2, pp. 277-283.
EBI accession No. EMBL: J05199; "*N. pharaonis* halorhodopsin (hop) gene, complete cds"; (Nov. 22, 1990).
EBI accession No. UNIPROT: A7U0Y6; "SubName: Full= Bacteriorhodopsin"; (Aug. 10, 2010).
EBI accession No. UNIPROT: B0R5N9; "Subname: Full= Bacteriorhodopsin"; (Apr. 8, 2008).
EBI accession No. UNIPROT: B4Y103; "SubName: Full= Channelrhodopsin-1"; (Sep. 23, 2008).
EBI accession No. UNIPROT: P15647; "RecName: Full= Halorhodopsin; Short=HR; Alt Name: Full=NpHR"; (Apr. 1, 1990).
Ehrlich I. et al. "Amygdala inhibitory circuits and the control of fear memory", Neuron, 2009, vol. 62: pp. 757-771.
Eijkelkamp, et al. "Neurological perspectives on voltage-gated sodium channels", Brain, 2012, 135:2585-2612.
Eisen, "Treatment of amyotrophic lateral sclerosis", Drugs Aging, 1999; vol. 14, No. 3, pp. 173-196.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Ernst, et al. "Photoactivation of Channelrhodopsin", J. Biol. Chem., 2008, vol. 283, No. 3, pp. 1637-1643.
Esposito et al. "The integrase family of tyrosine recombinases: evolution of a conserved active site domain", Nucleic Acids Research, 1997, vol. 25, No. 18, pp. 3605-3614.
Evanko "Optical excitation yin and yang" Nature Methods, 2007, 4:384.

(56) References Cited

OTHER PUBLICATIONS

Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fenno et al., "The development and application of optogenetics", Annual Review of Neuroscience, 2011, vol. 34, No. 1, pp. 389-412.
Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Garrido et al., "A targeting motif involved in sodium channel clustering at the axonal initial segment", Science, 2003, vol. 300, No. 5628, pp. 2091-2094.
Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine 02 receptor 1-4, 24-25 gene, promoter region and exon 1. Jan. 31, 1997.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al. , "The course of neural projection from the prefrontal cortex to the nucleus accumbens in the rat", Neuroscience, 1997, vol. 76, No. 3, pp. 689-706.
Goshen et al. "Dynamics of Retrieval Strategies for Remote Memories", Cell, 2011, col. 147: pp. 678-589.
Gottesman et al."Bacterial regulation: global regulatory networks," Ann. Rev. Genet. , 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Han, et a.; "Virogenetic and optogenetic mechanisms to define potential therapeutic targets in psychiatric disorders"; Neuropharmacology; vol. 62, pp. 89-100 (2012).
Han, et al., "Millisecond-Timescale Optical Control of Neural Dynamics in the Nonhuman Primate Brain"; Neuron; vol. 62, pp. 191-198 (Apr. 30, 2009).
Han, et al., "Multiple-Color Optical Activation, Silencing, and Desynchronization of Neural Activity with Single-Spike Temporal Resolution", PLoS One, 2007, vol. 2, No. 3, pp. 1-12.
Han; et al., "Two-color, bi-directional optical voltage control of genetically-targeted neurons", CoSyne Abstract Presentation, Presented Feb. 24, 2007.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas rhodopsin*", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.

(56) References Cited

OTHER PUBLICATIONS

Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetlycholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane," PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 5I, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers" Journal of Cell Science, 2005, vol. 118, p. 1935-1943.
Hosokawa, T. et al. "Imaging spatio-temporal patterns of long-term potentiation in mouse hippocampus." Philos. Trans. R. Soc. Lond. B., 2003, vol. 358, pp. 689-693.
Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.
Isenberg et al.; "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene GAL4 and analysis of its dosage effects on the galactose/melibiose regulon," PNAS, 1982, vol. 79, pp. 6971-6975.
Kaiser; "Clinical research. Death prompts a review of gene therapy vector"; Science; 317(5838):580, 1 page (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.

Kandel, E.R.,et al. "Electrophysiology of Hippocampal Neurons: II. After-Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines" , Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Kay; "State-of-the-art gene-based therapies: the road ahead"; Nature Reviews Genetics; vol. 12, pp. 316-328 (May 2011).
Kelder et al., "Glycoconjugates in human and transgenic animal milk", Advances in Exp. Med. and Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Diverging neural pathways assemble a behavioural state from separable features in anxiety" Nature, 2013, 496(7444):219-23.
Kim et al., "Light-Driven Activation of $\beta$2-Adrenergic Receptor Signaling by a Chimeric Rhodopsin Containing the $\beta$2-Adrenergic Receptor Cytoplasmic Loops," Biochemistry, 2005, vol. 44, No. 7, pp. 2284-2292.
Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-10.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Knopfel, et al. "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "A comprehensive concept of optogenetics"; Progress in Brain Research; vol. 196, pp. 1-28 (2012).

(56) References Cited

OTHER PUBLICATIONS

Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kokel et al., "Photochemical activation of TRPA1 channels in neurons and animals", Nat Chem Biol, 2013, 9(4):257-263.
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423):212-217.
Landy, A. "Mechanistic and structural complexity in the site-specific recombination pathways of Int and FLP", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Li et al., "Surface Expression of Kv1 Channels is Governed by a C-Terminal Motif", J. Biol. Chem. (2000), 275(16):11597-11602.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.
Lin, "A user's guide to channelrhodopsin variants: features, limitations and future developments", Exp Physiol, 2010, vol. 96, No. 1, pp. 19-25.
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.

Lyznik, et al. "FLP-mediated recombination of FRT sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996, 274(5293):1678-1683.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.
Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.
Mourot et al., "Rapid Optical Control of Nociception with an Ion Channel Photoswitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.

(56) References Cited

OTHER PUBLICATIONS

Nagel, et al. "Channelrhodopsin-I: a light-gated proton channel in green algae", Science, 2002, vol. 296: pp. 2395-2398.

Nagel, et al. "Channelrhodopsin-2, a directly light-gated cation-selective membrane channel", PNAS, 2003, vol. 100, No. 24: pp. 13940-13945.

Nakagami, et al. "Optical Recording of Trisynaptic Pathway in Rat Hippocampal Slices with a Voltage-Sensitive Dye" Neuroscience, 1997, vol. 81, No. 1, pp. 1-8.

Naqvi, et al. "Damage to the insula disrupts addiction to cigarette smoking," Science; 2007, vol. 315 pp. 531-534.

Natochin, et al. "Probing rhodopsin-transducin interaction using *Drosophila* Rh1-bovine rhodopsin chimeras," Vision Res., 2006, vol. 46, No. 27: pp. 4575-4581.

Nieh et al., "Optogenetic dissection of neural circuits underlying emotional valence and motivated behaviors", Brain Research, E-pub 2012, 1511:73-92.

Nirenberg, et al. "The Light Response of Retinal Ganglion Cells is Truncated by a Displaced Amacrine Circuit", Neuron, 1997, vol. 18: pp. 637-650.

No Authors Listed; "Two bright new faces in gene therapy," Nature Biotechnology, 1996, vol. 14: p. 556.

Nonet, "Visualization of synaptic specializations in live C. elegans with synaptic vesicle protein-GFP fusions", J. Neurosci. Methods, 1999, 89:33-40.

Nunes-Duby, et al. "Similarities and differences among 105 members of the Int family of site-specific recombinases", Nucleic Acids Research, 1998, vol. 26, No. 2: pp. 391-406.

O'Gorman et al. "Recombinase-mediated gene activation and site-specific integration in mammalian cells", Science, 1991, 251(4999): pp. 1351-1355.

Olivares (2001) "Phage R4 integrase mediates site-specific integration in human cells", Gene, 2001, vol. 278, pp. 167-176.

Ory, et al. "A stable human-derived packaging cell line for production of high titer retrovirus/vesicular stomatitis virus G pseudotypes," PNAS, 1996, vol. 93: pp. 11400-11406.

Packer, et al.; "Targeting Neurons and Photons for Optogenetics"; Nature Neuroscience; vol. 16, No. 7, pp. 805-815 (Jul. 2013).

Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.

Palmer et al., "The Adult Rat Hippocampus Contains Primordial Neural Stem Cells", Molecular and Cellular Neuroscience, 1997, vol. 8, pp. 389-404.

Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.

Panda, et al. "Illumination of the Melanopsin Signaling Pathway", Science, 2005, vol. 307: pp. 600-604.

Pandya, et al.; "Where in the Brain Is Depression?"; Curr. Psychiatry Rep.; vol. 14, pp. 634-642 (2012).

Pape, et al., "Plastic Synaptic Networks of the Amygdala for the Acquisition, Expression, and Extinction of Conditioned Fear", 2010, Physiol Rev, vol. 90, pp. 419-463.

Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.

Pear "Transient Transfection Methods for Preparation of High-Titer Retroviral Supernatants" Supplement 68, Current Protocols in Molecular Biology, 1996, 9.1 1 .1-9.1 1 .18.

Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.

Peterlin, et al. "Optical probing of neuronal circuits with calcium indicators," PNAS, 2000, vol. 97, No. 7: pp. 3619-3624.

Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.

Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.

Pettit, et al. "Local Excitatory Circuits in the Intermediate Gray Layer of the Superior Colliculus", J Neurophysiol., 1999, vol. 81, No. 3: pp. 1424-1427.

Pinkham et al., "Neural bases for impaired social cognition in schizophrenia and autism spectrum disorders", Schizophrenia Research, 2008, vol. 99, pp. 164-175.

Potter, "Transfection by Electroporation." Supplement 62, Current Protocols in Molecular Biology, 1996, 9.3.1-9.3.6.

Pouille, et al. "Routing of spike series by dynamic circuits in the hippocampus", Nature, 2004, vol. 429: pp. 717-723.

Qiu et al. "Induction of photosensitivity by heterologous expression of melanopsin", Nature, 2005, vol. 433: pp. 745-749.

Ramalho, et al.; "Mouse genetic corneal disease resulting from transgenic insertional mutagenesis"; Br. J. Ophthalmol.; vol. 88, No. 3, pp. 428-432 (Mar. 2004).

Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.

Randic, et al. "Long-term Potentiation and Long-term Depression of Primary Afferent Neurotransmission in the Rat Spinal Cord", 1993, Journal of Neuroscience, vol. 13, No. 12, pp. 5228-5241.

Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).

Rathnasingham et al., "Characterization of implantable microfabricated fluid delivery devices," IEEE Transactions on Biomedical Engineering, 2004, vol. 51, No. 1: pp. 138-145.

Rein, et al., "The Optogenetic (r)evolution", Mol. Genet. Genomics, 2012, vol. 287, No. 2, pp. 95-109.

Remy, et al., "Depression in Parkinson's Disease: Loss of Dopamine and Noradrenaline Innervation in the Limbic System", Brain, 2005, vol. 128 (Pt 6), pp. 1314-1322.

Ristevski; "Making Better Transgenic Models: Conditional, Temporal, and Spatial Approaches"; Molecular Biotechnology; vol. 29, No. 2, pp. 153-163 (Feb. 2005).

Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.

Rivera et al., "BDNF-Induced TrkB Activation Down-Regulates the K+-Cl− cotransporter KCC2 and Impairs Neuronal Cl− Extrusion", The Journal of Cell Biology, 2002, vol. 159: pp. 747-752.

Rosenkranz, et al. "The prefrontal cortex regulates lateral amygdala neuronal plasticity and responses to previously conditioned stimuli", J. Neurosci., 2003, vol. 23, No. 35: pp. 11054-11064.

Rousche, et al., "Flexible polyimide-based intracortical electrode arrays with bioactive capability," IEEE Transactions on Biomedical Engineering, 2001, vol. 48, No. 3, pp. 361-371.

Rubinson et at. "A lentivirus-based system to functionally silence genes in primary mammalian cells, stem cells and transgenic mice by RNA interference," Nature Genetics, 2003, vol. 33, p. 401-406.

Rudiger et at. "Specific arginine and threonine residues control anion binding and transport in the light-driven chloride pump halorhodopsin," The EMBO Journal, 1997, vol. 16, No. 13, pp. 3813-3821.

Sajdyk, et al., "Excitatory Amino Acid Receptors in the Basolateral Amygdala Regulate Anxiety Responses in the Social Interaction Test", Brain Research, 1997, vol. 764, pp. 262-264.

Salzman, et al. "Cortical microstimulation influences perceptual judgements of motion direction", Nature, 1990, vol. 346, pp. 174-177.

(56) References Cited

OTHER PUBLICATIONS

Samuelson; "Post-traumatic stress disorder and declarative memory functioning: a review"; Dialogues in Clinical Neuroscience; vol. 13, No. 3, pp. 346-351 (2011).
Santana et al., "Can Zebrafish Be Used as Animal Model to Study Alzheimer's Disease?" Am. J. Neurodegener. Dis. (2012), 1(1):32-48.
Sato et al. "Role of Anion-binding Sites in cytoplasmic and extracellular channels of Natronomonas pharaonis halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008,vol. 33, pp. 368-377.
Schroll et al., "Light-induced activation of distinct modulatory neurons triggers appetitive or aversive learning in Drosophila larvae", Current Biology, Sep. 2006, 16(17):1741-1747.
Sclimenti, et al. "Directed evolution of a recombinase for improved genomic integration at a native human sequence," Nucleic Acids Research, 2001, vol. 29, No. 24: pp. 5044-5051.
Sheikh et al., "Neurodegenerative Diseases: Multifactorial Conformational Diseases and Their Therapeutic Interventions", Journal of Neurodegenerative Diseases (2013), Article ID 563481:1-8.
Shepherd, et al. "Circuit Analysis of Experience-Dependent Plasticity in the Developing Rat Barrel Cortex", Neuron, 2003, vol. 38: pp. 277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Sigmund; "Viewpoint: Are Studies in Genetically Altered Mice Out of Control?"; Arterioscler Thromb Vasc Biol.; vol. 20, No. 6, pp. 1425-1429 (Jun. 2000).
Silver, et al. "Amino terminus of the yeast GAL4 gene product is sufficient for nuclear localization" PNAS, 1984, vol. 81, No. 19: pp. 5951-5955.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al.; "Intramolecular Proton Transfer in Channelrhodopsins"; Biophysical Journal; vol. 104, No. 4, pp. 807-807 (Feb. 2013).
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.

Sohal et al., "Parvalbumin neurons and gamma rhythms enhance cortical circuit performance", Nature, 2009, vol. 459, No. 7247, pp. 698-702.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Suzuki et al., "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a Chlamydomonas reinhardtii Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic Xenopus laevis", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", Nippon Ganka Gakkai Zasshi, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in Aplysia: Spread of Stimulus Information and Cross-Correlation Analysis," The Journal of Neuroscience, 1994, vol. 14, No. 7, pp. 4167-4184.

(56) References Cited

OTHER PUBLICATIONS

Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.1-19.39.
Wall, "Transgenic livestock: Progress and prospects for the future", Theriogenology, 1996, vol. 45, pp. 57-68.
Wang, et al. "Direct-current Nanogenerator Driven by Ultrasonic Waves," Science, 2007, vol. 316, pp. 102-105.
Wang, et al., "High-speed mapping of synaptic connectivity using photostimulation in Channelrhodopsin-2 transgenic mice", PNAS, 2007, vol. 104, No. 19, pp. 8143-8148.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Wang, et al., "Mrgprd-Expressing Polymodal Nociceptive Neurons Innervate Most Known Classes of Substantia Gelatinosa Neurons", J Neurosci, 2009, 29(42):13202-13209.
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Williams et al., "From optogenetic technologies to neuromodulation therapies", Sci Transl Med., 2013, 5(177):177.
Witten et. al., "Cholinergic Interneurons Control Local Circuit Activity and Cocaine Conditioning", Science, 2010, vol. 330, No. 6011: pp. 1677-1681.

Witten et. al., Supporting Online Material for: "Cholinergic Interneurons Control Local Circuit Activity and Cocaine Conditioning", Science, 2010, vol. 330: 17 pages.
Written opinion of PCT Application No. PCT/US2011/059383 (dated May 9, 2012).
Xiong et al., "Interregional connectivity to primary motor cortex revealed using MRI resting state images", Hum Brain Mapp, 1999, 8(2-3):151-156.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human $\beta,\beta$-Carotene-15, 15'-Dioxygenase that is Highly Expressed in the Retinal Pigment Epithelium", Genomics, 2001, vol. 72: pp. 193-202.
Yizhar et al., "Optogenetics in neural systems", Neuron Primer, vol. 71, No. 1, pp. 9-34 (Jul. 14, 2011).
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang "Multimodal fast optical interrogation of neural circuitry," Nature, 2007, vol. 446, pp. 633-641.
Zhang, et al. "Channelrhodopsin-2 and optical control of excitable cells," Nature Methods,2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008,vol. 11, No. 6, pp. 631-633.
Zhang, et al., "The Microbial Opsin Family of Optogenetic Tools", Cell, 2011, vol. 147, No. 7, pp. 1146-1457.
Zhang, et al.; "Optogenetic interrogation of neural circuits: Technology for probing mammalian brain structures"; Nature Protocols; vol. 5, No. 3, pp. 439-456 (Feb. 18, 2010).
Zhao, et al., "Improved Expression of Halorhodopsin for Light-Induced Silencing of Neuronal Activity", Brain Cell Biology, 2008, vol. 36 (1-4), pp. 141-154.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Definition of Implant; Merriam-Webster Dictionary; retrieved Nov. 7, 2016 (http://www.merriam-webster.com/dictionary/implant).
Ferenczi, et al.; "Optogenetic approaches addressing extracellular modulation of neural excitability"; Scientific Reports; vol. 6, 20 pages (Apr. 5, 2016).
Li, et al.; "A Method for Activation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Lin, et al.; "Study of the Circuitry of Nucleus Accumbens and its Effect on Addiction by Optogenetic Methods: 964"; Neurosurgery; vol. 67, No. 2, pp. 557 (Aug. 2010).

(56) References Cited

OTHER PUBLICATIONS

Tsuchida; "Nervous Control of Micturition"; The Japanese Journal of Urology; vol. 80, No. 9, pp. 1257-1277 (1989).
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Bibel, et al.; "Differentiation of mouse embryonic stem cells into a defined neuronal lineage"; Nature Neuroscience; vol. 7, No. 9, pp. 1033-1009 (Sep. 2004).
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).
Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Boyden, et al.; "A history of optogenetics: the development of tools for controlling brain circuits with light"; F1000 Biology Reports; vol. 3, No. 11, 12 pages (May 3, 2011).
Knox, et al.; "Heterologous Expression of *Limulus* Rhodopsin"; The Journal of Biological Chemistry; vol. 278, No. 42, pp. 40493-40502 (Oct. 17, 2003).
Lin, et al.; "Characterization of Engineered Channelrhodopsin Variants with Improved Properties and Kinetics"; Biophysical Journal; vol. 96, No. 5, pp. 1803-1814 (Mar. 2009).
Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).
Masaki, et al.; "β2-Adrenergic Receptor Regulation of the Cardiac L-Type $Ca^{2+}$ Channel Coexpressed in a Fibroblast Cell Line"; Receptor; vol. 5, pp. 219-231 (1996).
Smith, et al.; "Proton binding sites involved in the activation of acid-sensing ion channel ASIC2a"; Neuroscience Letters; vol. 426, pp. 12-17 (2007).
Friedman, et al.; "VTA Dopamine Neuron Bursting is Altered in an Animal Model of Depression and Corrected by Desipramine"; J. Mol. Neurosci.; vol. 34, pp. 201-209 (2008).
Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).
Weiss, et al.; "Galanin: A Significant Role in Depression?"; Annals New York Academy of Sciences; vol. 863, No. 1, pp. 364-382 (1998).
Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).
Ahmad, et al. "Heterplogous expression of bovine rhodopsin in Drosophila photoreceptor cells" Invest Ophthalmol Vis Sci. 2006, 3722-3728.
Clare "Targeting Ion Channels for Drug Discovery" Discov Med. 2010 vol. 9 No. 46 pp. 1-6.
Clare "Functional Expression of Ion Channels in Mammalian Systems" Protein Science Encyclopedia A.R. Fersht (Ed.) 2008 pp. 79-109.
Reeves et al., "Structure and function in rhodosin: A tetracycline-inducible system in stable mammalian cell lines for high-level expression of opsin mutants" PNAS, 2002 vol. 99 No. 21 pp. 13413-13418.

* cited by examiner

Arch-TS-p2A-ASIC2a-EYFP atggaccccatcgctctgcaggctggttacgacctgctgggtgacggcagacctgaaactctgtggctgggcatcggcactctgctgatgctg
attggaaccttctactttctggtccgcggatggggagtcaccgataaggatgcccgggaatattacgctgtgactatcctggtgcccggaatcg
catccgccgcatatctgtctatgttctttggtatcgggcttactgaggtgaccgtcggggcgaaatgttggatatctattatgccaggtacgcc
gactggctgtttaccaccccacttctgctgctggatctggcccttctcgctaaggtggatcgggtgaccatcggcaccctggtgggtgtggacg
ccctgatgatcgtcactggcctcatcggagccttgagccacacggccatagccagatacagttggtggttgttctctacaatttgcatgatagtg
gtgctctattttctggctacatccctgcgatctgctgcaaaggagcggggccccgaggtggcatctaccttaacaccctgacagctctggtctt
ggtgctgtggaccgcttaccctatcctgtggatcataggcactgagggcgctggcgtggtgggcctgggcatcgaaactctgctgtttatggt
gttggacgtgactgccaaggtcggctttggctttatcctgttgagatcccgggctattctgggcgacaccgaggcaccagaacccagtgccgg
tgccgatgtcagtgccgccgacaagagcaggatcaccagcgagggcgagtacatcccctggaccagatcgacatcaacgtgggcgcgcc
cggctccggagccacgaacttctctctgttaaagcaagcaggagacgtggaagaaaaccccggtcccatggacctgaaggagtcaccaagc
gagggatcactgcagccatcaagcattcagatttcgctaatacaagcacactgcacggcatccggcatatcttcgtgtacggcccactgaccat
tcggagagtcctgtgggcagtggcctttgtcggaagcctgggactgctgctggtggagagctccgaaagagtcagttactatttctcatatca
gcacgtgactaaggtggacgaggtggtcgctcagtccctggtgtttccgcagtcaccctgtgcaacctgaatgggttcaggttttctcgcctg
accacaaacgacctgtaccacgccggagagctgctggctctgctggatgtgaatctgcagatcccagaccccatctggccgatccaaccgtg
ctggaagcactgaggcagaaggccaacttcaaacactacaagcccaaacagttcagcatgctggagtttctgcaccgcgtgggacatgacct
gaaagatatgatgctgtattgcaagttcaaaggccaggagtgtgggcatcaggacttcactaccgtgtttacaaagtacggcaaatgttacatg
ttcaactccggggaagatggaaaacctctgctgacaactgtgaagggcgggacagggaatggactggagatcatgctggacattcagcag
gatgagtacctgccaatctggggagaaactgaggaaaccacattcgaggccggcgtgaaggtccagatccactcacagagcgagcccctt
cattcaggaactggagatttggagtggcaccaggattccagacatttgtcgctactcaggagcagcgcctgacctatctgccacccccttggggc
gagtgccgatctagtgaaatggggctggacttcttttcctgtgtactctatcaccgcctgccgaattgattgtgagacacggtatatcgtggaaaa
ctgcaattgtaggatggtccacatgcctggcgacgcccccattctgcactcccgaacagcataaagagtgtgctgaacctgcactgggctgct
ggctgagaaggatagtaactactgcctgtgtagaacaccctgtaacctgactaggtataataaggaactgagcatggtgaagatcccttccaa
aacatctgcaaagtacctggagaagaagttcaacaagtctgagaagtacatcagtgaaaacattctggtgctggacatcttctttgaagctctga
attacgagaccattgaacagaagaaagcatatgaggtggccgctctgctgggggatattggaggccagatgggactgttcatcggcgccag
cctgctgacaattctggagctgtttgactacatctatgagctgattaaggaaaaactgctggatctgctggggaaggaggaagaggaaggat
cacacgacgaaaacatgagcacttgcgataccatgcctaatcacagcgagaccatctcccatacagtgaatgtcccactgcagactgcactgg
gcaccctggaggaaattgcctgtgcggccgcc<mark>gtgagcaagggcgaggagctgttcaccggggtggtgcccatcctggtcgagctggacg
gcgacgtaaacggccacaagttcagcgtgtccggcgagggcgagggcgatgccacctacggcaagctgaccctgaagttcatctgcaccac
cggcaagctgcccgtgccctggcccaccctcgtgaccaccttcggctacggcctgcagtgcttcgcccgctaccccgaccacatgaagcagca
cgacttcttcaagtccgccatgcccgaaggctacgtccaggagcgcaccatcttcttcaaggacgacggcaactacaagacccgcgcgagg
tgaagttcgagggcgacaccctggtgaaccgcatcgagctgaagggcatcgacttcaaggaggacggcaacatcctggggcacaagctgg
agtacaactacaacagccacaacgtctatatcatggccgacaagcagaagaacggcatcaaggtgaacttcaagatccgccacaacatcgag
gacggcagcgtgcagctcgccgaccactaccagcagaacacccccatcggcgacggccccgtgctgctgcccgacaaccactacctgagct
accagtccgccctgagcaaagaccccaacgagaagcgcgatcacatggtcctgctggagttcgtgaccgccgccgggatcactctcggcatg
gacgagctgtacaagtaa</mark> (SEQ ID NO: 63)

Arch = underlined
TS = *italic*
p2A = white-on-black
ASIC2a = *italic underlined*
EYFP = *italic white-on-black*

FIG. 5

Arch-TS-p2A-ASIC2a-TS-EYFP-ER atggaccccatcgctctgcaggctggttacgacctgctgggtgacggcagacctgaaactctgtggctgggcatcggcactctgctgatgctg
attggaaccttctactttctggtccgcggatggggagtcaccgataaggatgcccgggaatattacgctgtgactatcctggtgcccggaatcg
catccgccgcatatctgtctatgttctttggtatcggcttactgaggtgaccgtcggggcgaaatgttggatatctattatgccaggtacgcc
gactggctgtttaccaccccacttctgctgctggatctggcccttctcgctaaggtggatcgggtgaccatcggcacctggtgggtgtggacg
ccctgatgatcgtcactggcctcatcggagccttgagccacacggccatagccagatacagttggtggttgttctctacaatttgcatgatagtg
gtgctctatttctggctacatccctgcgatctgctgcaaaggagcggggccccgaggtggcatctaccttttaacaccctgacagctctggtctt
ggtgctgtggaccgcttacctatcctgtggatcataggcactgagggcgctggcgtggtgggcctgggcatcgaaactctgctgtttatggt
gttggacgtgactgccaaggtcggctttggctttatcctgttgagatcccggctattctgggcgacaccgaggcaccagaacccagtgccgg
tgccgatgtcagtgccgccgacaagagcaggatcaccagcgagggcgagtacatcccccfggaccagatcgacatcaacgtgggcgcgcc
c*ggctccggagccacgaacttctctctgttaaagcaagcaggagacgtggaagaaaacccggtccc*atggacctgaaggagtcaccaagc
gagggatcactgcagccatcaagcattcagatttttcgctaatacaagcacactgcacggcatccggcatatcttcgtgtacggcccactgaccat
tcggagagtcctgtgggcagtggcctttgtcggaagcctggactgctgctggtggagagctccgaaagagtcagttactatttctcatatca
gcacgtgactaaggtggacgaggtggtcgctcagtcctggtgtttccgcagtcaccctgtgcaacctgaatgggttcaggttttctcgcctg
accacaaacgacctgtaccacgccggagagctgctggctctgctggatgtgaatctgcagatcccagaccccatctggccgatccaaccgtg
ctggaagcactgaggcagaaggccaacttcaaacactacaagcccaaacagttcagcatgctggagtttctgcaccgcgtgggacatgacct
gaaagatatgatgctgtattgcaagtttcaaaggccaggagtgtgggcatcaggacttcactaccgtgtttacaaagtacggcaaatgttacatg
ttcaactccggggaagatggaaaacctctgctgacaactgtgaagggcgggacagggaatggactggagatcatgctggacattcagcag
gatgagtacctgccaatctggggagaaactgaggaaaccacattcgaggccggcgtgaaggtccagatccactcacagagcgagcccccttt
cattcaggaactgggatttggagtggcaccaggattccagacatttgtcgctactcaggagcagcgcctgacctatctgccacccccttgggcc
gagtgccgatctagtgaaatggggctggacttcttcctgtgtactctatcaccgcctgccgaattgattgtgagacacggtatatcgtggaaaa
ctgcaattgtaggatggtccacatgcctggcgacgccccattctgcactccgaacagcataaagagtgtgctgaacctgcactggggctgct
ggctgagaaggatagtaactactgcctgtgtagaacaccctgtaacctgactaggtataataaggaactgagcatggtgaagatcccttccaa
aacatctgcaaagtacctggagaagaagttcaacaagtctgagaagtacatcagtgaaaacattctggtgctggacatcttctttgaagctctga
attacgagaccattgaacagaagaaagcatatgaggtggccgctctgctggggatattggaggccagatgggactgttcatcggcgccag
cctgctgacaattctggagctgtttgactacatctatgagctgattaaggaaaaactgctggatctgctggggaaggaggaagaggaaggat
cacacgacgaaaacatgagcacttgcgataccatgcctaatcacagcgagaccatctcccatacagtgaatgtcccactgcagactgcactgg
gcaccctggaggaaattgcctgtgcggccgcc*aagagcaggatcaccagcgagggcgagtacatcccctggaccagatcgacatcaacgtggtgagcaagggcgaggagctgttcaccggggtggtgcccatcctggtcgagctggacggcgacgtaaacggccacaagttcagcgtgtc
cggcgagggcgagggcgatgccacctacggcaagctgaccctgaagttcatctgcaccaccggcaagctgcccgtgccctggcccaccctc
gtgaccaccttcggctacggcctgcagtgcttcgcccgctaccccgaccacatgaagcagcacgacttcttcaagtccgccatgcccgaaggct
acgtccaggagcgcaccatcttcttcaaggacgacggcaactacaagacccgcgccgaggtgaagttcgagggcgacaccctggtgaaccg
catcgagctgaagggcatcgacttcaaggaggacggcaacatcctggggcacaagctggagtacaactacaacagccacaacgtctatatc
atggccgacaagcagaagaacggcatcaaggtgaacttcaagatccgccacaacatcgaggacggcagcgtgcagctcgccgaccactac
cagcagaacacccccatcggcgacggccccgtgctgctgcccgacaaccactacctgagctaccagtccgccctgagcaaagaccccaacga
gaagcgcgatcacatggtcctgctggagttcgtgaccgccgcgggatcactctcggcatggacgagctgtacaag*tctgctacgagaacg*
*aggtgtaa* (SEQ ID NO:64)

Arch = underline
TS = *italic*
p2A = white-on-black
ASIC2a = *italic underline*
TS = double underline
EYFP = *italic white-on-black*
ER = *italic double underline*

FIG. 6 amino acid sequence of eArch:

MDPIALQAGYDLLGDGRPETLWLGIGTLLMLIGTFYFLVRGWGVTDKDAREYYAVTIL
VPGIASAAYLSMFFGIGLTEVTVGGEMLDIYYARYADWLFTTPLLLLDLALLAKVDRV
TIGTLVGVDALMIVTGLIGALSHTAIARYSWWLFSTICMIVVLYFLATSLRSAAKERGPE
VASTFNTLTALVLVLWTAYPILWIIGTEGAGVVGLGIETLLFMVLDVTAKVGFGFILLR
SRAILGDTEAPEPSAGADVSAAD (SEQ ID NO:1).

amino acid sequence of eArch3.0-EYFP:
MDPIALQAGYDLLGDGRPETLWLGIGTLLMLIGTFYFLVRGWGVTDKDAREYYAVTIL
VPGIASAAYLSMFFGIGLTEVTVGGEMLDIYYARYADWLFTTPLLLLDLALLAKVDRV
TIGTLVGVDALMIVTGLIGALSHTAIARYSWWLFSTICMIVVLYFLATSLRSAAKERGPE
VASTFNTLTALVLVLWTAYPILWIIGTEGAGVVGLGIETLLFMVLDVTAKVGFGFILLR
SRAILGDTEAPEPSAGADVSAADRPVVAVSKAAAKSRITSEGEYIPLDQIDNVVSKGEE
LFTGVVPILVELDGDVNGHKFSVSGEGEGDATYGKLTLKFICTTGKLPVPWPTLVTTFG
YGLQCFARYPDHMKQHDFFKSAMPEGYVQERTIFFKDDGNYKTRAEVKFEGDTLVNR
IELKGIDFKEDGNILGHKLEYNYNSHNVYIMADKQKNGIKVNFKIRHNIEDGSVQLADH
YQQNTPIGDGPVLLPDNHYLSYQSALSKDPNEKRDHMVLLEFVTAAGITLGMDELYKF
CYENEV (SEQ ID NO:2).

ArchT 3.0

MDPIALQAGYDLLGDGRPETLWLGIGTLLMLIGTFYFIVKGWGVTDKEAREYYSITILVP
GIASAAYLSMFFGIGLTEVTVAGEVLDIYYARYADWLFTTPLLLLDLALLAKVDRVSIGT
LVGVDALMIVTGLIGALSHTPLARYSWWLFSTICMIVVLYFLATSLRAAAKERGPEVAST
FNTLTALVLVLWTAYPILWIIGTEGAGVVGLGIETLLFMVLDVTAKVGFGFILLRSRAIL
GDTEAPEP (SEQ ID NO:3)

amino acid sequence of GtR3:

ASSFGKALLEFVFIVFACITLLLGINAAKSKAASRVLFPATFVTGIASIAYFSMASGGGWVI
APDCRQLFVARYLDWLITTPLLLIDLGLVAGVSRWDIMALCLSDVLMIATGAFGSLTVG
NVKWVWWFFGMCWFLHIIFALGKSWAEAAKAKGGDSASVYSKIAGITVITWFCYPVV
WVFAEGFGNFSVTFEVLIYGVLDVISKAVFGLILMSGAATGYESI (SEQ ID NO:4).

Amino acid sequence of a *Oxyrrhis marina* proton pump (rhodopsin type II)

```
maplaqdwty aewsavynal sfgiagmgsa tiffwlqlpn vtknyrtalt itgivtliat
yhyfrifnsw vaafnvglgv ngayevtvsg tpfndayryv dwlltvplii velilvmklp
aketvclawt lgiasavmva lgypgeiqdd lsvrwfwwac amvpfvyvvg tlvvglgaat
akqpegvvdl vsaaryltvv swltypfvyi vkniglagst atmyeqigys aadvtakavf
gvliwaiana ksrleeegkl ra (SEQ ID NO:5)
```

FIG. 13A

Amino acid sequence of *L. maculans* rhodopsin

```
mivdqfeevl mktsqlfplp tatqsaqpth vapvptvlpd tpiyetvgds gsktlwvvfv
lmliasaaft alswkipvnr rlyhvittii tltaalsyfa matghgvaln kivirtqhdh
vpdtyetvyr qvyyaryidw aittplllld lgllagmsga hifmaivadl imvltglfaa
fgsegtpqkw gwytiaciay ifvvwhlvln gganarvkge klrsffvaig aytlilwtay
pivwgladga rkigvdgeii ayavldvlak gvfgawllvt hanlresdve lngfwangln
regairiged dga (SEQ ID NO:6)
```

Mac 3.0
```
MIVDQFEEVLMKTSQLFPLPTATQSAQPTHVAPVPTVLPDTPIYETVGDSGSKTLWVVFV
LMLIASAAFTALSWKIPVNRRLYHVITTIITLTAALSYFAMATGHGVALNKIVIRTQHDH
VPDTYETVYRQVYYARYIDWAITTPLLLLDLGLLAGMSGAHIFMAIVADLIMVLTGLFAA
FGSEGTPQKWGWYTIACIAYIFVVWHLVLNGGANARVKGEKLRSFFVAIGAYTLILWTAY
PIVWGLADGARKIGVDGEIIAYAVLDVLAKGVFGAWLLVTHANLRESDVELNGFWANGLN
REGAIRIGEDDGARPVVAVSK (SEQ ID NO:7)
```

FIG. 13B

Amino acid sequence of ChR2:

MDYGGALSAVGRELLFVTNPVVVNGSVLVPEDQCYCAGWIESRGTNGAQTASNVLQWLAAGFSIL
LLMFYAYQTWKSTCGWEEIYVCAIEMVKVILEFFFEFKNPSMLYLATGHRVQWLRYAEWLLTCPV
ILIHLSNLTGLSNDYSRRTMGLLVSDIGTIVWGATSAMATGYVKVIFFCLGLCYGANTFFHAAKA
YIEGYHTVPKGRCRQVVTGMAWLFFVSWGMFPILFILGPEGFGVLSVYGSTVGHTIIDLMSKNCW
GLLGHYLRVLIHEHILIHGDIRKTTKLNIGGTEIEVETLVEDEAEAGAVP (SEQ ID NO:8).

amino acid sequence of a SFO:

MDYGGALSAVGRELLFVTNPVVVNGSVLVPEDQCYCAGWIESRGTNGAQTASNVLQW
LAAGFSILLLMFYAYQTWKSTCGWEEIYVCAIEMVKVILEFFFEFKNPSMLYLATGHRVQ
WLRYAEWLLTSPVILIHLSNLTGLSNDYSRRTMGLLVSDIGTIVWGATSAMATGYVKVIF
FCLGLCYGANTFFHAAKAYIEGYHTVPKGRCRQVVTGMAWLFFVSWGMFPILFILGPEG
FGVLSVYGSTVGHTIIDLMSKNCWGLLGHYLRVLIHEHILIHGDIRKTTKLNIGGTEIEVET
LVEDEAEAGAVP (SEQ ID NO:9).

amino acid sequence of an SSFO:

MDYGGALSAVGRELLFVTNPVVVNGSVLVPEDQCYCAGWIESRGTNGAQTASNVLQW
LAAGFSILLLMFYAYQTWKSTCGWEEIYVCAIEMVKVILEFFFEFKNPSMLYLATGHRVQ
WLRYAEWLLTSPVILIHLSNLTGLSNDYSRRTMGLLVSAIGTIVWGATSAMATGYVKVIF
FCLGLCYGANTFFHAAKAYIEGYHTVPKGRCRQVVTGMAWLFFVSWGMFPILFILGPEG
FGVLSVYGSTVGHTIIDLMSKNCWGLLGHYLRVLIHEHILIHGDIRKTTKLNIGGTEIEVET
LVEDEAEAGAVP (SEQ ID NO:10).

amino acid sequence of C1V1:

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWEEIYVATIEMIKFIIEYFHEFDEPAVIYSSNGNKTVWLRYAEWLLTCPVLLIHL
SNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISPYGSAIGHSI
LDLIAKNMWGVLGNYLRVKIHEHILLYGDIRKKQKITIAGQEMEVETLVAEEED (SEQ
ID NO:11).

amino acid sequence of C1V1 (E122T):

MSRRPWLLALALAVALAAGSAGASTGSDATVPVATQDGPDYVFHRAHERMLFQTSYTL
ENNGSVICIPNNGQCFCLAWLKSNGTNAEKLAANILQWITFALSALCLMFYGYQTWKST
CGWETIYVATIEMIKFIIEYFHEFDEPAVIYSSNGNKTVWLRYAEWLLTCPVLLIHLSNLT
GLKDDYSKRTMGLLVSDVGCIVWGATSAMCTGWTKILFFLISLSYGMYTYFHAAKVYIE
AFHTVPKGICRELVRVMAWTFFVAWGMFPVLFLLGTEGFGHISPYGSAIGHSILDLIAKN
MWGVLGNYLRVKIHEHILLYGDIRKKQKITIAGQEMEVETLVAEEED (SEQ ID NO:12).

FIG. 13C amino acid sequence of C1V1 (E162T):

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWEEIYVATIEMIKFIIEYFHEFDEPAVIYSSNGNKTVWLRYATWLLTCPVLLIHL
SNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISPYGSAIGHSI
LDLIAKNMWGVLGNYLRVKIHEHILLYGDIRKKQKITIAGQEMEVETLVAEEED (SEQ
ID NO:13).

amino acid sequence of C1V1 (E122T/E162T):

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWETIYVATIEMIKFIIEYFHEFDEPAVIYSSNGNKTVWLRYATWLLTCPVLLIHL
SNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISPYGSAIGHSI
LDLIAKNMWGVLGNYLRVKIHEHILLYGDIRKKQKITIAGQEMEVETLVAEEED (SEQ
ID NO:14).

Amino acid sequence of *Dunaliella salina* channelrhodopsin

```
mrrresqlay  lclfvliagw  aprltesapd  laerrppser  ntpyanikkv  pnitepnanv
qldgwalyqd  fyylagsdke  wvvgpsdqcy  crawskshgt  dreqeaavvw  ayivfaiciv
qlvyfmfaaw  katvgweevy  vniielvhia  lviwvefdkp  amlylndgqm  vpwlrysawl
lscpvlihl   snltglkgdy  skrtmgllvs  digtivfgts  aalappnhvk  vilftiglly
glftfftaak  vyieayhtvp  kgqcrnlvra  mawtyfvswa  mfpilfilgr  egfghityfg
ssighfilei  fsknlwsllg  hglryrirqh  iiihgnltkk  nkiniagdnv  eveeyvdsnd
kdsdv (SEQ  ID NO:15)
```

FIG. 13D amino acid sequence of NpHR without the (native) signal peptide:

VTQRELFEFVLNDPLLASSLYINIALAGLSILLFVFMTRGLDDPRAKLIAVSTILVPVVSIAS
YTGLASGLTISVLEMPAGHFAEGSSVMLGGEEVDGVVTMWGRYLTWALSTPMILLALG
LLAGSNATKLFTAITFDIAMCVTGLAAALTTSSHLMRWFWYAISCACFLVVLYILLVEW
AQDAKAAGTADMFNTLKLLTVVMWLGYPIVWALGVEGIAVLPVGVTSWGYSFLDIVA
KYIFAFLLLNYLTSNESVVSGSILDVPSASGTPADD (SEQ ID NO:16).

amino acid sequence of eYFP-NpHR3.0:

MTETLPPVTESAVALQAEVTQRELFEFVLNDPLLASSLYINIALAGLSILLFVFMTRGLDD
PRAKLIAVSTILVPVVSIASYTGLASGLTISVLEMPAGHFAEGSSVMLGGEEVDGVVTMW
GRYLTWALSTPMILLALGLLAGSNATKLFTAITFDIAMCVTGLAAALTTSSHLMRWFWY
AISCACFLVVLYILLVEWAQDAKAAGTADMFNTLKLLTVVMWLGYPIVWALGVEGIAV
LPVGVTSWGYSFLDIVAKYIFAFLLLNYLTSNESVVSGSILDVPSASGTPADDAAAKSRIT
SEGEYIPLDQIDINVVSKGEELFTGVVPILVELDGDVNGHKFSVSGEGEGDATYGKLTLKF
ICTTGKLPVPWPTLVTTFGYGLQCFARYPDHMKQHDFFKSAMPEGYVQERTIFFKDDGN
YKTRAEVKFEGDTLVNRIELKGIDFKEDGNILGHKLEYNYNSHNVYIMADKQKNGIKVN
FKIRHNIEDGSVQLADHYQQNTPIGDGPVLLPDNHYLSYQSALSKDPNEKRDHMVLLEF
VTAAGITLGMDELYKFCYENEV (SEQ ID NO:17).

amino acid sequence of eYFP-NpHR3.1:

MVTQRELFEFVLNDPLLASSLYINIALAGLSILLFVFMTRGLDDPRAKLIAVSTILVPVVSI
ASYTGLASGLTISVLEMPAGHFAEGSSVMLGGEEVDGVVTMWGRYLTWALSTPMILLA
LGLLAGSNATKLFTAITFDIAMCVTGLAAALTTSSHLMRWFWYAISCACFLVVLYILLVE
WAQDAKAAGTADMFNTLKLLTVVMWLGYPIVWALGVEGIAVLPVGVTSWGYSFLDIV
AKYIFAFLLLNYLTSNESVVSGSILDVPSASGTPADDAAAKSRITSEGEYIPLDQIDINVVS
KGEELFTGVVPILVELDGDVNGHKFSVSGEGEGDATYGKLTLKFICTTGKLPVPWPTLVT
TFGYGLQCFARYPDHMKQHDFFKSAMPEGYVQERTIFFKDDGNYKTRAEVKFEGDTLV
NRIELKGIDFKEDGNILGHKLEYNYNSHNVYIMADKQKNGIKVNFKIRHNIEDGSVQLAD
HYQQNTPIGDGPVLLPDNHYLSYQSALSKDPNEKRDHMVLLEFVTAAGITLGMDELYKF
CYENEV (SEQ ID NO:18).

Amino acid sequence of C1C2

MSRRPWLLALALAVALAAGSAGASTGSDATVPVATQDGPDYVFHRAHERMLFQTSYTLE
NNGSVICIPNNGQCFCLAWLKSNGTNAEKLAANILQWITFALSALCLMFGYQTWKSTC
GWEEIYVATIEMIKFIIEYFHEFDEPAVIYSSNGNKTVWLRYAEWLLTCPVILIHLSNL
TGLANDYNKRTMGLLVSDIGTIVWGTTAALSKGYVRVIFFLMGLCYGIYTFFNAAKVYI
EAYHTVPKGRCRQVVTGMAWLFFVSWGMFPILFILGPEGFGVLSVYGSTVGHTIIDLMS
KNCWGLLGHYLRVLIHEHILIHGDIRKTTKLNIGGTEIEVETLVEDEAEAGAV (SEQ
ID NO:29)

FIG. 13E

Amino acid sequence of ReaChR
MVSRRPWLLALALAVALAAGSAGASTGSDATVPVATQDGPDYVFHRAHERMLFQTSYTL
ENNGSVICIPNNGQCFCLAWLKSNGTNAEKLAANILQWVTFALSVACLGWYAYQAWRAT
CGWEEVYVALIEMMKSIIEAFHEFDSPATLWLSSGNGVVWMRYGEWLLTCPVILIHLSN
LTGLKDDYSKRTMGLLVSDVGCIVWGATSAMCTGWTKILFFLISLSYGMYTYFHAAKVY
IEAFHTVPKGLCRQLVRAMAWLFFVSWGMFPVLFLLGPEGFGHISPYGSAIGHSILDLI
AKNMWGVLGNYLRVKIHEHILLYGDIRKKQKITIAGQEMEVETLVAEEEDKYESS
(SEQ ID NO:30)

FIG. 13F

Champ 1.0:

MDPIALQAGYDLLGDGRPETLWLGIGTLLMLIGTFYFLVRGWGVTDKDAREYYAVTILV
PGIASAAYLSMFFGIGLTEVTVGGEMLDIYYARYADWLFTTPLLLLDLALLAKVDRVTIG
TLVGVDALMIVTGLIGALSHTAIARYSWWLFSTICMIVVLYFLATSLRSAAKERGPEVAS
TFNTLTALVLVLWTAYPILWIIGTEGAGVVGLGIETLLFMVLDVTAKVGFGFILLRSRAIL
GDTEAPEPSAGADVSAADKSRITSEGEYIPLDQIDINVGAPGSGATNFSLLKQAGDVEENP
MDLKESPSEGSLQPSSIQIFANTSTLHGIRHIFVYGPLTIRRVLWAVAFVGSLGLLLVESSERVSY
YFSYQHVTKVDEVVAQSLVFPAVTLCNLNGFRFSRLTTNDLYHAGELLALLDVNLQIPDPHLA
DPTVLEALRQKANFKHYPKPKQFSMLEFLHRVGHDLKDMMLYCKFKGQECGHQDFTTVFTK
YGKCYMFNSGEDGKPLLTTVKGGTGNGLEIMLDIQQDEYLPIWGETEETTFEAGVKVQIHSQS
EPPFIQELGFGVAPGFQTFVATQEQRLTYLPPPWGECRSSEMGLDFFPVYSITACRIDCETRYI
VENCNCRMVHMPGDAPFCTPEQHKECAEPALGLLAEKDSNYCLCRTPCNLTRYNKELSMVKI
PSKTSAKYLEKKFNKSEKYISENILVLDIFFEALNYETIEQKKAYEVAALLGDIGGQMGLFIGASL
LTILELFDYIYELIKEKLLDLLGKEEEEGSHDENMSTCDTMPNHSETISHTVNVPLQTALGTLEE
IAC*AAAVSKGEELFTGVVPILVELDGDVNGHKFSVSGEGEGDATYGKLTLKFICTTGKLPVPW
PTLVTTFGYGLQCFARYPDHMKQHDFFKSAMPEGYVQERTIFFKDDGNYKTRAEVKFEGDT
LVNRIELKGIDFREDGNILGHKLEYNYNSHNVYIMADKQKNGIKVNFKIRHNIEDGSVQLADHY
QQNTPIGDGPVLLPDNHYLSYQSALSKDPNEKRDHMVLLEFVTAAGITLGMDELYK*TGTENET
** (SEQ ID NO:31)

KEY:

Arch = underline

ASIC2a = *italic*

TS = white-on-black

ER = *italic white-on-black* eYFP = *italic underline* p2A = double underline

FIG. 13G

Champ 2.0:

<u>MDPIALQAGYDLLGDGRPETLWLGIGTLLMLIGTFYFLVRGWGVTDKDAREYYAVTILV</u>
<u>PGIASAAYLSMFFGIGLTEVTVGGEMLDIYYARYADWLFTTPLLLLDLALLAKVDRVTIG</u>
<u>TLVGVDALMIVTGLIGALSHTAIARYSWWLFSTICMIVVLYFLATSLRSAAKERGPEVAS</u>
<u>TFNTLTALVLVLWTAYPILWIIGTEGAGVVGLGIETLLFMVLDVTAKVGFGFILLRSRAIL</u>
<u>GDTEAPEPSAGADVSAAD</u>KSRITSEGEYIPLDQIDINVGAPGSGATNFSLLKQAGDVEENP
*MDLKESPSEGSLQPSSIQIFANTSTLHGIRHIFVYGPLTIRRVLWAVAFVGSLGLLLVESSERVSY*
*YFSYQHVTKVDEVVAQSLVFPAVTLCNLNGFRFSRLTTNDLYHAGELLALLDVNLQIPDPHLA*
*DPTVLEALRQKANFKHYKPKQFSMLEFLHRVGHDLKDMMLYCKFKGQECGHQDFTTVFTK*
*YGKCYMFNSGEDGKPLLTTVKGGTGNGLEIMLDIQQDEYLPIWGETEETTFEAGVKVQIHSQS*
*EPPFIQELGFGVAPGFQTFVATQEQRLTYLPPPWGECRSSEMGLDFFPVYSITACRIDCETRYI*
*VENCNCRMVHMPGDAPFCTPEQHKECAEPALGLLAEKDSNYCLCRTPCNLTRYNKELSMVKI*
*PSKTSAKYLEKKFNKSEKYISENILVLDIFFEALNYETIEQKKAYEVAALLGDIGGQMGLFIGASL*
*LTILELFDYIYELIKEKLLDLLGKEEEEGSHDENMSTCDTMPNHSETISHTVNVPLQTALGTLEE*
*IACAAA*KSRITSEGEYIPLDQIDINV*VSKGEELFTGVVPILVELDGDVNGHKFSVSGEGEGDA*
*TYGKLTLKFICTTGKLPVPWPTLVTTFGYGLQCFARYPDHMKQHDFFKSAMPEGYVQERTIF*
*FKDDGNYKTRAEVKFEGDTLVNRIELKGIDFREDGNILGHKLEYNYNSHNVYIMADKQKNGIK*
*VNFKIRHNIEDGSVQLADHYQQNTPIGDGPVLLPDNHYLSYQSALSKDPNEKRDHMVLLEFVT*
*AAGITLGMDELYK*<u>FCTENET</u>** (SEQ ID NO:32)

KEY:

Arch = <u>underline</u>

ASIC2a = *italic*

TS = white-on-black

ER = *italic white-on-black* eYFP = *<u>italic underline</u>* p2A = <u><u>double underline</u></u>

FIG. 13H

Champ 3.0

MDPIALQAGYDLLGDGRPETLWLGIGTLLMLIGTFYFLVRGWGVTDKDAREYYAVTILV
PGIASAAYLSMFFGIGLTEVTVGGEMLDIYYARYADWLFTTPLLLLDLALLAKVDRVTIG
TLVGVDALMIVTGLIGALSHTAIARYSWWLFSTICMIVVLYFLATSLRSAAKERGPEVAS
TFNTLTALVLVLWTAYPILWHGTEGAGVVGLGIETLLFMVLDVTAKVGFGFILLRSRAIL
GDTEAPEPSAGADVSAADKSRITSEGEYIPLDQIDINVGAP*MDLKESPSEGSLQPSSIQIFAN
TSTLHGIRHIFVYGPLTIRRVLWAVAFVGSLGLLLVESSERVSYYFSYQHVTKVDEVVAQSLVFPA
VTLCNLNGFRFSRLTTNDLYHAGELLALLDVNLQIPDPHLADPTVLEALRQKANFKHYKPKQF
SMLEFLHRVGHDLKDMMLYCKFKGQECGHQDFTTVFTKYGKCYMFNSGEDGKPLLTTVKG
GTGNGLEIMLDIQQDEYLPIWGETEETTFEAGVKVQIHSQSEPPFIQELGFGVAPGFQTFVAT
QEQRLTYLPPPWGECRSSEMGLDFFPVYSITACRIDCETRYIVENCNCRMVHMPGDAPFCTPE
QHKECAEPALGLLAEKDSNYCLCRTPCNLTRYNKELSMVKIPSKTSAKYLEKKFNKSEKYISENI
LVLDIFFEALNYETIEQKKAYEVAALLGDIGGQMGLFIGASLLTILELFDYIYELIKEKLLDLLGK
EEEEGSHDENMSTCDTMPNHSETISHTVNVPLQTALGTLEEIACAAA*****KSRITSEGEYIPLDQI
DINV****VSKGEELFTGVVPILVELDGDVNGHKFSVSGEGEGDATYGKLTLKFICTTGKLPVPWPT
LVTTFGYGLQCFARYPDHMKQHDFFKSAMPEGYVQERTIFFKDDGNYKTRAEVKFEGDTLV
NRIELKGIDFREDGNILGHKLEYNYNSHNVYIMADKQKNGIKVNFKIRHNIEDGSVQLADHYQ
QNTPIGDGPVLLPDNHYLSYQSALSKDPNEKRDHMVLLEFVTAAGITLGMDELYK*TQYENE**
(SEQ ID NO:33)

KEY:

Arch = <u>underline</u>

ASIC2a = *italic*

TS = white-on-black

ER = *italic white-on-black* eYFP = *<u>italic underline</u>* p2A = <u>double underline</u>

FIG. 13I

Champ 4.0:

MDPIALQAGYDLLGDGRPETLWLGIGTLLMLIGTFYFLVRGWGVTDKDAREYYAVTILV
PGIASAAYLSMFFGIGLTEVTVGGEMLDIYYARYADWLFTTPLLLLDLALLAKVDRVTIG
TLVGVDALMIVTGLIGALSHTAIARYSWWLFSTICMIVVLYFLATSLRSAAKERGPEVAS
TFNTLTALVLVLWTAYPILWIIGTEGAGVVGLGIETLLFMVLDVTAKVGFGFILLRSRAIL
GDTEAPEPSAGADVSAADKSRITSEGEYIPLDQIDINVGAPGSGATNFSLLKQAGDVEENP
GPMDLKESPSEGSLQPSSIQIFANTSTLHGIRHIFVYGPLTIRRVLWAVAFVGSLGLLLVESSERV
SYYFSYQHVTKVDEVVAQSLVFPAVTLCNLNGFRFSRLTTNDLYHAGELLALLDVNLQIPDPHL
ADPTVLEALRQKANFKHYKPKQFSMLEFLHRVGHDLKDMMLYCKFKGQECGHQDFTTVFT
KYGKCYMFNSGEDGKPLLTTVKGGTGNGLEIMLDIQQDEYLPIWGETEETTFEAGVKVQIHS
QSEPPFIQELGFGVAPGFQTFVATQEQRLTYLPPPWGECRSSEMGLDFFPVYSITACRIDCETR
YIVENCNCRMVHMPGDAPFCTPEQHKECAEPALGLLAEKDSNYCLCRTPCNLTRYNKELSMV
KIPSKTSAKYLEKKFNKSEKYISENILVLDIFFEALNYETIEQKKAYEVAALLGDIGGQMGLFIGA
SLLTILELFDYIYELIKEKLLDLLGKEEEEGSHDENMSTCDTMPNHSETISHTVNVPLQTALGTL
EEIACAAAKSRITSEGEYIPLDQIDINVVSKGEELFTGVVPILVELDGDVNGHKFSVSGEGEG
DATYGKLTLKFICTTGKLPVPWPTLVTTFGYGLQCFARYPDHMKQHDFFKSAMPEGYVQERT
IFFKDDGNYKTRAEVKFEGDTLVNRIELKGIDFREDGNILGHKLEYNYNSHNVYIMADKQKNG
IKVNFKIRHNIEDGSVQLADHYQQNTPIGDGPVLLPDNHYLSYQSALSKDPNEKRDHMVLLEF
VTAAGITLGMDELYKPGYNEL* (SEQ ID NO:34)

KEY:

Arch = underline

ASIC2a = *italic*

TS = white-on-black

ER = *italic white-on-black* eYFP = *italic underline* p2A = double underline

FIG. 13J

Amino acid Sequence of *Coccomyxa subellipsoidea* (*Chlorella vulgaris*) C-169 Rhodopsin MAVHQIGEGGLVMYWVTFGLMAFSALAFAVMTFTRPLNKRSHGYITLAIVTIAAIAYYAMAAS
GGKALVSNPDGNLRDIYYARYIDWFFTPLLLLDIILLTGIPIGVTLWIVLADVAMIMLGLFGALS
TNSYRWGYYGVSCAFFFVVLWGLFFPGAKGARARGGQVPGLYFGLAGYLALLWFGYPIVWGL
AEGSDYISVTAEAASYAGLDIAAKVVFGWAVMLSHPLIARNQTDGSLLINSTNDPFVASTTHIPE
RQGGIFGGLMGKKRGAGTPLATNEGVPRKAAPTAATTTAGNPATAAEVRTPRELMARL (SEQ
ID NO:62)

FIG. 13K

ASIC

```
  1  mdlkespseg slqpssiqif antstlhgir hifvygpliti rrvlwavafv gslglilves
 61  servsyyfsy qhvtkvdevv aqslvfpavt lcnlngfrfs rlttndlyha gellalldvn
121  lqipdphlad ptvlealrqk anfkhykpkq fsmleflhrv ghdlkdmmly ckfkgqecgh
181  qdfttvftky gkcymfnsge dgkplittvk ggtgngleim ldiqqdeylp iwgeteettf
241  eagvkvqihs qseppfiqel gfgvapgfqt fvatgeqrit ylpppwgecr ssemgldffp
301  vysitacrid cetryivenc ncrmvhmpgd apfctpeqhk ecaepalgil aekdsnycic
361  rtpcnltryn kelsmvkips ktsakylekk fnksekyise nilvldiffe alnyetieqk
421  kayevaallg diggqmglfi gaslitiel fdyiyelike klidllgkee eegshdenms
481  tcdtmpnhse tishtvnvpl qtalgtleei ac (SEQ ID NO:19)
```

*Helicobacter pylori* potassium channel

```
  1  mfeklkfffki kkddedqpev nlnseiyeqf kvfrlplili qllvllgtlg yfalenysim
 61  qaffqttytm tatgfgalne sqfgpisifl cyhneytiel skqfrsaqip tsilmfcgtg iiafsvailv svvnkgtltr
121  likekgmiyk iarlkdhyvi                       fvvvdndpsf eeeaikhkyp
181  yyiigdphtn lamlkthlss argvvalski lpvnvalmvs vrlfekelkr kpyyiiasah
241  sdeglekikk lgadmvvspt klmaqrvsam avrpdmenil erfinkkdtl ldleevivpk
301  tswlvlrklk eahfreiaka fvigitqkdg kyipmpdget iiasesklim vgtsegvatc
361  kqlitshqkp kevdyisl (SEQ ID NO:20)
```

FIG. 14A

Sodium-calcium exchanger SLC24
GenBank NP_065077
*Homo sapiens*

```
  1 mdlqgsttit slekwcldes lsgcrrhysv kkklklirvl glfmglvais tvsfsisafs
 61 etdtqstgea svvsgprvaq gyhqrtlidl ndkildytpq pplskegese nstdhaqgdy
121 pkdifsleer rkgaiilhvi gmiymfiala ivcdeffvps ltviteklgi sddvagatfm
181 aaggsapelf tsligvfiah snvgigtivg savfnilfvi gmcalfsrei inltwplfr
241 dvsfyivdli mliiffldnv imwweslill tayfcyvvfm kfnvqvekwv kqminrnkvv
301 kvtapeaqak psaardkdep tlpakpriqr ggssaslhns lmrnsifqlm ihtldplaee
361 lgsygklkyy dtmteegrfr ekasilhkia kkkchvdene rqngaanhve kielpnstst
421 dvemtpssda sepvqngnls hniegaeaqt adeeedqpls lawpsetrkq vtflivfpiv
481 fplwitlpdv rkpssrkffp itffgsitwi avfsylmvww ahqvgetigi seeimgltil
541 aagtsipdli tsvivarkgl gdmavsssvg snifditvgl plpwllytvi hrfqpvavss
601 nglfcaivli fimllfvils iaickwrmnk ilgfimfgly fvflvvsvll edriltcpvs
661 i (SEQ ID NO:21)
```

FIG. 14B

Sodium-calcium exchanger SCL8A3
GenBank CAC40984
*Homo sapiens*

```
  1  mawlrlqplt saflhfglvt fvlflnglra eaggsgdvps tgqnnescsg ssdckegvil
 61  piwypenpsl gdkiarvivy fvaliymflg vsiiadrfma sievitsqer evtikkpnge
121  tsttirvwn etvsnltima lgssapeill slievcghgf iagdlgpsti vgsaafnmfi
181  iigicvyvip dgetrkikhl rvffitaaws ifayiwlymi lavfspgvvq vweglitlff
241  fpvcvilawv adkrllfyky mhkkyrtdkh rgiiietegd hpkgiemdgk mmnshfldgn
301  lvplegkevd esrremiril kdlkqkhpek didqlveman yyalshqqks rafyriqatr
361  mmtgagnilk khaaegakka ssmsevhtde pedfiskvff dpcsyqclen cgaviltvvr
421  kggdmsktmy vdyktedgsa nagadyefte gtvvlkpget qkefsvgiid ddifeedehf
481  fvrlsnvrie eeqpeegmpp aifnslplpr avlaspcvat vtildddhag iftfecdtih
541  vsesigvmev kvlrtsgarg tvivpfirtve gtakgggedf edtygelefk ndetvktihi
601  kviddeayek nknyfiemmg prmvdmsfqk alllspdrkl tmeeeakri aemgkpvlge
661  hpkleviiee syefkttvdk likktnlalv vgthswrdqf meaitvsaag dededesgee
721  ripscfdyvm hfltvfwkvl facvppteyc hgwacfavsi liigmitaii gdlashfgct
781  iglkdsvtav vfvafgtsvp dtfaskaaal qdvyadasig nvtgsnavnv flgiglawsv
841  aaiywalqgq efhvsagtla fsvtlftifa fvcisvllyr rrphlggelg gprgcklatt
901  wlfvslwlly iifatleayc yikgf (SEQ ID NO:22)
```

FIG. 14C

Sodium-hydrogen exchanger (NhaA)
GenBank ZP_16216900
*Moraxella catarrhalis*

```
  1 mfaqfkrfle leaaggivla aaallamiia nspldemyha fihapvvvqi gtfqiakdah
 61 hwindglmai ffflvgleik realigeisd vkqilmpala avggmimpal iyaafnqsnp
121 eqlagwaipa atdiafaigv lsllgnrvpn alkvflvsia ifddigaivi ialfytsdls
181 lsslavagvc fpflfilnkm nvvrltpyli iglvmwaafl ksgvhatlag vllaffiplr
241 nksdpehspl eelehdlhnt vafgvlpifa fanagiglag tgidslihsv plgiaagifi
301 gkqigvmtav ficlkiglas lpkgttikql ygvslicgig ftmslfisgl afgntpkdfd
361 prigiilgsi isgvigymil rgnipnadhp vlakdtgegf iptqhdaqa (SEQ ID NO:23)
```

KVLQT1 (KCNQ1)
GenBank AAC51776
*Homo sapiens*

```
  1 maaassppra erkrwgwgrl pgarrgsagl akkcpfslel aeggpaggal yapiapgapg
 61 pappaspaap aappvasdig prppvsldpr vsiystrrpv larthvqgrv ynflerptgw
121 kcfvyhfavf livlvcliifs vlstieqyaa latgtlfwme ivlvvffgte yvvrlwsagc
181 rskyvglwgr lrfarkpisi idlivvvasm vvlcvgskgq vfatsairgi rflqiirmlh
241 vdrqggtwri lgsvvfiihrq elittlyigf lgliifssyfv ylaekdavne sgrvefgsya
301 dalwgvvtv ttigyygdkvp qtwvgktias cfsvfaisff alpagilgsg falkvqqkqr
361 qkhfnrqipa aasliqtawr cyaaenpdss twkiyirkap rshtlispsp kpkksvvvkk
421 kkfkldkdng vtpgekmltv phitcdppee rrldhfsvdg ydssvrkspt llevsmphfm
481 rtnsfaedid legetlitpi thisqlrehh ratikvirrm qyfvakkkfq qarkpydvrd
541 vieqysgghi nlmvrikelq rrldqsigkp slfisvseks kdrgsntiga rinrvedkvt
601 qldqrlalit dmlhqllslh ggstpgsggp preggahitq pcgsggsvdp elflpsntlp
661 tyeqltvprr gpdegs (SEQ ID NO:24)
```

FIG. 14D

HERG (KCNH2)
GenBank AAA62473
*Homo sapiens*

```
   1  mpvrrghvap qntfldtiir kfeggsrkfi ianarvenca viycndgfce lcgysraevm
  61  qrpctcdflh gprtqrraaa qiaqallgae erkveiafyr kdgscflclv dvvpvknedg
 121  avimfilnfe vvmekdmvgs pahdtnhrgp ptswiapgra ktfriklpal laltaressv
 181  rsggaggaga pgavvvdvdl tpaapssesl aldevtamdn hvaglgpaee rralvgpgsp
 241  prsapgqlps prahslnpda sgsscslart rsrescasvr rassaddiea mragvlpppp
 301  rhastgamhp lrsglinsts dsdlvryrti skipqitlnf vdlkgdpfla sptsdreiia
 361  pkikerthnv tekvtqvisl gadvlpeykl qaprihrwti lhyspfkavw dwlilllviy
 421  tavftpysaa filketeegp patecgyacq plavvdlivd imfivdilin frttyvnane
 481  evvshpgria vhyfkgwfli dmvaaipfdl lifgsgseel iglilktarll rlvrvarkid
 541  ryseygaavl fllmctfali ahwlaciwya ignmeqphmd srigwlhnlg dqigkpynss
 601  giggpsikdk yvtalyftfs sltsvgfgnv spntnsekif sicvmligsl myasifgnvs
 661  aiiqrlysgt aryhtqmlrv refirfhqip nplrqrleey fqhawsytng idmnavlkgf
 721  peclqadicl hinrsliqhc kpfrgatkgc lralamkfkt thappgdtlv hagdlltaly
 781  fisrgsieil rgdvvvailg kndifgepln lyarpgksng dvraltycdl hkihrddile
 841  vidmypefsd hfwssleitf nlrdtnmipg spgstelegg fsrqrkrkls frrrtdkdte
 901  qpgevsalgp gragagpssr grpggpwges pssgpssspes sedegpgrss spirlvpfss
 961  prppgeppgg eplmedceks sdtcnplsga fsgvsnifsf wgdsrgrqyq elprcpaptp
1021  silniplssp grrprgdves ridalqrqin rletrlsadm atviqliqrq mtlvppaysa
1081  vttpgpgpts tsplipvspi ptlldslsq vsqfmaceel ppgapelpqe gptrrislpg
1141  qigaltsqpi hrhgsdpgs (SEQ ID NO:25)
```

FIG. 14E

KCNJ2/Kir2.1
*Homo sapiens*
GenBank NP_000882

```
  1 mgsvrtnrys ivsseedgmk latmavangf gngkskvhtr qqcrsrfvkk dghcnvqfin
 61 vgekgqryla difttcvdir wrwmlvifcl afvlswlffg cvfwliallh gdldaskegk
121 acvsevnsft aaflfsietq ttigygfrcv tdecpiavfm vvfqsivgci idafiigavm
181 akmakpkkrn etlvfshnav iamrdgklcl mwrvgnlrks hlveahvraq llksritseg
241 eyipldqidi nvgfdsgidr iflvspitiv heidedsply dlskqdidna dfeivvileg
301 mveatamttq crssylanei lwghryepvl feekhyykvd ysrfhktyev pntplcsard
361 laekkyilsn ansfcyenev altskeedds engvpestst dtppdidlhn qasvpleprp
421 lrresei (SEQ ID NO:26)
```

FIG. 14F

GenBank AAH35294
SLC34A1 sodium-phosphate co-transporter
*Homo sapiens*

```
  1 mlsygerlgs pavsplpvrg ghvmrgtafa yvpspqvlhr ipgtsayafp slgpvalaeh
 61 tcpcgevler heplpaklal eeeqkpesri vpklrqagam likvplmitf lylifvcsldm
121 lssafqlagg kvagdifkdn ailsnpvagl vvgilvtvlv qssststsii vsmvssgliie
181 vssaipiimg snigtsvtnt ivalmqagdr tdfrr (SEQ ID NO:27)
```

FIG. 14G

GenBank AAL32454
Sodium-potassium-chloride cotransporter
*Homo sapiens*

```
  1 vivlglyiyv tykkpdvnwg sstgqaltyln alqhsirlsg vedhvknfrp qclvmtgapn
 61 srpallhlvh dftknvglmi cghvhmgprr qamkemsidq akyqrwlikn kmkafyapvh
121 addiregaqy lmqaaglgrm kpntlvlgfk kdwlqadmrd vdmyinlfhd afdiqygvvv
181 irlkegldis hlqgqeells sqekspgtkd vvvsveyskk sdldtskpls ekpithkesk
241 gpivplnvad qklleastqf qkkqgkntid vwwlfddggl tllipylltt kkkwkdckir
301 vfiggkinri d (SEQ ID NO:28)
```

FIG. 14H

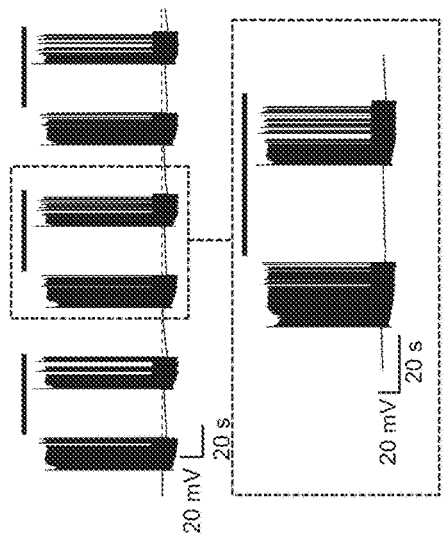
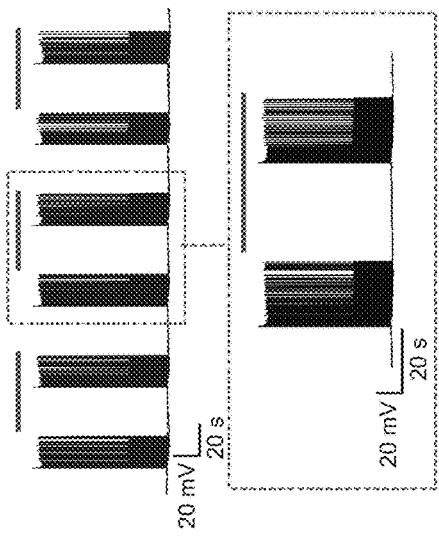
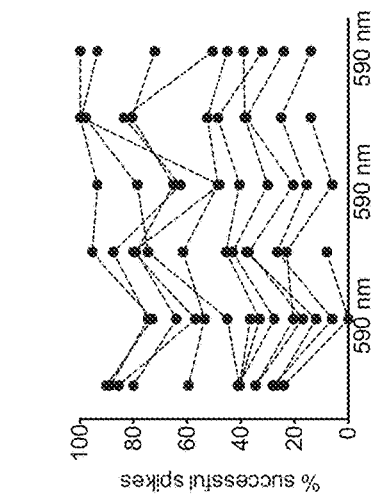
FIG. 18C
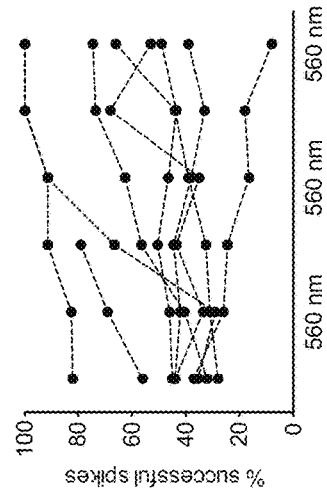
FIG. 18D
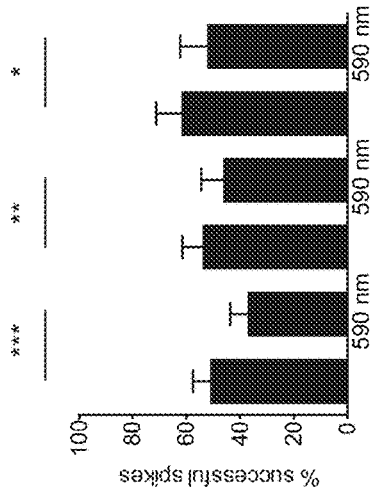
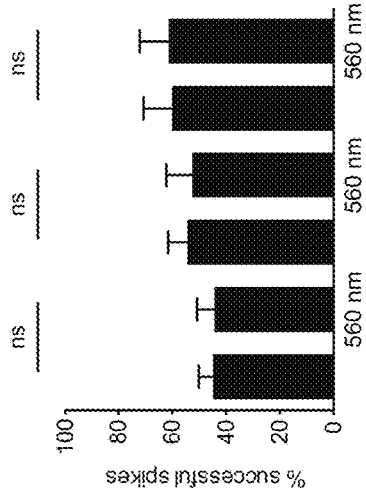

Electrical stimulation with tungsten bipolar concentric electrode.

ASIC3

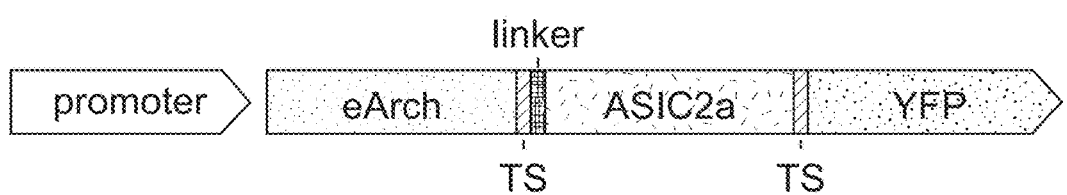
FIG. 27A
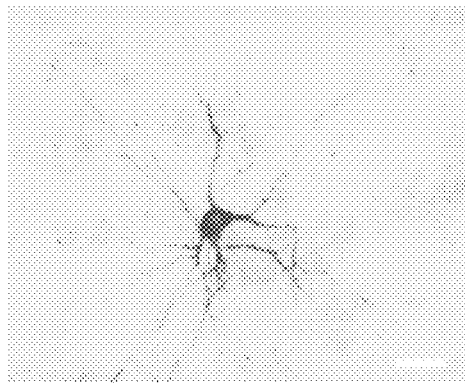 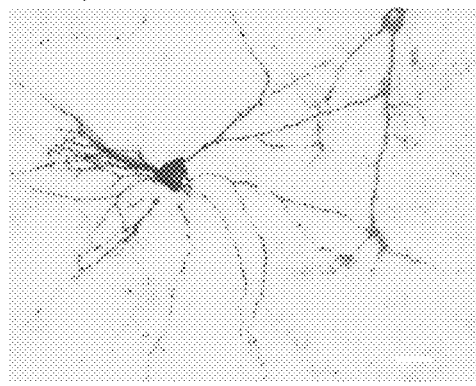
FIG. 27B

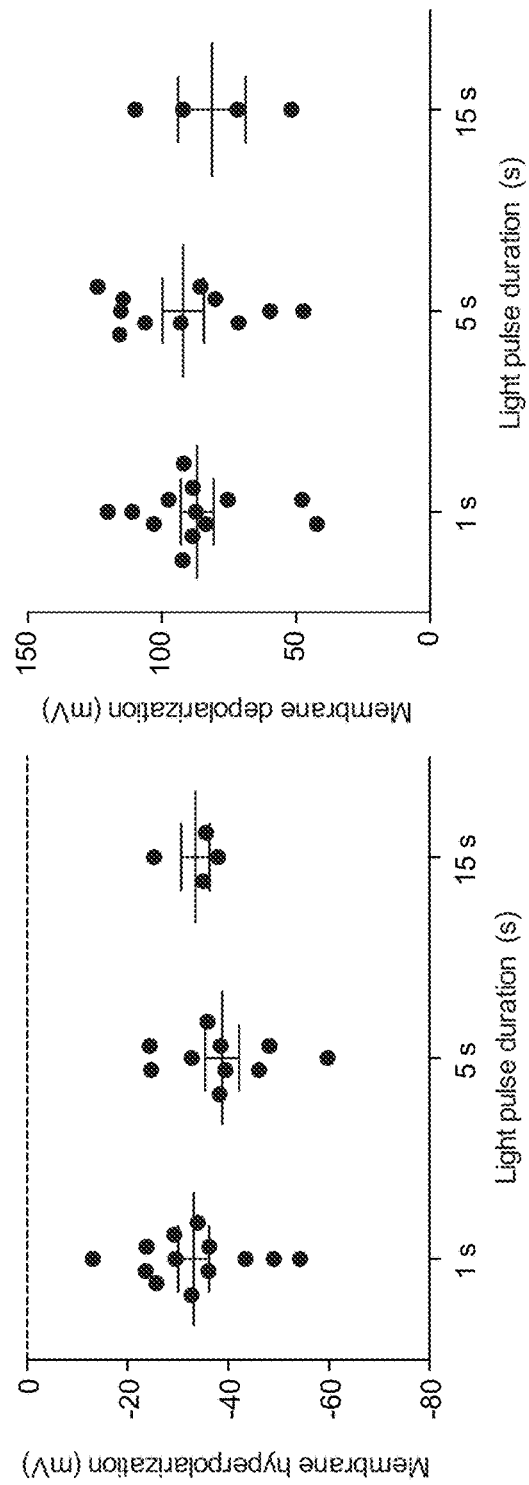
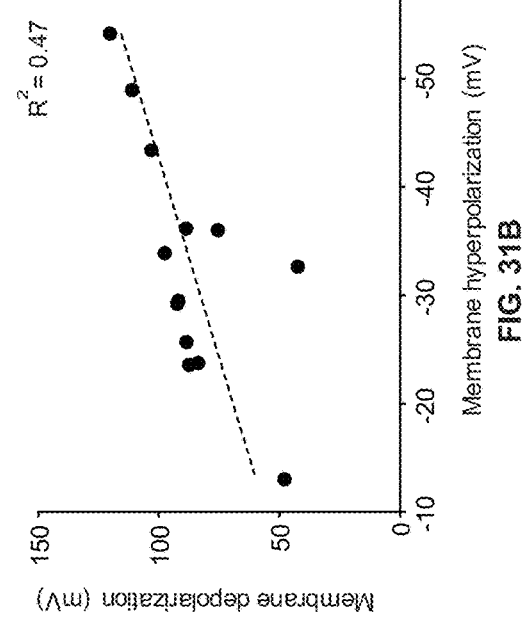
FIG. 31A
FIG. 31B

DEVICES, SYSTEMS AND METHODS FOR OPTOGENETIC MODULATION OF ACTION POTENTIALS IN TARGET CELLS

CROSS-REFERENCE

This application claims the benefit of U.S. Provisional Patent Application No. 61/817,221, filed Apr. 29, 2013, which application is incorporated herein by reference in its entirety.

INCORPORATION BY REFERENCE OF SEQUENCE LISTING PROVIDED AS A TEXT FILE

A Sequence Listing is provided herewith as a text file, "STAN-1030WO SeqList_ST25.txt" created on Apr. 29, 2014 and having a size of 208 KB. The contents of the text file are incorporated by reference herein in their entirety.

INTRODUCTION

Optogenetics refers to the combination of genetic and optical methods used to control specific events in target cells with the temporal precision (millisecond-timescale) needed to keep pace with functioning intact biological systems. Optogenetics involves the introduction of fast light-responsive ion channel or pump proteins into the plasma membranes of target cells to allow temporally precise manipulation of membrane potentials while maintaining cell-type resolution through the use of specific targeting mechanisms, such as tissue-specific promoters.

A major limiting step in optogenetic electrical inhibition is that the existing tools do not cause input resistance changes, and only generate relatively weak photocurrents because the existing ion pump proteins only move one ion per photon. Conversely, a major limiting step in optogenetic excitation is that when exciting a projection of a target cell, such as an axon, retrograde propagating action potentials can return to the cell body and proceed down collateral cell projections, thereby reducing specificity. As such, there is a need for devices, systems and methods that can be used to inhibit and/or intercept action potentials in target cells, thereby expanding the potential uses of optogenetic technology.

SUMMARY

Aspects of the disclosure include devices, systems and methods for optogenetic modulation of action potentials in target cells. The subject devices include light-generating devices, control devices, and delivery devices for delivering vectors to target cells. The subject systems include light-activated proteins, response proteins, nucleic acids comprising nucleotide sequences encoding these proteins, as well as expression systems that facilitate expression of these proteins in target cells. Also provided are methods of using the subject devices and systems to optogenetically inhibit and intercept action potentials in target cells, e.g., to treat a neurological or psychiatric condition in a human or non-human animal subject.

BRIEF DESCRIPTION OF THE DRAWINGS

FIG. 5 shows the nucleotide sequence of an example polynucleotide containing an Arch sequence (Arch), a trafficking sequence (TS), a ribosomal skip sequence (p2A), an ASIC2a sequence (ASIC2a), and a yellow fluorescent protein sequence (EYFP).

FIG. 6 shows the nucleotide sequence of an example polynucleotide containing an Arch sequence (Arch), a trafficking sequence (TS), a ribosomal skip sequence (p2A), an ASIC2a sequence (ASIC2a), a trafficking sequence (TS), a yellow fluorescent protein sequence (EYFP), and an endoplasmic reticulum export sequence (ER).

FIGS. 13A-K provide amino acid sequences of various light-responsive proteins.

FIGS. 14A-H provide amino acid sequences of exemplary response proteins.

FIGS. 18A-D depict the functional impact of bystander currents on action potential firing measured as a percentage of successfully evoked spikes during repeated light-off and light-on epochs.

FIGS. 27A-H depict expression of eArch3.0-ASIC2a (Champ) in in hippocampal neurons, photocurrents in such neurons, and related quantification.

FIGS. 31A-B depict Champ-mediated membrane hyperpolarization and depolarization in response to light pulses of increasing duration.

DEFINITIONS

Figure 1:
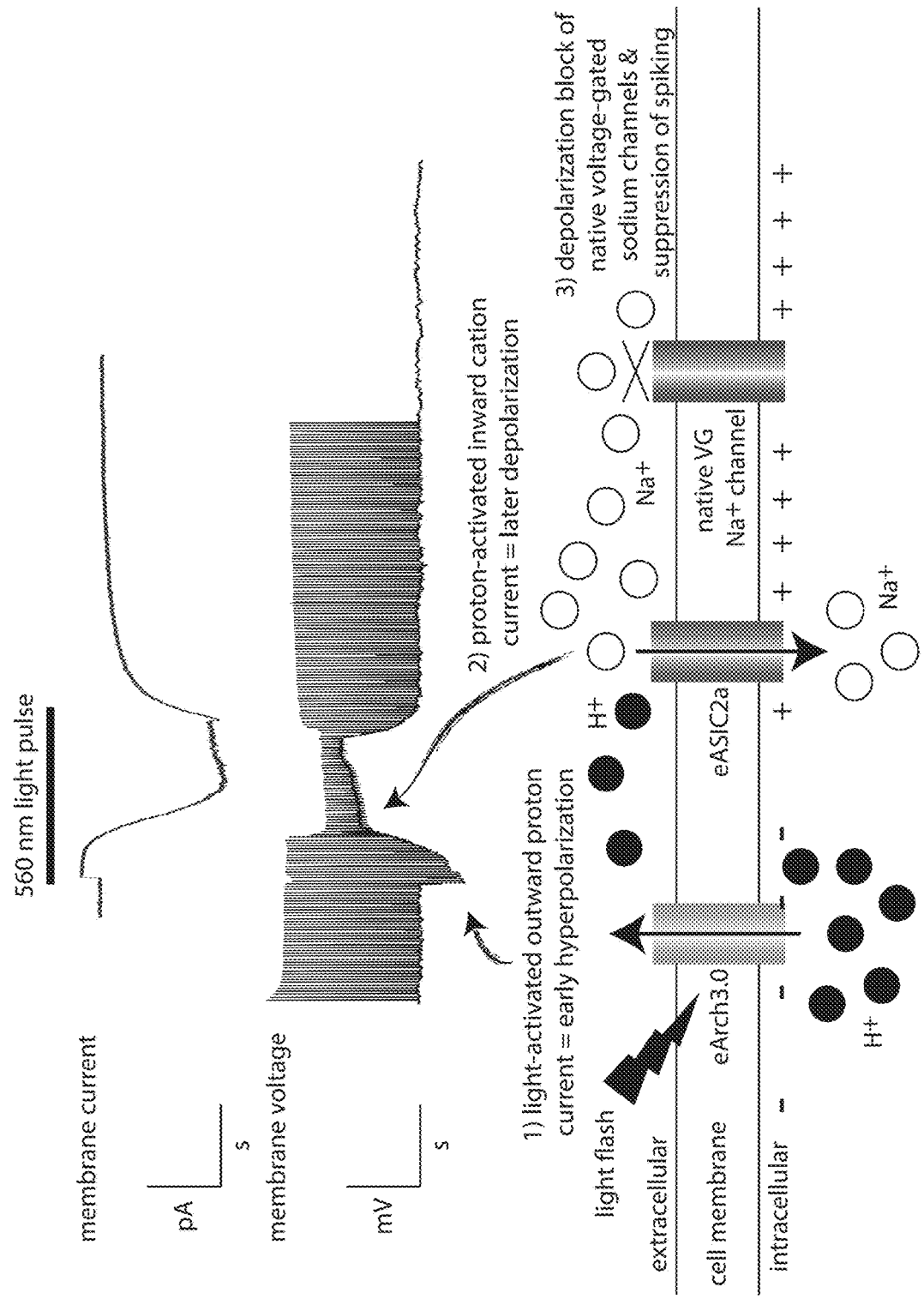
FIG. 1 is a schematic representation of a subject optogenetic system, showing a light-activated protein (eArch3.0) and a response protein (eASIC2a or ASIC2a) present in the membrane of a nerve cell. Also depicted are the membrane current as a function of time after the cell is illuminated with light of the indicated wavelength and the influence of light on evoked action potential spiking (membrane voltage) as a function of time.

As used herein, an "individual," "subject," or "patient" can be a mammal, including a human. Mammals include, but are not limited to, ungulates, canines, felines, bovines, ovines, non-human primates, lagomorphs (e.g., rabbits), and rodents (e.g., mice and rats). In one aspect, an individual is a human. In another aspect, an individual is a non-human mammal.

Amino acid substitutions in a native protein sequence may be "conservative" or "non-conservative" and such substituted amino acid residues may or may not be one encoded by the genetic code. A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain). The standard twenty amino acid "alphabet" is divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine).

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this disclosure, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about" The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of embodiments of the invention in greater detail, aspects of the systems and devices of various embodiments are reviewed first in greater detail, followed by a discussion of methods and kits according to certain embodiments of the invention.

DETAILED DESCRIPTION

Aspects of the disclosure include devices, systems and methods for optogenetic modulation of action potentials in target cells. The subject devices include light-generating devices, control devices, and delivery devices for delivering vectors to target cells. The subject systems include light-activated proteins, response proteins, nucleic acids comprising nucleotide sequences encoding these proteins, as well as expression systems that facilitate expression of these proteins in target cells. Also provided are methods of using the subject devices and systems to optogenetically inhibit and intercept action potentials in target cells, e.g., to treat a neurological or psychiatric condition in a human or animal subject.

Systems and Devices

Aspects of the present disclosure include systems and devices configured for optogenetically modulating action potentials in target cells. The subject systems generally include a light-activated protein, a response protein, and one or more devices for delivering light of an activating wavelength to a target cell. The subject systems further include nucleic acids comprising nucleotide sequences encoding the subject proteins, as well as additional components, such as transcriptional control elements (e.g., promoter sequences, such as tissue-specific or cell type-specific promoter sequences), trafficking sequences, signal sequences, endoplasmic reticulum export sequences, and the like. Also provided are devices for delivering the subject nucleic acids to target cells, and devices for controlling the delivery of light to the target cells. Each of these components is now further described in greater detail.

Light-Activated Proteins

As summarized above, aspects of the present disclosure include light-activated proteins that allow one or more ions to pass through the plasma membrane of a target cell when the protein is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. The subject light-activated proteins are in some embodiments specific to a particular species of ion, meaning that the subject light-activated proteins only allow ions of a particular species to pass through the membrane.

Examples of suitable light-responsive polypeptides include, e.g., the Halorhodopsin family of light-responsive chloride pumps (e.g., NpHR, NpHR2.0, NpHR3.0, NpHR3.1). As another example, the GtR3 proton pump can be used to promote neural cell membrane hyperpolarization in response to light. As another example, eArch (a proton pump) can be used to promote neural cell membrane hyperpolarization in response to light. As another example, an ArchT opsin protein or a Mac opsin protein can be used to promote neural cell membrane hyperpolarization in response to light.

Examples of suitable light-responsive polypeptides include, e.g., members of the Channelrhodopsin family of light-responsive cation channel proteins (e.g., ChR2, SFOs, SSFOs, C1V1s), which can be used to promote neural cell membrane depolarization or depolarization-induced synaptic depletion in response to a light stimulus.

Enhanced Intracellular Transport Amino Acid Motifs

The present disclosure provides for the modification of light-responsive opsin proteins expressed in a cell by the addition of one or more amino acid sequence motifs which enhance transport to the plasma membranes of mammalian cells. Light-responsive opsin proteins having components derived from evolutionarily simpler organisms may not be expressed or tolerated by mammalian cells or may exhibit impaired subcellular localization when expressed at high levels in mammalian cells. Consequently, in some embodiments, the light-responsive opsin proteins expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive protein transport to the plasma membranes of mammalian cells can be fused to the N-terminus, the C-terminus, or to both the N- and C-terminal ends of the light-responsive protein. Optionally, the light-responsive protein and the one or more amino acid sequence motifs may be separated by a linker. In some embodiments, the light-responsive protein can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQ-IDINV (SEQ ID NO:37).

Trafficking sequences that are suitable for use can comprise an amino acid sequence having 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:37)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Signal sequences that are suitable for use can comprise an amino acid sequence having 90%, 91%, 92%, 93%, 94%, 95%, 96%, 97%, 98%, 99%, or 100%, amino acid sequence identity to an amino acid sequence such as one of the following:
1) the signal peptide of hChR2 (e.g., MDYGGAL-SAVGRELLFVTNPVVNGS (SEQ ID NO:38))
2) the β2 subunit signal peptide of the neuronal nicotinic acetylcholine receptor (e.g., MAGHSNSMALFSFSLL-WLCSGVLGTEF (SEQ ID NO:39));
3) a nicotinic acetylcholine receptor signal sequence (e.g., MGLRALMLWLLAAAGLVRESLQG (SEQ ID NO:40)); and
4) a nicotinic acetylcholine receptor signal sequence (e.g., MRGTPLLLVVSLFSLLQD (SEQ ID NO:41)).

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Endoplasmic reticulum (ER) export sequences that are suitable for use in a modified opsin of the present disclosure include, e.g., VXXSL (where X is any amino acid) (SEQ ID NO:42) (e.g., VKESL (SEQ ID NO:43); VLGSL (SEQ ID NO:44); etc.); NANSFCYENEVALTSK (SEQ ID NO:45); FXYENE (SEQ ID NO:46) (where X is any amino acid), e.g., FCYENEV (SEQ ID NO:47); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In some embodiments, the signal peptide sequence in the protein can be deleted or substituted with a signal peptide sequence from a different protein.

Proton Pump Proteins

In some embodiments, a light-activated protein is an Archaerhodopsin (Arch) proton pump that can transport one or more protons across the plasma membrane of a cell when the cell is illuminated with light. The light can have a wavelength between about 530 and about 595 nm or can have a wavelength of about 560 nm. In some embodiments, the Arch protein can comprise an amino acid sequence that is at least about 90%, 91%, 92%, 93%, 94%, 95%, 96%, 97%, 98%, 99%, or 100% identical to the sequence shown in SEQ ID NO:1 (Arch). The Arch protein can additionally comprise substitutions, deletions, and/or insertions introduced into a native amino acid sequence to increase or decrease sensitivity to light, increase or decrease sensitivity to particular wavelengths of light, and/or increase or decrease the ability of the Arch protein to transport ions across the plasma membrane of a target cell. Additionally, the Arch protein can contain one or more conservative amino acid substitutions and/or one or more non-conservative amino acid substitutions. The Arch protein comprising substitutions, deletions, and/or insertions introduced into the native amino acid sequence suitably retains the ability to transport ions across the plasma membrane of a target cell in response to light.

In some embodiments, an Arch protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the Arch protein comprises an N-terminal signal peptide and a C-terminal ER export signal. In some embodiments, the Arch protein comprises an N-terminal signal peptide and a C-terminal trafficking signal. In some embodiments, the Arch protein comprises an N-terminal signal peptide, a C-terminal ER export signal, and a C-terminal trafficking signal. In some embodiments, the Arch protein comprises a C-terminal ER export signal and a C-terminal trafficking signal. In some embodiments, the C-terminal ER export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the light-responsive proton pump protein can be responsive to blue light and can be derived from *Guillardia theta,* wherein the proton pump protein can be capable of mediating a hyperpolarizing current in the cell when the cell is illuminated with blue light. The light can have a wavelength between about 450 and about 495 nm or can have a wavelength of about 490 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:4 (GtR3). The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:4 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4.

In some embodiments, a light-activated protein is an *Oxyrrhis marina* (Oxy) proton pump that can transport one or more protons across the plasma membrane of a cell when the cell is illuminated with light. The light can have a wavelength between about 500 and about 560 nm or can have a wavelength of about 530 nm. In some embodiments, the Oxy protein can comprise an amino acid sequence that is at least about 90%, 91%, 92%, 93%, 94%, 95%, 96%, 97%, 98%, 99%, or 100% identical to the sequence shown in SEQ ID NO:5. The Oxy protein can additionally comprise substitutions, deletions, and/or insertions introduced into a native amino acid sequence to increase or decrease sensitivity to light, increase or decrease sensitivity to particular wavelengths of light, and/or increase or decrease the ability of the Oxy protein to transport ions across the plasma membrane of a target cell. Additionally, the Oxy protein can contain one or more conservative amino acid substitutions and/or one or more non-conservative amino acid substitutions. The Oxy protein comprising substitutions, deletions, and/or insertions introduced into the native amino acid sequence suitably retains the ability to transport ions across the plasma membrane of a target cell in response to light.

In some embodiments, an Oxy protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the Oxy protein comprises an N-terminal signal peptide and a C-terminal ER export signal. In some embodiments, the Oxy protein comprises an N-terminal signal peptide and a C-terminal trafficking signal. In some embodiments, the Oxy protein comprises an N-terminal signal peptide, a C-terminal ER export signal, and a C-terminal trafficking signal. In some embodiments, the Oxy protein comprises a C-terminal ER export signal and a C-terminal trafficking signal. In some embodiments, the C-terminal ER export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the light-responsive proton pump protein can be responsive to light and can be derived from *Leptosphaeria maculans,* wherein the proton pump protein can be capable of pumping protons across the membrane of a cell when the cell is illuminated with 520 nm to 560 nm light. The light can have a wavelength between about 520 nm to about 560 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:6 or SEQ ID NO:7 (Mac; Mac 3.0). The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to pump protons across the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:6 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:6. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:6.

Further disclosure related to light-activated proton pump proteins can be found in International Patent Application No. PCT/US2011/028893, the disclosure of which is hereby incorporated by reference in its entirety.

Cation Channel Proteins

In some aspects, the light-responsive cation channel protein can be derived from *Chlamydomonas reinhardtii*, wherein the cation channel protein can be capable of transporting cations across a cell membrane when the cell is illuminated with light. In another embodiment, the light-responsive cation channel protein can comprise an amino acid sequence at least about 90%, 91%, 92%, 93%, 94%, 95%, 96%, 97%, 98%, 99%, or 100% identical to the sequence shown in SEQ ID NO:8. The light used to activate the light-responsive cation channel protein derived from *Chlamydomonas reinhardtii* can have a wavelength between about 460 and about 495 nm or can have a wavelength of about 480 nm. Additionally, light pulses having a temporal frequency of about 100 Hz can be used to activate the light-responsive protein. In some embodiments, activation of the light-responsive cation channel derived from *Chlamydomonas reinhardtii* with light pulses having a temporal frequency of about 100 Hz can cause depolarization-induced synaptic depletion of the neurons expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to transport cations across a cell membrane. In another embodiment, the light-responsive cation channel protein can comprise an amino acid sequence at least about 90%, 91%, 92%, 93%, 94%, 95%, 96%, 97%, 98%, 99%, or 100% identical to the C1C2 amino sequence shown in FIG. 13E, and set forth in SEQ ID NO:29. A crystal structure of C1C2 is presented in Kato et al. (2012) *Nature* 482:369. In another embodiment, the light-responsive cation channel protein can comprise an amino acid sequence at least about 90%, 91%, 92%, 93%, 94%, 95%, 96%, 97%, 98%, 99%, or 100% identical to the ReaChR amino sequence shown in FIG. 13F, and set forth in SEQ ID NO:30.

In some embodiments, the light-responsive cation channel comprises a T159C substitution of the amino acid sequence set forth in SEQ ID NO:8. In some embodiments, the light-responsive cation channel comprises a L132C substitution of the amino acid sequence set forth in SEQ ID NO:8. In some embodiments, the light-responsive cation channel comprises an E123T substitution of the amino acid sequence set forth in SEQ ID NO:8. In some embodiments, the light-responsive cation channel comprises an E123A substitution of the amino acid sequence set forth in SEQ ID NO:8. In some embodiments, the light-responsive cation channel comprises a T159C substitution and an E123T substitution of the amino acid sequence set forth in SEQ ID NO:8. In some embodiments, the light-responsive cation channel comprises a T159C substitution and an E123A substitution of the amino acid sequence set forth in SEQ ID NO:8. In some embodiments, the light-responsive cation channel comprises a T159C substitution, an L132C substitution, and an E123T substitution of the amino acid sequence set forth in SEQ ID NO:8. In some embodiments, the light-responsive cation channel comprises a T159C substitution, an L132C substitution, and an E123A substitution of the amino acid sequence set forth in SEQ ID NO:8. In some embodiments, the light-responsive cation channel comprises an L132C substitution and an E123T substitution of the amino acid sequence set forth in SEQ ID NO:8. In some embodiments, the light-responsive cation channel comprises an L132C substitution and an E123A substitution of the amino acid sequence set forth in SEQ ID NO:8. In some embodiments, the light-responsive cation channel comprises an H143R amino acid substitution of the amino acid sequence set forth in SEQ ID NO:8.

In some embodiments, a ChR2 protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the ChR2 protein comprises an N-terminal signal peptide and a C-terminal ER export signal. In some embodiments, the ChR2 protein comprises an N-terminal signal peptide and a C-terminal trafficking signal. In some embodiments, the ChR2 protein comprises an N-terminal signal peptide, a C-terminal ER export signal, and a C-terminal trafficking signal. In some embodiments, the ChR2 protein comprises a C-terminal ER export signal and a C-terminal trafficking signal. In some embodiments, the C-terminal ER export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

Step Function Opsins and Stabilized Step Function Opsins

In other embodiments, the light-responsive cation channel protein can be a step function opsin (SFO) protein or a stabilized step function opsin (SSFO) protein that can have specific amino acid substitutions at key positions throughout the retinal binding pocket of the protein. In some embodiments, the SFO protein can have a mutation at amino acid residue C128 of SEQ ID NO:8. In other embodiments, the SFO protein has a C128A mutation in SEQ ID NO:5. In other embodiments, the SFO protein has a C128S mutation in SEQ ID NO:8. In another embodiment, the SFO protein has a C128T mutation in SEQ ID NO:8. In some embodiments, the SFO protein can comprise an amino acid sequence at least about 90%, 91%, 92%, 93%, 94%, 95%, 96%, 97%, 98%, 99%, or 100% identical to the sequence shown in SEQ ID NO:9.

In some embodiments, the SSFO protein can have a mutation at amino acid residue D156 of SEQ ID NO:8. In other embodiments, the SSFO protein can have a mutation at both amino acid residues C128 and D156 of SEQ ID NO:8. In one embodiment, the SSFO protein has an C128S and a D156A mutation in SEQ ID NO:8. In another embodiment, the SSFO protein can comprise an amino acid sequence at least about 90%, 91%, 92%, 93%, 94%, 95%, 96%, 97%, 98%, 99%, or 100% identical to the sequence shown in SEQ ID NO:10. In another embodiment, the SSFO protein can comprise a C128T mutation in SEQ ID NO:8. In some embodiments, the SSFO protein comprises C128T and D156A mutations in SEQ ID NO:8.

In some embodiments the SFO or SSFO proteins provided herein can be capable of mediating a depolarizing current in the cell when the cell is illuminated with blue light. In other embodiments, the light can have a wavelength of about 445 nm. Additionally, in some embodiments the light can be delivered as a single pulse of light or as spaced pulses of light due to the prolonged stability of SFO and SSFO photocurrents. In some embodiments, activation of the SFO or SSFO protein with single pulses or spaced pulses of light can cause depolarization-induced synaptic depletion of the neurons expressing the SFO or SSFO protein. In some embodiments, each of the disclosed step function opsin and stabilized step function opsin proteins can have specific properties and characteristics for use in depolarizing the membrane of a neuronal cell in response to light.

Further disclosure related to SFO or SSFO proteins can be found in International Patent Application Publication No. WO 2010/056970, the disclosure of which is hereby incorporated by reference in its entirety.

C1V1 Chimeric Cation Channels

In other embodiments, the light-responsive cation channel protein can be a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein can further comprise a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein can further comprise a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1. In other embodiments, the C1V1 chimeric protein can comprise an amino acid sequence at least about 90%, 91%, 92%, 93%, 94%, 95%, 96%, 97%, 98%, 99%, or 100% identical to the sequence shown in SEQ ID NO:11.

In some embodiments, the C1V1 protein can mediate a depolarizing current in the cell when the cell is illuminated with green light. In other embodiments, the light can have a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, in some embodiments, light pulses having a temporal frequency of about 100 Hz can be used to activate the C1V1 protein.

C1V1 chimeric mutant variants

In some aspects, the present disclosure provides polypeptides comprising substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, provided herein are C1V1 chimeric light-responsive opsin proteins that can have specific amino acid substitutions at key positions throughout the retinal binding pocket of the VChR1 portion of the chimeric polypeptide. In some embodiments, the C1V1 protein can have a mutation at amino acid residue E122 of SEQ ID NO:11. In some embodiments, the C1V1 protein can have a mutation at amino acid residue E162 of SEQ ID NO:11. In other embodiments, the C1V1 protein can have a mutation at both amino acid residues E162 and E122 of SEQ ID NO:11. In other embodiments, the C1V1 protein can comprise an amino acid sequence at least about 90%, 91%, 92%, 93%, 94%, 95%, 96%, 97%, 98%, 99%, or 100% identical to the sequence shown in SEQ ID NO:12, SEQ ID NO:13, or SEQ ID NO:14.

In some aspects, the C1V1-E122 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In other embodiments, the C1V1-E122 mutant chimeric protein can mediate a depolarizing current in the cell when the cell is illuminated with red light. In some embodiments, the red light can have a wavelength of about 630 nm. In some embodiments, the C1V1-E122 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, in some embodiments, light pulses having a temporal frequency of about 100 Hz can be used to activate the C1V1-E122 mutant chimeric protein. In some embodiments, activation of the C1V1-E122 mutant chimeric protein with light pulses having a frequency of 100 Hz can cause depolarization-induced synaptic depletion of the neurons expressing the C1V1-E122 mutant chimeric protein.

In other aspects, the C1V1-E162 mutant chimeric protein is capable of mediating a depolarizing current in the cell when the cell is illuminated with light. In some embodiments the light can be green light. In other embodiments, the light can have a wavelength of between about 535 nm to about 540 nm. In some embodiments, the light can have a wavelength of about 542 nm. In other embodiments, the light can have a wavelength of about 530 nm. In some embodiments, the C1V1-E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, in some embodiments, light pulses having a temporal frequency of about 100 Hz can be used to activate the C1V1-E162 mutant chimeric protein. In some embodiments, activation of the C1V1-E162 mutant chimeric protein with light pulses having a frequency of 100 Hz can cause depolarization-induced synaptic depletion of the neurons expressing the C1V1-E162 mutant chimeric protein.

In yet other aspects, the C1V1-E122/E162 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In some embodiments, the C1V1-E122/E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. In some embodiments, the C1V1-E122/E162 mutant chimeric protein can exhibit less activation when exposed to violet light relative to C1V1 chimeric proteins lacking mutations at E122/E162 or relative to other light-responsive cation channel proteins. Additionally, in some embodiments, light pulses having a temporal frequency of about 100 Hz can be used to activate the C1V1-E122/E162 mutant chimeric protein. In some embodiments, activation of the C1V1-E122/E162 mutant chimeric protein with light pulses having a frequency of 100 Hz can cause depolarization-induced synaptic depletion of the neurons expressing the C1V1-E122/E162 mutant chimeric protein.

*Dunaliella Salina* Light-Responsive Proteins

In some embodiments, the light-responsive ion channel protein can be responsive to 470 nm-510 nm light and can be derived from *Dunaliella salina*, wherein the ion channel protein can be capable of mediating a hyperpolarizing current in the cell when the cell is illuminated with light. The light can have a wavelength between about 470 nm and about 510 nm or can have a wavelength of about 490 nm. In another embodiment, the light-responsive ion channel protein can comprise an amino acid sequence at least about 90%, 91%, 92%, 93%, 94%, 95%, 96%, 97%, 98%, 99%, or 100% identical to the sequence shown in SEQ ID NO:15. The light-responsive ion channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive ion channel protein to regulate the polarization state of the plasma membrane of the cell. Additionally, the light-responsive ion channel protein can contain one or more conservative amino acid substitutions and/or one or more non-conservative amino acid substitutions. The light-responsive ion channel protein comprising substitutions, deletions, and/or insertions introduced into the native amino acid sequence suitably retains the ability to transport ions across the plasma membrane of a neuronal cell in response to light.

In other aspects of the methods disclosed herein, the light-responsive ion channel protein can comprise a core amino acid sequence at least about 90%, 91%, 92%, 93%, 94%, 95%, 96%, 97%, 98%, 99%, or 100% identical to the sequence shown in SEQ ID NO:15 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton ion channel comprises an N-terminal signal peptide and a C-terminal ER export signal. In some embodiments, the light-responsive ion channel protein comprises an N-terminal signal peptide and a C-terminal trafficking signal. In some embodiments, the light-responsive ion channel protein comprises an N-terminal signal peptide, a C-terminal ER Export signal, and a C-terminal trafficking signal. In some embodiments, the light-responsive ion channel protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive channel proteins described herein, such as a light-responsive ion channel protein comprising a core amino acid sequence at least about 90%, 91%, 92%, 93%, 94%, 95%, 96%, 97%, 98%, 99%, or 100% identical to the sequence shown in SEQ ID NO:15. Also provided herein are expression vectors (such as a viral vector described herein) comprising a polynucleotide encoding the proteins described herein, such as a light-responsive channel protein comprising a core amino acid sequence at least about 90%, 91%, 92%, 93%, 94%, 95%, 96%, 97%, 98%, 99%, or 100% identical to the sequence shown in SEQ ID NO:15.

Chloride Ion Pumps

In some aspects, said one or more light-responsive chloride pump proteins expressed on the plasma membranes of the neurons described above can be derived from *Natronomonas pharaonis*. In some embodiments, the light-responsive chloride pump proteins can be responsive to amber light as well as red light and can mediate a hyperpolarizing current in the neuron when the light-responsive chloride pump proteins are illuminated with amber or red light. The wavelength of light which can activate the light-responsive chloride pumps can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the light-responsive chloride pump protein can hyperpolarize a neural membrane for at least about 90 minutes when exposed to a continuous pulse of light. In some embodiments, the light-responsive chloride pump protein can comprise an amino acid sequence at least about 85%, 90%, 91%, 92%, 93%, 94%, 95%, 96%, 97%, 98%, 99%, or 100% identical to the sequence shown in SEQ ID NO:16. Additionally, the light-responsive chloride pump protein can comprise substitutions, deletions, and/or insertions introduced into a native amino acid sequence to increase or decrease sensitivity to light, increase or decrease sensitivity to particular wavelengths of light, and/or increase or decrease the ability of the light-responsive protein to regulate the polarization state of the plasma membrane of the cell. In some embodiments, the light-responsive chloride pump protein contains one or more conservative amino acid substitutions. In some embodiments, the light-responsive protein contains one or more non-conservative amino acid substitutions. The light-responsive protein comprising substitutions, deletions, and/or insertions introduced into the native amino acid sequence suitably retains the ability to hyperpolarize the plasma membrane of a neuronal cell in response to light.

Additionally, in other aspects, the light-responsive chloride pump protein can comprise a core amino acid sequence at least about 85%, 90%, 91%, 92%, 93%, 94%, 95%, 96%, 97%, 98%, 99%, or 100% identical to the sequence shown in SEQ ID NO:16 and an endoplasmic reticulum (ER) export signal. This ER export signal can be fused to the C-terminus of the core amino acid sequence or can be fused to the N-terminus of the core amino acid sequence. In some embodiments, the ER export signal is linked to the core amino acid sequence by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal can comprise the amino acid sequence FXYENE (SEQ ID NO:46), where X can be any amino acid. In another embodiment, the ER export signal can comprise the amino acid sequence VXXSL (SEQ ID NO:42), where X can be any amino acid. In some embodiments, the ER export signal can comprise the amino acid sequence FCYENEV (SEQ ID NO:47).

Endoplasmic reticulum (ER) export sequences that are suitable for use in a modified opsin of the present disclosure include, e.g., VXXSL (where X is any amino acid) (SEQ ID NO:42) (e.g., VKESL (SEQ ID NO:43); VLGSL (SEQ ID NO:44); etc.); NANSFCYENEVALTSK (SEQ ID NO:45); FXYENE (where X is any amino acid) (SEQ ID NO:46), e.g., FCYENEV (SEQ ID NO:47); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In other aspects, the light-responsive chloride pump proteins described herein can comprise a light-responsive protein expressed on the cell membrane, wherein the protein comprises a core amino acid sequence at least about 90%, 91%, 92%, 93%, 94%, 95%, 96%, 97%, 98%, 99%, or 100% identical to the sequence shown in SEQ ID NO:16 and a trafficking signal (e.g., which can enhance transport of the light-responsive chloride pump protein to the plasma membrane). The trafficking signal may be fused to the C-terminus of the core amino acid sequence or may be fused to the N-terminus of the core amino acid sequence. In some embodiments, the trafficking signal can be linked to the core amino acid sequence by a linker which can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:37).

In some aspects, the light-responsive chloride pump protein can comprise a core amino acid sequence at least about 90%, 91%, 92%, 93%, 94%, 95%, 96%, 97%, 98%, 99%, or 100% identical to the sequence shown in SEQ ID NO:16 and at least one (such as one, two, three, or more) amino acid sequence motifs which enhance transport to the plasma membranes of mammalian cells selected from the group consisting of an ER export signal, a signal peptide, and a membrane trafficking signal. In some embodiments, the light-responsive chloride pump protein comprises an N-terminal signal peptide, a C-terminal ER Export signal, and a C-terminal trafficking signal. In some embodiments, the C-terminal ER Export signal and the C-terminal trafficking signal can be linked by a linker. The linker can comprise any of about 5, 10, 20, 30, 40, 50, 75, 100, 125, 150, 175, 200, 225, 250, 275, 300, 400, or 500 amino acids in length. The linker can also further comprise a fluorescent protein, for example, but not limited to, a yellow fluorescent protein, a red fluorescent protein, a green fluorescent protein, or a cyan fluorescent protein. In some embodiments the ER Export signal can be more C-terminally located than the trafficking signal. In other embodiments the trafficking signal is more C-terminally located than the ER Export signal. In some embodiments, the signal peptide comprises the amino acid sequence MTETLPPVTESAVALQAE (SEQ ID NO:48). In another embodiment, the light-responsive chloride pump protein comprises an amino acid sequence at least 95% identical to SEQ ID NO:17.

Moreover, in other aspects, the light-responsive chloride pump proteins can comprise a core amino acid sequence at least about 90%, 91%, 92%, 93%, 94%, 95%, 96%, 97%, 98%, 99%, or 100% identical to the sequence shown in SEQ ID NO:16, wherein the N-terminal signal peptide of SEQ ID NO:16 is deleted or substituted. In some embodiments, other signal peptides (such as signal peptides from other opsins) can be used. The light-responsive protein can further comprise an ER transport signal and/or a membrane trafficking signal described herein. In some embodiments, the light-responsive chloride pump protein comprises an amino acid sequence at least 95% identical to SEQ ID NO:18.

In some embodiments, the light-responsive opsin protein is a NpHR opsin protein comprising an amino acid sequence at least 95%, at least 96%, at least 97%, at least 98%, at least 99% or 100% identical to the sequence shown in SEQ ID NO:16. In some embodiments, the NpHR opsin protein further comprises an endoplasmic reticulum (ER) export signal and/or a membrane trafficking signal. For example, the NpHR opsin protein comprises an amino acid sequence at least 95% identical to the sequence shown in SEQ ID NO:16 and an endoplasmic reticulum (ER) export signal. In some embodiments, the amino acid sequence at least 95% identical to the sequence shown in SEQ ID NO:16 is linked to the ER export signal through a linker. In some embodiments, the ER export signal comprises the amino acid sequence FXYENE (SEQ ID NO:46), where X can be any amino acid. In another embodiment, the ER export signal comprises the amino acid sequence VXXSL (SEQ ID NO:42), where X can be any amino acid. In some embodiments, the ER export signal comprises the amino acid sequence FCYENEV (SEQ ID NO:47). In some embodiments, the NpHR opsin protein comprises an amino acid sequence at least 95% identical to the sequence shown in SEQ ID NO:16, an ER export signal, and a membrane trafficking signal. In other embodiments, the NpHR opsin protein comprises, from the N-terminus to the C-terminus, the amino acid sequence at least 95% identical to the sequence shown in SEQ ID NO:16, the ER export signal, and the membrane trafficking signal. In other embodiments, the NpHR opsin protein comprises, from the N-terminus to the C-terminus, the amino acid sequence at least 95% identical to the sequence shown in SEQ ID NO:16, the membrane trafficking signal, and the ER export signal. In some embodiments, the membrane trafficking signal is derived from the amino acid sequence of the human inward rectifier potassium channel Kir2.1. In some embodiments, the membrane trafficking signal comprises the amino acid sequence KSRITSEGEYIPLDQIDINV (SEQ ID NO:37). In some embodiments, the membrane trafficking signal is linked to the amino acid sequence at least 95% identical to the sequence shown in SEQ ID NO:16 by a linker. In some embodiments, the membrane trafficking signal is linked to the ER export signal through a linker. The linker may comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the light-responsive opsin protein further comprises an N-terminal signal peptide. In some embodiments, the light-responsive opsin protein comprises the amino acid sequence of SEQ ID NO:17. In some embodiments, the light-responsive opsin protein comprises the amino acid sequence of SEQ ID NO:18.

Also provided herein are polynucleotides encoding any of the light-responsive chloride ion pump proteins described herein, such as a light-responsive protein comprising a core amino acid sequence at least about 90%, 91%, 92%, 93%, 94%, 95%, 96%, 97%, 98%, 99%, or 100% identical to the sequence shown in SEQ ID NO:16, an ER export signal, and a membrane trafficking signal. In another embodiment, the polynucleotides comprise a sequence which encodes an amino acid at least 95% identical to SEQ ID NO:17 and SEQ ID NO:18. The polynucleotides may be in an expression vector (such as, but not limited to, a viral vector described herein). The polynucleotides may be used for expression of the light-responsive chloride ion pump proteins.

Further disclosure related to light-responsive chloride pump proteins can be found in U.S. Patent Application Publication Nos: 2009/0093403 and 2010/0145418 as well as in International Patent Application No: PCT/US2011/028893, the disclosures of each of which are hereby incorporated by reference in their entireties.

Chlorella Vulgaris Type 1 Rhodopsin

In some embodiments, a suitable light-responsive polypeptide is a rhodopsin from Coccomyxa subellipsoidea (Chlorella vulgaris). In some embodiments, a suitable light-responsive polypeptide comprises an amino acid sequence that is at least about 85%, 90%, 91%, 92%, 93%, 94%, 95%, 96%, 97%, 98%, 99%, or 100% identical to the sequence shown in SEQ ID NO:62. Additionally, the light-responsive polypeptide can comprise substitutions, deletions, and/or insertions introduced into a native amino acid sequence to increase or decrease sensitivity to light, increase or decrease sensitivity to particular wavelengths of light, and/or increase or decrease the ability of the light-responsive protein to regulate the polarization state of the plasma membrane of the cell. In some embodiments, the light-responsive polypeptide contains one or more conservative amino acid substitutions. In some embodiments, the light-responsive polypeptide contains one or more non-conservative amino acid substitutions. The light-responsive polypeptide comprising substitutions, deletions, and/or insertions introduced into the native amino acid sequence suitably retains the ability to hyperpolarize the plasma membrane of a neuronal cell in response to light.

In some cases, a suitable light-responsive polypeptide comprises an amino acid sequence that is at least about 85%, 90%, 91%, 92%, 93%, 94%, 95%, 96%, 97%, 98%, 99%, or 100% identical to the sequence shown in SEQ ID NO:62; and comprises an ER export signal (e.g., FCYENEV (SEQ ID NO:47)). In some cases, a suitable light-responsive polypeptide comprises an amino acid sequence that is at least about 85%, 90%, 91%, 92%, 93%, 94%, 95%, 96%, 97%, 98%, 99%, or 100% identical to the sequence shown in SEQ ID NO:62; and comprises a membrane trafficking signal (e.g., KSRITSEGEYIPLDQIDINV (SEQ ID NO:37)). In some cases, a suitable light-responsive polypeptide comprises an amino acid sequence that is at least about 85%, 90%, 91%, 92%, 93%, 94%, 95%, 96%, 97%, 98%, 99%, or 100% identical to the sequence shown in SEQ ID NO:62; and comprises a membrane trafficking signal (e.g., KSRITSEGEYIPLDQIDINV (SEQ ID NO:37)) and an ER export signal (e.g., FCYENEV (SEQ ID NO:47)).

(SEQ ID NO: 62)
MAVHQIGEGGLVMYWVTFGLMAFSALAFAVMTFTRPLNKRSHGYITLAIV

TIAAIAYYAMAASGGKALVSNPDGNLRDIYYARYIDWFFTTPLLLLDIIL

-continued

```
LTGIPIGVTLWIVLADVAMIMLGLFGALSTNSYRWGYYGVSCAFFFVVLW

GLFFPGAKGARARGGQVPGLYFGLAGYLALLWFGYPIVWGLAEGSDYISV

TAEAASYAGLDIAAKVVFGWAVMLSHPLIARNQTDGSLLINSTNDPFVAS

TTHIPERQGGIFGGLMGKKRGAGTPLATNEGVPRKAAPTAATTTAGNPAT

AAEVRTPRELMARL.
```

Response Proteins

As summarized above, aspects of the present disclosure include response proteins that allow one or more ions to pass through a membrane when the response protein detects the presence of one or more ions that have passed through a subject light-activated protein. Response proteins may be characterized as ion pump proteins, which facilitate the passage of a small number of ions through the membrane per action cycle, or as ion channel proteins, which allow a stream of ions to freely flow through the membrane. The subject response proteins are specific to a particular species of ion or to a particular group of ions (e.g., cations) meaning that the subject response proteins only allow ions of a particular species or group to pass through the membrane. In some cases, the response protein is a heterologous protein for a given cell, e.g., the response protein is one that is not normally expressed in the cell. In other cases, the response protein is native to a given cell, e.g., the response protein is one that is normally expressed in the cell. A response protein can be a mammalian protein (e.g., a human protein, a non-human protein), a bacterial protein, an archael protein, etc.

In some embodiments, the response protein is an ion channel. In some cases, the response protein is a cation channel, e.g., a potassium channel or a calcium channel. In some cases, the response protein is an anion channel, e.g., a chloride ion channel or a sodium channel. In other instances, the response protein is a proton pump. Response proteins can be voltage-gated or ligand-gated.

Non-limiting examples of suitable response proteins include, e.g., a voltage-gated potassium channel (e.g., KVLQT1); a potassium channel (e.g., HERG); an inward rectifier K$^+$ channel (e.g., Kir2.1); an acid sensing sodium ion channel; and the like. In some cases, the response protein is an ion exchanger (antiporter), e.g. the sodium-calcium exchanger (NCX), the potassium-dependent sodium-calcium exchanger (SLC24) or the sodium-hydrogen exchanger (NhaA). In some cases, the response protein is an ion co-transporter of the symport variety, e.g. the sodium-potassium-chloride co-transporter (NKCC1 and NKCC2) or the sodium-phosphate co-transporter (SLC34A1).

For example, a suitable response protein can comprise an amino acid sequence having at least about 90%, 91%, 92%, 93%, 94%, 95%, 96%, 97%, 98%, 99%, or 100% amino acid sequence identity to a contiguous stretch of from about 100 amino acid (aa) to about 200 aa, from about 200 aa to about 300 aa, from about 300 aa to about 400 aa, from about 400 aa to about 500 aa, from about 500 aa to about 600 aa, from about 600 aa to about 700 aa, from about 700 aa to about 800 aa, from about 800 aa to about 900 aa, from 900 aa to about 1000 aa, from about 1000 aa to about 1100 aa, up to the full length, of the amino acid sequence shown in one of FIGS. 14A-H (SEQ ID NOs:19-28).

Acid Sensing Ion Channel Variant 2a (ASIC2a)

In some embodiments, a response protein is an Acid Sensing Ion Channel variant 2a (ASIC2a) sodium ion channel protein that allows a plurality of sodium ions to flow across the plasma membrane of a target cell when the ASIC2a protein detects acidic conditions, such as the presence of a plurality of hydrogen ions on or near the external surface of the plasma membrane. In some embodiments, the ASIC2a protein can comprise an amino acid sequence that is at least about 90%, 91%, 92%, 93%, 94%, 95%, 96%, 97%, 98%, 99%, or 100% identical to the sequence shown in SEQ ID NO:19. The ASIC2a protein can additionally comprise substitutions, deletions, and/or insertions introduced into a native amino acid sequence to increase or decrease sensitivity to acidic conditions, and/or increase or decrease the ability of the ASIC2a protein to regulate the flow of sodium ions across the plasma membrane of a target cell. Additionally, the ASIC2a protein can contain one or more conservative amino acid substitutions and/or one or more non-conservative amino acid substitutions. The ASIC2a protein comprising substitutions, deletions, and/or insertions introduced into the native amino acid sequence suitably retains the functionality of the ASIC2a protein.

In some embodiments, an ASIC2a protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the ASIC2a protein comprises an N-terminal signal peptide and a C-terminal ER export signal. In some embodiments, the ASIC2a protein comprises an N-terminal signal peptide and a C-terminal trafficking signal. In some embodiments, the ASIC2a protein comprises an N-terminal signal peptide, a C-terminal ER export signal, and a C-terminal trafficking signal. In some embodiments, the ASIC2a protein comprises a C-terminal ER export signal and a C-terminal trafficking signal. In some embodiments, the C-terminal ER export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

Helicobacter Pylori Potassium Channel (HpKchA)

In some embodiments, a response protein is a Helicobacter pylori potassium ion channel protein (HpKchA) that allows a plurality of potassium ions to flow across the plasma membrane of a target cell when the HpKchA protein detects acidic conditions, such as the presence of a plurality of hydrogen ions on or near the external surface of the plasma membrane. In some embodiments, the HpKchA protein can comprise an amino acid sequence that is at least about 90%, 91%, 92%, 93%, 94%, 95%, 96%, 97%, 98%, 99%, or 100% identical to the sequence shown in SEQ ID NO:20. The HpKchA protein can additionally comprise substitutions, deletions, and/or insertions introduced into a native amino acid sequence to increase or decrease sensitivity to acidic conditions, and/or increase or decrease the ability of the HpKchA protein to regulate the flow of potassium ions across the plasma membrane of a target cell. Additionally, the HpKchA protein can contain one or more conservative amino acid substitutions and/or one or more non-conservative amino acid substitutions. The HpKchA protein comprising substitutions, deletions, and/or insertions introduced into the native amino acid sequence suitably retains the functionality of the HpKchA protein.

In some embodiments, an HpKchA protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the HpKchA protein comprises an N-terminal signal peptide and a C-terminal ER export signal. In some embodiments, the HpKchA protein comprises an N-terminal signal peptide and a C-terminal trafficking signal. In some embodiments, the HpKchA protein comprises an N-terminal signal peptide, a C-terminal ER export signal, and a C-terminal trafficking signal. In some embodiments, the HpKchA protein comprises a C-terminal ER export signal and a C-terminal trafficking signal. In some embodiments, the C-terminal ER export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

Fusion Proteins

In some cases, the light-responsive protein and the response protein are present together in a single polypeptide chain, e.g., the light-responsive protein and the response protein are a fusion protein. The present disclosure provides a two-component optogenetic fusion polypeptide comprising a light-responsive polypeptide and a response polypeptide.

In some embodiments, a subject two-component optogenetic fusion polypeptide comprises, in order from amino terminus to carboxyl terminus: a) a light-responsive polypeptide (as described above); and b) a response protein (as described above). In some embodiments, a subject two-component optogenetic fusion polypeptide comprises, in order from amino terminus to carboxyl terminus: a) a response protein; and b) a light-responsive polypeptide. In some embodiments, a subject two-component optogenetic fusion polypeptide comprises, in order from amino terminus to carboxyl terminus: a) a light-responsive polypeptide; b) a linker peptide; and c) a response protein. In some embodiments, a subject two-component optogenetic fusion polypeptide comprises, in order from amino terminus to carboxyl terminus: a) a light-responsive polypeptide; b) a membrane trafficking signal; and c) a response protein. In some embodiments, a subject two-component optogenetic fusion polypeptide comprises, in order from amino terminus to carboxyl terminus: a) a light-responsive polypeptide; b) a membrane trafficking signal; c) a response protein; and d) a membrane trafficking signal. In some embodiments, a subject two-component optogenetic fusion polypeptide comprises, in order from amino terminus to carboxyl terminus: a) a light-responsive polypeptide; b) a membrane trafficking signal; c) a self-cleaving polypeptide; d) a response protein; and e) a membrane trafficking signal.

In some embodiments, a subject two-component optogenetic fusion polypeptide comprises, in order from amino terminus to carboxyl terminus: a) a light-responsive polypeptide; b) a membrane trafficking signal; c) a spacer polypeptide; d) a response protein; and d) an ER export signal. In some embodiments, a subject two-component optogenetic fusion polypeptide comprises, in order from amino terminus to carboxyl terminus: a) a light-responsive polypeptide; b) a membrane trafficking signal; c) a spacer polypeptide; d) a response protein; e) a membrane trafficking signal; and f) an ER export signal. In some embodiments, a subject two-component optogenetic fusion polypeptide comprises, in order from amino terminus to carboxyl terminus: a) a light-responsive polypeptide; b) a membrane trafficking signal; c) a response protein; d) a membrane trafficking signal; and e) an ER export signal. In some embodiments, a subject two-component optogenetic fusion polypeptide comprises, in order from amino terminus to carboxyl terminus: a) a light-responsive polypeptide; b) a membrane trafficking signal; c) a self-cleaving polypeptide; d) a response protein; e) a membrane trafficking signal; and f) an ER export signal.

Suitable self-cleaving polypeptides include, e.g., a 2A peptide such as a P2A peptide: ATNFSLLKQAGDVEENPGP (SEQ ID NO:49); a T2A peptide: EGRGSLLTCGDVEENPGP (SEQ ID NO:50); an E2A peptide: QCTNYALLKLAGDVESNPGP (SEQ ID NO:51); an F2A peptide: VKQTLNFDLLKLAGDVESNPGP (SEQ ID NO:52); and the like. In some cases, the self-cleaving peptide is a P2A peptide: ATNFSLLKQAGDVEENPGP (SEQ ID NO:49). In some cases, a P2A peptide comprises the amino acid sequence GSGATNFSLLKQAGDVEENPGP (SEQ ID NO:61).

In some embodiments, a subject two-component optogenetic fusion polypeptide comprises, in order from amino terminus to carboxyl terminus: a) an eArch polypeptide comprising an amino acid sequence having at least 80%, at least 85%, at least 90%, at least 95%, at least 98%, at least 99%, or 100%, amino acid sequence identity to the eArch polypeptide amino acid sequence set forth in SEQ ID NO:1; b) a membrane trafficking signal; c) an ASIC2a polypeptide comprising an amino acid sequence having at least 80%, at least 85%, at least 90%, at least 95%, at least 98%, at least 99%, or 100%, amino acid sequence identity to the ASIC2a polypeptide amino acid sequence set forth in SEQ ID NO:19; and d) a membrane trafficking signal. In some cases, the membrane trafficking signal is: KSRITSEGEYIPLDQIDINV (SEQ ID NO:37). In some of these embodiments, the two-component optogenetic fusion polypeptide further comprises an ER export signal (e.g., FCYENEV (SEQ ID NO:47).

In some embodiments, a subject two-component optogenetic fusion polypeptide comprises, in order from amino terminus to carboxyl terminus: a) an eArch polypeptide comprising an amino acid sequence having at least 80%, at least 85%, at least 90%, at least 95%, at least 98%, at least 99%, or 100%, amino acid sequence identity to the eArch polypeptide amino acid sequence set forth in SEQ ID NO:1; b) a membrane trafficking signal (e.g., KSRITSEGEYIPLDQIDINV (SEQ ID NO:37)); c) a polypeptide linker of from about 5 amino acids to about 100 amino acids, e.g., a polypeptide linker of from about 20 amino acids to about 25 amino acids in length; d) an ASIC2a polypeptide comprising an amino acid sequence having at least 80%, at least 85%, at least 90%, at least 95%, at least 98%, at least 99%, or 100%, amino acid sequence identity to the ASIC2a polypeptide amino acid sequence set forth in SEQ ID NO:19; and e) a membrane trafficking signal (e.g., KSRITSEGEYIPLDQIDINV (SEQ ID NO:37)). In some of these embodiments, the two-component optogenetic fusion polypeptide further comprises an ER export signal (e.g., FCYENEV (SEQ ID NO:47).

In some embodiments, a subject two-component optogenetic fusion polypeptide comprises, in order from amino terminus to carboxyl terminus: a) an eArch polypeptide comprising an amino acid sequence having at least 80%, at least 85%, at least 90%, at least 95%, at least 98%, at least 99%, or 100%, amino acid sequence identity to the eArch polypeptide amino acid sequence set forth in SEQ ID NO:1; b) a membrane trafficking signal (e.g., KSRITSEGEYI-PLDQIDINV (SEQ ID NO:37)); c) a polypeptide linker of from about 5 amino acids to about 100 amino acids, e.g., a polypeptide linker of from about 40 amino acids to about 45 amino acids in length; d) an ASIC2a polypeptide comprising an amino acid sequence having at least 80%, at least 85%, at least 90%, at least 95%, at least 98%, at least 99%, or 100%, amino acid sequence identity to the ASIC2a polypeptide amino acid sequence set forth in SEQ ID NO:19; and e) a membrane trafficking signal (e.g., KSRITSEGEYI-PLDQIDINV (SEQ ID NO:37)). In some of these embodiments, the two-component optogenetic fusion polypeptide further comprises an ER export signal (e.g., FCYENEV (SEQ ID NO:47).

In some embodiments, a subject two-component optogenetic fusion polypeptide comprises, in order from amino terminus to carboxyl terminus: a) an eArch polypeptide comprising an amino acid sequence having at least 80%, at least 85%, at least 90%, at least 95%, at least 98%, at least 99%, or 100%, amino acid sequence identity to the eArch polypeptide amino acid sequence set forth in SEQ ID NO:1; b) a membrane trafficking signal; c) a self-cleaving peptide (e.g., ATNFSLLKQAGDVEENPGP (SEQ ID NO:49)); d) an ASIC2a polypeptide comprising an amino acid sequence having at least 80%, at least 85%, at least 90%, at least 95%, at least 98%, at least 99%, or 100%, amino acid sequence identity to the ASIC2a polypeptide amino acid sequence set forth in SEQ ID NO:19; and e) a membrane trafficking signal. In some cases, the membrane trafficking signal is: KSRITSEGEYIPLDQIDINV (SEQ ID NO:37). In some of these embodiments, the two-component optogenetic fusion polypeptide further comprises an ER export signal (e.g., FCYENEV (SEQ ID NO:47).

Suitable linkers include "flexible linkers". If present, the linker polypeptide is generally of sufficient length to allow some flexible movement between the polypeptides connected by the linker. Suitable linkers can be readily selected and can be of any of a suitable of different lengths, such as from 5 amino acids to 100 amino acids, e.g., from 5 amino acids (aa) to 10 aa, from 10 aa to 15 aa, from 15 aa to 25 aa, from 25 aa to 40 aa, from 40 aa to 60 aa, from 60 aa to 80 aa, or from 80 aa to 100 aa. In some cases, the polypeptide linker, if present, is from 20 aa to 25 aa in length. In some cases, the polypeptide linker, if present, is from 40 aa to 45 aa in length.

Exemplary polypeptide linkers include glycine polymers $(G)_n$, glycine-serine polymers (including, for example, $(GS)_n$, $(GSGGS)_n$ (SEQ ID NO:53) and $(GGGS)_n$ (SEQ ID NO:54), where n is an integer of at least one, e.g., 1, 2, 3, 4, 5, or from 5 to 10), glycine-alanine polymers, alanine-serine polymers, and other polypeptide linkers known in the art. Exemplary flexible linkers include, but are not limited GGSG (SEQ ID NO:55), GGSGG (SEQ ID NO:56), GSGSG (SEQ ID NO:57), GSGGG (SEQ ID NO:58), GGGSG (SEQ ID NO:59), GSSSG (SEQ ID NO:60), and the like. The ordinarily skilled artisan will recognize that design of a linker polypeptide can include linkers that are all or partially flexible, such that the linker can include a flexible linker as well as one or more portions that confer less flexible structure.

In some cases, a subject two-component optogenetic fusion polypeptide comprises an amino acid sequence having at least 85%, at least 85%, at least 90%, at least 95%, at least 98%, at least 99%, or 100%, amino acid sequence identity to the amino acid sequence set forth in SEQ ID NO:31 (Champ 1.0). In some cases, a subject two-component optogenetic fusion polypeptide comprises an amino acid sequence having at least 85%, at least 85%, at least 90%, at least 95%, at least 98%, at least 99%, or 100%, amino acid sequence identity to the amino acid sequence set forth in SEQ ID NO:32 (Champ 2.0). In some cases, a subject two-component optogenetic fusion polypeptide comprises an amino acid sequence having at least 85%, at least 85%, at least 90%, at least 95%, at least 98%, at least 99%, or 100%, amino acid sequence identity to the amino acid sequence set forth in SEQ ID NO:33 (Champ 3.0). In some cases, a subject two-component optogenetic fusion polypeptide comprises an amino acid sequence having at least 85%, at least 85%, at least 90%, at least 95%, at least 98%, at least 99%, or 100%, amino acid sequence identity to the amino acid sequence set forth in SEQ ID NO:34 (Champ 4.0).

In some cases, a subject two-component optogenetic fusion polypeptide comprises an amino acid sequence having at least 85%, at least 85%, at least 90%, at least 95%, at least 98%, at least 99%, or 100%, amino acid sequence identity to the amino acid sequence set forth in SEQ ID NO:31 (Champ 1.0) without the yellow fluorescent protein (eYFP) sequence. In some cases, a subject two-component optogenetic fusion polypeptide comprises an amino acid sequence having at least 85%, at least 85%, at least 90%, at least 95%, at least 98%, at least 99%, or 100%, amino acid sequence identity to the amino acid sequence set forth in SEQ ID NO:32 (Champ 2.0) without the yellow fluorescent protein (eYFP) sequence. In some cases, a subject two-component optogenetic fusion polypeptide comprises an amino acid sequence having at least 85%, at least 85%, at least 90%, at least 95%, at least 98%, at least 99%, or 100%, amino acid sequence identity to the amino acid sequence set forth in SEQ ID NO:33 (Champ 3.0) without the yellow fluorescent protein (eYFP) sequence. In some cases, a subject two-component optogenetic fusion polypeptide comprises an amino acid sequence having at least 85%, at least 85%, at least 90%, at least 95%, at least 98%, at least 99%, or 100%, amino acid sequence identity to the amino acid sequence set forth in SEQ ID NO:34 (Champ 4.0) without the yellow fluorescent protein (eYFP) sequence.

The present disclosure provides a nucleic acid comprising a nucleotide sequence encoding a fusion polypeptide as described above. The present disclosure provides a recombinant expression vector comprising a nucleic acid comprising a nucleotide sequence encoding a fusion polypeptide as described above. In some cases, the nucleotide sequence encoding the fusion polypeptide is operably linked to a neuron-specific transcriptional control element. Suitable expression vectors and neuron-specific transcriptional control elements are described herein. The present disclosure provides a cell genetically modified with a recombinant expression vector comprising a nucleic acid comprising a nucleotide sequence encoding a fusion polypeptide as described above. In some embodiments, the cell is a neuron.

Exemplary Systems

The present disclosure provides various compositions, which include, but are not limited to, the following:

a) a composition comprising: i) a nucleic acid comprising a nucleotide sequence encoding a light-responsive polypeptide, where the light-responsive polypeptide is a proton pump; and ii) a nucleic acid comprising a nucleotide sequence encoding a response protein, wherein the response protein is an ion channel, e.g., an anion channel;

b) a composition comprising: i) a nucleic acid comprising a nucleotide sequence encoding a light-responsive polypeptide, where the light-responsive polypeptide is a proton pump; and ii) a nucleic acid comprising a nucleotide sequence encoding a response protein, wherein the response protein is a chloride ion channel;

c) a composition comprising: i) a nucleic acid comprising a nucleotide sequence encoding a light-responsive polypeptide, where the light-responsive polypeptide is a proton pump; and ii) a nucleic acid comprising a nucleotide sequence encoding a response protein, wherein the response protein is an ion channel, e.g., a cation channel;

d) a composition comprising: i) a nucleic acid comprising a nucleotide sequence encoding a light-responsive polypeptide, where the light-responsive polypeptide is a proton pump; and ii) a nucleic acid comprising a nucleotide sequence encoding a response protein, wherein the response protein is a potassium ion channel;

e) a composition comprising: i) a nucleic acid comprising a nucleotide sequence encoding a light-responsive polypeptide, where the light-responsive polypeptide is a proton pump; and ii) a nucleic acid comprising a nucleotide sequence encoding a response protein, wherein the response protein is a sodium ion channel;

f) a composition comprising: i) a nucleic acid comprising a nucleotide sequence encoding a light-responsive polypeptide, where the light-responsive polypeptide is a channelrhodopsin; and ii) a nucleic acid comprising a nucleotide sequence encoding a response protein, wherein the response protein is an ion channel, e.g., an anion channel;

g) a composition comprising: i) a nucleic acid comprising a nucleotide sequence encoding a light-responsive polypeptide, where the light-responsive polypeptide is a channelrhodopsin; and ii) a nucleic acid comprising a nucleotide sequence encoding a response protein, wherein the response protein is a chloride ion channel;

h) a composition comprising: i) a nucleic acid comprising a nucleotide sequence encoding a light-responsive polypeptide, where the light-responsive polypeptide is a channelrhodopsin; and ii) a nucleic acid comprising a nucleotide sequence encoding a response protein, wherein the response protein is an ion channel, e.g., a cation channel;

i) a composition comprising: i) a nucleic acid comprising a nucleotide sequence encoding a light-responsive polypeptide, where the light-responsive polypeptide is a channelrhodopsin; and ii) a nucleic acid comprising a nucleotide sequence encoding a response protein, wherein the response protein is a potassium channel;

j) a composition comprising: i) a nucleic acid comprising a nucleotide sequence encoding a light-responsive polypeptide, where the light-responsive polypeptide is a channelrhodopsin; and ii) a nucleic acid comprising a nucleotide sequence encoding a response protein, wherein the response protein is a sodium channel;

k) a composition comprising: i) a nucleic acid comprising a nucleotide sequence encoding a light-responsive polypeptide, where the light-responsive polypeptide is a channelrhodopsin; and ii) a nucleic acid comprising a nucleotide sequence encoding a response protein, wherein the response protein is a proton pump;

l) a composition comprising: i) a nucleic acid comprising a nucleotide sequence encoding a light-responsive polypeptide, where the light-responsive polypeptide is a proton pump; and ii) a nucleic acid comprising a nucleotide sequence encoding a response protein, wherein the response protein is a proton pump;

m) a composition comprising: i) a nucleic acid comprising a nucleotide sequence encoding a light-responsive polypeptide, where the light-responsive polypeptide is a chloride ion pump; and ii) a nucleic acid comprising a nucleotide sequence encoding a response protein, wherein the response protein is an anion channel;

n) a composition comprising: i) a nucleic acid comprising a nucleotide sequence encoding a light-responsive polypeptide, where the light-responsive polypeptide is a chloride ion pump; and ii) a nucleic acid comprising a nucleotide sequence encoding a response protein, wherein the response protein is a cation channel;

o) a composition comprising: i) a nucleic acid comprising a nucleotide sequence encoding a light-responsive polypeptide, where the light-responsive polypeptide is a chloride ion pump; and ii) a nucleic acid comprising a nucleotide sequence encoding a response protein, wherein the response protein is a potassium channel;

p) a composition comprising: i) a nucleic acid comprising a nucleotide sequence encoding a light-responsive polypeptide, where the light-responsive polypeptide is a chloride ion pump; and ii) a nucleic acid comprising a nucleotide sequence encoding a response protein, wherein the response protein is a sodium channel; and q) a composition comprising: i) a nucleic acid comprising a nucleotide sequence encoding a light-responsive polypeptide, where the light-responsive polypeptide is a chloride ion pump; and ii) a nucleic acid comprising a nucleotide sequence encoding a response protein, wherein the response protein is a proton pump.

The present disclosure provides various compositions, which include, but are not limited to, the following:

a) a composition comprising i) a nucleic acid comprising a nucleotide sequence encoding a light-responsive polypeptide, where the light responsive polypeptide is a ion pump or channel, and ii) a nucleic acid comprising a nucleotide sequence encoding a response protein wherein the response protein an ion exchanger, transporter, antiporter, or symport co-transporter;

b) a composition comprising: i) a nucleic acid comprising a nucleotide sequence encoding a light-responsive polypeptide, where the light-responsive polypeptide is a proton pump; and ii) a nucleic acid comprising a nucleotide sequence encoding a response protein, wherein the response protein is a sodium-phosphate co-transporter;

c) a composition comprising: i) a nucleic acid comprising a nucleotide sequence encoding a light-responsive polypeptide, where the light-responsive polypeptide is a proton pump; and ii) a nucleic acid comprising a nucleotide sequence encoding a response protein, wherein the response protein is a sodium-potassium-chloride co-transporter;

d) a composition comprising: i) a nucleic acid comprising a nucleotide sequence encoding a light-responsive polypeptide, where the light-responsive polypeptide is a proton pump; and ii) a nucleic acid comprising a nucleotide sequence encoding a response protein, wherein the response protein is an ion exchanger (antiporter), e.g. a sodium-calcium exchanger, a potassium-dependent sodium-calcium exchanger, or a sodium-hydrogen exchanger;

e) a composition comprising: i) a nucleic acid comprising a nucleotide sequence encoding a light-responsive polypeptide, where the light-responsive polypeptide is a channelrhodopsin; and ii) a nucleic acid comprising a nucleotide sequence encoding a response protein, wherein the response protein is a sodium-phosphate co-transporter;

f) a composition comprising: i) a nucleic acid comprising a nucleotide sequence encoding a light-responsive polypeptide, where the light-responsive polypeptide is a channelrhodopsin; and ii) a nucleic acid comprising a nucleotide sequence encoding a response protein, wherein the response protein is a sodium-potassium-chloride co-transporter;

g) a composition comprising: i) a nucleic acid comprising a nucleotide sequence encoding a light-responsive polypeptide, where the light-responsive polypeptide is a channelrhodopsin; and ii) a nucleic acid comprising a nucleotide sequence encoding a response protein, wherein the response protein is an ion exchanger (antiporter), e.g. a sodium-calcium exchanger, a potassium-dependent sodium-calcium exchanger, or a sodium-hydrogen exchanger.

The present disclosure provides various compositions, which include, but are not limited to, the following:

a) a composition comprising a nucleic acid comprising a nucleotide sequence encoding a two-component optogenetic fusion polypeptide, as described above;

b) a composition comprising a nucleic acid comprising a two-component optogenetic fusion polypeptide that comprises, in order from amino terminus to carboxyl terminus: i) a light-responsive polypeptide (as described above); and ii) a response protein (as described above).

c) a composition comprising a nucleic acid comprising a two-component optogenetic fusion polypeptide that comprises, in order from amino terminus to carboxyl terminus: i) a response protein; and ii) a light-responsive polypeptide.

d) a composition comprising a nucleic acid comprising a two-component optogenetic fusion polypeptide that comprises, in order from amino terminus to carboxyl terminus: i) a light-responsive polypeptide; ii) a linker peptide; and ii) a response protein.

e) a composition comprising a nucleic acid comprising a two-component optogenetic fusion polypeptide that comprises, in order from amino terminus to carboxyl terminus: i) a light-responsive polypeptide; ii) a membrane trafficking signal; and iii) a response protein.

f) a composition comprising a nucleic acid comprising a two-component optogenetic fusion polypeptide that comprises, in order from amino terminus to carboxyl terminus: i) a light-responsive polypeptide; ii) a membrane trafficking signal; iii) a response protein; and iv) a membrane trafficking signal.

g) a composition comprising a nucleic acid comprising a two-component optogenetic fusion polypeptide that comprises, in order from amino terminus to carboxyl terminus: i) a light-responsive polypeptide; ii) a membrane trafficking signal; iii) a self-cleaving polypeptide; iv) a response protein; and v) a membrane trafficking signal.

h) a composition comprising a nucleic acid comprising a two-component optogenetic fusion polypeptide that comprises, in order from amino terminus to carboxyl terminus: i) an eArch polypeptide comprising an amino acid sequence having at least 80%, at least 85%, at least 90%, at least 95%, at least 98%, at least 99%, or 100%, amino acid sequence identity to the eArch polypeptide amino acid sequence set forth in SEQ ID NO:1; ii) a membrane trafficking signal; iii) an ASIC2a polypeptide comprising an amino acid sequence having at least 80%, at least 85%, at least 90%, at least 95%, at least 98%, at least 99%, or 100%, amino acid sequence identity to the ASIC2a polypeptide amino acid sequence set forth in SEQ ID NO:19; and iv) a membrane trafficking signal. In some cases, the membrane trafficking signal is: KSRITSEGEYIPLDQIDINV (SEQ ID NO:37). In some of these embodiments, the two-component optogenetic fusion polypeptide further comprises an ER export signal (e.g., FCYENEV (SEQ ID NO:47).

i) a composition comprising a nucleic acid comprising a two-component optogenetic fusion polypeptide that comprises, in order from amino terminus to carboxyl terminus: i) an eArch polypeptide comprising an amino acid sequence having at least 80%, at least 85%, at least 90%, at least 95%, at least 98%, at least 99%, or 100%, amino acid sequence identity to the eArch polypeptide amino acid sequence set forth in SEQ ID NO:1; ii) a membrane trafficking signal (e.g., KSRITSEGEYIPLDQIDINV (SEQ ID NO:37)); iii) a polypeptide linker of from about 5 amino acids to about 100 amino acids, e.g., a polypeptide linker of from about 20 amino acids to about 25 amino acids in length; iv) an ASIC2a polypeptide comprising an amino acid sequence having at least 80%, at least 85%, at least 90%, at least 95%, at least 98%, at least 99%, or 100%, amino acid sequence identity to the ASIC2a polypeptide amino acid sequence set forth in SEQ ID NO:19; and v) a membrane trafficking signal (e.g., KSRITSEGEYIPLDQIDINV (SEQ ID NO:37)). In some of these embodiments, the two-component optogenetic fusion polypeptide further comprises an ER export signal (e.g., FCYENEV (SEQ ID NO:47).

j) a composition comprising a nucleic acid comprising a two-component optogenetic fusion polypeptide that comprises, in order from amino terminus to carboxyl terminus: i) an eArch polypeptide comprising an amino acid sequence having at least 80%, at least 85%, at least 90%, at least 95%, at least 98%, at least 99%, or 100%, amino acid sequence identity to the eArch polypeptide amino acid sequence set forth in SEQ ID NO:1; ii) a membrane trafficking signal (e.g., KSRITSEGEYIPLDQIDINV (SEQ ID NO:37)); iii) a polypeptide linker of from about 5 amino acids to about 100 amino acids, e.g., a polypeptide linker of from about 40 amino acids to about 45 amino acids in length; iv) an ASIC2a polypeptide comprising an amino acid sequence having at least 80%, at least 85%, at least 90%, at least 95%, at least 98%, at least 99%, or 100%, amino acid sequence identity to the ASIC2a polypeptide amino acid sequence set forth in SEQ ID NO:19; and v) a membrane trafficking signal (e.g., KSRITSEGEYIPLDQIDINV (SEQ ID NO:37)). In some of these embodiments, the two-component optogenetic fusion polypeptide further comprises an ER export signal (e.g., FCYENEV (SEQ ID NO:47).

k) a composition comprising a nucleic acid comprising a two-component optogenetic fusion polypeptide that comprises, in order from amino terminus to carboxyl terminus: i) an eArch polypeptide comprising an amino acid sequence having at least 80%, at least 85%, at least 90%, at least 95%, at least 98%, at least 99%, or 100%, amino acid sequence identity to the eArch polypeptide amino acid sequence set forth in SEQ ID NO:1; ii) a membrane trafficking signal; iii) a self-cleaving peptide (e.g., ATNFSLLKQAGDVEENPGP (SEQ ID NO:49)); iv) an ASIC2a polypeptide comprising an amino acid sequence having at least 80%, at least 85%, at least 90%, at least 95%, at least 98%, at least 99%, or 100%, amino acid sequence identity to the ASIC2a polypeptide amino acid sequence set forth in SEQ ID NO:19; and v) a membrane trafficking signal. In some cases, the membrane trafficking signal is: KSRITSEGEYIPLDQIDINV (SEQ ID NO:37). In some of these embodiments, the two-component optogenetic fusion polypeptide further comprises an ER export signal (e.g., FCYENEV (SEQ ID NO:47).

In some cases, the above-noted nucleic acids are expression vectors comprising a nucleotide sequence encoding a light-responsive protein and/or a response protein. In some cases, a subject composition comprises a first expression vector that comprises a nucleotide sequence encoding a light-responsive protein; and a second expression vector that comprises a nucleotide sequence encoding a response protein. In some cases, a subject composition comprises a single expression vector that includes a nucleotide sequence encoding a light-responsive protein and a nucleotide sequence encoding a response protein. Where the composition comprises a single expression vector, in some cases, the nucleotide sequence encoding the light-responsive protein and the nucleotide sequence encoding the response protein are under transcriptional control (operably linked) to the same transcriptional control element (e.g., promoter). Where the composition comprises a single expression vector, in some cases, the nucleotide sequence encoding the light-responsive protein and the nucleotide sequence encoding the response protein are under transcriptional control (operably linked) to two different promoters.

The present disclosure provides a system for modulating the membrane potential of a cell, the system comprising: i) a first nucleic acid comprising a nucleotide sequence encoding a light-activated protein that is adapted to allow a first ion to pass through a cell membrane in response to light; ii) a second nucleic acid comprising a nucleotide sequence encoding a response protein that responds to the passage of the first ion through the cell membrane by allowing a second ion to pass through the cell membrane; and iii) a device configured to illuminate a target location with a light. Any of the above-noted combinations of nucleic acids can be included in a subject system.

Polynucleotides and Vectors

Aspects of the present disclosure include nucleic acids, such as polynucleotides, that comprise a nucleotide sequence that encodes one or more of the subject proteins described herein (e.g., one or more light-activated proteins or response proteins as described above). In some embodiments, a subject polynucleotide comprises an expression cassette, wherein the expression cassette contains a plurality of components (e.g., a plurality of coding sequences) that are utilized to express one or more proteins encoded by the polynucleotide in a target cell.

In some embodiments, a portion of a polynucleotide encoding a subject protein is operably linked to a promoter sequence. Any suitable promoter that functions in a target cell can be used for expression of the subject polynucleotides. In certain embodiments, a promoter sequence can be a promoter that is specific to a particular target cell type or to a particular tissue type, such as a particular neuron or a pan-neuronal promoter. Initiation control regions of promoters, which are useful to drive expression of polynucleotides in a specific animal cell, are numerous and familiar to those skilled in the art. Virtually any promoter capable of driving expression of the subject polynucleotides can be used. In some embodiments, the promoter used to drive expression of a subject protein can be the Thy1 promoter (See, e.g., Llewellyn, et al., 2010, Nat. Med., 16(10):1161-1166). In some embodiments, the promoter used to drive expression of a subject protein can be a human synapsin (hSyn) promoter, a human elongation factor 1-α (EF1α) promoter, a cytomegalovirus (CMV) promoter, a CMV early enhancer/chicken β actin (CAG) promoter, a synapsin-I promoter (e.g., a human synapsin-I promoter), a human synuclein 1 promoter, a human Thy1 promoter, a calcium/calmodulin-dependent kinase II alpha (CAMKIIα) promoter, or any other promoter capable of driving expression of the a subject nucleic acid sequence in a target cell.

In some embodiments, a promoter may be an inducible promoter. For example, the promoter may be induced by a trans-acting factor that responds to an exogenously administered drug. Examples of inducible promoters include, but are not limited to, tetracycline-on or tetracycline-off promoters, or tamoxifen-inducible CreER.

In some embodiments, a subject polynucleotide may comprise a ribosomal skip sequence that can be used to generate two separate proteins from the same transcript. In such embodiments, a subject polynucleotide will typically include a coding sequence that encodes a light-activated protein as well as a response protein. In these embodiments, a ribosomal skip sequence may be placed between the two coding sequences to produce two distinct proteins (namely, the light-activated protein and the response protein) from the same transcript.

Also provided herein are vectors comprising the subject polynucleotides or any variant thereof as described herein. Vectors according to the present disclosure also include vectors comprising a nucleotide sequence that encodes an RNA (e.g., an mRNA) that when transcribed from the polynucleotides of the vector will result in the accumulation of a subject protein on the plasma membranes of target cells. Vectors which may be used include, without limitation, lentiviral, HSV, adenoviral, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, a vector may be a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome that contains the rep gene involved in viral replication and expression of the viral genes; and the right-hand part of the genome that contains the cap gene encoding the capsid proteins of the virus. AAV vectors may be prepared using standard methods in the art. Adeno-associated viruses of any serotype are suitable (see, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore. M E Bloom, R M Linden, C R Parrish, Eds.) p5-14, Hudder Arnold, London, UK (2006); and D E Bowles, J E Rabinowitz, R J Samulski "The Genus Dependovirus" (J R Kerr, S F Cotmore. M E Bloom, R M Linden, C R Parrish, Eds.) p15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication-defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596, 535, the disclosure of which is hereby incorporated by reference in its entirety.

FIG. 5 provides an example of a subject polynucleotide. The depicted polynucleotide, from 5' to 3', comprises a light-activated protein sequence (Arch), a trafficking sequence (ts), a ribosomal skip sequence (p2A), a response protein sequence (ASIC2a), and a yellow fluorescent protein sequence (EYFP). FIG. 6 provides an different example of a subject polynucleotide. The depicted polynucleotide, from 5' to 3', comprises a light-activated protein sequence (Arch), a trafficking sequence (ts), a ribosomal skip sequence (p2A), a response protein sequence (ASIC2a), a trafficking sequence (ts), a yellow fluorescent protein sequence (EYFP), and an endoplasmic reticulum export sequence (ER).

Figure 7:
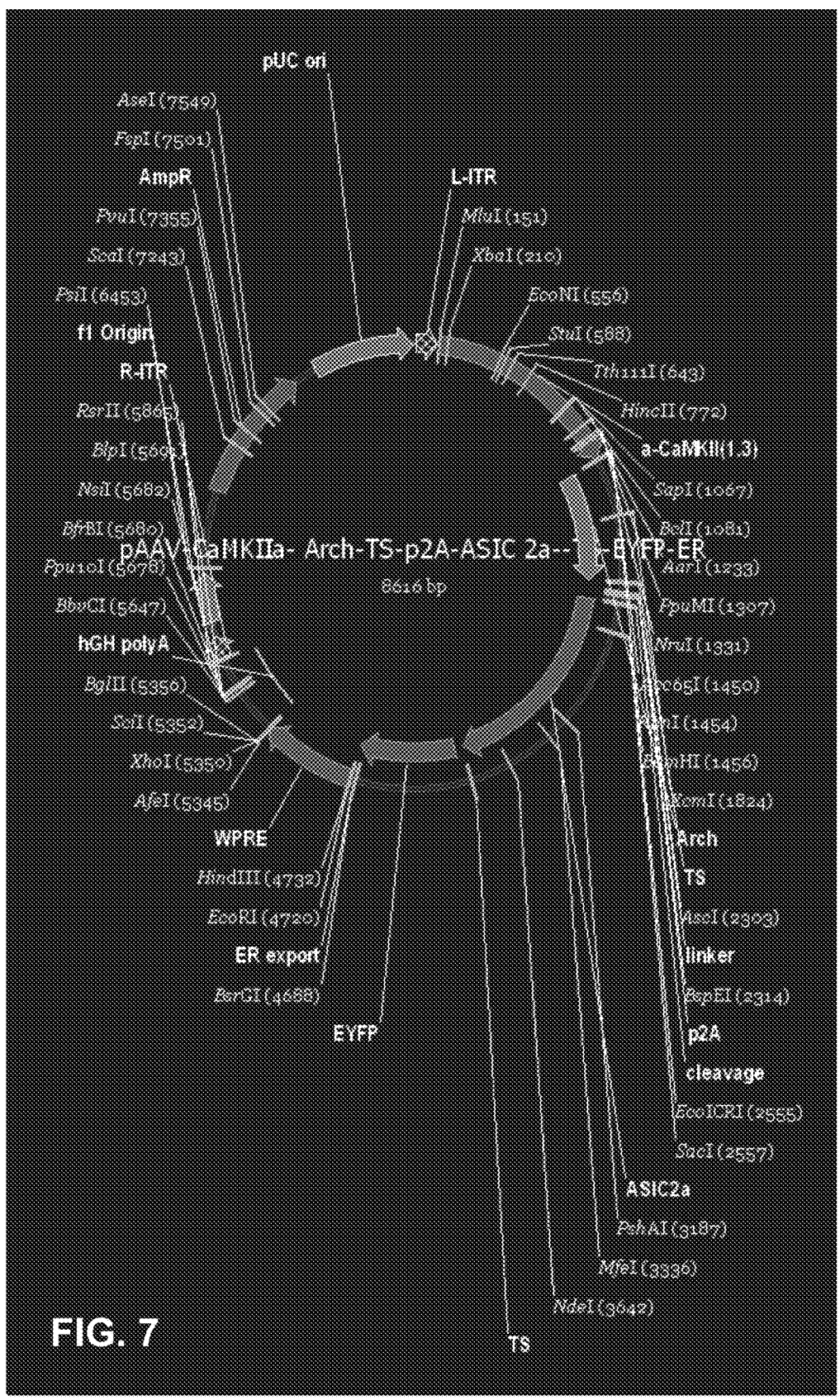
FIG. 7 shows a map of an example vector containing an Arch sequence and an ASIC2a sequence, as well as additional components, such as a CaMKIIa promoter.
Figure 8:
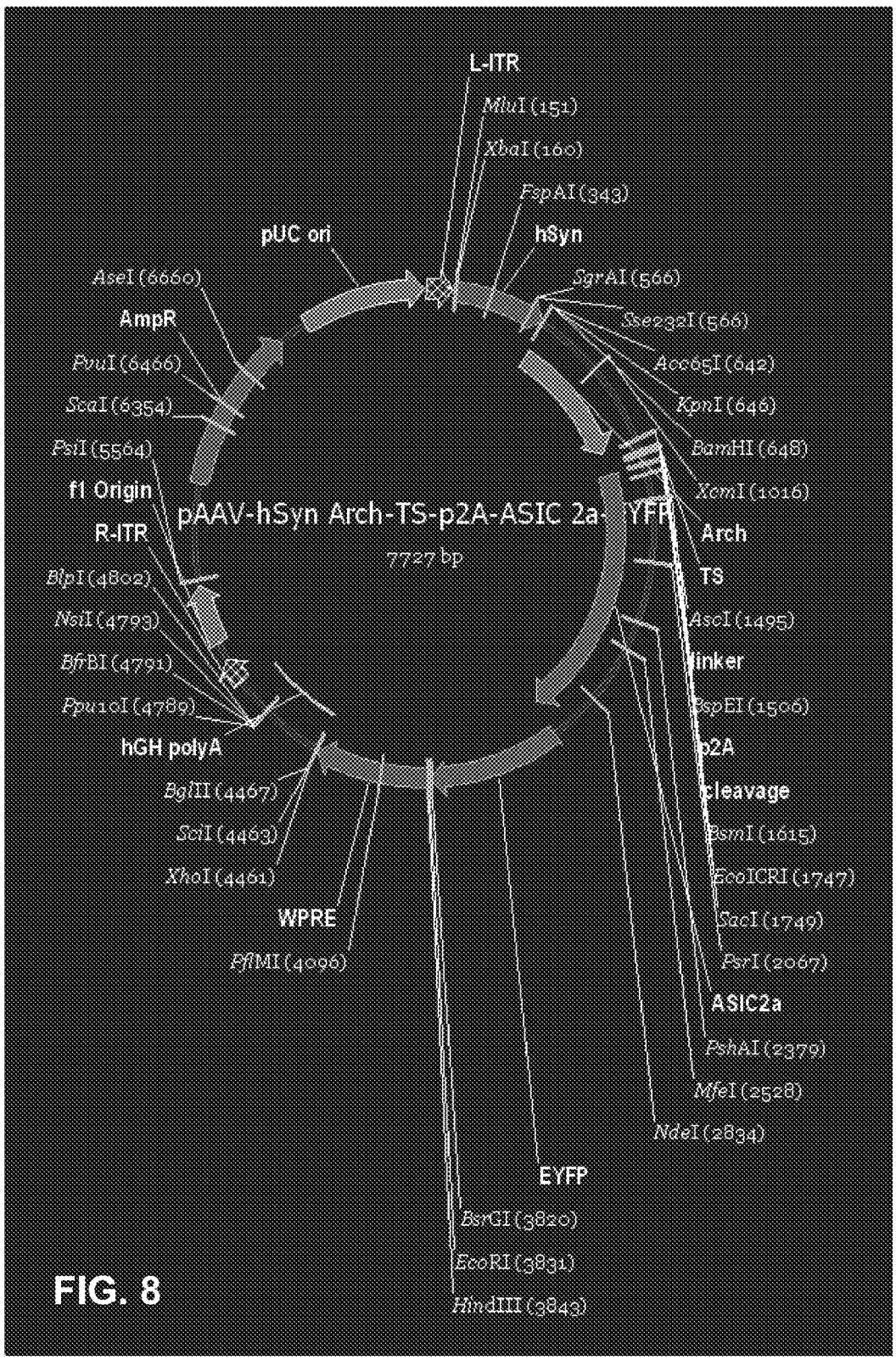
FIG. 8 shows a map of an example vector containing an Arch sequence and an ASIC2a sequence, as well as additional components, such as an hSyn promoter.

FIG. 7 provides an example of a subject vector. The depicted vector includes, from 5' to 3', a CamKII promoter sequence, an Arch coding sequence, a trafficking sequence (ts), a ribosomal skip sequence (p2A), an ASIC2a coding sequence, a trafficking sequence (ts), a yellow fluorescent protein sequence (EYFP), and an endoplasmic reticulum export sequence (ER). FIG. 8 provides another example of a subject vector. The depicted vector includes, from 5' to 3', an hSyn promoter sequence, an Arch coding sequence, a trafficking sequence (ts), a ribosomal skip sequence (p2A), an ASIC2a coding sequence, and a yellow fluorescent protein sequence (EYFP).

Pharmaceutical Compositions

Aspects of the present disclosure include pharmaceutical compositions that comprise the subject polynucleotides, vectors, or components thereof. The subject pharmaceutical compositions may be administered to a subject for purposes genetically modifying a target cell so that the target cell expresses one or more subject proteins. A subject pharmaceutical composition may, in some embodiments, comprise a pharmaceutically acceptable excipient. In some embodiments, a pharmaceutical composition may comprise components to facilitate delivery of the subject polynucleotides or vectors to a target cell, including but not limited to transfection reagents or components thereof, such as lipids, polymers, and the like.

In some embodiments, a subject pharmaceutical composition will be suitable for injection into a subject, e.g., will be sterile. For example, in some embodiments, a subject pharmaceutical composition will be suitable for injection into a subject, e.g., where the composition is sterile and is free of detectable pyrogens and/or other toxins.

Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public as well, and may be incorporated into the pharmaceutical compositions of the present disclosure without limitation.

Target Cells and Tissues

As summarized above, aspects of the present disclosure include delivering the subject polynucleotides, or components thereof, to target cells. Target cells are generally cells that carry or transmit electrical impulses, such as nerve cells. In some embodiments, a target cell may be, e.g., a sensory neuron, a motor neuron, or an interneuron. Target cells of the disclosure may include cells of the central nervous system and/or cells of the peripheral nervous system. In some embodiments, a target tissue may include a plurality of nerve fibers, a nerve, a nerve cell ganglion, a neuromuscular junction, a tissue that is innervated by nerves, including but not limited to muscle, skin, or endocrine tissue, or an anatomical region, such as a portion or sub-portion of the brain or spinal cord. In some embodiments, a target tissue may be a portion of an individual cell, such as specific axon of a nerve cell.

Once the subject polynucleotides have been delivered to a target cell or tissue, the polynucleotides enter the target cells and are expressed. In some embodiments, the subject polynucleotides may contain tissue-specific promoters so that expression only occurs in target cells wherein the tissue-specific promoter is active. In this way, if a subject polynucleotide is delivered to cells other than a target cell, the polynucleotide will not be expressed in the non-target cells because the tissue-specific promoter will be inactive in those cells. In some embodiments, a subject polynucleotide may contain an inducible promoter, such that expression of the polynucleotide only takes place when an exogenously administered drug is present is a sufficient concentration within the cell to activate the promoter.

In some cases, the present disclosure provides methods for modulating activity of a target cell that expresses a light-responsive protein and a response protein, as described above, where the method involves activating the light-responsive protein with light. In some cases, the present disclosure provides methods for modulating activity of a target cell that is proximal to a cell that expresses a light-responsive protein and a response protein, as described above, where the method involves activating the light-responsive protein with light. Thus, the target cell may not express the light-responsive protein and the response protein, but the activity of the target cell is modulated upon activating with light the light-responsive protein in a cell proximal to the target cell. A target cell that is "proximal" to a cell that expresses a light-responsive protein and a response protein, as described above, includes a cell that is in direct physical contact with the cell that expresses a light-responsive protein and a response protein, as described above. A target cell that is "proximal" to a cell that expresses a light-responsive protein and a response protein, as described above, includes a cell that is not in direct physical contact with the cell that expresses a light-responsive protein and a response protein, as described above, but whose activity is modulated by the cell that expresses a light-responsive protein and a response protein, as described above, e.g., modulated by neurotransmitter produced by the cell that expresses a light-responsive protein and a response protein, as described above; etc.

Devices

As summarized above, aspects of the present disclosure include various devices that can be used to carry out aspects of the subject methods. Devices that find use in the subject methods include delivery devices that can be used to deliver the subject polynucleotides to target cells and tissues, light-generating devices that can be used to illuminate target cells that express the subject light-activated proteins, and control devices that can be used to control the delivery of light to specific target cells or tissues. Each of these devices is further described below.

Delivery Devices

Aspects of the present disclosure include delivery devices that can be used to deliver a subject pharmaceutical composition to a target cell. The subject delivery devices may provide regular, irregular, programmed, or clinician- or patient-activated doses of the subject pharmaceutical compositions to one or more target cells to ensure that the target cells continue to express the subject proteins.

The subject delivery devices may generally include various components, such as reservoirs, pumps, actuators, tubing components, needles, catheters, and any other suitable components for delivering the subject pharmaceutical compositions to a target cell or tissue of a patient. Delivery devices may also include components that facilitate computerized operation, such as a power source, a processor comprising a memory, a user input device, and/or a graphical user interface. In some embodiments, a delivery device may be completely or partially implantable within a patient. In some embodiments, a delivery device may be operated by a caregiver, wherein the device is introduced into a portion of the patient's body, e.g., into the patient's brain, and a subject pharmaceutical composition is delivered to a target tissue, e.g., a portion of the patient's brain. In some embodiments, following delivery of the pharmaceutical composition, the device may be removed. In other embodiments, the device may be kept in place for later delivery of additional pharmaceutical compositions.

Light-Generating Devices

Aspects of the present disclosure include light-generating devices that can be used to deliver light to target cells that express one or more of the subject proteins. Light-generating devices in accordance with embodiments of the present disclosure can generally produce light of a variety of different wavelengths from one or more light sources on the device. In some embodiments, a light-generating device may include a light cuff or sleeve that can be placed around or near target cells expressing one or more subject proteins. In some embodiments, a portion of the light source or the entire light source may be implantable. The subject light-generating devices may be of any useful configuration for stimulating the light-activated proteins disclosed herein. In some embodiments, for example, a light-generating device may comprise components that facilitate exclusive illumination of a target cell or tissue. For example, in some embodiments, a light-generating device may exclusively direct light to a target cell, a portion of a target cell, e.g., a particular axon of a nerve cell, or a specific anatomical structure, such as, e.g. a bundle of nerve fibers, a target tissue, or a portion of the spinal cord. By "exclusively direct light" is meant that the light-generating device only delivers light to the specific target structure, and does not illuminate other structures. For examples, in some embodiments, a light-generating device may be configured to illuminate an axon of a nerve cell, but not illuminate any other portion of the nerve cell. In this way, the light from the light-generating device only affects light-activated proteins in the specific target structure that is illuminated.

In some embodiments, a light-generating device may not completely surround the region containing a target cell expressing a light-activated protein, but, rather, can have a U-shape. In some embodiments, a light-generating device can have an attachment arm that can be used to guide the light-generating device to a specific region or target structure, e.g., a specific neuronal region. The attachment arm can be removed following implantation of the light-generating device or can be left in place to fix the position of the light-generating device in proximity to the target cells of interest.

In some embodiments, the subject light-generating devices may comprise an inner body, the inner body having at least one means for generating light which is connected to a power source. In some embodiments, the power source can be an internal battery for powering the light-generating device. In some embodiments, an implantable light-generating device may comprise an external antenna for receiving wirelessly transmitted electromagnetic energy from an external source for powering device. The wirelessly transmitted electromagnetic energy can be a radio wave, a microwave, or any other electromagnetic energy source that can be transmitted from an external source to power the light-generating device. In some embodiments, the light-generating device is controlled by, e.g., an integrated circuit produced using semiconductor or other processes known in the art.

In some embodiments, the light-generating device may comprise a light emitting diode (LED). In some embodiments, the LED can generate blue and/or green light. In other embodiments, the LED can generate amber and/or yellow light. In some embodiments, several micro LEDs are embedded into the inner body of the light-generating device. In other embodiments, the light-generating device is a solid state laser diode or any other means capable of generating light. The light-generating device can generate light having a wavelength and intensity sufficient to activate a subject light-activated protein. In some embodiments, a light-generating device produces light having an intensity of any of about 0.05 mW/mm$^2$, 0.1 mW/mm$^2$, 0.2 mW/mm$^2$, 0.3 mW/mm$^2$, 0.4 mW/mm$^2$, 0.5 mW/mm$^2$, about 0.6 mW/mm$^2$, about 0.7 mW/mm$^2$, about 0.8 mW/mm$^2$, about 0.9 mW/mm$^2$, about 1.0 mW/mm$^2$, about 1.1 mW/mm$^2$, about 1.2 mW/mm$^2$, about 1.3 mW/mm$^2$, about 1.4 mW/mm$^2$, about 1.5 mW/mm$^2$, about 1.6 mW/mm$^2$, about 1.7 mW/mm$^2$, about 1.8 mW/mm$^2$, about 1.9 mW/mm$^2$, about 2.0 mW/mm$^2$, about 2.1 mW/mm$^2$, about 2.2 mW/mm$^2$, about 2.3 mW/mm$^2$, about 2.4 mW/mm$^2$, about 2.5 mW/mm$^2$, about 3 mW/mm$^2$, about 3.5 mW/mm$^2$, about 4 mW/mm$^2$, about 4.5 mW/mm$^2$, about 5 mW/mm$^2$, about 5.5 mW/mm$^2$, about 6 mW/mm$^2$, about 7 mW/mm$^2$, about 8 mW/mm$^2$, about 9 mW/mm$^2$, or about 10 mW/mm$^2$, inclusive, including values in between these numbers. In some embodiments, the light-generating device produces light having an intensity of at least about 10 Hz, such as up to about 25 Hz, such as up to about 50 Hz, such as up to about 75 Hz, such as up to about 100 Hz.

The subject light-generating devices are generally capable of generating light having a wavelength ranging from about 350 nm, up to about 360 nm, up to about 370 nm, up to about 380 nm, up to about 390 nm, up to about 400 nm, up to about 410 nm, up to about 420 nm, up to about 430 nm, up to about 440 nm, up to about 450 nm, up to about 460 nm, up to about 470 nm, up to about 480 nm, up to about 490 nm, up to about 500 nm, up to about 510 nm, up to about 520 nm, up to about 530 nm, up to about 540 nm, up to about 550 nm, up to about 560 nm, up to about 570 nm, up to about 580 nm, up to about 590 nm, up to about 600 nm, up to about 610 nm, up to about 620 nm, up to about 630 nm, up to about 640 nm, up to about 650 nm, up to about 660 nm, up to about 670 nm, up to about 680 nm, up to about 690 nm, up to about 700 nm, up to about 710 nm, up to about 720 nm, up to about 730 nm, up to about 740 nm, and/or up to about 750 nm.

In some embodiments, a subject light-generating device may include one or more optical fibers that can transmit light from a light source and deliver the light to a target structure. The optical fibers may comprise plastic or glass materials, and in some embodiments may be suitably flexible to facilitate placement of the light-generating device in locations that could not be accommodated by rigid structures. For example, in some embodiments, a light-generating device may comprise a light source that generates light, as well as one or more optical fibers that can be placed in various locations on or in the patient's body. Light from the light source can pass through the optical fiber, passing around corners and bends in the optical fiber, and emerge at the end of the optical fiber to deliver light to a target structure.

In some embodiments, the subject light-generating devices may comprise a plurality of light sources that can be used to illuminate a target tissue with different wavelengths of light. For example, in some embodiments, a light-generating device may comprise a first light source that generates light of a first wavelength, e.g., red light, and a second light source that generates light of a second wavelength, e.g., green light. Such light-generating devices may be used to simultaneously illuminate the same target tissue with light of both wavelengths, or may alternately illuminate the target tissue with light of the first wavelength and light of the second wavelength. In some embodiments, such light generating devices may be used to deliver light from the same light source different target tissues. For example, in some embodiments a light-generating device may deliver light of a first wavelength to a first target tissue, and may deliver light of a second wavelength to a different target tissue.

Control Devices

Aspects of the present disclosure include control devices that can control, or modulate, the amount of light that is emitted from the subject light-generating devices. In some embodiments, a control device may be configured to modulate the wavelength and/or the intensity of light that is delivered to a target tissue from a light-generating device. In some embodiments, a control device may be configured to modulate the frequency and/or duration of light that is delivered to a target tissue from a light-generating device. For example, in some embodiments, a control device may be configured to deliver pulses of light from the light-generating device to a target tissue. The control device can modulate the frequency and/or duration of the light pulses such that the target tissue is illuminated with light from the light-generating device, e.g., at a regular or irregular rate, according to a user input, etc. In some embodiments, a control device can produce pulses of light from the light-generating device that have a duration ranging from about 1 millisecond or less, up to about 1 second, up to about 10 seconds, up to about 20 seconds, up to about 30 seconds, up to about 40 seconds, up to about 50 seconds, up to about 60 seconds or more. In some embodiments, a control device can produce pulses of light from the light-generating device that have a frequency of 1 pulse per millisecond, up to about 1 pulse per second, up about 1 pulse per minute, up to about 1 pulse per 10 minutes, up to about 1 pulse per 20 minutes, up to about 1 pulse per 30 minutes.

In some embodiments, a subject control device may comprise a power source that can be mounted to a transmitting coil. In some embodiments, a battery can be connected to the power source for providing power thereto. A switch can be connected to the power source, allowing an operator (e.g., a patient or caregiver) to manually activate or deactivate the power source. In some embodiments, upon activation of the switch, the power source can provide power to the light-generating device through electromagnetic coupling between the transmitting coil on the control device and an external antenna of an implantable light-generating device (such as a light cuff or sleeve). The transmitting coil can establish an electromagnetic coupling with the external antenna of the implantable light-generating device when in proximity thereof, for supplying power to the light-generating device and for transmitting one or more control signals to the light-generating device. In some embodiments, the electromagnetic coupling between the transmitting coil of the control device and the external antenna of the implantable light-generating device can be radio-frequency magnetic inductance coupling. When radio-frequency magnetic inductance coupling is used, the operational frequency of the radio wave can be between about 1 and 20 MHz, inclusive, including any values in between these numbers (for example, about 1 MHz, about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, about 15 MHz, about 16 MHz, about 17 MHz, about 18 MHz, about 19 MHz, or about 20 MHz). However, other coupling techniques may be used, such as an optical receiver, infrared, or a biomedical telemetry system (See, e.g., Kiourti, "Biomedical Telemetry: Communication between Implanted Devices and the External World, Opticon1826, (8): Spring, 2010).

Figure 9:
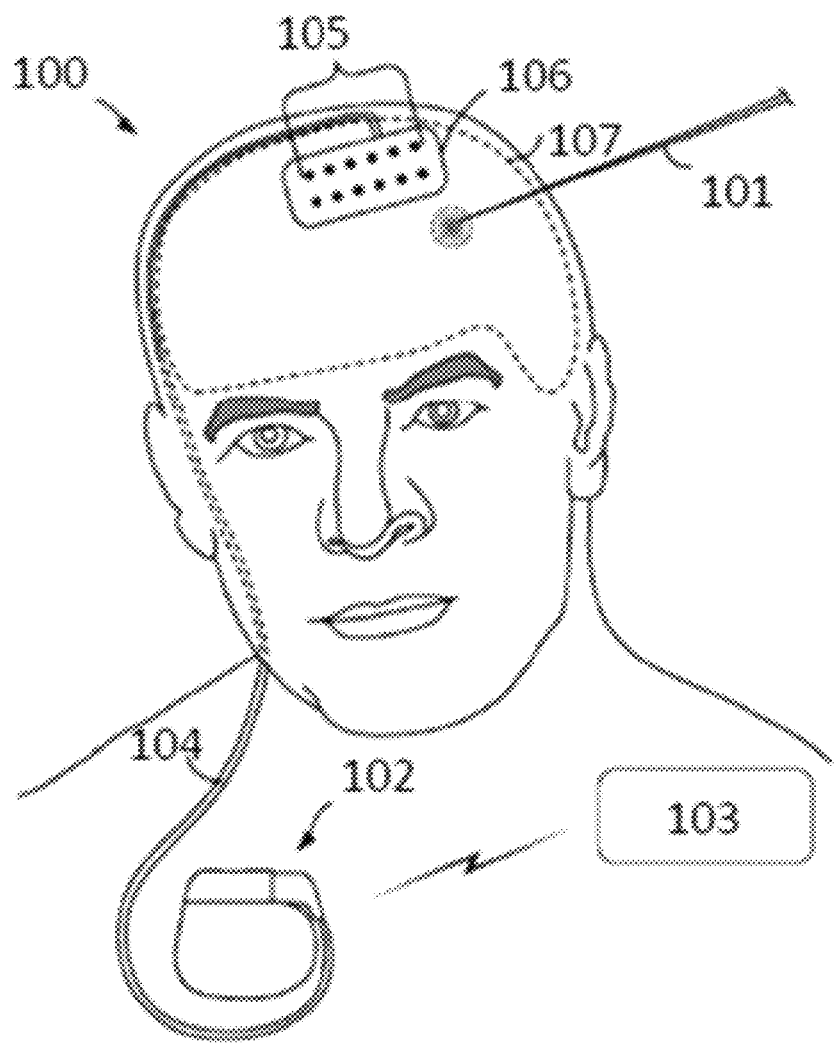
FIG. 9 shows a first example of an optical stimulation system in accordance with embodiments of the present disclosure.

Turning now to FIG. 9, a first example of an optical stimulation system 100 is depicted. The optical stimulation system 100 comprises a delivery device 101 for delivering a subject polynucleotide to a target tissue, e.g., brain tissue 107 of a patient. Also provided are a light-generating device 102, a control device 103, and optical fibers 104 for conveying light generated by the light-generating device 102 to a light array 105 positioned on a light cuff 106.

Figure 10:
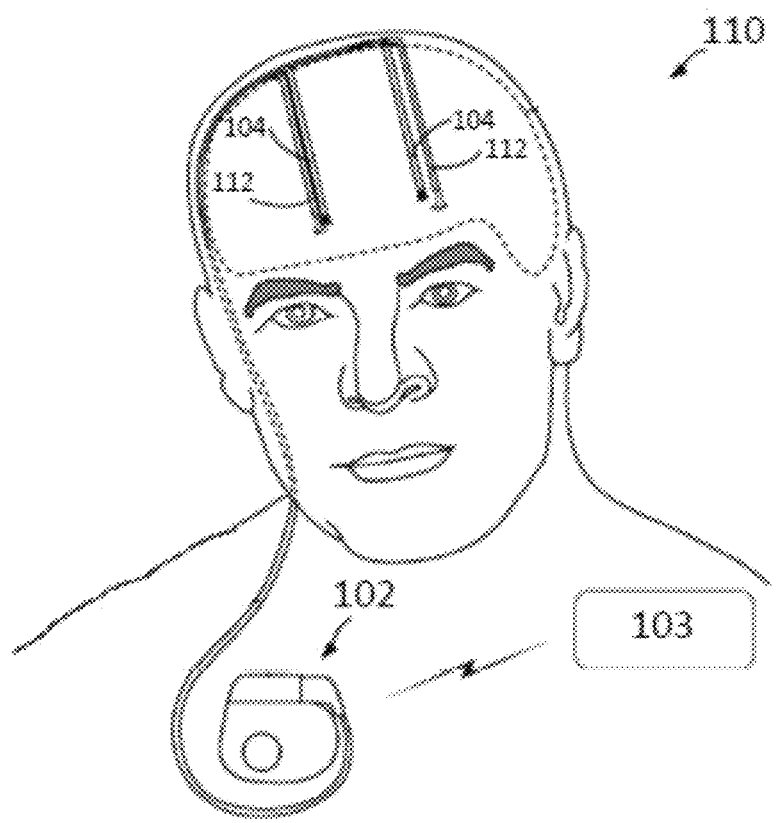
FIG. 10 shows a second example of an optical stimulation system in accordance with embodiments of the present disclosure.

Turning now to FIG. 10, a second example of an optical stimulation system 110 is depicted. The optical stimulation system 110 comprises a catheter 112 for delivering a subject polynucleotide to a target tissue, e.g., brain tissue 107 of a patient. Also provided are a light-generating device 102, a control device 103, and optical fibers 104 for conveying light generated by the light-generating device 102 to the end of the optical fibers 104.

Figure 11:
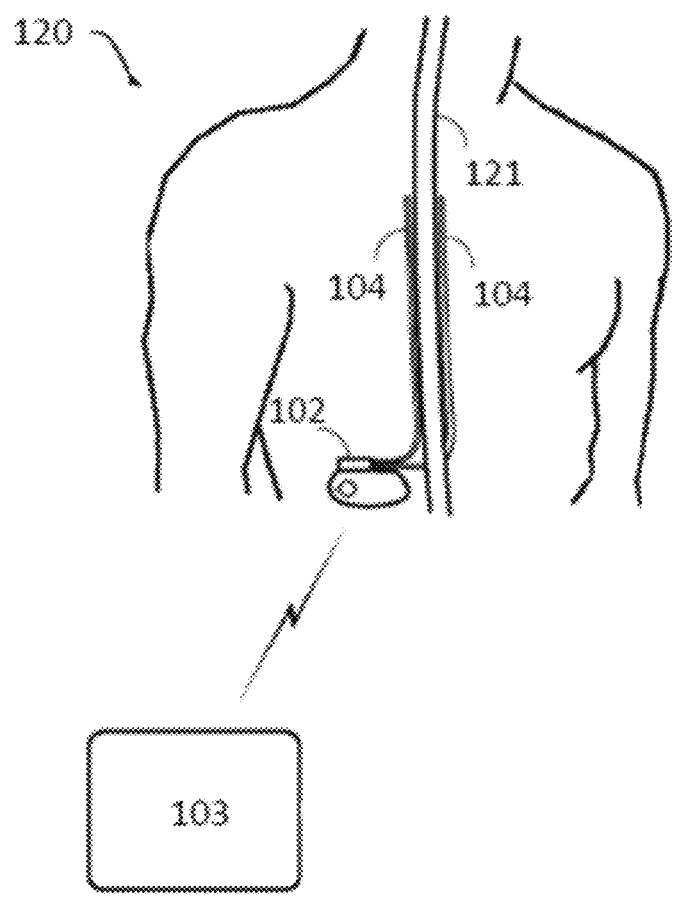
FIG. 11 shows a third example of an optical stimulation system in accordance with embodiments of the present disclosure.

Turning now to FIG. 11, a third example of an optical stimulation system 120 is depicted. The optical stimulation system 120 comprises a light-generating device 102, a control device 103, and optical fibers 104 for conveying light generated by the light-generating device 102 to various positions along the spinal cord 121 of the patient.

Methods

Aspects of the present disclosure include methods for optogenetic modulation of action potentials in target cells. The subject methods generally involve introducing a light-activated protein and a response protein into a target cell and illuminating the target cell with light of an activating wavelength. Illumination of the target cell with light of an activating wavelength causes the light-activated protein to allow one or more of a first species of ions to pass through the plasma membrane of the target cell. The presence of the first species of ions that passed through the light-activated protein causes the response protein to allow a second species of ions to pass through the plasma membrane of the target cell. The passage of the second species of ions through the plasma membrane of the target cell has a desired effect, such as, e.g., modulating the membrane potential of the plasma membrane, activating or inactivating an ion channel, etc. In some embodiments, the passage of the second ion species through the plasma membrane may be used to modulate one or more neurological responses or processes in a patient, and may therefore by used to treat a disease or condition in the patient. As such, in some embodiments, the subject methods involve treating a patient for a condition, such as a neurological condition, using the systems and devices provided herein. The subject methods are now described in greater detail below.

As discussed above, in some cases, a target cell does not express the light-responsive protein and the response protein, but the activity of the target cell is modulated upon activating with light the light-responsive protein in a cell proximal to the target cell. A target cell that is "proximal" to a cell that expresses a light-responsive protein and a response protein, as described above, includes a cell that is in direct physical contact with the cell that expresses a light-responsive protein and a response protein, as described above. A target cell that is "proximal" to a cell that expresses a light-responsive protein and a response protein, as described above, includes a cell that is not in direct physical contact with the cell that expresses a light-responsive protein and a response protein, as described above, but whose activity is modulated by the cell that expresses a light-responsive protein and a response protein, as described above, e.g., modulated by neurotransmitter produced by the cell that expresses a light-responsive protein and a response protein, as described above; etc.

Modulating Membrane Potentials in Target Cells

In some embodiments, the subject methods involve modulating membrane potentials in target cells using the subject systems and devices. In some embodiments, a nucleic acid encoding a subject light-activated protein and a subject response protein is introduced into a target cell such that the target cell expresses both the light-activated protein and the response protein. The target cell is then illuminated with light of an activating wavelength using a light-generating device. Illumination of the light-activated protein results in the movement of one or more ions of a first species through the plasma membrane of the cell in response to light. In some embodiments, for example, the light-activated protein is a proton pump, and in response to light moves proteins from the internal side of the plasma membrane to the external side of the plasma membrane.

Once the first ion species has been moved across the plasma membrane of the target cell, the response protein responds to the presence of the first ion species by transporting a second ion species across the plasma membrane of the target cell. In some embodiments, for example, the response protein is an acid sensing ion channel, such as, e.g., ASIC2a, which detects the presence of acidic conditions, such as the presence of protons on the external side of the plasma membrane, and responds by opening an ion channel, such as a sodium ion channel, that allows ions of a second species to pass through the plasma membrane. The passage of the second species of ions through the plasma membrane modulates the membrane potential of the cell by changing the charge distribution across the plasma membrane. For example, in some embodiments, the passage of the second species of ions through the plasma membrane results in a build-up of positive charge inside the cell, which modulates the membrane potential of the cell. As such, using the subject light-activated proteins in combination with the subject response proteins, the methods of the present disclosure can be used to modulate the membrane potential of a target cell in response to light of an activating wavelength.

Inhibiting Activity of Voltage-Gated Ion Channels

In some embodiments, the subject methods involve inhibiting the activity of voltage-gated sodium channels (VGSCs) that may be present in a nerve cell. VGSCs are a class of ion channels that are activated by changes in the membrane potential of nerve cells, and are generally involved with rapid, coordinated depolarization of nerve cell membranes in response to a given stimulus. For example, VGSCs are frequently found along the axons of nerve cells, and generally facilitate propagation of an action potential along the axon.

VGSCs function by allowing sodium ions to flow into the nerve cell from outside the plasma membrane. The flow of positively-charged sodium ions into the nerve cell changes the membrane potential and thereby propagates an action potential along the length of the nerve cell. Following activation, the VGSCs inactivate in a time-dependent manner. Once inactivated, the VGSC remains in a refractory inactivated state until the cell membrane potential repolarizes. As such, inactivation of VGSCs is a powerful technique for controlling nerve cell activity because, once inactivated, the VGSCs cannot regain activity until the nerve cell has repolarized.

In some embodiments, the subject methods involve inhibiting the activity of VGSCs by introducing into a nerve cell a light-activated protein, such as a light-activated proton pump (e.g., Arch), and a response protein, such as an acid sensing sodium ion channel (e.g., ASIC2a). Polynucleotides encoding these proteins are introduced into the nerve cell, and the proteins are expressed by the nerve cell and inserted into the plasma membrane of the nerve cell. Next, the nerve cell is illuminated with light of an activating wavelength from a light-generating device to cause the light-activated proton pump to transport protons through the plasma membrane from inside the cell to the outside of the cell. When the protons are present on or near the external surface of the plasma membrane, the response protein detects the presence of the protons and responds by opening a sodium ion channel. The sodium ion channel allows sodium ions to pass through the plasma membrane from outside the cell to the inside of the cell.

Once inside the nerve cell, the sodium ions depolarize the membrane sufficiently to inactivate one or more VGSCs in the plasma membrane. The inactivation of the VGSCs prevents the VGSCs from generating further action potentials in the nerve cell until the membrane repolarizes, which is facilitated by the cessation of light and decay of the response protein current, and the refractory period ends. As such, the propagation of action potentials along the nerve cell is blocked for the duration of the light pulse, the response protein current decay, and the refractory period. Accordingly, the subject methods may be used to block the propagation of an action potential along a nerve cell by introducing the subject proteins into the nerve cell plasma membrane and illuminating the cell with light of an activating wavelength from a light-generating device to inactivate one or more VGSCs in the nerve cell. Since the duration of action potential blockade outlasts the duration of the light pulse, inhibition of action potentials may be achieved using pulsed light delivery, rather than continuous light delivery.

In some embodiments, the subject methods involve inhibiting the activity of one or more voltage-gated calcium channels (VGCCs) that may be present in a target tissue. For example, in some cells and tissues, voltage-gated calcium channels (VGCCs) play analogous roles to those described above regarding voltage-gated sodium channels (VGSCs), and also exhibit voltage-dependent inactivation. Moreover, VGCCs also mediate neurotransmitter release, modulator and hormone release, and muscle contraction. Accordingly, in some embodiments, the subject methods involve inhibiting the activity of VGCCs by introducing into a target cell a light-activated protein, such as a light-activated proton pump (e.g., Arch), and a response protein, such as an acid sensing sodium ion channel (e.g., ASIC2a). Polynucleotides encoding these proteins are introduced into the target cell, and the proteins are expressed by the target cell and inserted into the plasma membrane of the target cell. Next, the target cell is illuminated with light of an activating wavelength from a light-generating device to cause the light-activated proton pump to transport protons through the plasma membrane from inside the cell to the outside of the cell. When the protons are present on or near the external surface of the plasma membrane, the response protein detects the presence of the protons and responds by opening a sodium ion channel. The sodium ion channel allows sodium ions to pass through the plasma membrane from outside the cell to the inside of the cell.

Once inside the target cell, the sodium ions depolarize the membrane sufficiently to inactivate one or more VGCCs in the plasma membrane. The inactivation of the VGCCs prevents the VGCCs from, e.g., generating further action potentials in the target cell; mediating the release of neurotransmitters, modulators, or hormones; mediating muscle contraction; and the like until the membrane repolarizes, which is facilitated by the cessation of light and decay of the response protein current, and the refractory period ends. As such, various functions of the VGCCs in the target cell are blocked for the duration of the light pulse, the response protein current decay, and the refractory period. Accordingly, the subject methods may be used to block various functions of VGCCs in a target cell by introducing the subject proteins into the target cell plasma membrane and illuminating the cell with light of an activating wavelength from a light-generating device to inactivate one or more VGCCs in the target cell. Since the duration of the VGCC blockade outlasts the duration of the light pulse, inhibition of VGCCs may be achieved using pulsed light delivery, rather than continuous light delivery.

Inhibiting and/or Blocking Retrograde Action Potentials in Nerve Cells

In some embodiments, the subject methods involve inhibiting and/or blocking the propagation of a retrograde action potential along a portion of a nerve cell (e.g., along an axon of a nerve cell) using the subject systems and devices. For example, in some embodiments, the subject methods involve introducing into a nerve cell a light-activated protein, such as a light-activated proton pump (e.g., Arch), and a response protein, such as an acid sensing sodium ion channel (e.g., ASIC2a). Polynucleotides encoding the proteins are introduced into the nerve cell, and the proteins are expressed by the nerve cell and inserted into the plasma membrane of the nerve cell.

Next, a light-generating device is positioned such that only a target portion of the nerve cell (e.g., only the axon, or only a portion of the axon, of the nerve cell) is illuminated with light of an activating wavelength when the light-generating device is activated. Next, the light-generating device is activated to deliver light to the desired portion of the nerve cell to cause the light-activated proton pump to transport protons through the plasma membrane from inside the cell to the outside of the cell. When the protons are present on or near the external surface of the plasma membrane, the response protein detects the presence of the protons and responds by opening a sodium ion channel. The sodium ion channel allows sodium ions to pass through the plasma membrane from outside the cell to the inside of the cell.

Once inside the cell, the sodium ions depolarize the membrane sufficiently to inactivate one or more VGSCs in the plasma membrane in the portion of the cell that is illuminated with light from the light-generating device. The inactivation of the VGSCs in the designated area of the nerve cell prevents the VGSCs from generating further action potentials in the nerve cell until the membrane repolarizes, which is facilitated by the cessation of light and decay of the response protein current, and the refractory period ends. As such, the propagation of action potentials along the nerve cell in the illuminated area is blocked for the duration of the light pulse, the response protein current decay and the refractory period. Accordingly, the subject methods may be used to block the propagation of an action potential along a particular portion of a nerve cell by introducing the subject proteins into the nerve cell plasma membrane and illuminating only a specific portion of the nerve cell with light of an activating wavelength from a light-generating device to inactivate one or more VGSCs in the illuminated portion of nerve cell or axon. Since the duration of action blockade outlasts the duration of the light pulse, inhibition of action potentials may be achieved using pulsed light delivery, rather than continuous light delivery. Accordingly, the subject methods may be used to block or inhibit the propagation of action potentials along a particular portion of a nerve cell or axon by delivering light of an activating wavelength to the specific portion of the nerve cell. Importantly, action potentials may still propagate through other portions of the nerve cell or axon that are not illuminated with light of a wavelength that activates the subject light-activated protein. In this way, specificity is achieved for restricting action potential propagation (anterograde and/or orthograde, and elicited naturally, optically, or electrically) to subdomains of the axonal arborization or cell.

Methods of Treatment

In some embodiments, the subject methods may be used to treat a patient for a condition or disorder, such as a neurological condition or disorder, by optogenetically modulating the action potentials of target cells within the patient. In some embodiments, the subject methods involve introducing a light-activated protein, such as such as a light-activated proton pump (e.g., Arch), and a response protein, such as an acid sensing sodium ion channel (e.g., ASIC2a) in a target tissue within the patient. In some embodiments, introduction of the subject proteins into the target tissue is accomplished using a subject delivery device. The polynucleotides encoding the subject proteins are introduced into the target tissue, and the proteins are expressed by nerve cells in the target tissue and inserted into the plasma membrane of the nerve cells.

Next, a light-generating device is positioned to illuminate the target tissue with light of an activating wavelength when the light-generating device is activated. The light-generating device is activated (either by the patient or by a caregiver) to deliver light to the target tissue to cause the light-activated proton pump to transport protons through the plasma membrane from inside a cell in the target tissue to the outside of the cell. When the protons are present on or near the external surface of the plasma membrane, the response protein detects the presence of the protons and responds by opening a sodium ion channel. The sodium ion channel allows sodium ions to pass through the plasma membrane from outside the cell to the inside of the cell.

Once inside the cell, the sodium ions depolarize the membrane sufficiently to inactivate one or more VGSCs in the plasma membrane in the portion of the cell that is illuminated with light from the light-generating device. The inactivation of the VGSCs in the designated area of the nerve cell prevents the VGSCs from generating further action potentials in the nerve cell until the membrane repolarizes, which is facilitated by the cessation of light and decay of the response protein current, and the refractory period ends. As such, the propagation of action potentials along the nerve cell is blocked for the duration of the light pulse, the response protein current decay and the refractory period. Accordingly, the subject methods may be used to block the propagation of an action potential in a nerve cell by introducing the subject proteins into the nerve cell plasma membrane and illuminating the nerve cell with light of an activating wavelength from a light-generating device to inactivate one or more VGSCs in the illuminated portion of nerve cell. As the duration of action blockade outlasts the duration of the light pulse, inhibition of action potentials may be achieved using pulsed light delivery, rather than continuous light delivery.

In some embodiments, the subject methods involve treating a subject for a disorder by inhibiting the activity of one or more voltage-gated calcium channels (VGCCs) that may be present in a target tissue. For example, in some cells and tissues, voltage-gated calcium channels (VGCCs) play analogous roles to those described above regarding voltage-gated sodium channels (VGSCs), and also exhibit voltage-dependent inactivation. Moreover, VGCCs also mediate neurotransmitter release, modulator and hormone release, and muscle contraction. Accordingly, in some embodiments, the subject methods involve treating a subject by inhibiting the activity of VGCCs by introducing into a target cell a light-activated protein, such as a light-activated proton pump (e.g., Arch), and a response protein, such as an acid sensing sodium ion channel (e.g., ASIC2a). Polynucleotides encoding these proteins are introduced into the target cell, and the proteins are expressed by the target cell and inserted into the plasma membrane of the target cell. Next, the target cell is illuminated with light of an activating wavelength from a light-generating device to cause the light-activated proton pump to transport protons through the plasma membrane from inside the cell to the outside of the cell. When the protons are present on or near the external surface of the plasma membrane, the response protein detects the presence of the protons and responds by opening a sodium ion channel. The sodium ion channel allows sodium ions to pass through the plasma membrane from outside the cell to the inside of the cell.

Once inside the target cell, the sodium ions depolarize the membrane sufficiently to inactivate one or more VGCCs in the plasma membrane. The inactivation of the VGCCs prevents the VGCCs from, e.g., generating further action potentials in the target cell; mediating the release of neurotransmitters, modulators, or hormones; mediating muscle contraction; and the like until the membrane repolarizes, which is facilitated by the cessation of light and decay of the response protein current, and the refractory period ends. As such, various functions of the VGCCs in the target cell are blocked for the duration of the light pulse, the response protein current decay, and the refractory period. Accordingly, the subject methods may be used to treat a subject for a disorder by blocking various functions of VGCCs in a target cell by introducing the subject proteins into the target cell plasma membrane and illuminating the cell with light of an activating wavelength from a light-generating device to inactivate one or more VGCCs in the target cell. Since the duration of the VGCC blockade outlasts the duration of the light pulse, inhibition of VGCCs may be achieved using pulsed light delivery, rather than continuous light delivery.

Accordingly, the subject methods may be used to treat any disease or condition in which blocking or inhibiting the propagation of an action potential along an excitable or nerve cell, or along a particular portion of an excitable or nerve cell, would have a therapeutic effect for the patient, or wherein blocking the function of a VGCC would have a therapeutic effect for the patient. Examples of therapeutic applications of the subject methods include, without limitation, therapy for cardiac rhythm disorders, such as pacing, cardioversion, defibrillation, resynchronization, or other cardiac-related conditions; gastrointestinal therapy, such as therapy to address obesity, motility disorders (e.g., gastroparesis), dyspepsia, or other therapies, therapy for pelvic floor tissue (e.g., sacral or pudendal nerve tissue) to support pelvic floor therapy such as pain therapy, urinary or fecal incontinence therapy, sexual dysfunction, or other therapies; cranial nerve therapy, such as therapy to relieve occipital neuralgia, trigeminal neuralgia, facial pain, migraine headaches; therapy for the treatment of pain, such as nociceptive pain or neuropathic pain; therapy for neurological and/or psychiatric conditions; therapy for endocrine conditions; or the like.

Specificity can be achieved as above for restricting action potential propagation (anterograde and/or orthograde, and elicited naturally, optically, or electrically) to subdomains of the axonal arborization or cell.

Combination Treatment Methods

In some embodiments, the subject methods involve combination treatments that involve activating or initiating an action potential in a first tissue, and also involve blocking or inhibiting the propagation of an action potential within a second tissue. For example, in some embodiments, the subject methods involve introducing a first light-activated protein into a first tissue, such as a nerve cell, by introducing into the cell a polynucleotide that encodes a first light-activated protein. The first light-activated protein is capable of transporting one or more ions across the plasma membrane of cells in the target tissue to trigger an action potential in the first tissue in response to light of an activating wavelength.

Simultaneously, a second light-activated protein, such as a light-activated proton pump (e.g., Arch), and a response protein, such as an acid sensing sodium ion channel (e.g., ASIC2a) are also introduced into the tissue. Next, a light-generating device is positioned near the target tissue to illuminate the target tissue. The light-generating device comprises a plurality of light sources, such that the target tissue, or portions thereof, can be illuminated with light of different wavelengths. A portion of the light-generating device is positioned to exclusively illuminate a portion of the target tissue in which it is desirable to block or inhibit action potentials. For example, a portion of the light-generating device, such as a particular light cuff or sleeve, may be positioned to exclusively illuminate, e.g., a particular portion of a nerve cell, such as an axon of the nerve cell, with a particular wavelength of light.

Next, the light-generating device is activated to deliver light of a wavelength that activates the first light-activated protein in the target tissue. This illumination generates an action potential in the target tissue that propagates through nerve cells in the target tissue. Simultaneously, the light-generating device is activated to deliver light of a wavelength that activates the second light-activated protein to the specific portion of the target tissue in which it is desirable to block or inhibit action potentials. This illumination causes the light-activated proton pump to transport protons through the plasma membrane from inside the cell to the outside of the cell. When the protons are present on or near the external surface of the plasma membrane, the response protein detects the presence of the protons and responds by opening a sodium ion channel. The sodium ion channel allows sodium ions to pass through the plasma membrane from outside the cell to the inside of the cell depolarizing the cell sufficiently to render native voltage-gated sodium channels inactive, a phenomenon known as depolarization block.

Figure 12:
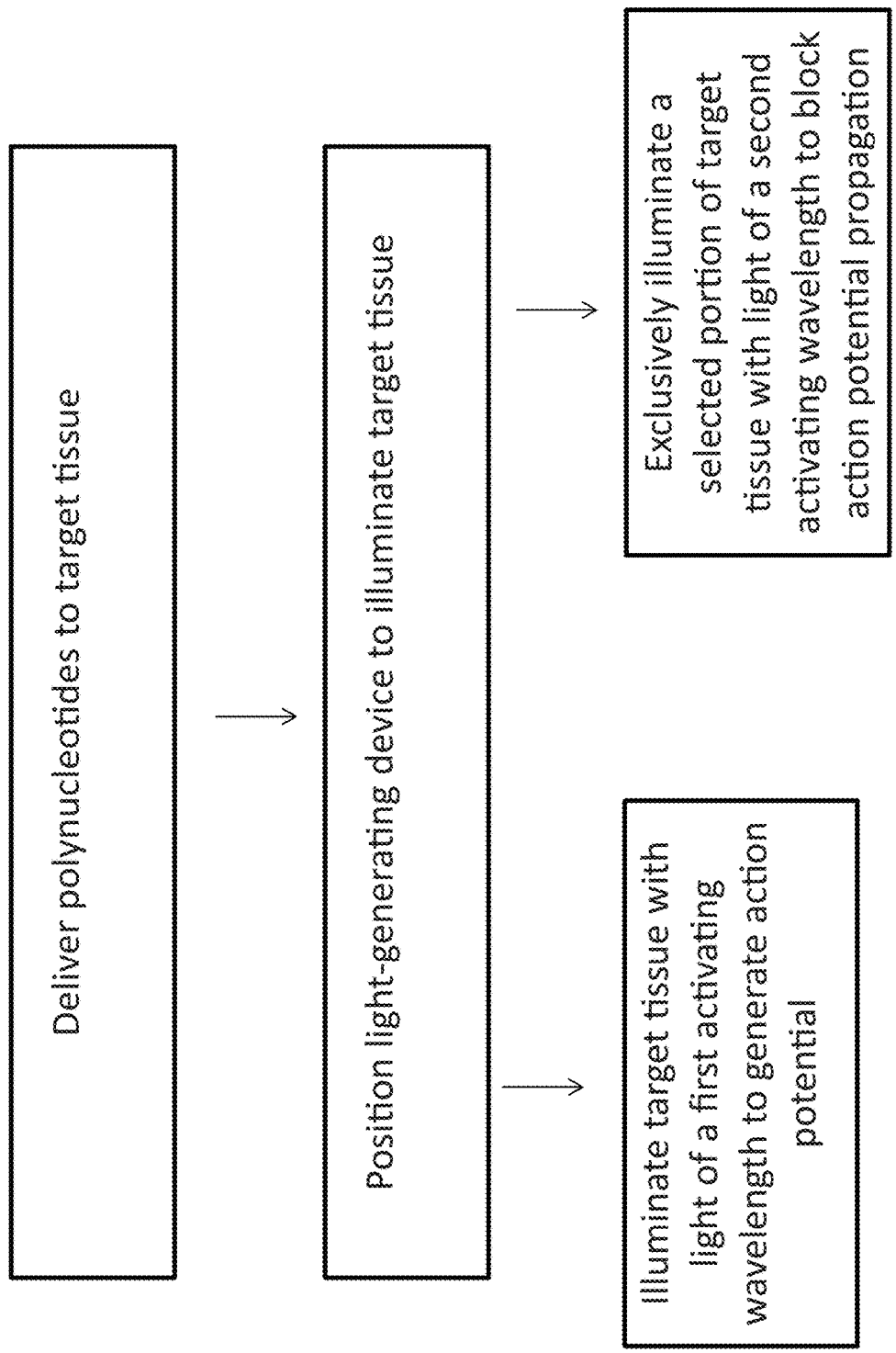
FIG. 12 shows a flow diagram that illustrates the steps of an example method in accordance with embodiments of the present disclosure.

The voltage-dependent inactivation of the VGSCs in the designated portion of the target tissue prevents the VGSCs from generating further action potentials in the nerve cell until the membrane repolarizes, which is facilitated by the cessation of light and decay of the response protein current, and the refractory period ends. As such, the propagation of action potentials along the nerve cell in the specified area is profoundly blocked for the duration of the light pulse, the decay of the response protein current, and the refractory period. Accordingly, the subject methods may be used to control the flow of action potentials through a target tissue by initiating an action potential in a target tissue using light of a first activating wavelength, and simultaneously blocking or inhibiting the propagation of the action potential through a specific portion of the target tissue by inactivating VGSCs in the specific portion of the target tissue. Additionally, since the duration of action blockade outlasts the duration of the light pulse, inhibition of action potentials may be achieved using pulsed light delivery, rather than continuous light delivery. In this way, the subject methods provide for directing and controlling the flow of action potentials through a target tissue using the subject systems and devices. FIG. 12 provides a flow diagram that illustrates the steps of an example of the subject methods.

Kits

Also provided are kits that at least include the subject systems and devices or components thereof, e.g., as described above, and instructions for how to use the subject systems and/or devices to optogenetically modulate action potentials in a target tissue. In some embodiments, a kit may include one or more of the subject polynucleotides, vectors, or pharmaceutical compositions. Kits in accordance with embodiments of the present disclosure may also include one or more devices, such as one or more delivery devices, one or more light-generating device, and/or one or more control devices.

The instructions for using the systems and devices as discussed above are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or sub-packaging) etc. In other embodiments, the instructions are present as an electronic storage data file present on a suitable computer-readable storage medium, e.g., a digital storage medium, e.g., a CD-ROM, diskette, etc. The instructions may take any form, including complete instructions for how to use the systems and devices or as a website address with which instructions posted on the Internet may be accessed.

EXAMPLES

Example 1

Inhibition of Action Potentials Using eArch3.0 and ASIC2a in a Nerve Cell

A nerve cell was transfected with a polynucleotide that encodes a light-activated proton pump protein (eArch3.0) and an acid sensing sodium ion channel response protein (ASIC2a). The proteins were expressed in the nerve cell and were present in the plasma membrane of the nerve cell. A pulse of 560 nm light activated eArch3.0, causing a fast outward proton current, resulting in early hyperpolarization of the plasma membrane. The extracellular protons then activated an inward cation current carried by ASIC2a resulting in sustained membrane depolarization and subsequent inactivation of native voltage-gated sodium channels, causing depolarization block and suppression of evoked spiking. Results are shown in FIG. 1.

Example 2

Strong Inhibition of Action Potentials Using ASIC2a

Figure 2:
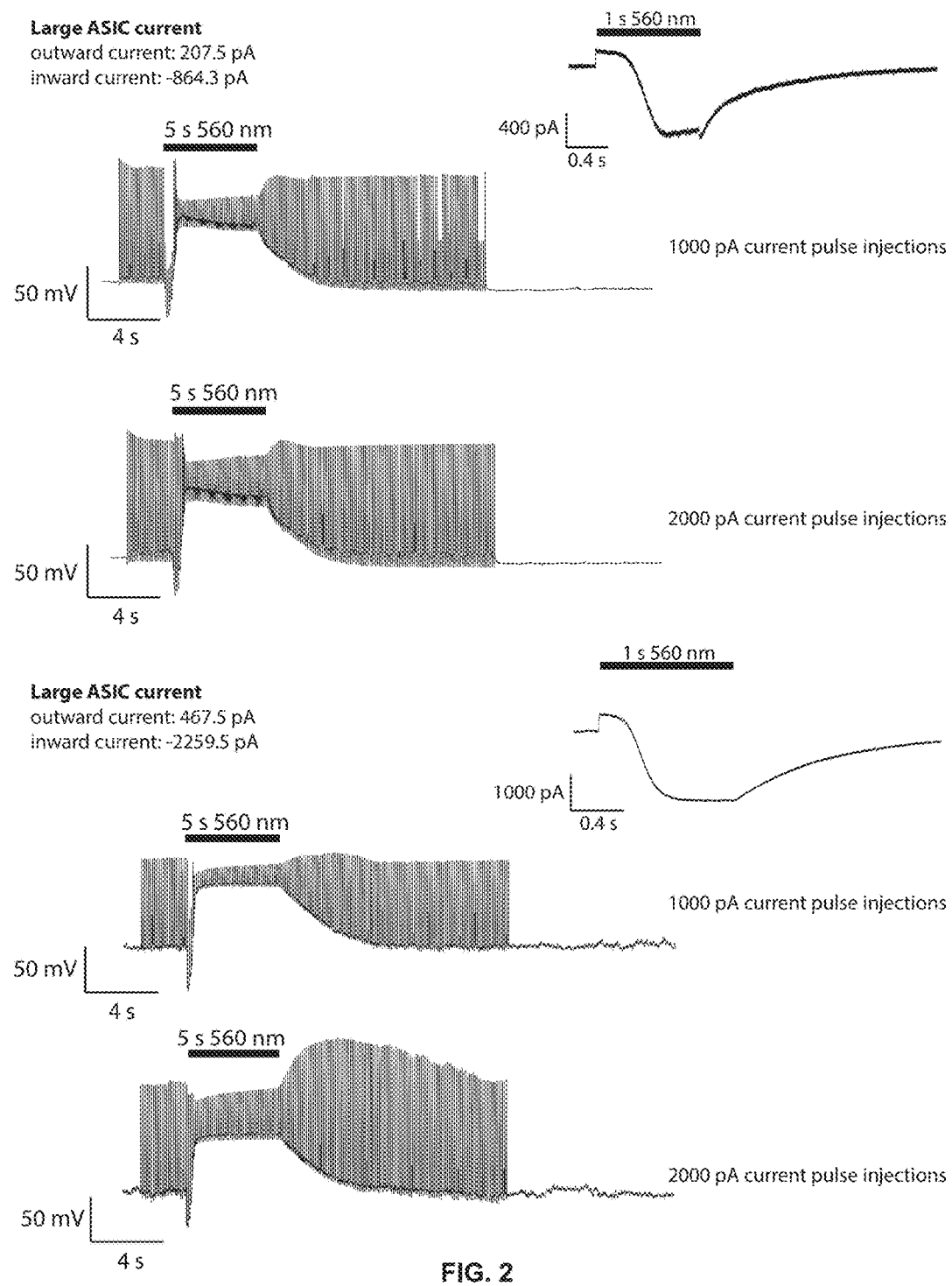
FIG. 2 shows several graphs that depict the influence of light on evoked action potential firing when ASIC2a currents are large. The graphs show examples of membrane voltage of an eArch-ASIC2a expressing nerve cell as a function of time when the nerve cell is illuminated with light of the indicated wavelength, during electrically-evoked action potential spiking

A hippocampal cultured neuron was transfected with a polynucleotide that encodes an acid sensing sodium ion channel response protein (ASIC2a). The protein was expressed in the nerve cell and was present in the plasma membrane of the nerve cell. A 1000 pA current was injected into the cell at 10 Hz, and whole cell patch clamp recordings were collected. In response to the 1000 pA current pulse injections, the outward current component inhibited spiking. During 2000 pA current pulse injections, however, only the depolarization block caused by the ASIC component was sufficient to inhibit spiking. The results are shown in FIG. 2. Insets show the voltage-clamp trace of each cell in response to a 1 second green light pulse.

Example 3

ASIC2a-mediated Inhibition of Action Potentials

A nerve cell was transfected with a polynucleotide that encodes a light-activated proton pump protein (eArch3.0) and an acid sensing sodium ion channel response protein (ASIC2a). The proteins were expressed in the nerve cell and were present in the plasma membrane of the nerve cell.

Figure 3:
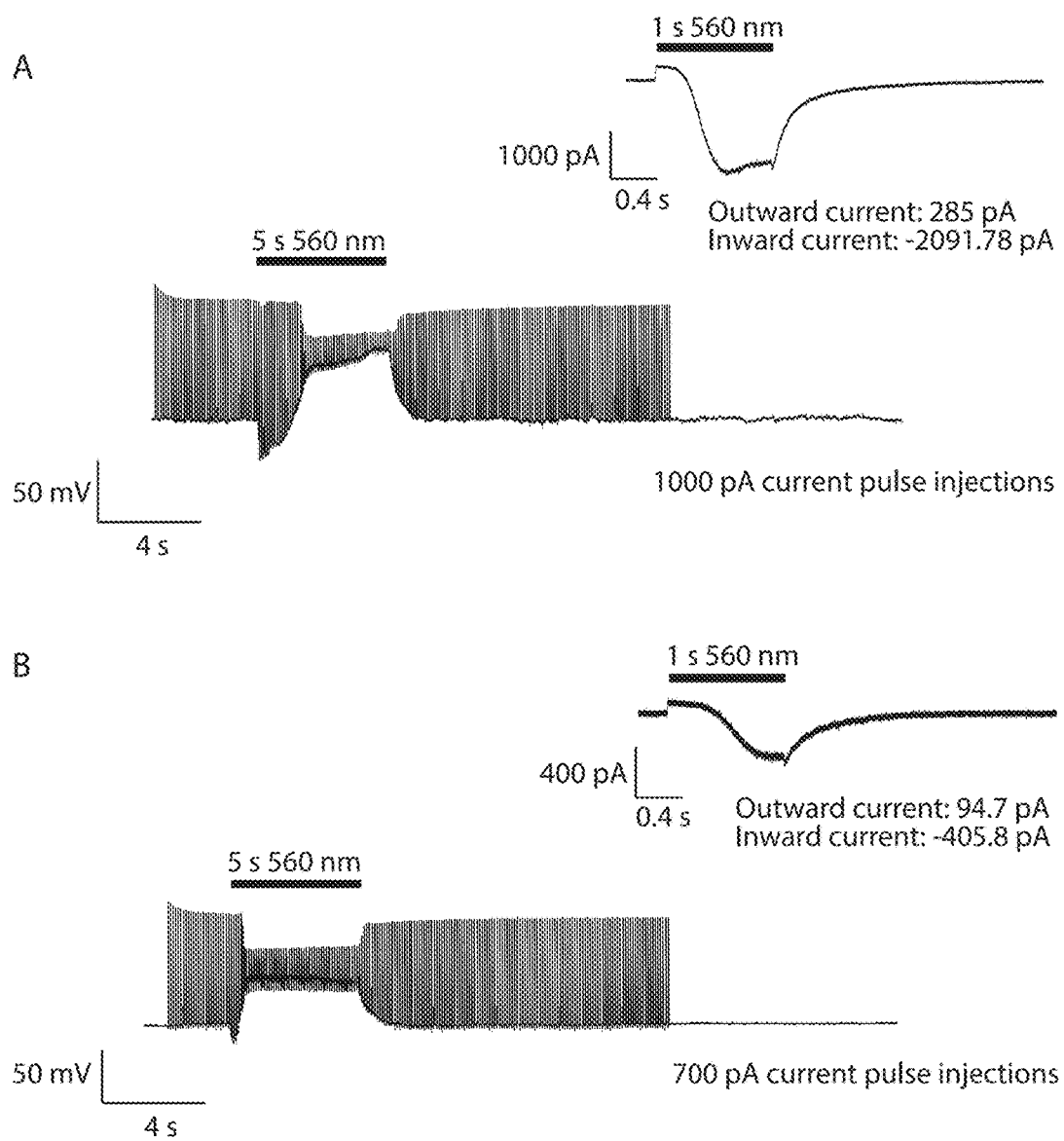
FIG. 3 shows several graphs that depict the influence of light on evoked action potential firing when ASIC2a currents are large. The graphs show examples of membrane voltage of an eArch-eASIC2a-expressing nerve cell as a function of time when the nerve cell is illuminated with light of the indicated wavelength, during electrically-evoked action potential spiking.

Spikes were evoked at baseline using suprathreshold (high reliability spiking) current pulse injections at 10 Hz. When light was applied, the eArch3.0-mediated hyperpolarization was insufficient to inhibit spiking, whereas the ASIC2a-mediated depolarization strongly suppressed spiking throughout the remainder of the light pulse, due to depolarization block. The insets to the right show the voltage-clamp response of the same neurons to a 1 second pulse of 560 nm light, with the amplitude of outward and inward currents provided. Results are shown in FIG. 3.

Example 4

Weak ASIC2a-mediated Inhibition of Action Potentials

Figure 4:
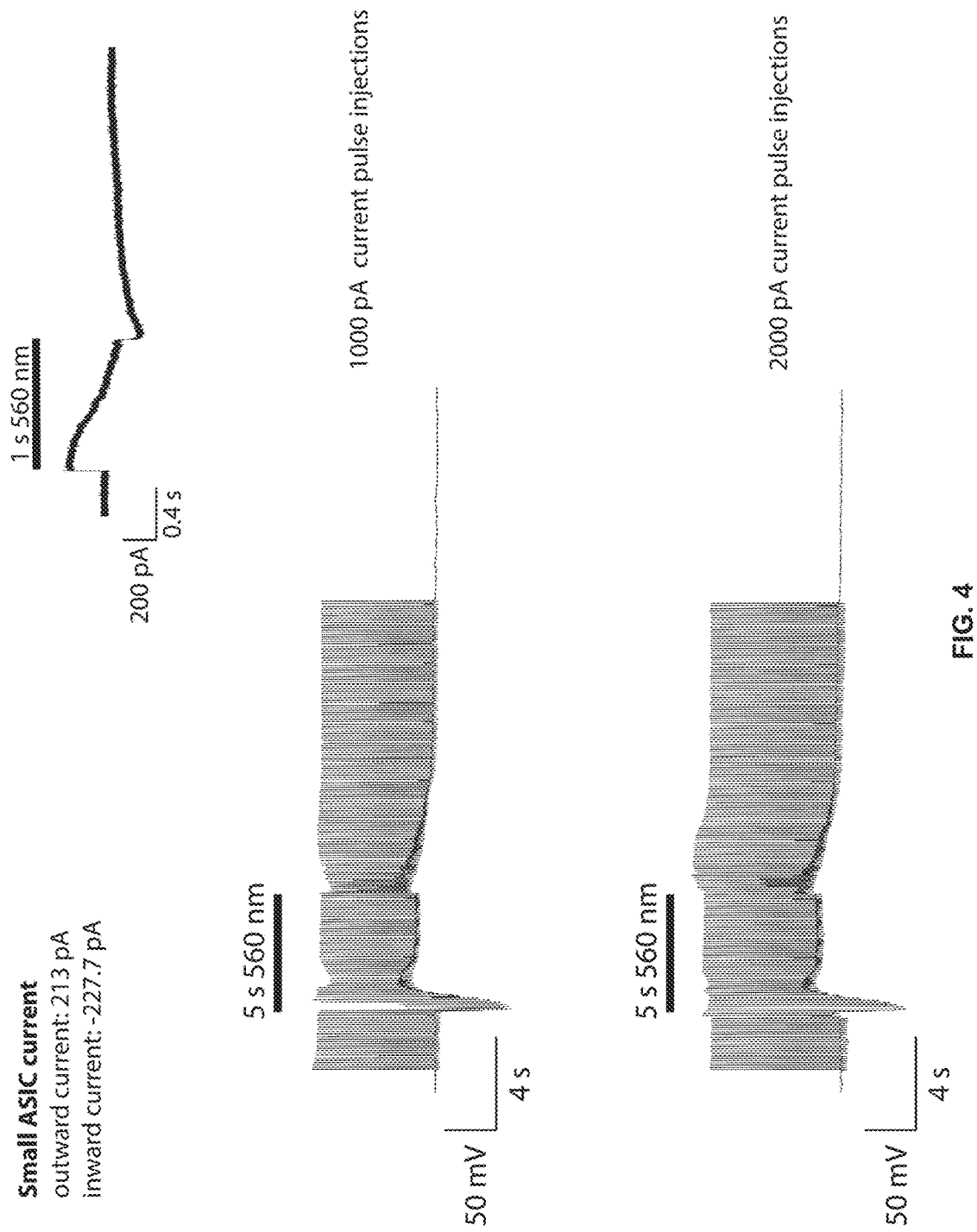
FIG. 4 shows several graphs that depict the influence of light on evoked action potential firing when the ASIC2a current in small. The graphs show examples of membrane voltage of an eArch-eASIC2a-expressing nerve cell as a function of time when the nerve cell is illuminated with light of the indicated wavelength, during electrically-evoked action potential spiking.

A nerve cell was transfected with a polynucleotide that encodes a light-activated proton pump protein (eArch3.0) and an acid sensing sodium ion channel response protein (ASIC2a). The proteins were expressed in the nerve cell and were present in the plasma membrane of the nerve cell. In this example, the inward:outward current ratio was small ($\approx 1$), therefore the depolarization caused by the ASIC component was insufficient to cause depolarization block and overcome the evoked spiking. Results are shown in FIG. 4.

Example 5

Volumetric Modulation of Excitability by Extracellular Protons

In this example, it is described how extracellular ions, in particular protons, can influence local neural activity in non-cell-autonomous fashion through activation of acid-sensitive membrane proteins. An approach for manipulating cellular function, which couples light-sensitive proton pumps to acid-sensitive ion channels, permitting longer lasting, ion-specific regulation of transmembrane currents with many possible permutations for flexible neural control, is described.

Methods

Bystander Experiments

All experiments were conducted under protocols approved by the Stanford Administrative Panel on Laboratory Animal Care.

Stereotactic injections: For expression of ChR2(H134R), eArch3.0 or eNpHR3.0 in CamKII-positive neurons, adeno-associated virus (AAV) serotype 2/5 was produced by the University of North Carolina Chapel Hill Vector Core at a genomic titer of ~4-16×10$^{12}$ pfu mL$^{-1}$. 1 µL of virus was stereotactically injected at two sites unilaterally into the CA1 region of the hippocampus of 3-4 week-old mice. Coordinates for all animals at injection site #1 were −2.2 anteroposterior, 1.5 mediolateral (left side) and −1.3 dorsoventral (in mm from bregma) and for injection site #2 were −1.7 anteroposterior, 1.25 mediolateral (left side) and −1.5 dorsoventral (in mm from bregma). For cortical bystander experiments, Thy1::ChR2 (line 18) mice (Arenkiel et al, 2007) were used (bred in-house).

Acute slice electrophysiology recordings: Acute brain slices were prepared from mice at 4-8 weeks post virus injection, or at 4 weeks of age for transgenic mice. After lethal anesthesia, transcardial perfusion was performed prior to decapitation, followed by rapid brain extraction and submersion of the brain in ice-cold sucrose-based slicing solution (234 mM sucrose, 11 mM glucose, 10 mM MgSO$_4$.7H$_2$O, 2.5 KCl, 1.25 mM NaH$_2$PO$_4$.H$_2$O, 0.5 mM CaCl$_2$.2H$_2$O). 300 µm thick slices of hippocampus were cut on a Leica vibratome (Leica VT1000S). After cutting, slices were submerged in a hypertonic recovery solution (artificial cerebrospinal fluid (ACSF) at an 8% increased concentration) at 33° C. for 15 mins before being transferred to standard ACSF (123 mM NaCl, 26 mM NaHCO$_3$, 11 mM glucose, 3 mM KCl, 2 mM CaCl$_2$.2H$_2$O, 1.25 mM NaH$_2$PO$_4$.H$_2$O, 1 mM MgCl$_2$.6H$_2$O) for a further 45 mins at 33° C., at which point they were transferred to room temperature.

Whole cell patch clamp recordings on cortical and hippocampus neurons were performed on an upright Leica DM-LFSA microscope. Slices were continually perfused in warmed (33° C.) ACSF at a rate of 7 ml min$^{-1}$ Patching was performed in the presence of synaptic transmission blockers 6-cyano-7-nitroquinoxaline-2,3-dione (CNQX, 50 µM) and D(−)-2-amino-5-phosphonovaleric acid (APV, 25 µM) and gabazine (25 µM) (Tocris Bioscience) except for during testing of electrically-evoked synaptic responses. For amiloride experiments, amiloride was added to the ACSF at a concentration of 500 µM (Tocris). Borosilicate glass (Sutter Instruments) pipette resistances were pulled to 3-6 MΩ and filled with potassium gluconate intracellular solution (130 mM K Gluconate, 10 mM KCl, 10 mM HEPES, 10 mM EGTA, 2 mM MgCl$_2$, pH adjusted with KOH to 7.3). Voltage and current clamp electrophysiological recordings and manipulations were performed using pClamp (Axon Instruments). Cells were held at −70 mV for all experiments. Cells with leak current greater than −300 pA or pipette resistance greater than 30 MΩ were excluded. Light (full-field illumination) was emitted from a 300 W DG-4 lamp (Sutter Instruments, Novato, Calif., USA) fitted with a Lambda 10-3 filter wheel (Sutter Instruments) with a 10-position wheel for filters of different wavelengths, or external filters (wavelength in nm/bandwidth in nm: 470/20; 560/25; 590/20). Light pulses were delivered through a 40×, 0.8 NA water-immersion objective at 4-7 mW/mm$^2$ light power density. Extracellular electrical stimulation was performed using a concentric bipolar electrode of platinum iridium (FHC, Bowdoin, Me., USA) or tungsten (World Precision Instruments, Sarasota, Fla. USA). Electrical pulses were delivered using a stimulus isolator (ISO-Flex, A.M.P.I) controlled by pClamp to deliver 200 µs square pulses at intensities ranging from 500 µA-2.5 mA and frequencies of 5-10 Hz.

Immunohistochemistry: For identification of bystanders in slice preparations, 0.3% biocytin was added to the intracellular pipette solution and following recording slices were fixed in 4% paraformaldehyde perfusion fix solution (Electron Microscopy Services, Hatfield, Pa., USA) for 24 hours then transferred to 1× phosphate buffered saline (Gibco, Life Technologies). Biocytin was stained with fluorescent streptavidin (Alexa Fluor 546 conjugate, Invitrogen, over 3 hours. For YFP staining, slices were incubated in anti-GFP primary antibody (Invitrogen, 1:500 dilution) for 24 hours. Cy5 secondary antibody (Jackson Laboratories, West Grove, Pa., 1:500 dilution) was applied in 2% NDS for 1 hour at room temperature for 3 hours followed by DAPI (1:50,000) for 30 mins, then mounted, and coverslipped with PVA-DABCO (Sigma). Images were obtained on a Leica confocal microscope (DM600B) at 1024×1024 pixel resolution using 5× and 10× dry objectives and 20×, 40× and 63× oil objectives.

Data analysis: Analysis of all of physiological results was performed using Clampfit software (Axon Instruments). Pipette (access) resistance ($R_a$) and membrane resistance ($R_m$) were monitored at 5 minute intervals to ensure stability of the recording and data was only included when leak current was less than 300 pA and $R_a$ less than 30 MΩ with less than 25% change in $R_a$ for the duration of periods of drug application and between sequential membrane tests. Reversal potentials were corrected for an estimated liquid junction potential of 14 mV. Statistical analysis was performed using GraphPad Prism 6.0 for Mac OS X. For comparisons between YFP controls and opsin or electrical stimulation groups we performed non-parametric unpaired 2-tailed Mann Whitney tests to compare mean ranks between groups, without assuming a Gaussian distribution. For comparison of the functional impact of light on bystander neuron spiking, we compared successive light-on vs light-off epochs for each opsin, using a non-parametric, paired Wilcoxin signed rank test, again without assuming a Gaussian distribution. Significance thresholds were set at $p<0.05$ (*), $p<0.01$ (), $p<0.001$ (*) and $p<0.0001$ (****).

Two-component optogenetics experiments. Construct design and expression in *Xenopus laevis* oocytes: The coding sequences for rat ASICs (in pRSSP6009) were provided by Stefan Grander (Aachen). The pRSSP6009 plasmid coding for ASICs and the pGEM plasmid coding for *Coccomyxa subellipsoidea* C-169 Rhodopsin $CsR_{T46N}$ were linearized by MulI site in pRSSP 6009 and by NheI in pGEM. After transcription into RNA using T7 (pGEM) or SP6 (pRSSP6009) mMessage mMachine Kit (Ambion Inc, Texas, USA) 32 ng of capped RNA encoding CsR pump and one type of ASIC were co-injected into *Xenopus leavis* oocytes with a molar ratio of 1:1 pump:channel for ASIC1 and ASIC2a and a molar ratio of 1:2 for ASIC3. Oocytes were incubated for 3 days at 18° C. in ORI solution with 1 µM all-trans retinal (Tsunoda & Hegemann, 2009).

Two-electrode voltage clamp measurements: TEVC measurements on *X. laevis* oocytes were performed using a GeneClamp 500 amplifier (Axon Instruments, Union City). Data acquisition, buffer exchange and light triggering were controlled with pClamp software via a Digidata 1322A interface (Molecular Devices, Sunnyvale). The light supplied by a 75 W Xenon lamp (Jena-Instruments, Jena, Germany) was passed through a K55 filter (Balzers, Liechtenstein) and applied to the oocytes using a light guide (diameter of 2 mm) The light intensity was $8.5 \times 10^{20}$ photons $s^{-1}$ $m^{-2}$ at the surface of the oocyte. The bulk buffer (chamber volume 300 µl) was continuously perfused at a flow rate of 1.8±0.2 ml $min^{-1}$. Data was acquired at 1 kHz and filtered at 0.5 kHz. If not otherwise specified the extracellular buffer was composed of 100 mM NaCl, 1 mM KCl, 1 mM $MgCl_2$, 0.1 mM $CaCl_2$ and 0.1 to 5 mM MOPS at pH 7.5. For pH titration, buffer solutions were adjusted with 5 mM MOPS/MES/Citrate over the range of pH 8.0 to 4.0, and were subsequently compared with photocurrents measured at 0.1 mM MOPS at pH 7.5

Construct design for hippocampal neurons: The protein sequence of rat ASIC2a (Genbank accession number NM_001034014.1) was human codon optimized and synthesized by Genscript. eArch3.0 and ASIC-YFP fusions were cloned into an AAV2 backbone either under a CaMKIIα or human synapsin promoter. The trafficking signal (TS) and endoplasmic reticulum export signal (ER) sequences were appropriately added to enhance membrane trafficking. All maps and sequence details are on the website: www(dot)optogenetics(dot)org.

Hippocampal neuron culture and calcium phosphate transfection (as per Mattis et al. (Nat Methods 2011; 9: 159-72)). Primary cultured hippocampal neurons were prepared from PO Sprague-Dawley rat pups (Charles River). CA1 and CA3 were isolated, digested with 0.4 mg $ml^{-1}$ papain (Worthington), and plated onto glass coverslips pre-coated with 1:30 Matrigel (Becton Dickinson Labware). Cultures were maintained in a 5% $CO_2$ humid incubator with Neurobasal-A medium (Invitrogen) containing 1.25% FBS (HyClone), 4% B-27 supplement (Gibco), 2 mM Glutamax (Gibco) and 2 mg $ml^{-1}$ fluorodeoxyuridine (FUDR) (Sigma), and grown on coverslips in a 24-well plate at a density of 65,000 cells per well. For each well, a DNA-$CaCl_2$ mix was prepared with 2 µg DNA (Qiagen endotoxin-free preparation) and 1.875 µl 2 M $CaCl_2$ (final $Ca^{2+}$ concentration 250 mM) in 15 µl $H_2O$. To DNA-$CaCl_2$ was added 15 µl of 2× HEPES-buffered saline (pH 7.05). After 20 min at room temperature (20-22° C.), the mix was added dropwise into each well (from which the growth medium had been removed and replaced with pre-warmed minimal essential medium (MEM)) and transfection proceeded for 45-60 min at 37° C., after which each well was washed with 3×1 ml warm MEM before the original growth medium was returned.

Electrophysiological recordings in cultured hippocampal neurons: Whole cell patch clamp recordings were performed on cultured hippocampal neurons 4-8 days post-transfection on an upright Leica DM-LFSA microscope (Mattis et al, 2011). Cells were continuously perfused in standard extracellular Tyrode's solution (NaCl: 125 mM, KCl 2 mM, $CaCl_2$ 2 mM, $MgCl_2$ 2 mM, glucose 30 mM, HEPES 25 mM, titrated to pH 7.3-7.4 with NaOH, 320 mOsm) or in low HEPES Tyrode's solution (NaCl: 125 mM, KCl 2 mM, $CaCl_2$ 2 mM, $MgCl_2$ 2 mM, glucose 55 mM, HEPES 0.1 mM, titrated to pH 7.3-7.4, 320 mOsm) at a rate of 1-2 ml $min^{-1}$, in the presence of synaptic transmission blockers 6-cyano-7-nitroquinoxaline-2,3-dione (CNQX), D(−)-2-amino-5-phosphonovaleric acid (APV) and gabazine (25 µM; Tocris Bioscience). Patch pipette borosilicate glass electrodes (Sutter Instruments) with tip resistance of 3-6 MΩ were filled with a potassium gluconate intracellular solution (K-gluconate 130 mM, KCl 10 mM, HEPES 10 mM, EGTA 10 mM, $MgCl_2$ 2 mM, titrated to pH 7.3 with KOH, 300 mOsm). Data acquisition, current and light manipulations were controlled using pClamp (Axon Instruments) via a Digidata 1440A interface and analyzed using ClampFit software (Axon Instruments). Cells were held at −70 mV for all voltage-clamp experiments. Resting membrane potentials were corrected for an estimated liquid junction potential of 16 mV. Full-field illumination for activation of optogenetic tools was delivered by a 300 W DG-4 lamp (Sutter instruments) via a 40×, 0.8 numerical aperture (NA) water-immersion objective. The light was first passed through a 560/25 nm filter within a Lambda 10-3 filter wheel (Sutter Instruments). Light power density was ~5 $mWmm^{-2}$ for all experiments. All experiments were performed at room temperature (24-25° C.).

Confocal images of cultured neurons: Confocal images were obtained by staining glass coverslips of transfected neurons with DAPI (1:50,000) which were then imaged using a Leica confocal microscope (DM600B) as 1,025×1, 024 pixel resolution, at 40× magnification, 1.25 NA (oil). Excitation/emission wavelengths for eYFP were 488 nm/500-545 nm.

Results

Electrophysiological Characterization of the Bystander Effect

Figure 15A:
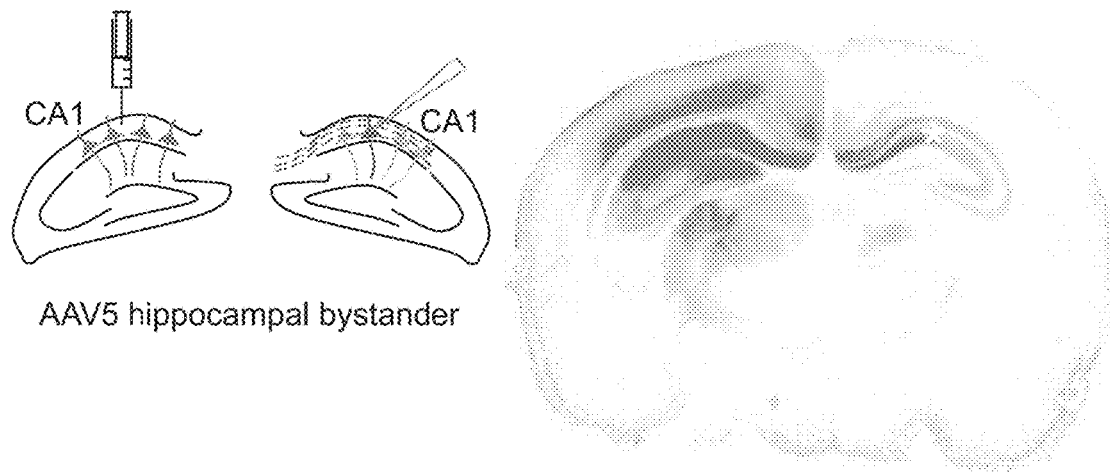
FIGS. 15A-L depicts the identification and delineation of the bystander effect.
Figure 15B:
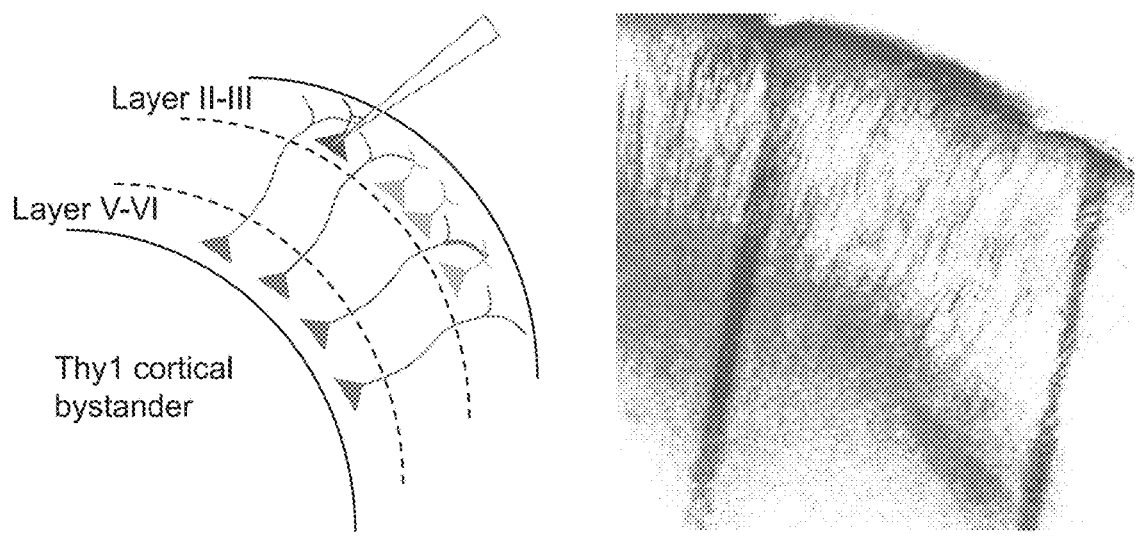
Figure 15C:
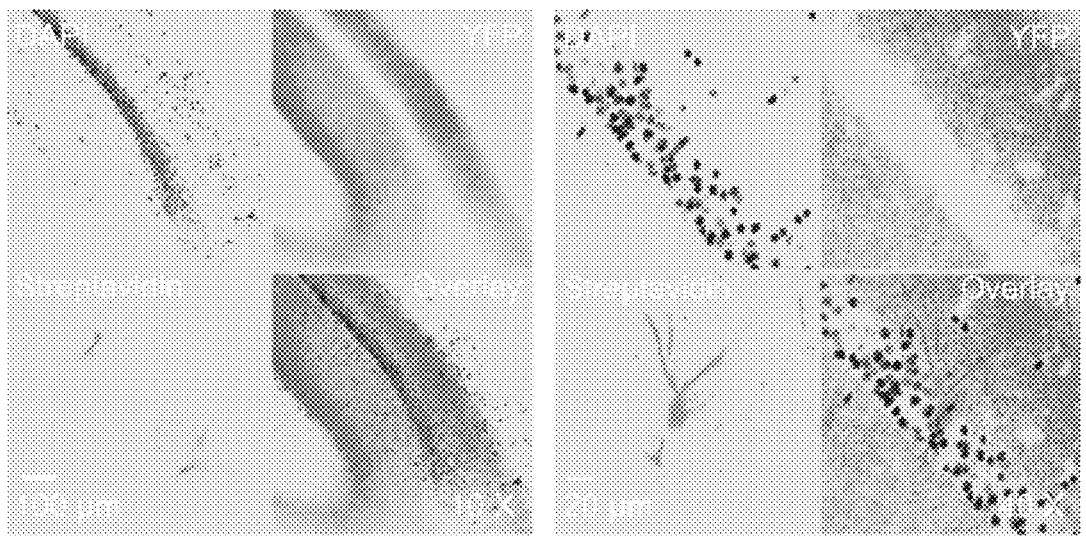
Figure 15D:
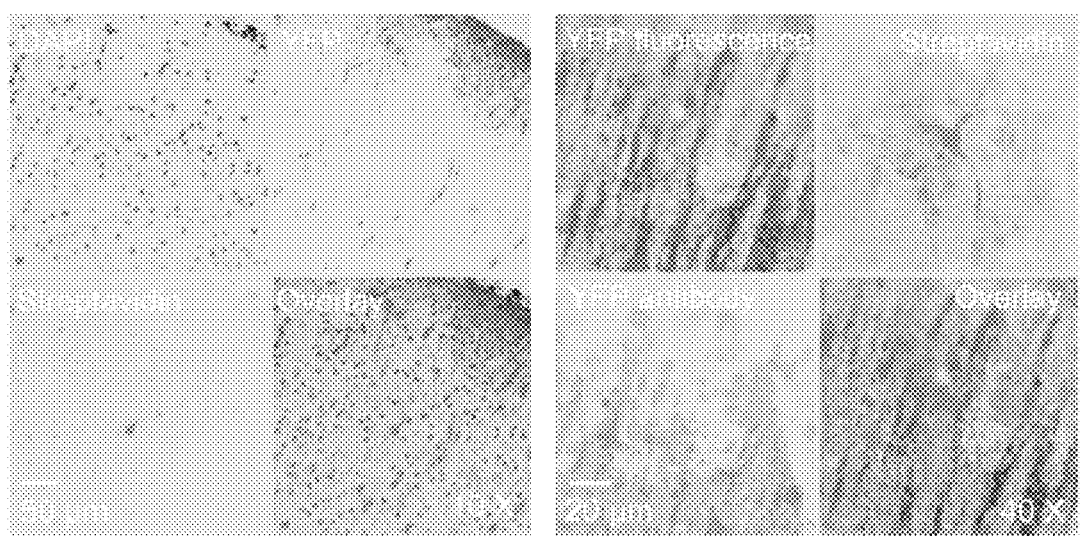

The existence of "bystander neurons", defined here as neurons indirectly exposed to, but not direct expressors of, optogenetically-mediated changes in neural activity was tested. Two optogenetic targeting strategies were employed:

first, an optogenetic construct containing one of CHR2 (H134R), eArch3.0, eNpHR3.0 or a YFP control, driven by the calmodulin kinase IIα promoter (AAV5-CamKII-(opsin)-eYFP), was injected unilaterally in the CA1 region of hippocampus. Due to the contralateral axonal projections of these neurons, one could then record from non-expressing neurons (bystander neurons) surrounded by opsin-expressing axons in the contralateral CA1 . (FIGS. 15A and 15C). Bystander responses to the depolarizing opsin CHR2 (H134R) (from now on referred to as ChR2), two hyperpolarizing opsins (enhanced for membrane targeted expression)—the proton pump archeorhodopsin (eArch3.0) and the chloride pump halorhodopsin (eNpHR3.0), and a YFP-control were compared in the hippocampal preparation, under matched experimental conditions. A second category of bystander neuron was identified using the transgenic mouse strain Thy1-ChR2 (line 18), where ChR2 is expressed in layer V cortical neurons and bystander neurons are located in superficial cortical layers, where they are surrounded by ChR2-expressing membrane processes but not expressing ChR2 themselves (FIGS. 15B and 15D).

Figure 15E:
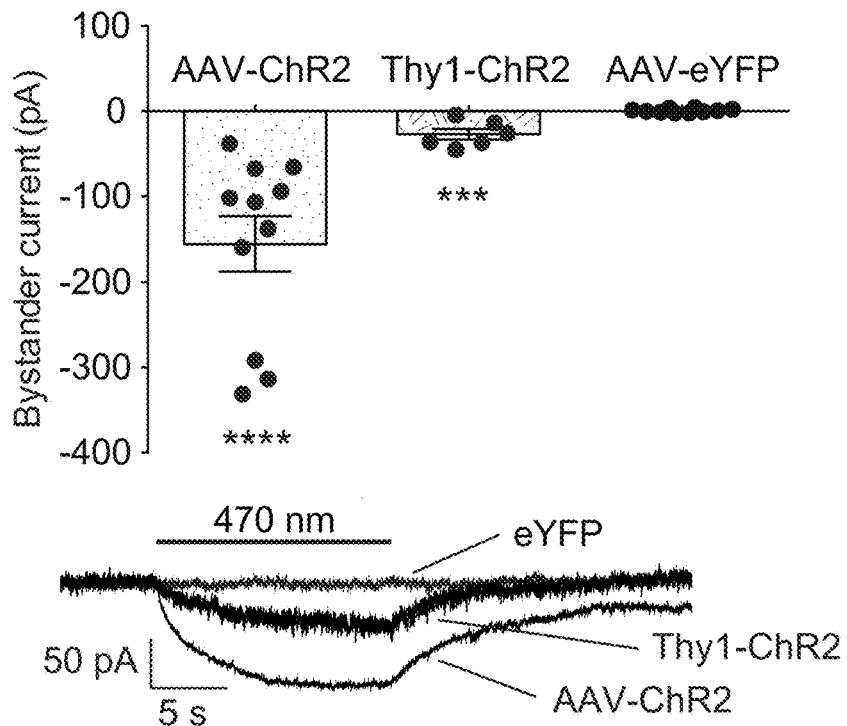
Figure 15F:
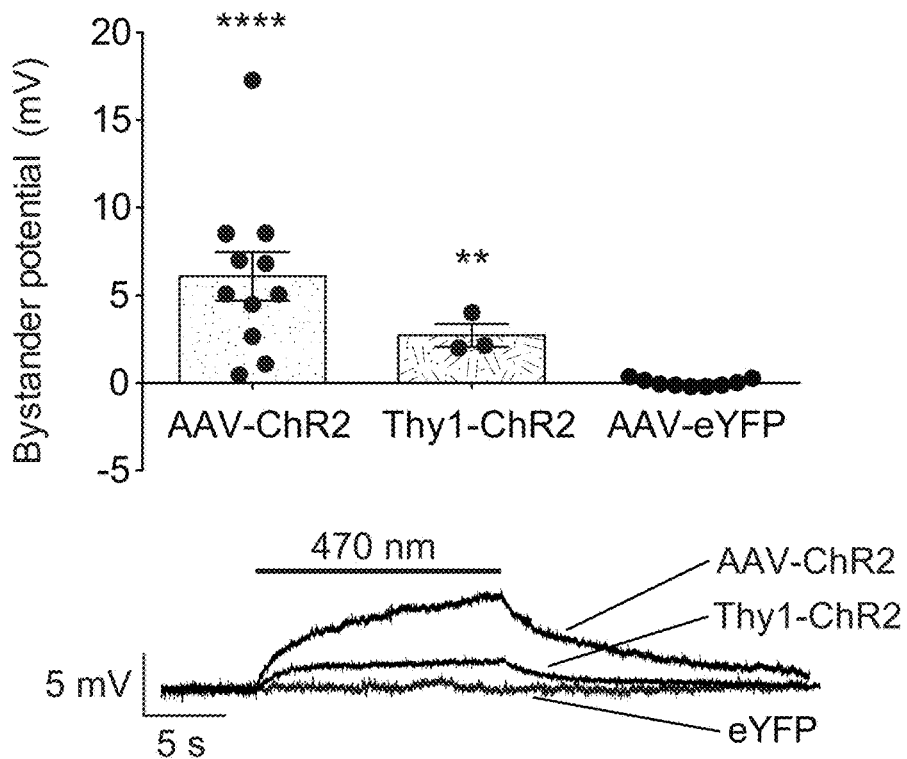
Figure 15G:
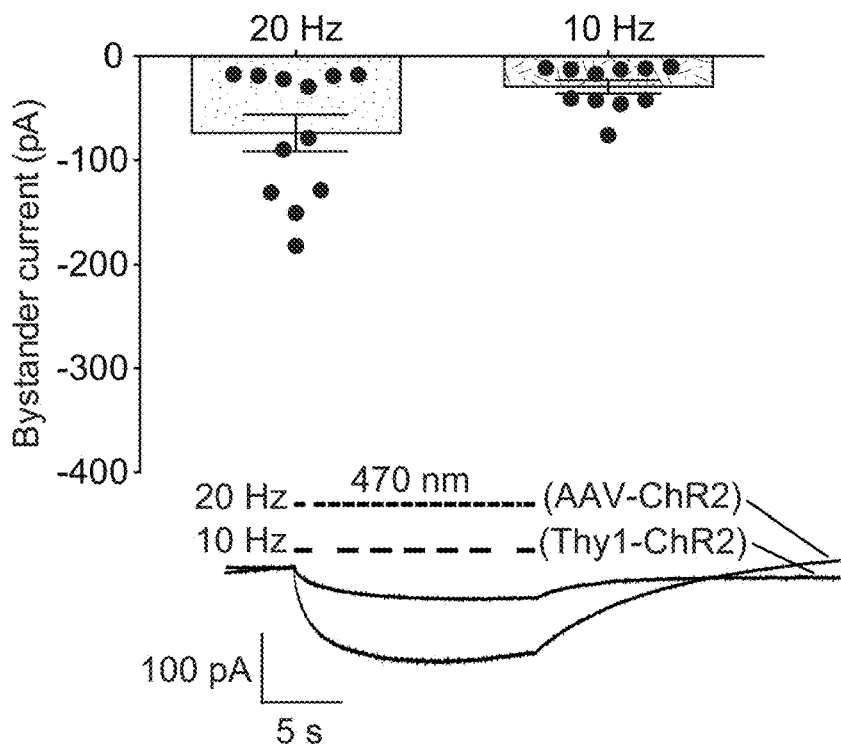
Figure 15H:
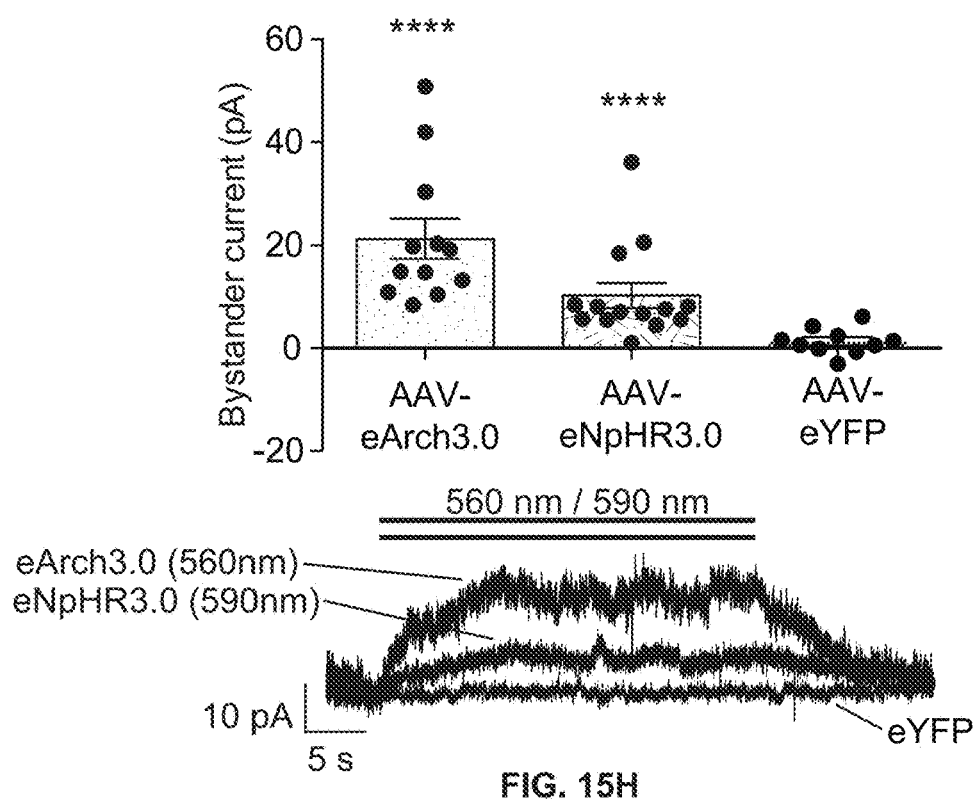
Figure 15I:
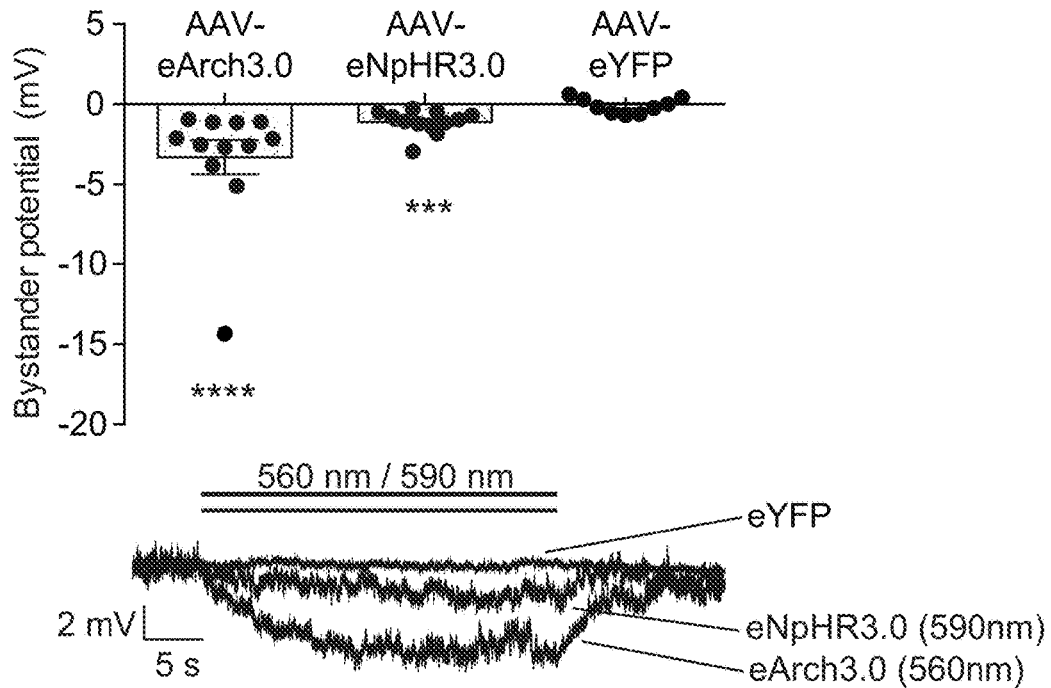
Figure 15J:
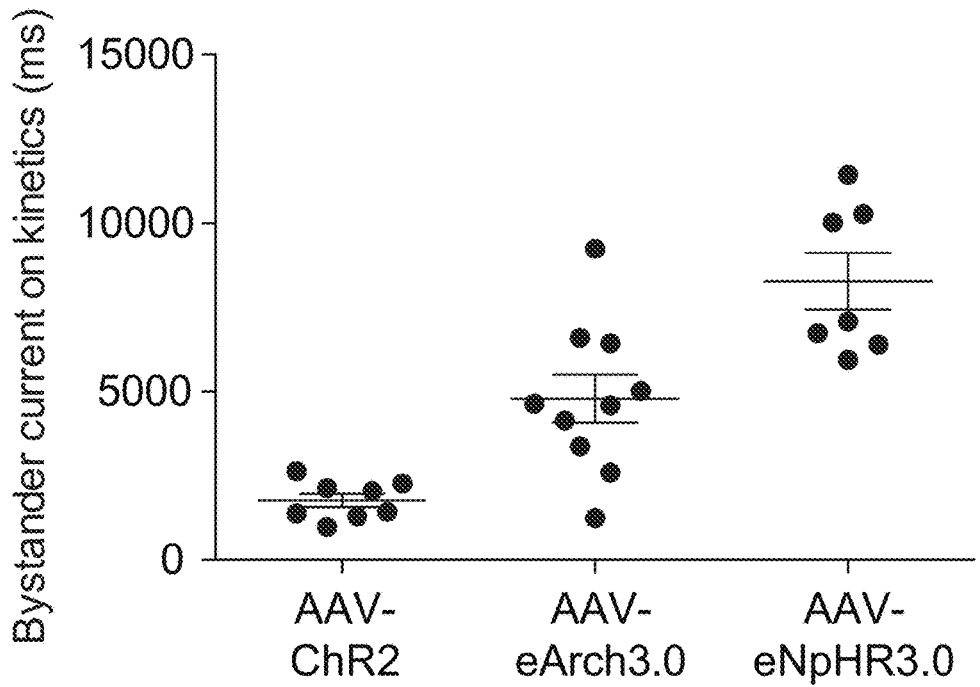
Figure 16:
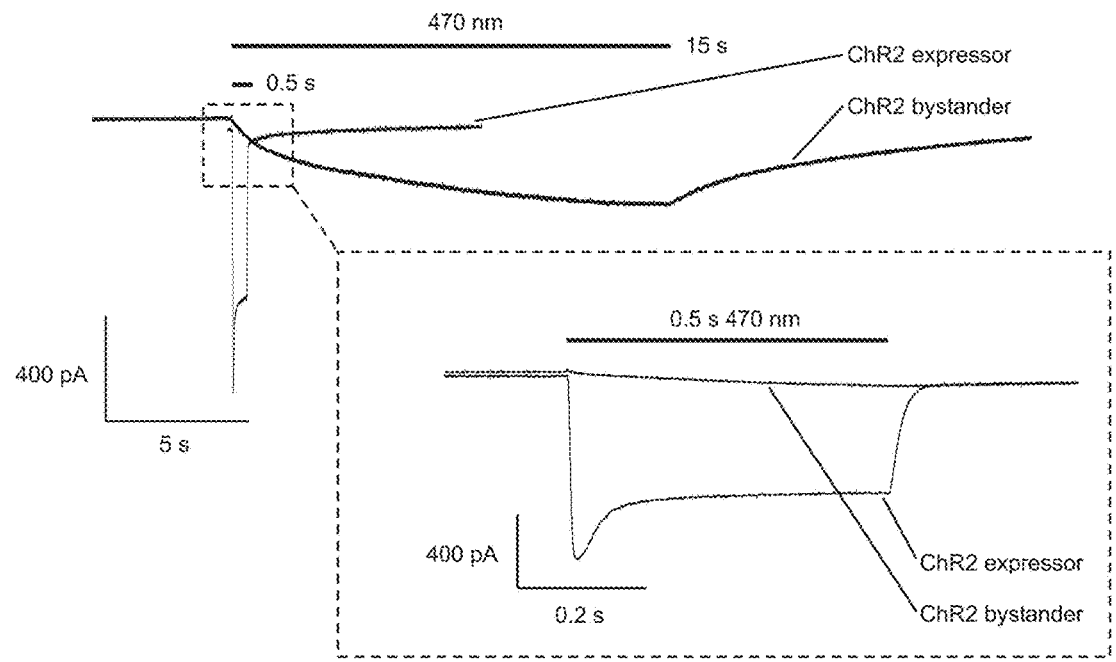
FIG. 16 depicts traces illustrating the difference in on-kinetics between a ChR2 expressing-cell photocurrent and a ChR2 bystander current (dashed box shows a zoom-in of the first 0.5 s of both traces).

Whole cell recordings from bystander neurons in the presence of ionotropic synaptic transmission blockers were performed in acute brain slices. In response to a 15 s blue light pulse, hippocampal ChR2 bystander neurons exhibited a depolarizing membrane current (mean=−155 pA) (FIG. 15E) with onset-kinetics several orders of magnitude slower (~2 s) than a direct ChR2 photocurrent (FIG. 15J and FIG. 16). Cortical Thy1-ChR2 bystander neurons displayed a smaller inward current (mean=−27 pA) consistent with the smaller direct ChR2 photocurrent magnitude in Thy1-ChR2-expressing neurons (FIG. 17). These inward currents corresponded to a mean membrane depolarization of 6.1 mV for hippocampal ChR2 bystanders and 2.7 mV for cortical Thy1-ChR2 bystanders (FIG. 15F). AAV5-YFP control bystanders did not exhibit a change in membrane current or voltage. Given that pulsed-light paradigms are commonly used for depolarizing optogenetic applications, we examined bystander responses to 20 and 10 Hz light pulse trains, and again observed similar slow inward currents (mean=−73 pA for 20 Hz and −29 pA for 10 Hz) (FIG. 15G).

We next examined the impact of hyperpolarizing optogenetic tools on hippocampal bystander neurons. During a 30 s light pulse, AAV5-eArch3.0 bystanders exhibited a slow (~5 s) hyperpolarizing current (mean=21 pA), several orders of magnitude slower than a direct eArch3.0 photocurrent and AAV5-eNpHR3.0 bystanders exhibited a smaller (mean=10 pA) and even slower (~8 s) hyperpolarizing current (FIGS. 15H and 15J). These outward currents corresponded to a small mean membrane hyperpolarization of −3.3 mV for eArch3.0 and −1.1 mV for eNpHR3.0 whereas no change in membrane current or voltage was observed for AAV5-YFP control bystanders under matched experimental conditions (FIG. 15I).

Figure 15K:
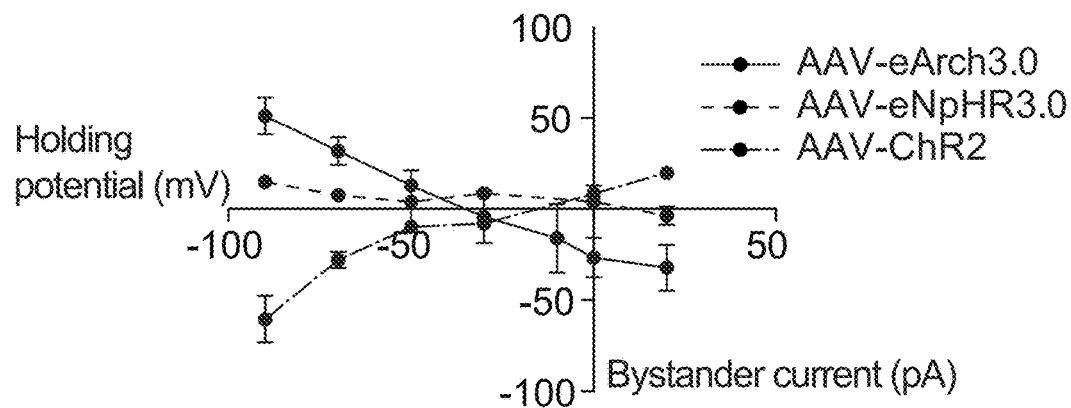
Figure 15L:
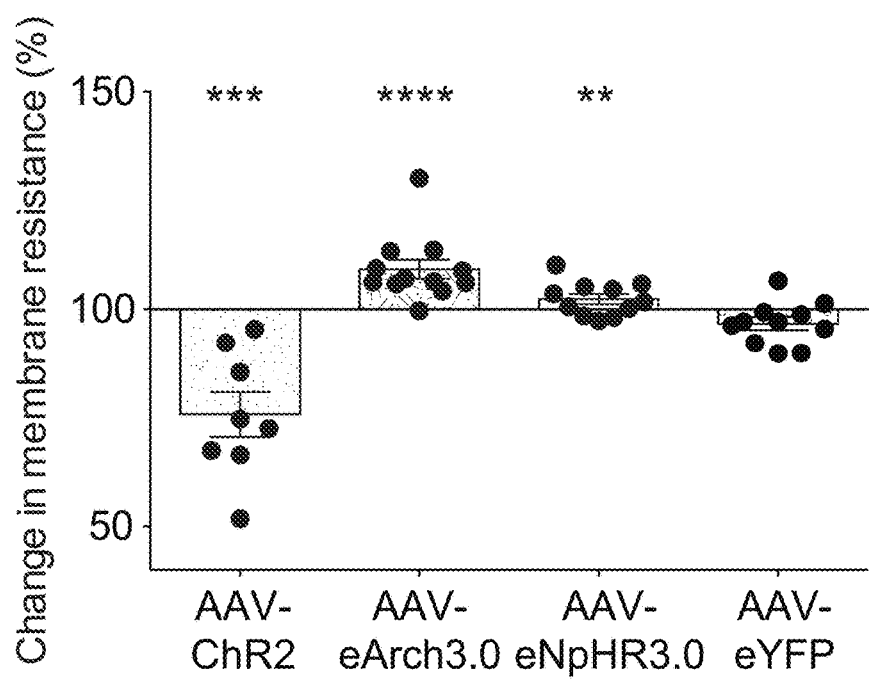

During the application of light, ChR2 bystander neurons experienced a 24% mean decrease in membrane resistance, whereas eArch3.0-bystander neurons experienced a 9% increase in membrane resistance and eNpHR3.0 a 2% increase. YFP controls showed a 3% decrease in membrane resistance (FIG. 15L). Current-voltage relationships demonstrated a significantly positive slope for depolarizing bystanders and significantly negative slope for hyperpolarizing bystanders converging at a reversal potential between −10 to −40 mV (FIG. 15K). Functional and mechanistic investigation of the bystander effect.

FIGS. 15A-L. Identification and delineation of the bystander effect. A Unilateral injection of AAV5-CamKII-(opsin)-eYFP into CA1 of hippocampus yielded non-expressing bystander neurons in the contralateral hippocampus. Confocal image showing YFP expression and location of bystander neurons (star) (5×, scale bar 1 mm). B Cortical bystander neurons in superficial layers of cortex of Thy1-ChR2 (line 18) transgenic mice. Confocal image showing YFP expression and location of bystander neurons (star) (10×, scale bar 100 µm). C Biocytin-filled hippocampal bystander neurons labeled with streptavidin in CA1 (scale bars 100 µm and 20 µm). D Biocytin-filled cortical bystander neuron labeled with streptavidin, surrounded by but not overlapping with YFP fluorescence confirmed by anti-YFP antibody staining (scale bars 50 µm and 20 µm). E Depolarizing bystander currents in response to 15 s 470 nm light pulses for AAV5-ChR2 hippocampal bystanders (mean+/−SEM=−155+/−32 pA, n=11, p<0.0001 compared to YFP), Thy1-ChR2 cortical bystanders (−27+/−6 pA, n=6, p<0.001 compared to AAV5-YFP) and AAV5-YFP controls (0.7+/−0.7 pA, n=10), Example voltage clamp traces shown below summary plot. F Depolarizing bystander potentials for AAV5-ChR2 hippocampal bystanders (6.1+/−1.4 mV, n=11, p<0.0001), Thy1-ChR2 bystanders (2.7+/−0.6 mV, n=3, p<0.01) and AAV5-YFP controls (0.02+/−0.07 mV, n=9). Example current clamp traces shown below summary plot. G Bystander currents in response to 470 nm light pulse trains at 20 Hz (−73+/−18 pA, n=12) and 10 Hz (−29+/−6 pA, n=11). Example voltage clamp traces shown below summary plot. H Hyperpolarizing bystander currents in response to 30 s 560 nm light for AAV5-eArch3.0 (21+/−4 pA, n=12, p<0.0001), 590 nm for AAVS-eNpHR3.0 (10+/−2 pA, n=14, p<0.0001) and AAVS-YFP controls (1.3+/−0.8 pA, n=10, 560 nm light). Example voltage clamp traces shown below summary plot. I Hyperpolarizing bystander potentials for AAVS-eArch3.0 (−3.3+/−1.1 mV, n=12, p<0.0001), AAVS-eNpHR3.0 (−1.1+/−0.2 mV, n=12, p<0.001) and AAV5-YFP controls (−0.1+/−0.2 mV, n=9). Example current clamp traces shown below the summary plot. J Onset kinetics ($\tau_{on}$) for depolarizing (ChR2: 1800+/−200 ms, n=8) and hyperpolarizing (eArch3.0: 4800+/−710 ms n=10, eNpHR3.0: 8300+/−850 ms, n=7) bystanders. K Current-voltage relationships for depolarizing ChR2 bystander currents ($R^2$ for slope (difference from 0)=0.71, p<0.0001)) and hyperpolarizing bystander currents (eArch3.0: $R^2$ for slope=0.43, p<0.0001, eNpHR3.0: $R^2$ for slope=0.26, p=0.0001) (n=5-12). L Change in membrane resistance from baseline in response to 30 s pulse of light for ChR2 (470 nm, 24% decrease in membrane resistance, n=8, p<0.001), eArch3.0 (560 nm, 9% increase in membrane resistance, n=12, p<0.0001) eNpHR3.0 (590 nm, 2% increase in membrane resistance, n=11, p<0.01) and YFP control bystanders (560 nm, 3% decrease in membrane resistance, n=11). All bar charts indicate mean values and error bars represent standard error of the mean (SEM). Individual data points indicate results from single cells. All statistical comparisons are between test (opsin) groups and YFP controls using the Mann Whitney (non-parametric) paired t-test.

FIG. 16: Kinetics of photocurrents and bystanders. Example traces illustrating the difference in on-kinetics between a ChR2 expressing-cell photocurrent and a ChR2 bystander current in response to a 470 nm light pulse (0.5 s and 15 s respectively). Dashed box shows a zoom-in of the first 0.5 s of both traces.

Figure 17A:
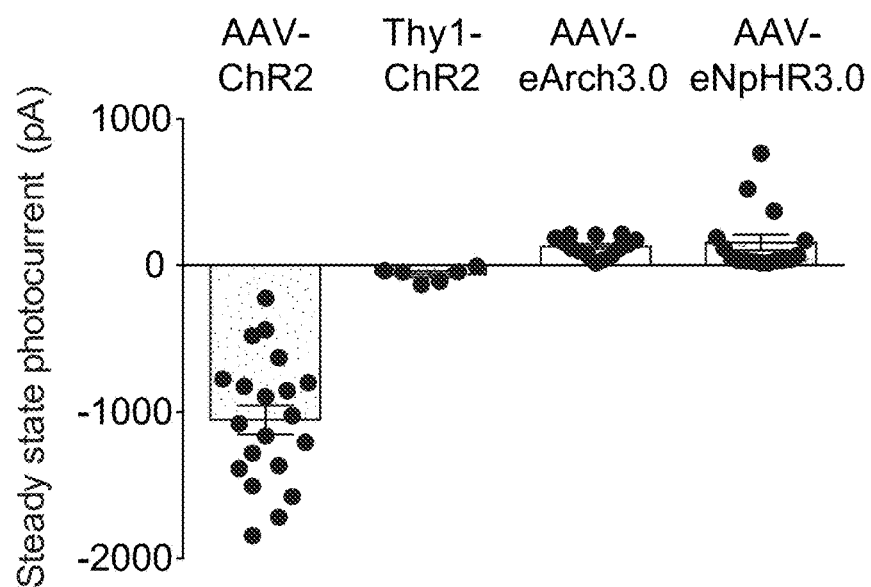
FIGS. 17A-B depict photocurrent magnitudes and traces for opsin-expressing neurons.
Figure 17B:
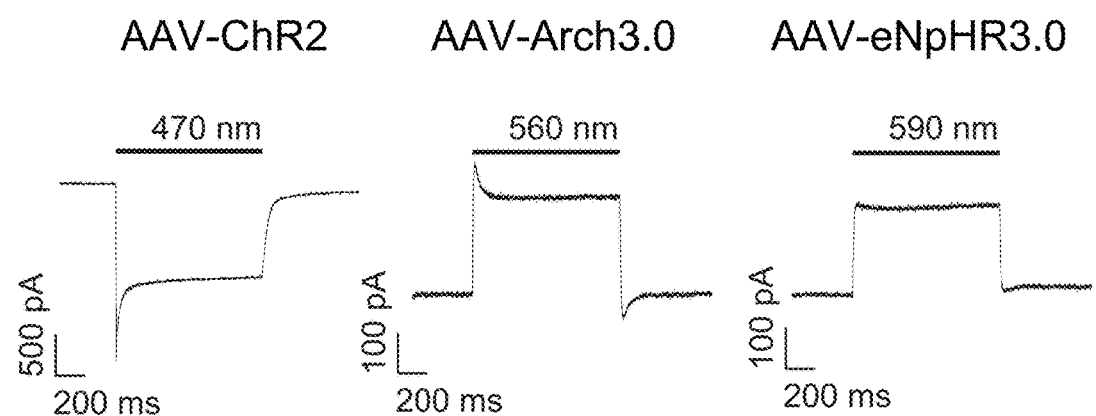

FIGS. 17A and 17B: Photocurrent magnitudes. A Steady state photocurrent magnitudes (in response to 1 s light) for opsin-expressing neurons present in same preparations as bystander neurons: AAV-ChR2 (n=20, 470 nm), Thy1-ChR2 (n=6, 470 nm), AAV-eArch3.0 (n=14, 560 nm), AAV-eNpHR3.0 (n=16, 590 nm). Bars indicate mean and SEM, filled circles indicate individual cell photocurrents. B Example photocurrent traces for AAV5-ChR2 (blue), AAV-eArch3.0 (green) and AAV-eNpHR3.0 (amber) expressing neurons.

Figure 18A:
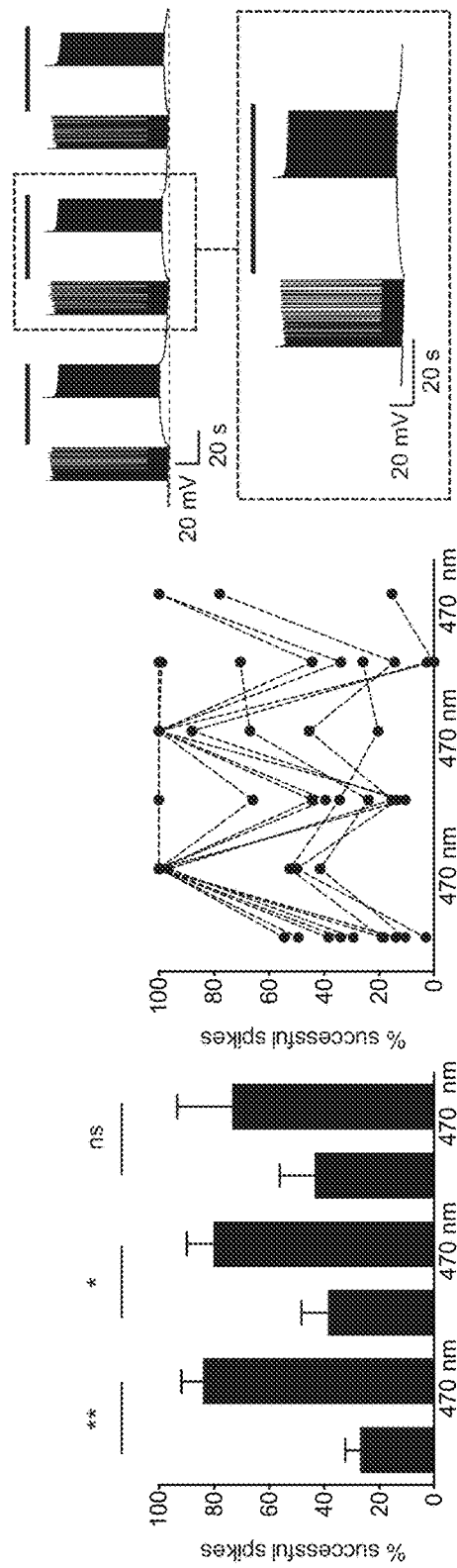
Figure 18B:
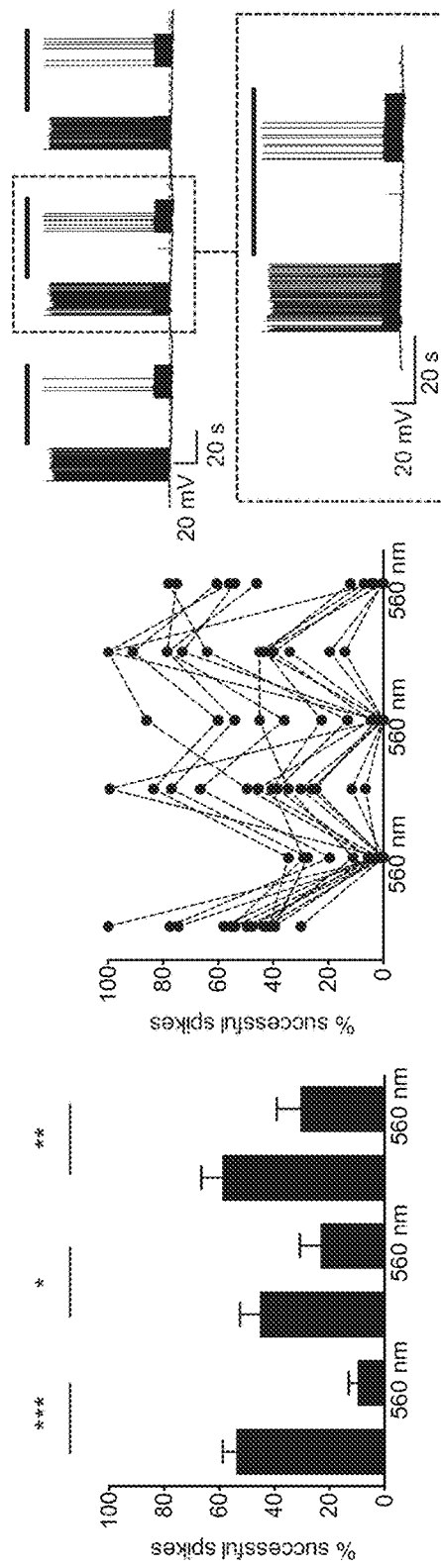

The influence of the bystander effect on evoked action potential firing was investigated (FIG. 18). During epochs of illumination (470 nm, 560 nm or 590 nm), the proportion of action potentials evoked in bystander neurons was modulated in a bidirectional manner, approximately doubling in the case of AAV5-ChR2 bystanders and halving in the case of AAV5-eArch3.0 bystanders (FIGS. 18A and 18B). AAV5-eNpHR3.0 bystanders also experienced a modest but significant reduction in spiking success during illumination whereas no modulation by light epochs was observed in AAV5-YFP controls (FIGS. 18C and 18D).

FIGS. 18A-D. Functional impact of bystander currents on action potential firing. Spikes were evoked in the bystander neuron by intracellular injection of electrical current pulses at 10 Hz titrated to achieve a ~50% success rate at baseline. Light pulses were applied and the change in evoked spiking was recorded. Plots show percentage of successfully evoked spikes during repeated light-off and light-on epochs for A AAV-ChR2 (n=4-10), B AAV-eArch3.0 (n=13-14), C AAV-eNpHR3.0 (n=9-14) and D AAV-YFP control bystander neurons Summary plots and individual cell data are shown with example traces. Dashed box shows zoom-in of the center light-off/light-on epochs. Bar charts indicate mean values and error bars represent SEM. All statistical comparisons (Wilcoxon matched pairs signed rank test) are between the light-on epoch and the preceding light-off epoch.

Figure 19A:
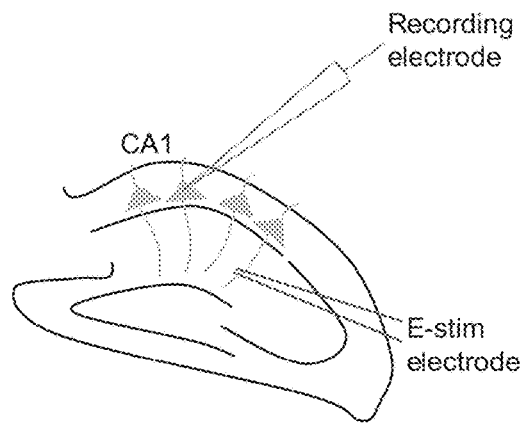
FIGS. 19A-G depict electrical stimulation-elicited bystander effects and the effects of ASIC antagonist amiloride administration.
Figure 19B:
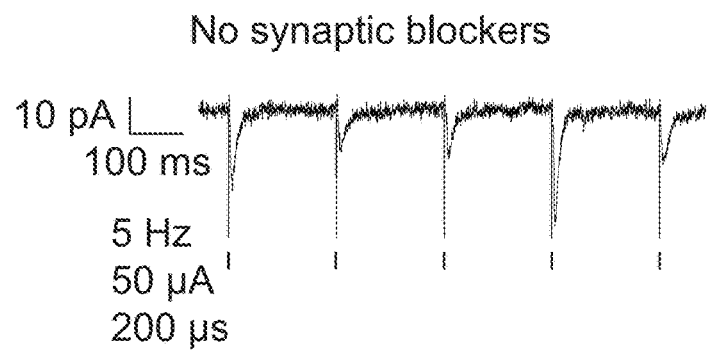
Figure 19C:
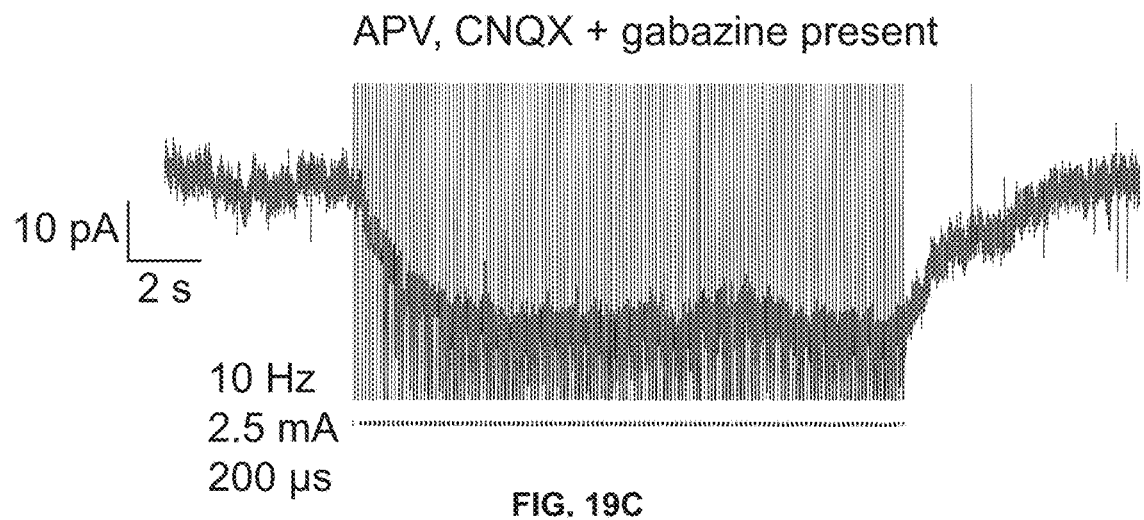
Figure 19D:
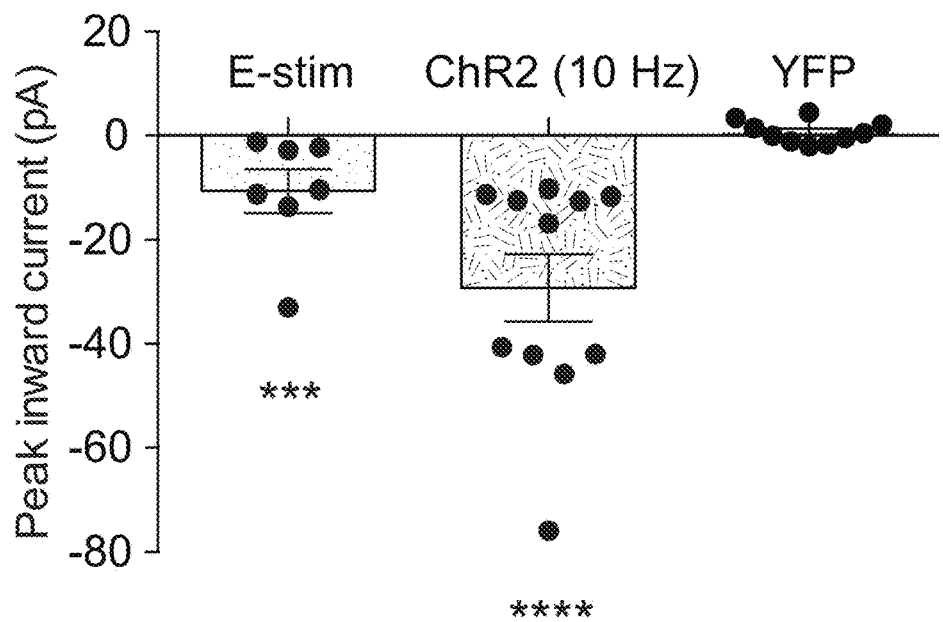
Figure 19E:
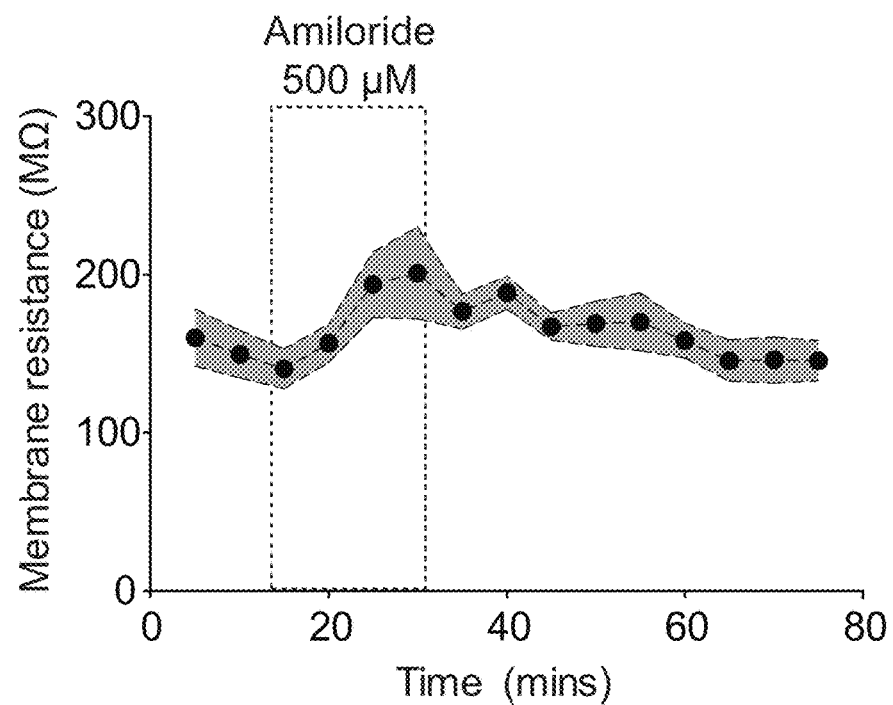
Figure 19F:
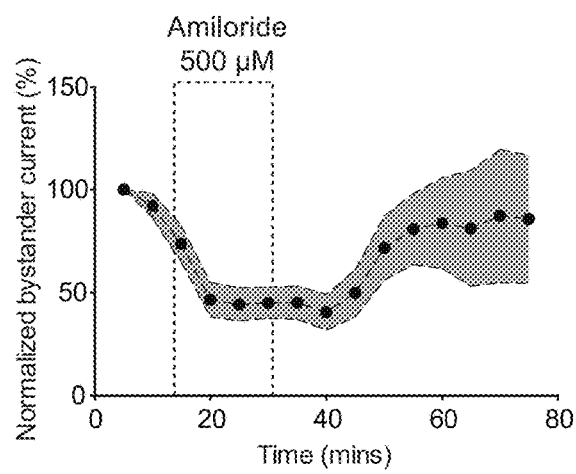
Figure 19G:
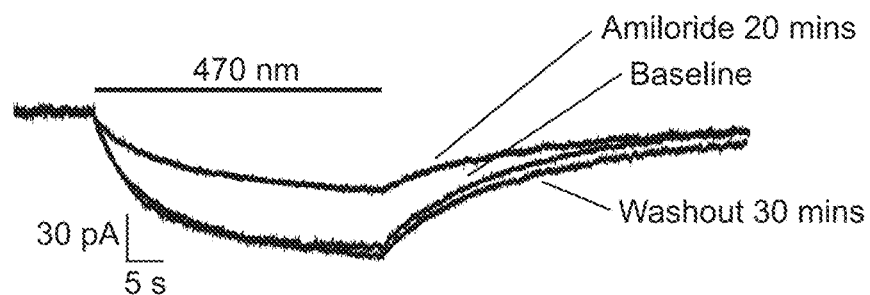
Figure 20:
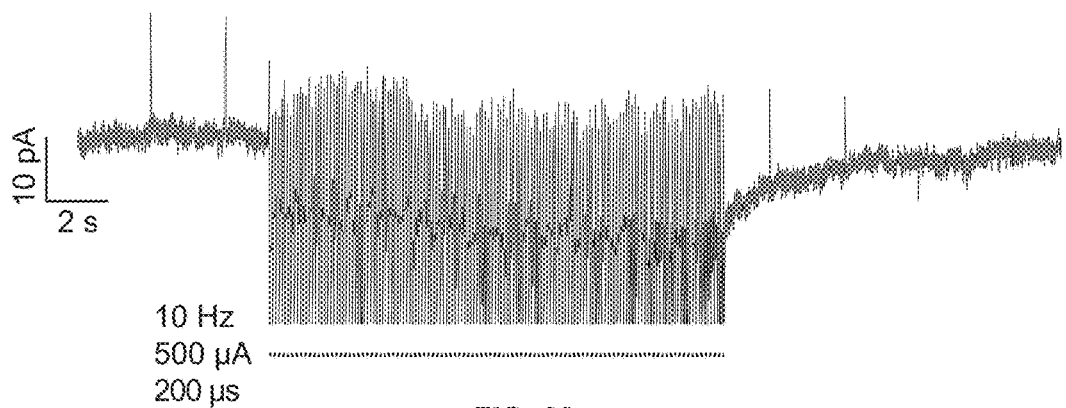
FIG. 20 depicts an exemplary bystander current in response to electrical stimulation of Schaffer collaterals to CA1 region of hippocampus using a tungsten concentric bipolar electrode.

Having observed that the bystander effect tracked the direction of change in local neural activity we questioned whether the effect could be observed during manipulation of neural activity using electrical stimulation. Although electrical stimulation is not constrained to a genetically specified cell type or projection, we endeavored to create "electrical bystanders" by stimulating axonal inputs (Schaffer collaterals) to the CA1 region of hippocampus (FIG. 19A). The ability of the stimulation paradigm to induce synaptic release (FIG. 19B) was confirmed, then ionotropic synaptic transmission blockers were applied to isolate the impact of electrical axonal stimulation on the extracellular milieu. To mimic the intensity of the optogenetic manipulations, high amplitude (0.5-2.5 mA) extracellular current pulses at a frequency of 10 Hz for a period of 20 s were used (FIG. 19C). Electrical artifacts challenged the assessment of whole-cell current responses during stimulation, however the mean change in holding current immediately post-stimulation compared to baseline was significantly more negative than the YFP control group (−11 pA) (FIG. 19D), displaying a slow recovery comparable to the ChR2 optogenetic bystander currents. The possibility of a unique electrochemical reaction between the electrode metal and the extracellular fluid was controlled for by performing the experiments using both tungsten and platinum-iridium electrodes; similar effects were found with both electrode-types (FIG. 20).

Figure 21A:
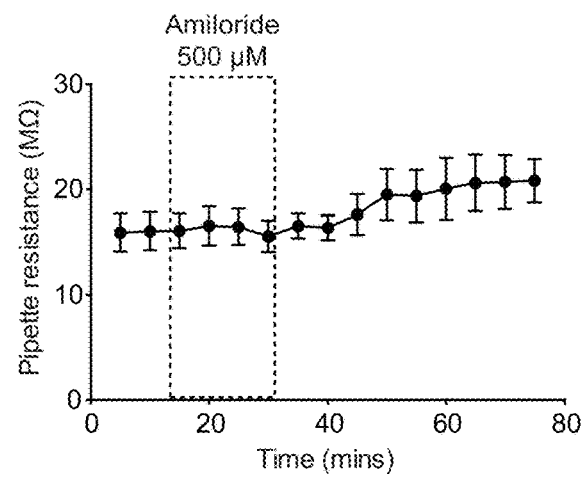
FIGS. 21A-C depict control experiments pertaining to amiloride administration.
Figure 21B:
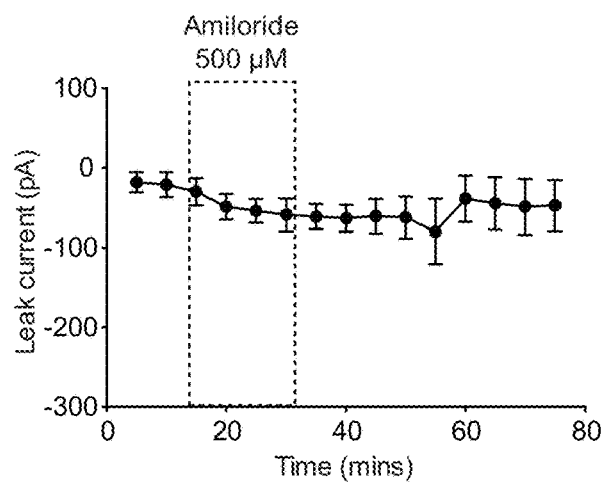
Figure 21C:
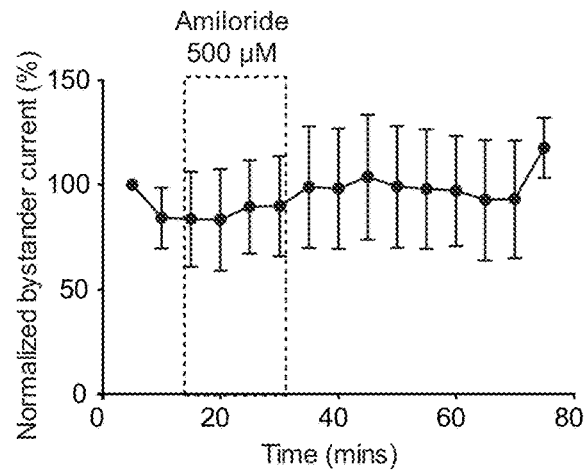
Figure 22A:
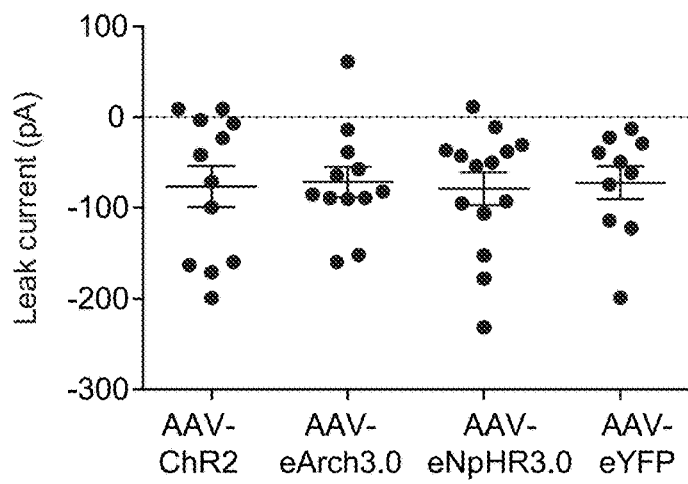
FIGS. 22A-C depict measures of cell health for bystander neurons.
Figure 22B:
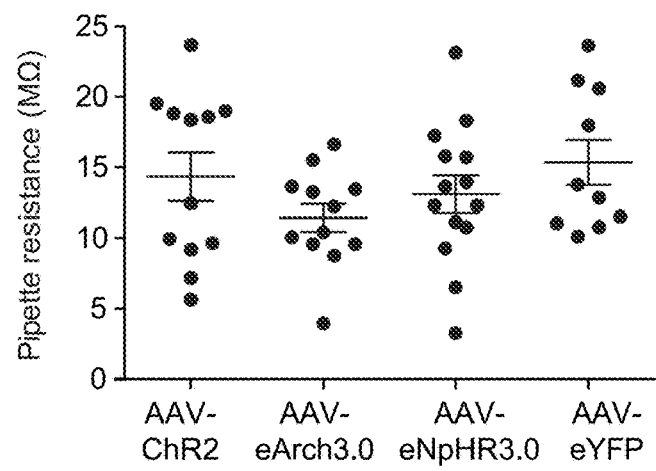
Figure 22C:
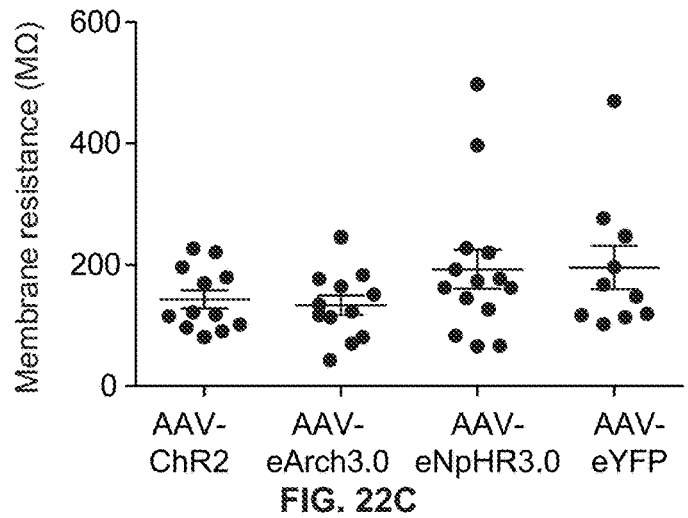

It was hypothesized that the bystander effect could be driven by changes in local extracellular pH. Neural activity and synaptic release can modulate extracellular pH and many membrane proteins are modulated by extracellular protons such as acid-sensing ion channels (ASICs), which may be partially open at rest and are plentiful in the brain. The contribution of ASICs to the ChR2 bystander current was tested by using pharmacological blockade by the ASIC inhibitor, amiloride. A bystander current (15 s light pulse) was evoked in hippocampal ChR2 bystander neurons every 5 minutes for up to 75 minutes. Following two baseline measurements, 500 μM amiloride was applied for 20 minutes, then returned to ACSF alone for a "washout" period. During amiloride application, an increase in membrane resistance (in the absence of any illumination) (FIG. 15E) was observed, with a concurrent reduction in the magnitude of the light-evoked bystander current to ~50% of the baseline value, which slowly recovered during the washout period (FIGS. 15F and 15G). To control for the effect of holding cells in whole-cell patch clamp configuration for long periods, the experiment was repeated in the absence of amiloride application and no consistent reduction in bystander current magnitude over time was seen (FIG. 21C). Measures of cell health confirmed the integrity of the pipette access and cell membrane for the duration of the recordings (FIGS. 22A and 22B).

Coupling Proton Pumps to Acid-Sensing Ion Channels

Figure 23A:
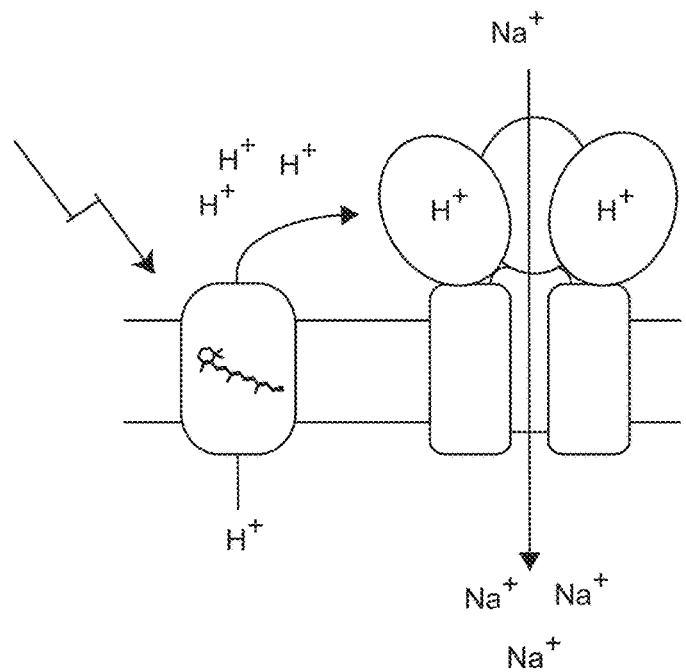
FIGS. 23A-D depict optical activation of three acid-sensitive ion channels using the Two Component Optogenetic (TCO) approach.

The response of acid-sensing ion channels to extracellular protons was exploited through a concept that we term "two-component optogenetics" (TCO). A modular system was devised, in which a light-sensitive protein such as a proton pump (e.g. *Coccomyxa subellipsoidea* C-169 (CsR) or Archaerhodopsin (Arch)) is co-expressed with a secondary-coupled ion channel, such as an acid-sensing ion channel (ASIC), to evoke a light-triggered secondary current carried by a specific ionic species, as illustrated in FIG. 23A.

Oocytes: To test this approach in *Xenopus laevis* oocytes, we chose a light-driven proton pump of the arctic green alga *Coccomyxa subellipsoidea* C-169 (CsR) (Blanc et al, 2012), which has improved expression in oocytes compared to the well-characterized bacteriorhodopsin or archaerhodopsin, used for hyperpolarization of neurons. The CsR mutant T46N was used, which exhibits less voltage dependence than the wild type, with large photocurrents at negative voltages (FIG. 24).

Figure 23B:
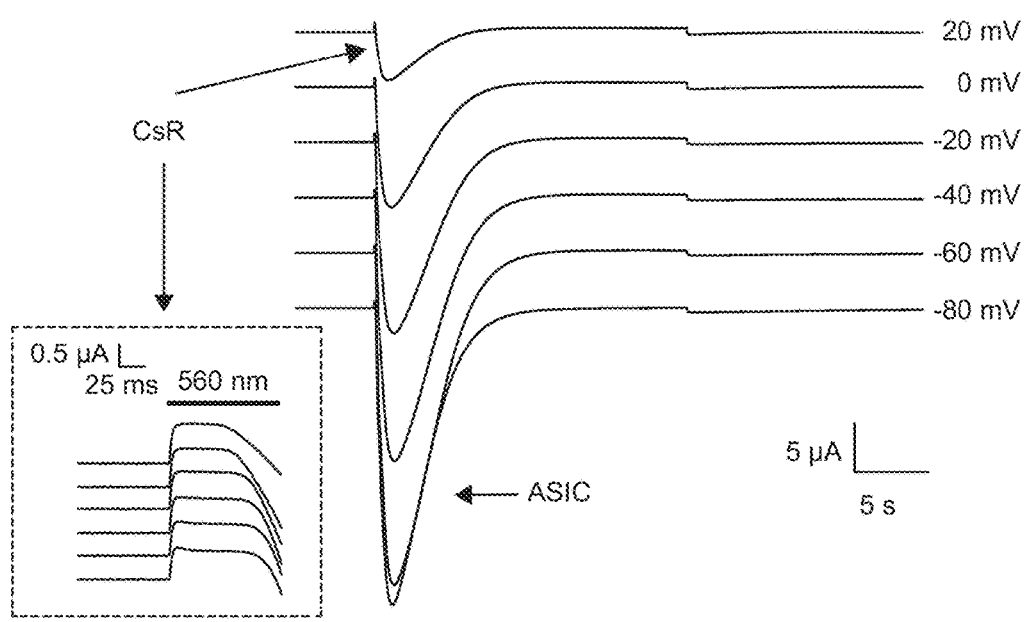
Figure 23C:
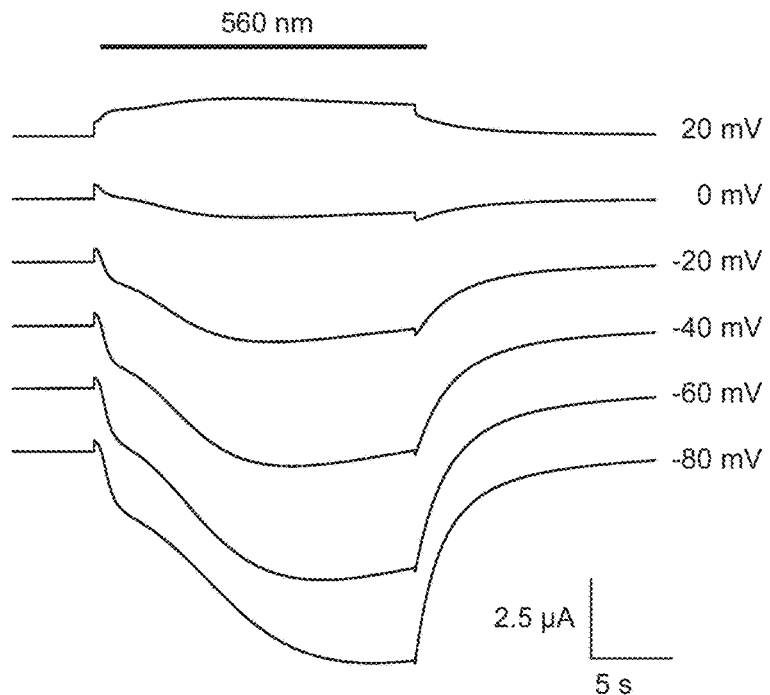
Figure 23D:
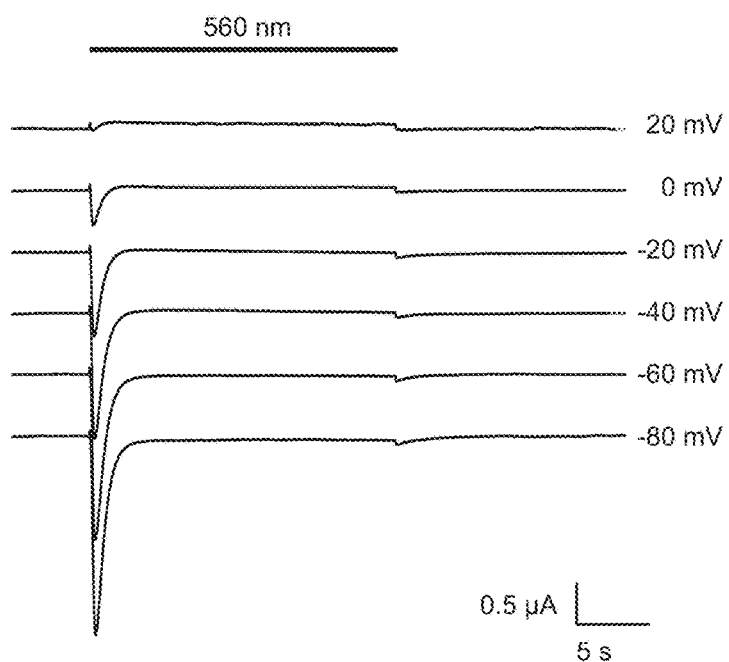
Figure 24A:
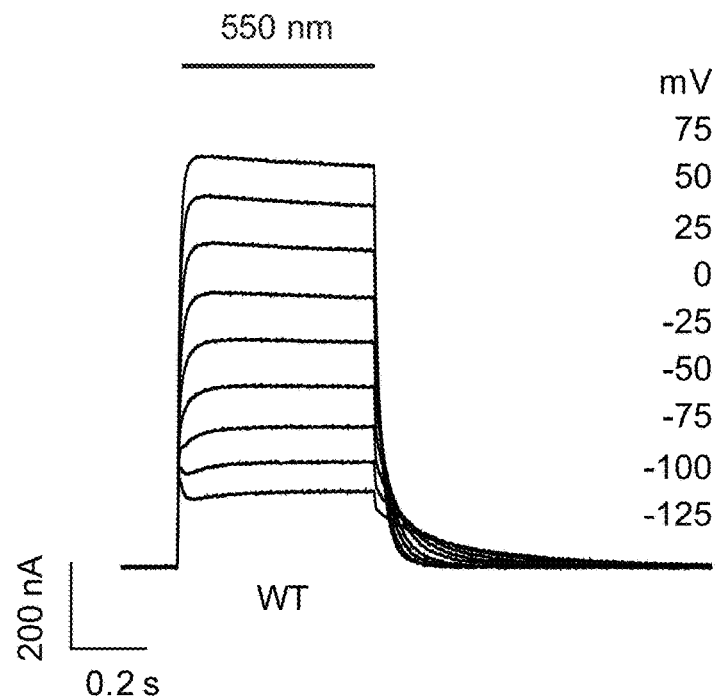
FIGS. 24A-E depict photocurrents of Chlorellarhodopsin (CsR) and related current quantification.
Figure 24B:
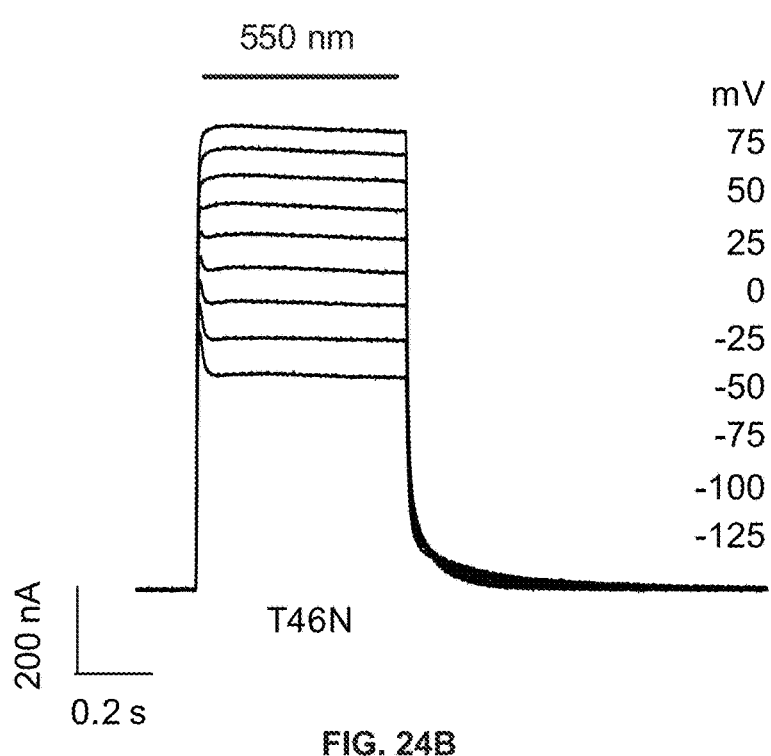
Figure 24C:
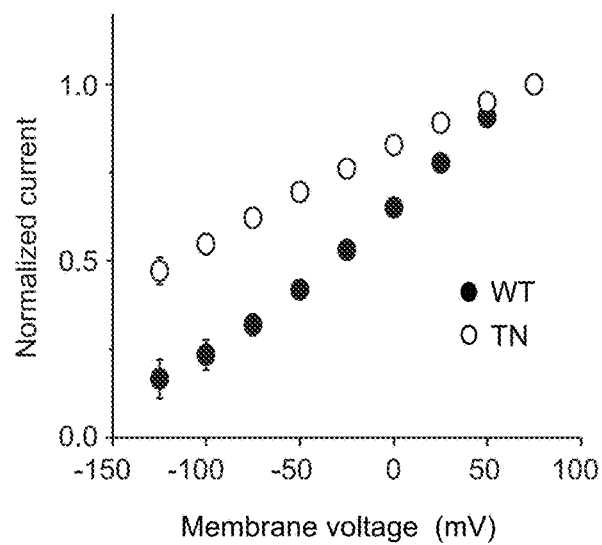
Figure 24D:
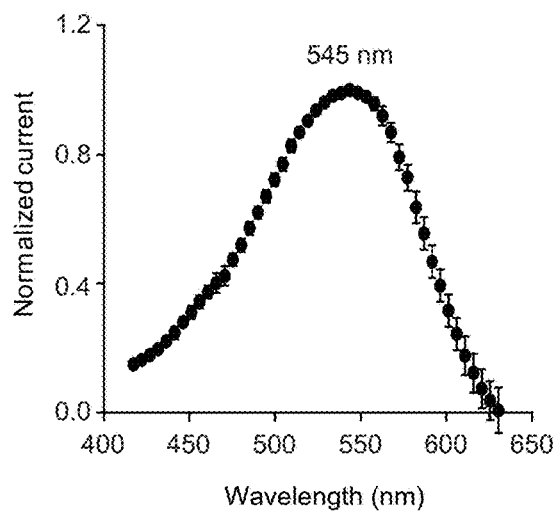
Figure 24E:
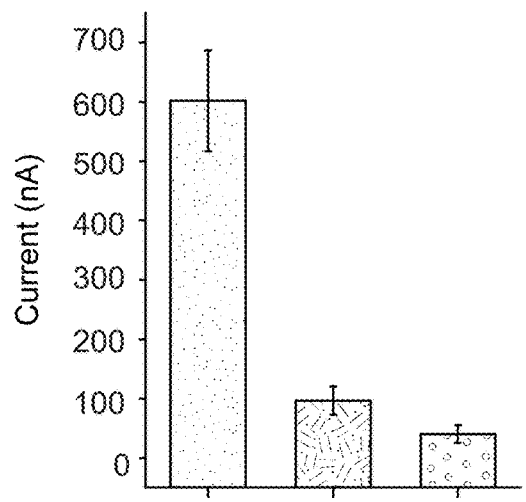
Figure 25A:
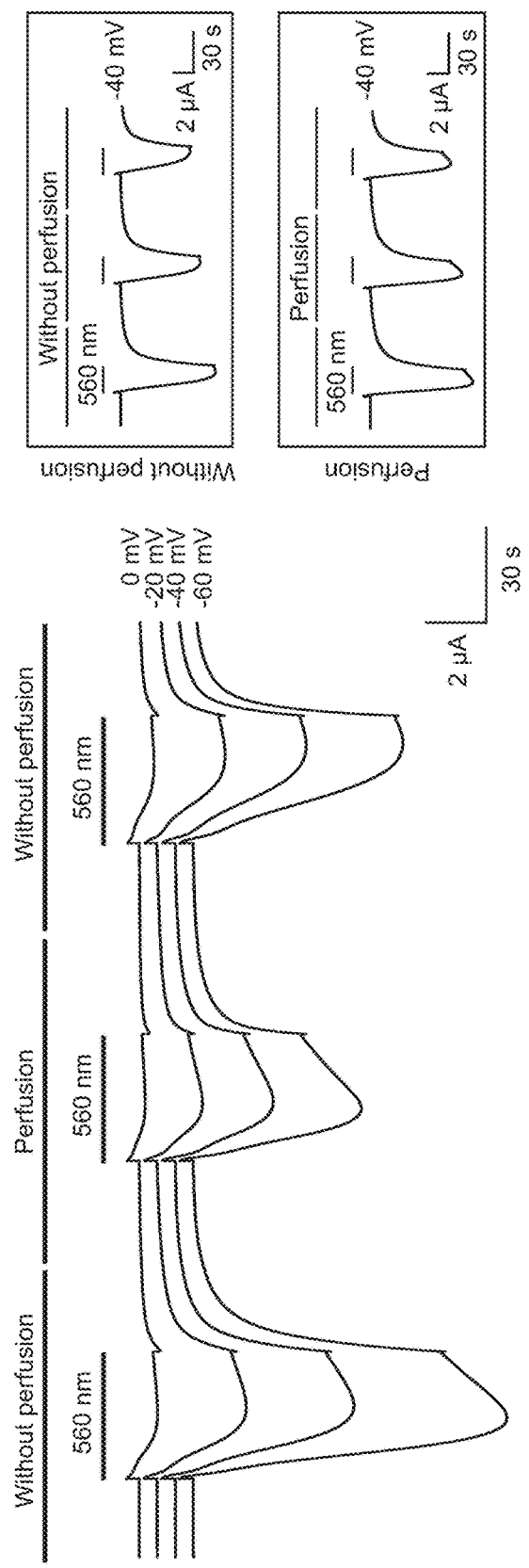
FIGS. 25A-E depict CsR-ASIC1a photocurrents with and without permanent perfusion in *Xenopus laevis* oocytes and related quantification.
Figure 25B:
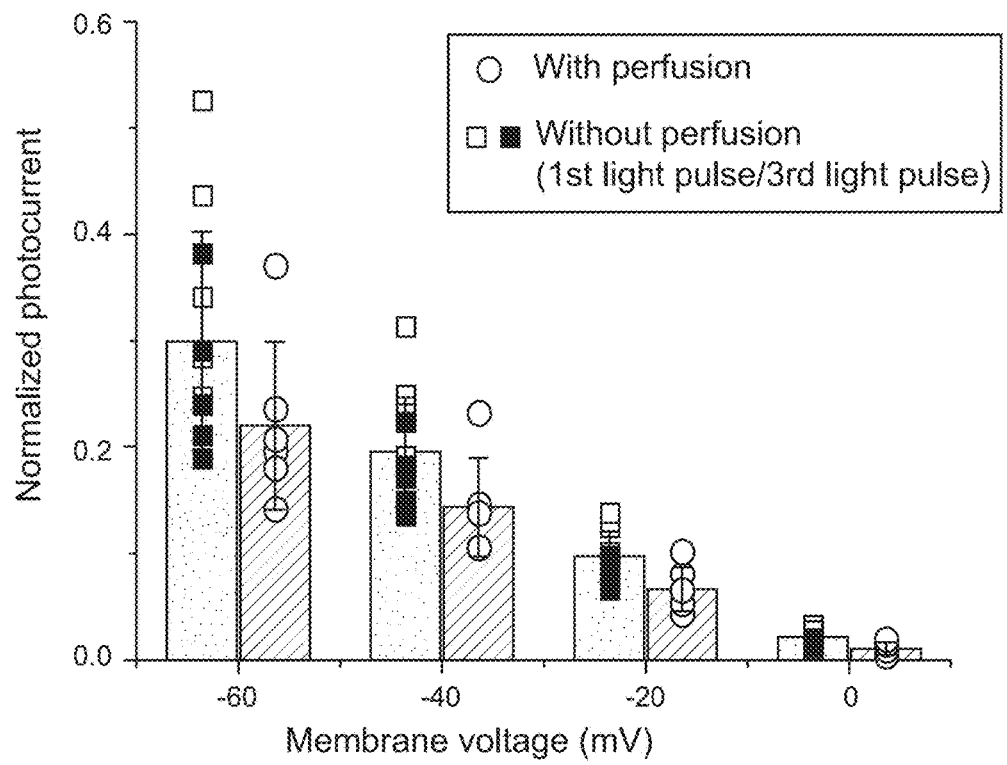
Figure 25C:
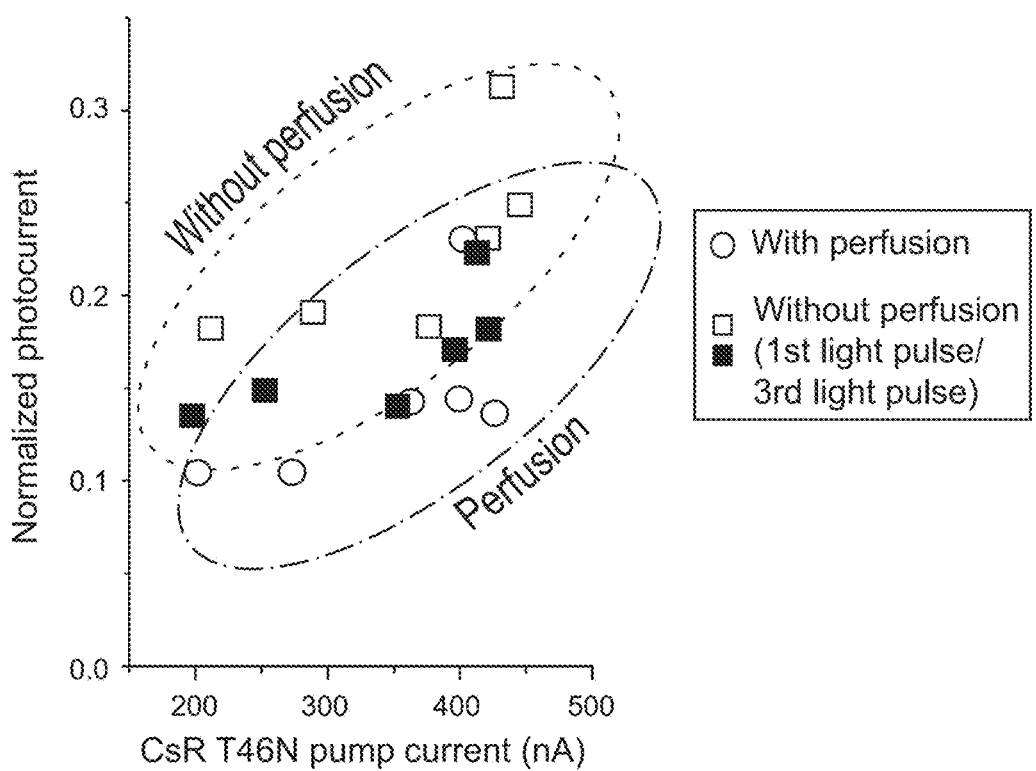
Figure 25D:
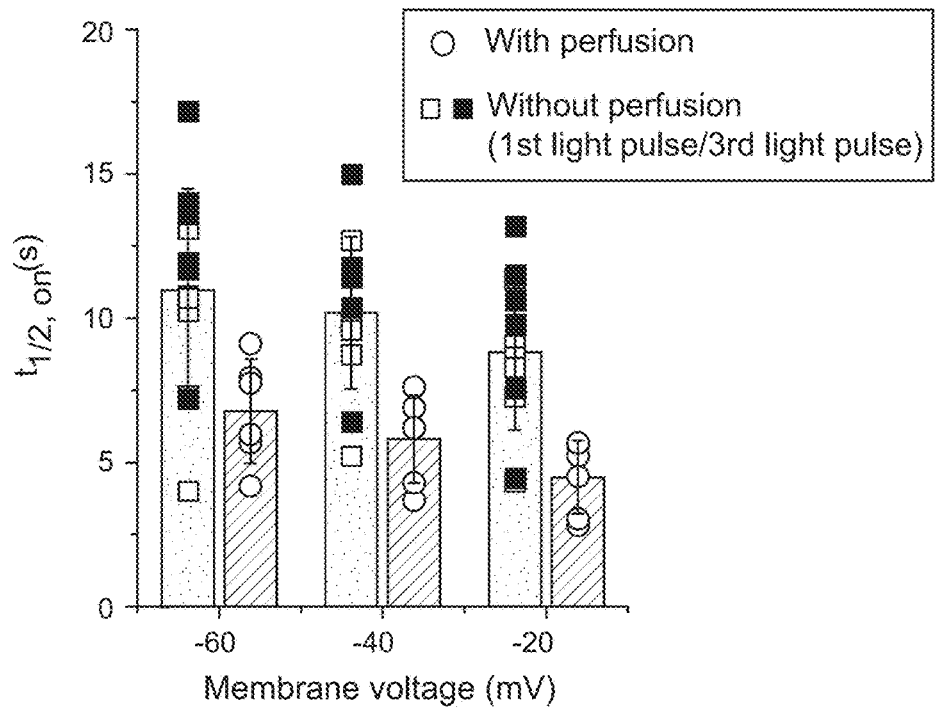
Figure 25E:
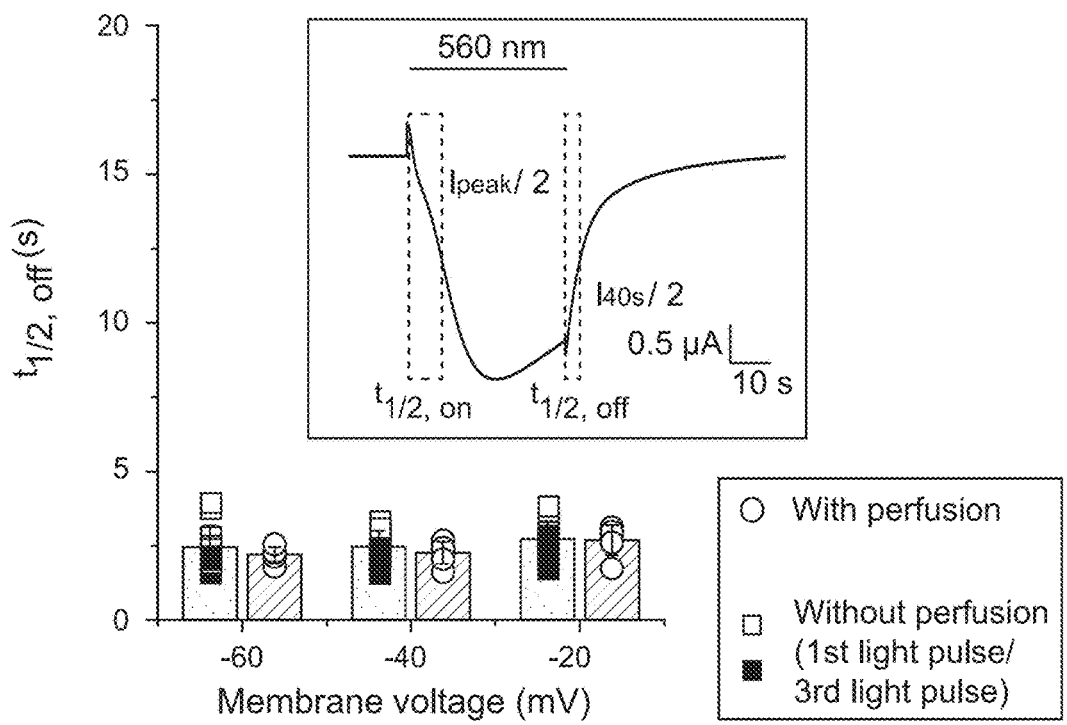

In *Xenopus laevis* oocytes we co-expressed CsR with each of three different rat acid-sensing ion channels ASIC1a, ASIC2a or ASIC3. These channels are characterized by a steep pH-dependence of the proton-activated currents, more or less below the physiological pH. Immediately after light onset a small outward current carried by proton pumping of CsR was observed, followed by a large inward current carried by the co-expressed acid-sensing ion channel (FIGS. 23B-D). For both ASIC1a and ASIC3, the secondary activated inward current peaked within 1-2 s after light onset then rapidly decayed to the initial pump current, due to the high proton sensitivity and fast desensitization of ASIC1a and ASIC3 as described previously (Zhang & Canessa, 2002) (FIGS. 23B and 23D). In contrast ASIC2a mediated a long-lasting light activated inward current (FIG. 23C). The rise of the ASIC2a current was multiphasic at all voltages, a property not observed in previous studies in which the channel was directly activated by acidification of the bulk solution. This is possibly due to the indirect activation of the channel by the proton pump. In accordance with a low $pH_{50}$ of 5 and the reported slow and incomplete desensitization of ASIC2a (Zhang & Canessa 2002), the light-induced currents decayed only very slowly during illumination. Following light offset the current decayed to zero within ~20 seconds and could be reactivated by illumination any time (FIG. 25A).

FIGS. 23A-D. Optical activation of three acid-sensitive ion channels. A Principle of the Two Component Optogenetic (TCO) approach. Upon illumination the light-activated proton pump may moderately acidify the local extracellular medium and activate acid-sensitive ion channels, ASICs, via their proton-sensing domain. This results in a remote but large sodium influx that can be used for sustained cell depolarization at moderate light intensities. In *Xenopus* oocytes, a light-driven proton pump of *Coccomyxa subellipsoidea* (CsR) was used. B-D Macroscopic currents of CsR$_{T46N}$ coexpressed with rat ASIC1a, rat ASIC2a or rat ASIC3 in oocytes at a molar RNA ratio of 1:1 (for ASIC3 of 2:1). Cells were illuminated with 560 nm light at different holding voltages at 0.1 mM MOPS and pH 7.5 under constant perfusion. The small outward directed pump currents (CsR) triggers large inward sodium currents (ASIC). Inset zooming to the initial pump activity directly after starting to illuminate CsR$_{T46N}$-ASIC1a with green light. Note that ASIC1a and ASIC3 show strong inactivation in sustained light, whereas ASIC2a shows moderate to no inactivation at all.

FIGS. 24A-E. Photocurrents of Chlorellarhodopsin (CsR). A, B Light induced pump currents of CsR WT (A) and T46N (B) in *Xenopus* oocytes. The T46N mutant exhibits greater currents at negative membrane voltage compared to WT. C Current—voltage relationships, I(E), and D action spectra with maxima at 545 nm. E Comparison of CsR photocurrents (545 nm excitation) with those of bacteriorhodopsin (BR, 570 nm excitation) expressed under identical conditions. Current amplitudes of CsR are on average 10 fold greater than those of BR.

FIGS. 25A-D. Characterization of CsR-ASIC1a with and without permanent perfusion in *Xenopus laevis* oocytes. In "perfusion" conditions a measuring chamber of 300 µl was continuously perfused with 1.8±0.2 ml/min of standard measuring buffer containing 100 mM NaCl, 1 mM KCl, 1 mM MgCl$_2$, 0.1 mM CaCl$_2$, 0.1 mM MOPS (pH 7.5). In measurements "without perfusion" the buffer supply was disconnected and the peristaltic pump switched off. A Representative CsR$_{T46N}$-ASIC2a photocurrents at 40 s light pulses of 560 nm in a succession of conditions "without perfusion", with continuous "perfusion" and "without perfusion" at different voltages. Insets: Repetitive photocurrent "without perfusion" and with "continuous perfusion" at −40 mV. B Comparison of normalized peak photocurrent with "perfusion" (open circles) and "without perfusion" (squares). Empty squares describe the response to the first light pulse and filled squares to the third light pulse (see A). C Normalized peak photocurrent at −40 mV in dependence on the initial CsR$_{T46N}$ pump current in "perfusion" condition and "without perfusion" for 1$^{st}$ light pulse empty for 3$^{rd}$ light pulse (see A and B)). All currents were normalized to ASIC2a current at pH4 and −40 mV (see FIG. 5). D CsR$_{T46N}$-ASIC2a on-kinetics quantified by the time to reach the half maximal photocurrent t$_{1/2,on}$ with perfusion (circles) and without perfusion (filled and empty squares, see B and C) E CsR$_{T46N}$-ASIC2a off-kinetics quantified by the time to reduce the photocurrent by half after light switched off t$_{1/2,off}$ with perfusion (circles) and without perfusion (filled and empty squares, see B and C). Inset: Description of t$_{1/2,on}$ and t$_{1/2,off}$ (red) on a representative photocurrent at −40 mV.

Figure 26A:
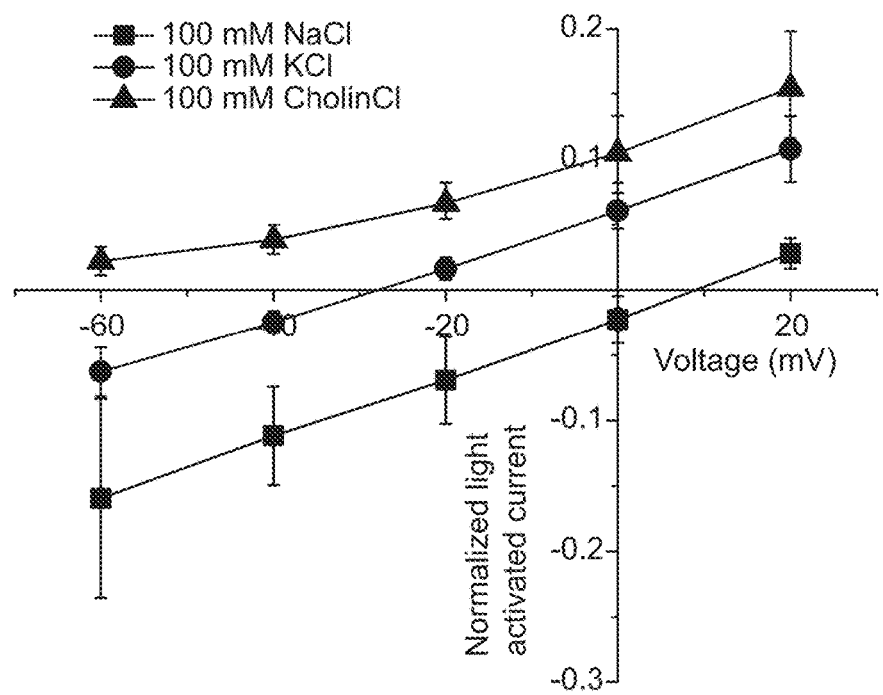
FIGS. 26A-E depict the effects of various parameters (pH, buffer, light intensity, etc.) on CsR-ASIC2a photocurrents measured by two-electrode voltage clamp (TEVC) in oocytes.

The observed light activated inward currents were inversely proportional to the membrane voltage due to the increased driving force for Na$^+$ at negative voltages and voltage independent gating and permeability of ASIC2a (Zhang & Canessa, 2002) (FIG. 23A; FIG. 26A). Changing the concentration of the major extracellular cation from Na$^+$ to K$^-$ or choline shifted the reversal potential and greatly decreased the magnitude of the inward current component, confirming the Na$^+$ selectivity of the ASIC2a response as a major feature of the TCO pair (FIG. 26A).

Figure 26B:
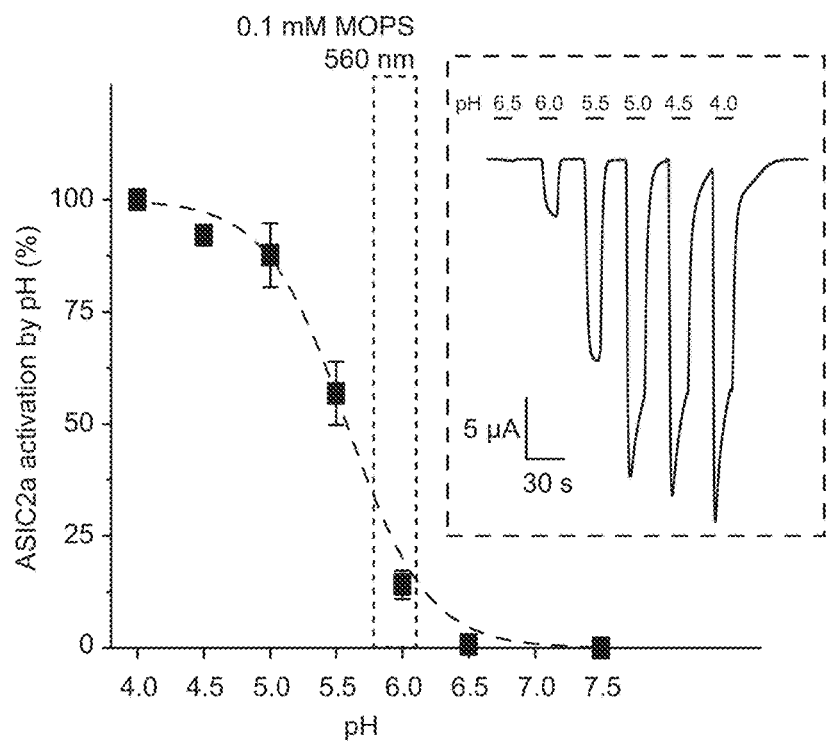
Figure 26C:
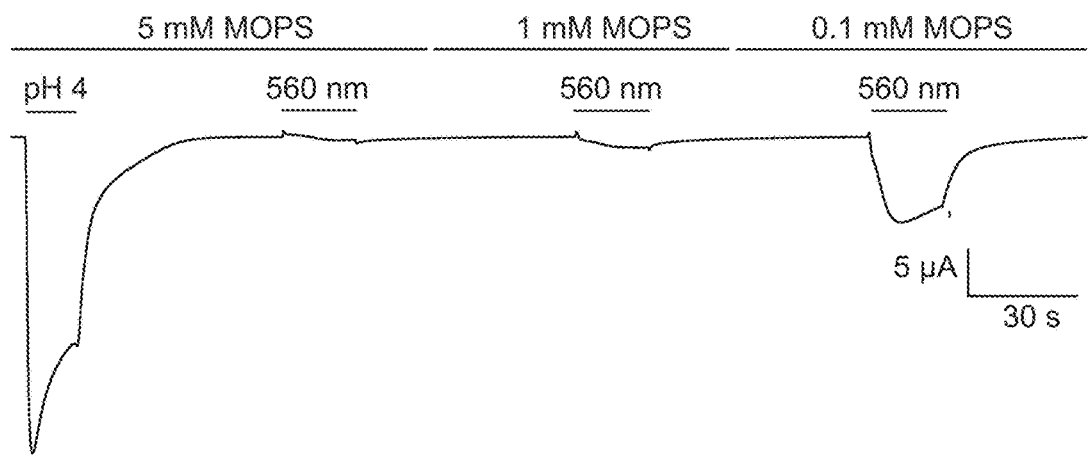

To determine the fraction of ASIC2a channels that are activated by light, we titrated the ASIC2a currents by rapid buffer exchange. It was found that the maximal current (when holding the membrane potential at −60 mV) was only reached at pH 4 (FIG. 26B). Normalization of light-activated currents to this value revealed that approximately 25% of ASICs are activated by CsR-mediated acidification (FIGS. 26B-D) and allowed an approximation of the acidification sensed by ASICs at the cell surface (FIG. 26B green bar). It was also noticed that at pH values of 5.5 or below, ASIC2a inactivates more severely than at pH 6. Thus for neuronal applications, the degree of inactivation may serve as a useful indicator for the external pH value that may have been reached.

Figure 26D:
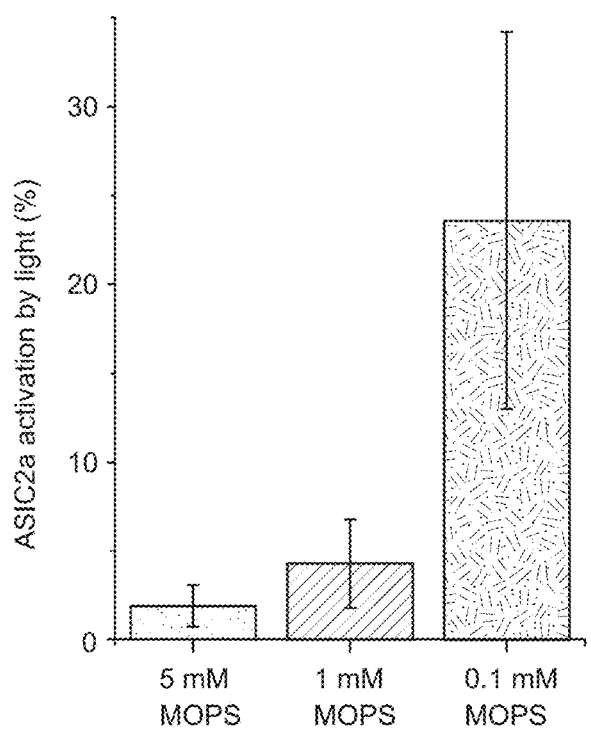
Figure 26E:
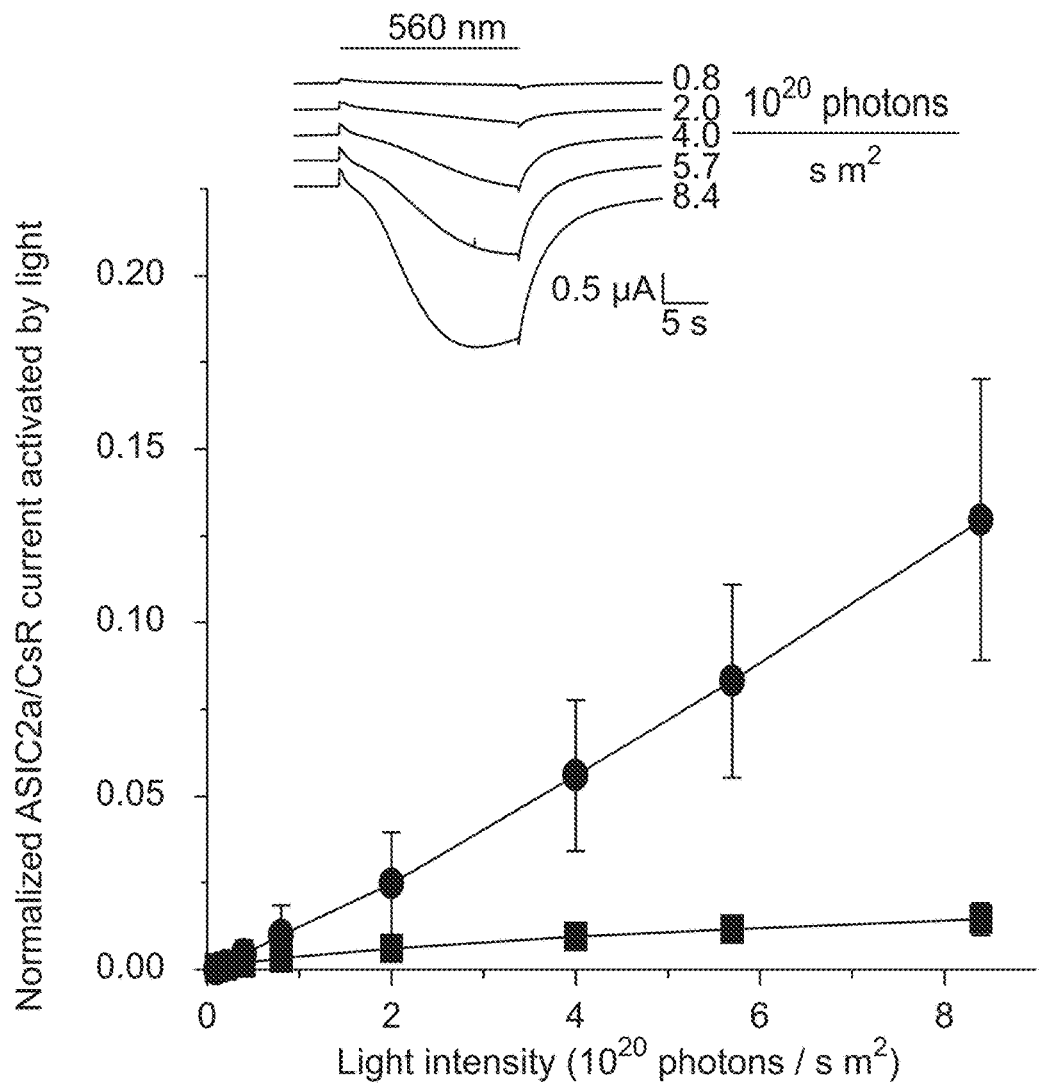

ASIC activation strongly depended on the number of active proton pumps as probed by application of light at different intensities (FIG. 26E). Furthermore efficient activation was expected to depend on the external buffering capacity for protons, namely buffer strength and extracellular volume. Indeed increasing the buffer strength from 0.1 mM to 5 mM strongly decreased the ASIC2a mediated inward current (FIG. 26C) and correspondingly the fraction of light activated ASIC2a channels from ~25% at 0.1 mM MOPS to ~2% at 5 mM MOPS (FIG. 26D). In contrast the extracellular bulk volume seemed of low importance. Consecutive exchange of the bulk medium during illumination by continuous perfusion only slightly decreased the light activated ASIC2a current compared to conditions with a constant bulk phase (FIG. 25).

FIG. 26A-E. Characterization of CsR-ASIC2a by two-electrode voltage clamp (TEVC) in oocytes. A Current-voltage dependency of normalized photocurrents in 100 mM NaCl, 100 mM KCl or 100 mM CholineCl extracellular medium (all media contained additionally 1 mM NaCl/KCl, 1 mM MgCl$_2$, 0.1 mM CaCl$_2$ and 0.1 mM MOPS, pH 7.5, n=5, normalized to ASIC2a current activated by pH 4). B ASIC2a currents measured during pH titration in darkness and comparison with photocurrents measured at pH 7.5. The boxed region highlights the percent activation of ASIC2a by illumination with green light at 0.1 mM MOPS (data shown in FIG. 5B). Inset: representative pH activated current trace of ASIC2a at −40 mV. C Macroscopic currents of CsR$_{T46N}$-ASIC2a activated by pH 4 or green light at different buffer concentrations (5 mM MOPS, 1 mM MOPS and 0.1 mM MOPS, −40 mV, constant perfusion) D Percent activation of ASIC2a by the light driven proton pump CsR$_{T46N}$ in different buffer concentrations (5 mM MOPS, 1 mM MOPS and 0.1 mM MOPS, −40 mV, n=9, 100% activation taken as the peak ASIC current produced by pH 4). E Normalized ASIC2a and CsR$_{T46N}$ photocurrents measured at different light intensities (0.1 mM MOPS, −40 mV, n=5, normalized to ASIC2a current activated by pH 4). Inset: representative current traces at −40 mV.

Figure 27C:
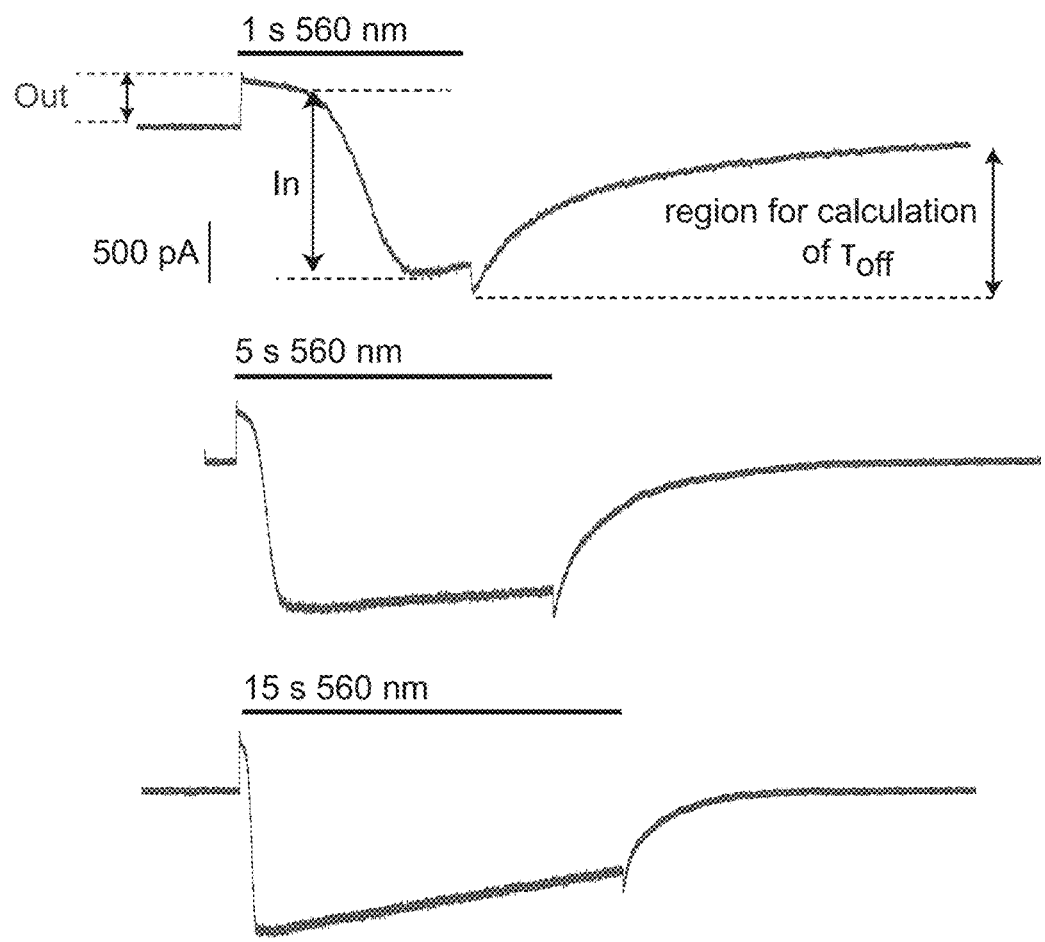
Figure 27D:
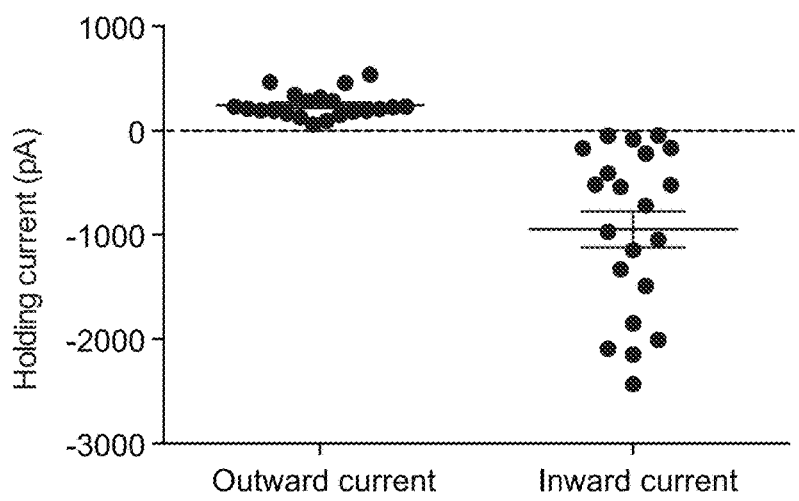
Figure 27E:
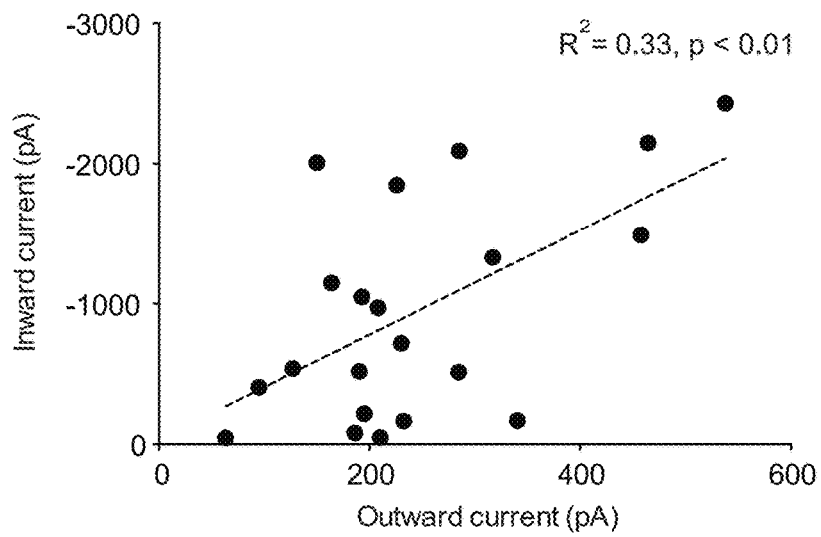
Figure 28A:
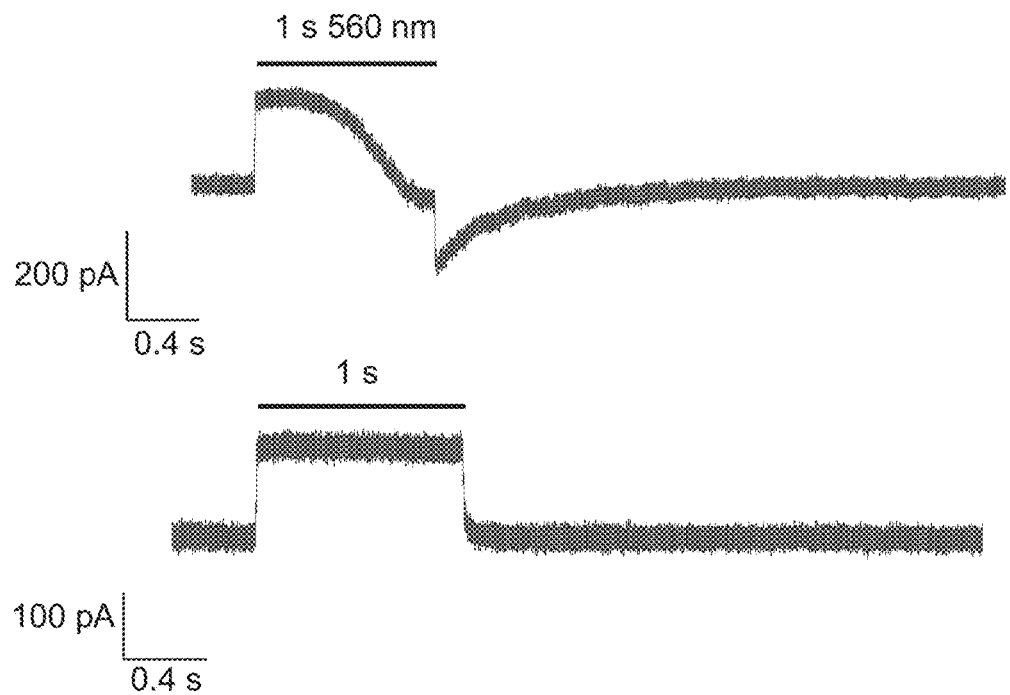
FIGS. 28A-F depict various measures of the variable presence of the ASIC2a component in cultured hippocampal neurons.
Figure 28B:
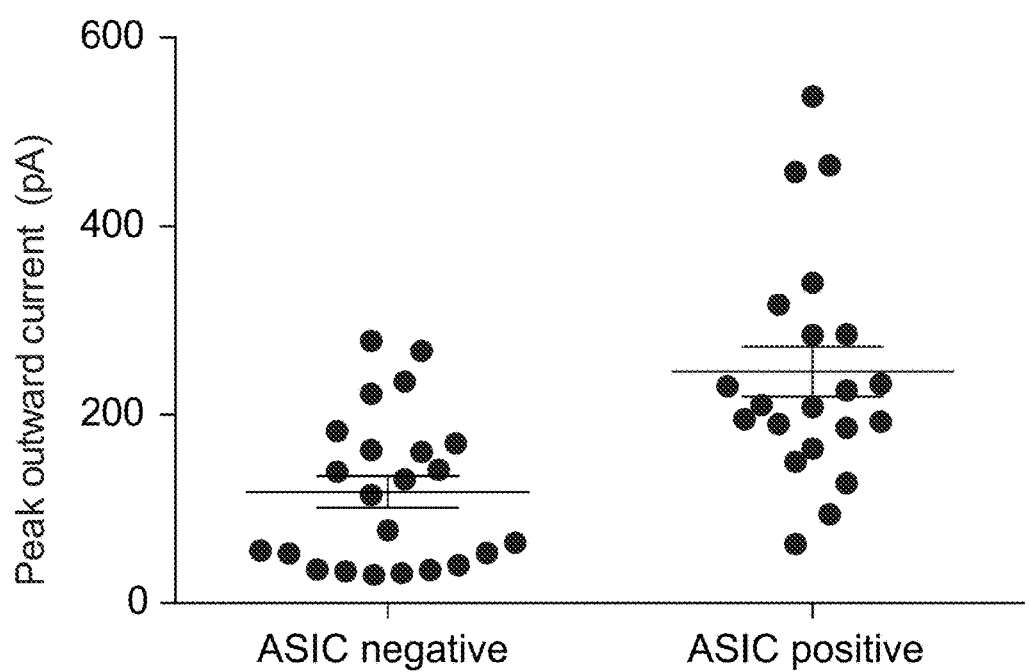
Figure 28C:
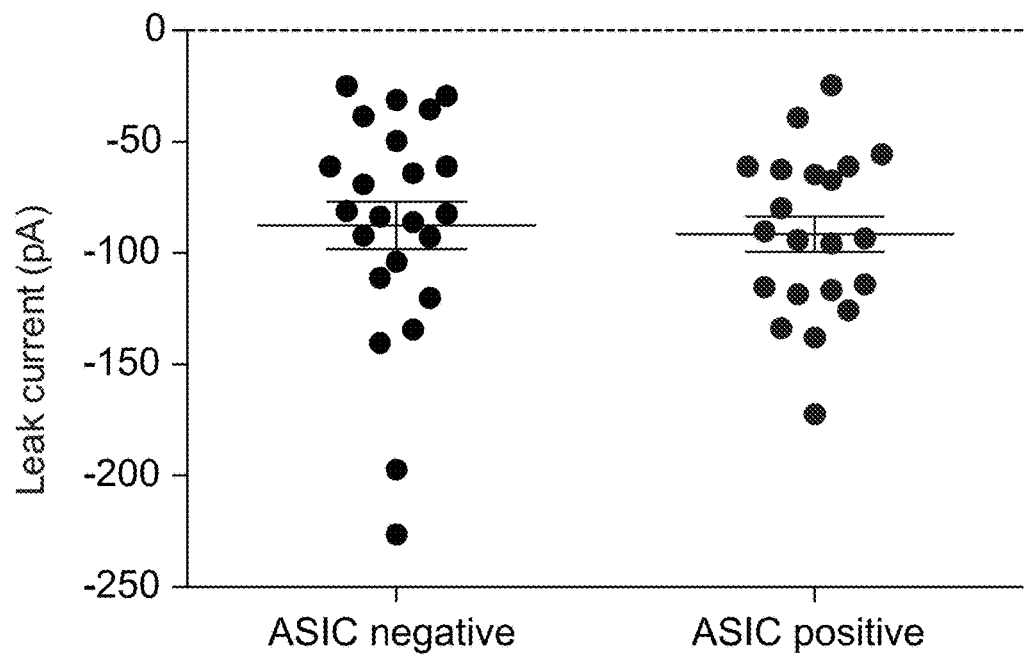
Figure 28D:
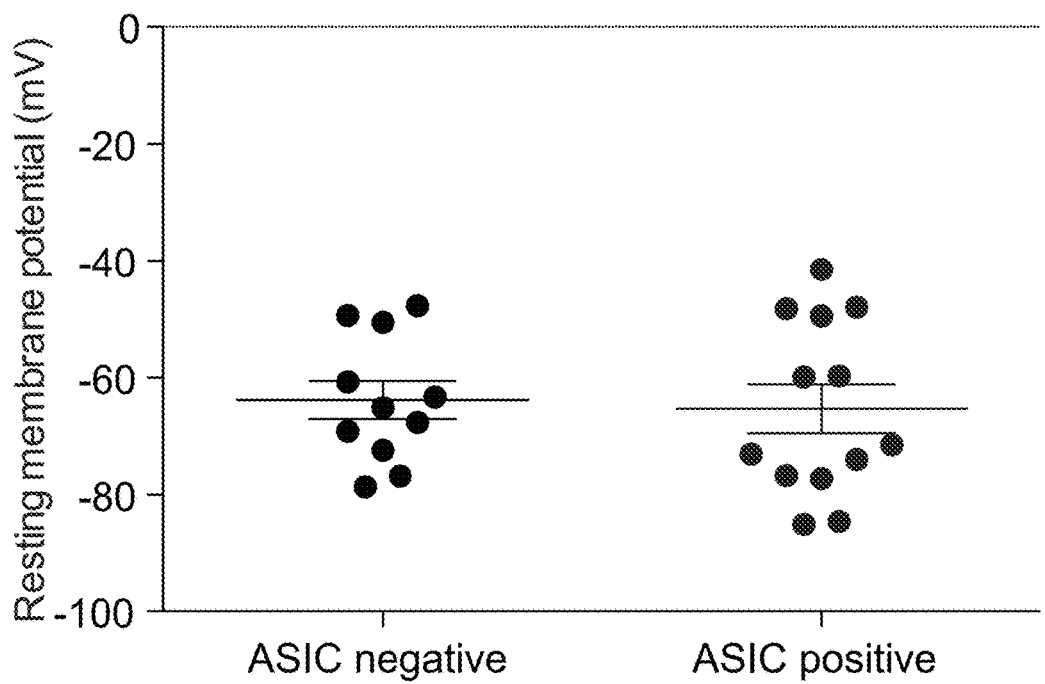
Figure 28E:
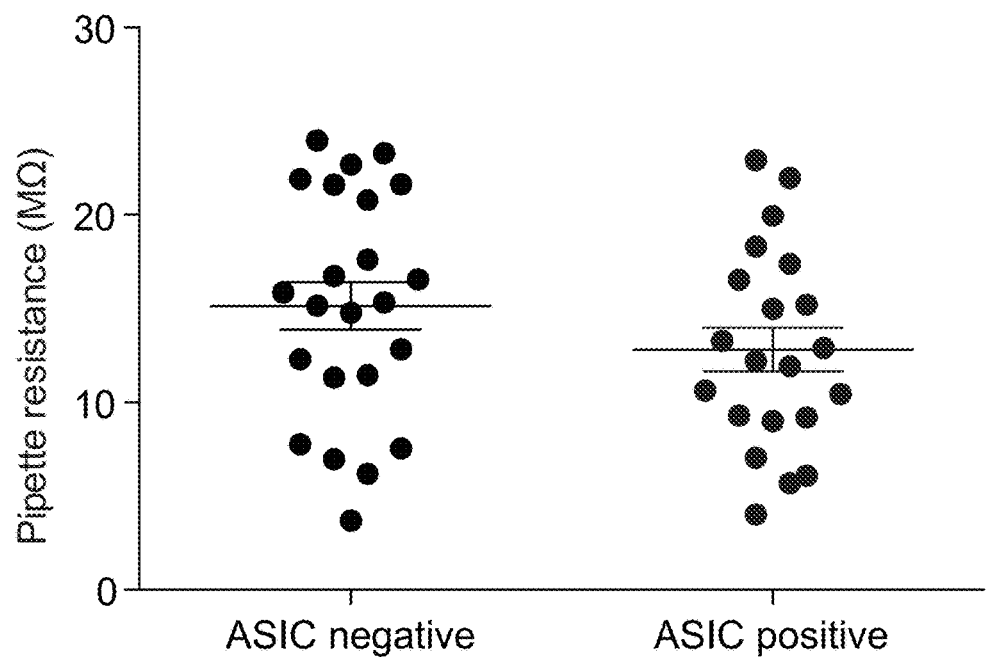
Figure 28F:
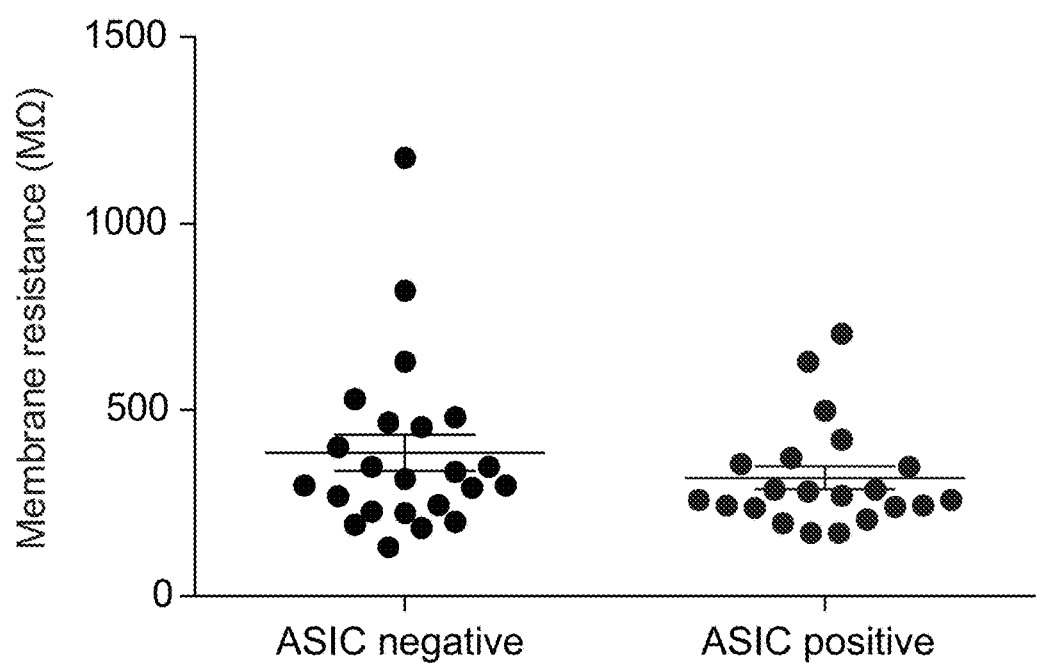
Figure 29A:
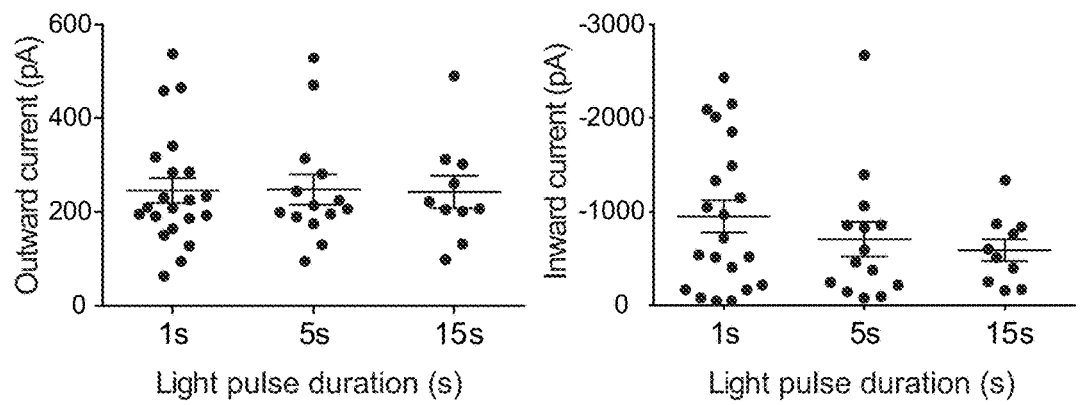
FIGS. 29A-B depict the effects of light pulse duration on Champ currents and kinetics.

Neurons: For application to neuroscience, ASIC2a was tested in cultured hippocampal neurons. The channels were co-expressed with the light-driven proton pump eArch3.0, one of the highest-expressing pumps in neurons (Chow et al, 2010, Mattis et al, 2011). A single eArch3.0-ASIC2a construct was developed, termed Champ (Channel/pump), fusing the proton pump and ASIC2a channel at the DNA level, separating the two genes only by a linker sequence (FIG. 27A). The combination of eArch3.0-ASIC2a (Champ1.0) was enhanced for better membrane localization (Champ2.0) via trafficking signal (TS) and endoplasmic reticulum (ER) export motifs (Gradinaru et al, 2010) (FIGS. 27A and 27B). We performed whole-cell patch clamp recordings from cultured hippocampal pyramidal neurons, expressing the constructs under the human synapsin (hSyn) or calmodulin kinase IIα (CamKIIα) promoters and saw a characteristic biphasic membrane current in response to 560 nm light in voltage-clamp recordings (FIG. 27C). The mean current magnitudes were 246 pA for the outward proton pump-mediated component and −950 pA for the inward ASIC-mediated component (FIG. 27D). The biphasic current was observed in 48% of YFP-positive neurons (FIGS. 28A and 28B) and there was no evidence of adverse effects on cell health in neurons expressing the dual component construct (FIGS. 28C-F). The inward current magnitude was linearly related to the magnitude of the outward proton pump current (FIG. 27E). Peak inward and outward current magnitude did not vary significantly with the duration of light pulses (1 s to 15 s) in a HEPES buffered solution (FIGS. 29A and 29B), suggesting that maximal currents were achievable within 1 s, however off-kinetics, as fitted by a two-term exponential, increased with increasing light pulse duration (FIGS. 29C and 29D). For longer light pulses (15 s), a clear decay in the inward current magnitude over the course of the light pulse to approximately 80% of the initial value was observed (FIG. 27C and FIG. 30B), which may be explained by increases in extracellular acidity under sustained light conditions.

In a separate experiment we tested the effect of decreasing the concentration of HEPES buffer in the extracellular Tyrode's solution (from 25 mM to 0.1 mM) on the magnitude of the currents (FIG. 30). In a low (0.1 mM) HEPES solution, 7/11 (~60%) neurons exhibited the characteristic biphasic membrane response (compared to 5/10 (50%) neurons in standard (25 mM) Tyrode's under otherwise matched conditions). There was a trend towards an increase in current magnitude in low HEPES solution, particularly during longer light pulses (15 s) (FIG. 30D-F) however this was accompanied by a decrease in the stability of the response with greater decay of the peak inward current over the duration of the light pulse (FIGS. 30A and 30B), likely due to the larger drop in extracellular pH in the weakly buffered solution.

Figure 27F:
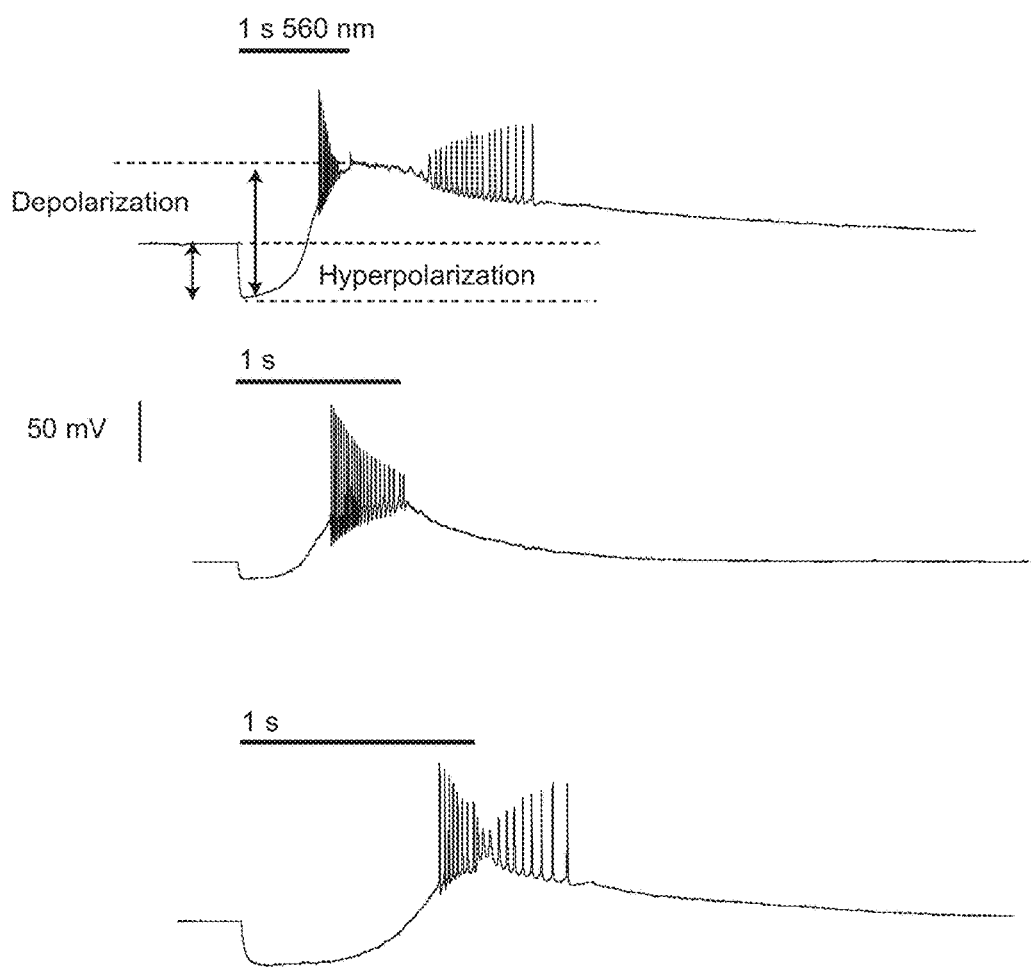
Figure 27G:
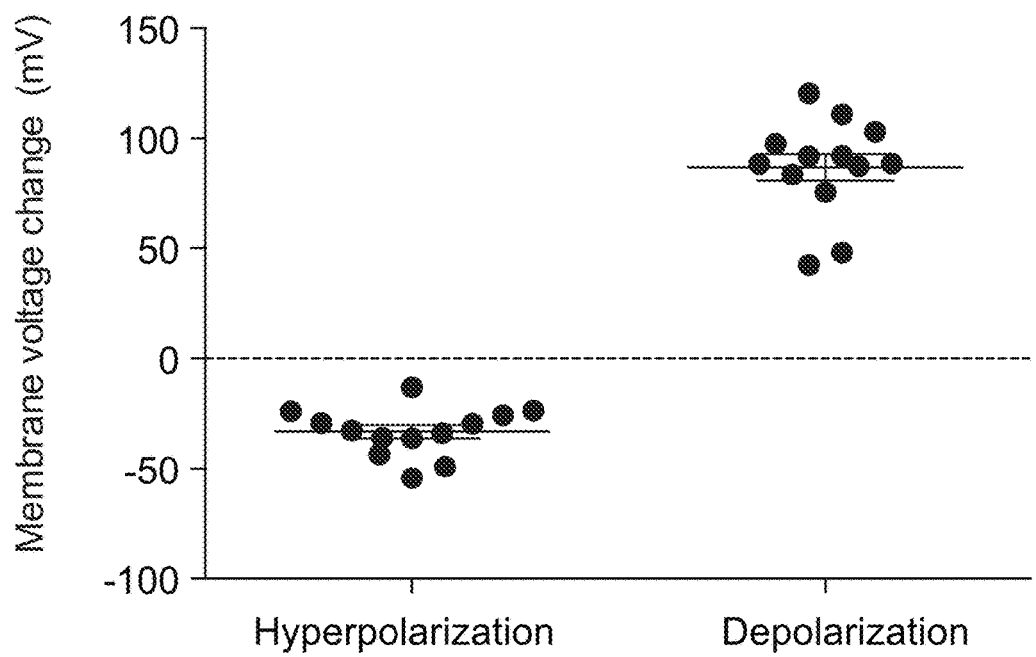
Figure 27H:
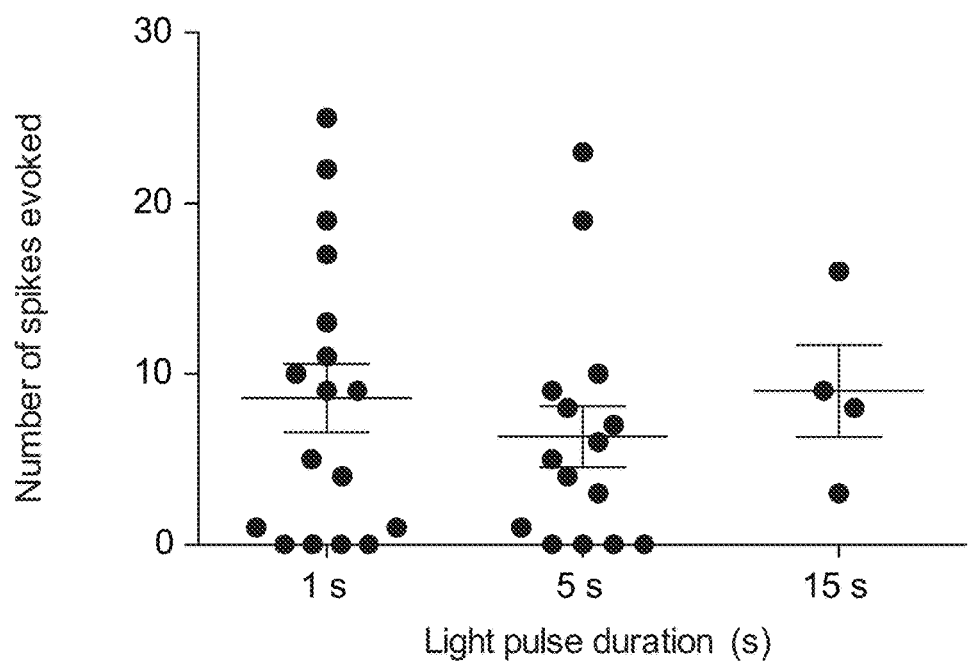

Current clamp recordings of membrane potential responses of TCO-expressing neurons revealed that 560 nm light evoked an initial hyperpolarization (−33 mV) of the membrane potential, followed by a subsequent depolarization (87 mV) (FIGS. 27F and 27G) which was sufficient to generate action potentials (~9 spikes) and persisted beyond the termination of the light pulse (FIGS. 27F and 27H). The extent of ASIC-mediated depolarization was proportional to the initial pump-mediated hyperpolarization (FIG. 31B), echoing the linear relationship between the inward and outward current components seen in voltage-clamp recordings. The light pulse duration did not significantly alter the magnitude of membrane potential change beyond 1 s light (FIG. 31).

FIGS. 27A-H. eArch3.0-ASIC2a (Champ) expression in hippocampal neurons. A Confocal images of yellow fluorescent protein (YFP) fluorescence from cultured hippocampal neurons expressing ASIC2a labeled with YFP in combination with the enhanced light-driven proton pump Arch3.0 at 40× magnification. Scale bars represent 30 µm. The construct expressed well under both the CamKIIα and human synapsin (hSyn) promoter. B Cartoon illustration of the two-component construct containing eArch (enhanced by trafficking sequence, TS) and ASIC2a, separated by a linker sequence and labeled with YFP. C Representative voltage clamp traces of the Champ current (eArch3.0-ASIC2a current in response to 1 s, 5 s and 15 s pulses of 560 nm light (timing of light pulse is indicated by horizontal line). Regions of the trace used to measure outward and inward current components and off-kinetics are indicated by dashed lines and arrows. D Magnitude of outward (mean+/−SEM=246+/−27 pA) and inward (−950+/−172 pA) components of the Champ current in response to a 1 s pulse of 560 nm light (n=21). E Relationship between the inward and outward components of the current response to 1 s pulse of 560 nm light (n=21). Linear regression analysis yields $R^2=0.33$, $p<0.01$ for difference of slope from zero. F Examples of a variety of membrane potential responses to 1 s pulses of 560 nm light (light pulse timing indicated by horizontal lines) from 4 different eArch-ASIC2a (Champ) expressing cells recorded in current clamp. Regions of the trace used to measure hyperpolarizing and depolarizing components of the response are indicated. G Magnitude of hyperpolarizing (eArch3.0-mediated, −33+/−3 mV) and depolarizing (ASIC2a-mediated, 87+/−6 mV) components of the light response (n=13) H Number of spikes evoked in response to 1 s (n=17), 5 s (n=15) and 15 s (n=4) light pulses.

FIGS. 28A-F. Variable presence of the ASIC2a component in cultured hippocampal neurons. A Example of an eArch3.0-ASIC2a current when the ASIC2a component is small (upper trace) and example of an ASIC negative current, in which only the eArch3.0 (outward) component is present, with no inward ASIC2a component (lower trace). B Magnitude of outward current components for ASIC negative cells (eArch3.0 component present only, n=23) and ASIC positive cells (both outward (eArch3.0) and inward (ASIC2a) components present, n=21). C Leak current for all ASIC negative (n=23) and ASIC positive (n=21) cells. D Resting membrane potential for all ASIC negative (n=11) and ASIC positive (n=13) cells. E Pipette (access) resistance for all ASIC negative (n=23) and ASIC positive (n=21) cells. F Membrane resistance for all ASIC negative (n=23) and ASIC positive (n=21) cells.

Figure 29B:
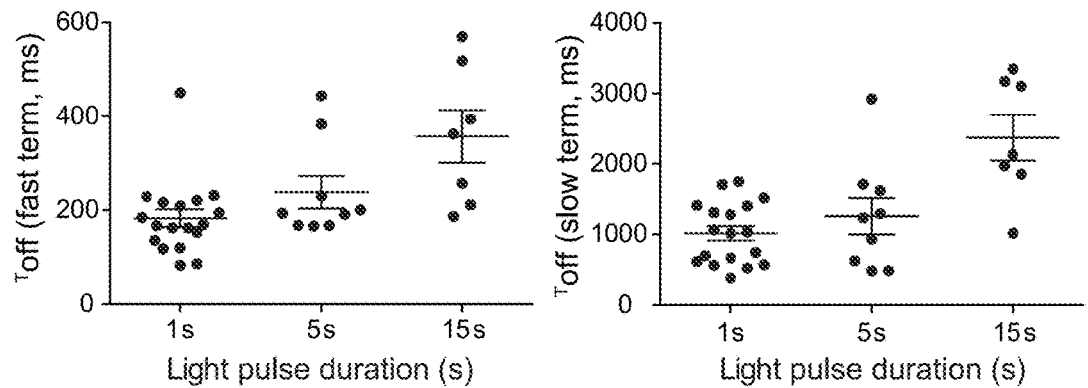
Figure 30A:
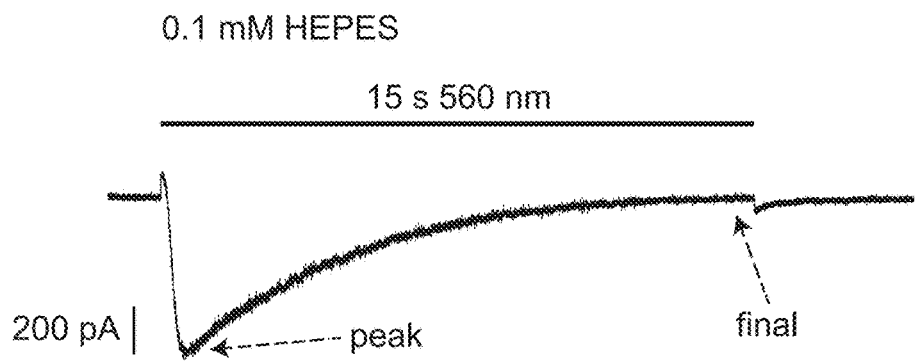
FIGS. 30A-F depict the effects of HEPES concentration in Tyrode's solution on Champ photocurrents
Figure 30B:
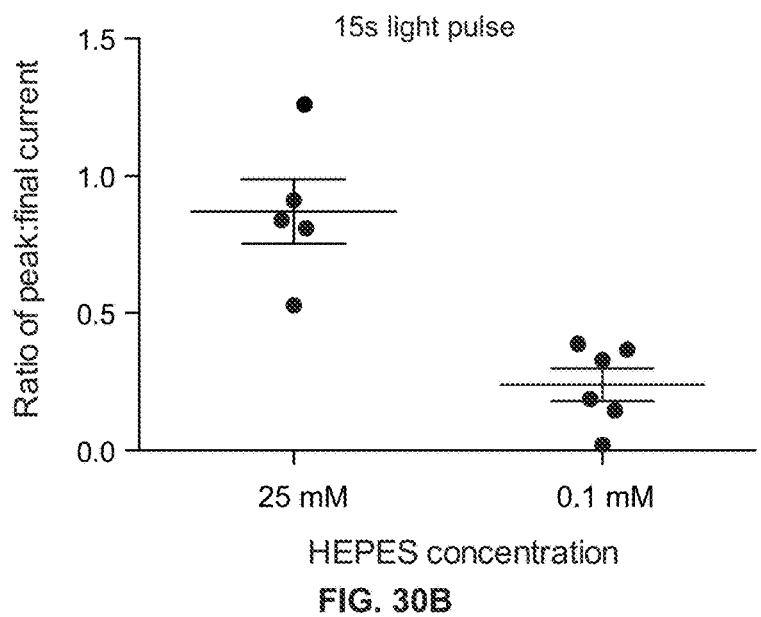
Figure 30C:
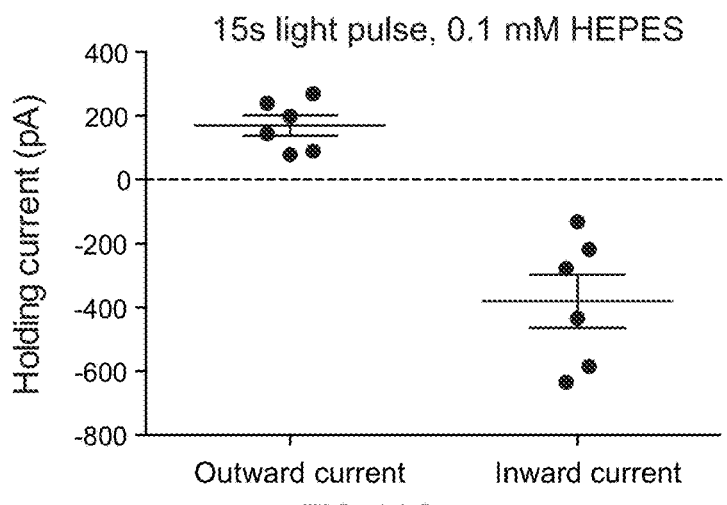
Figure 30D:
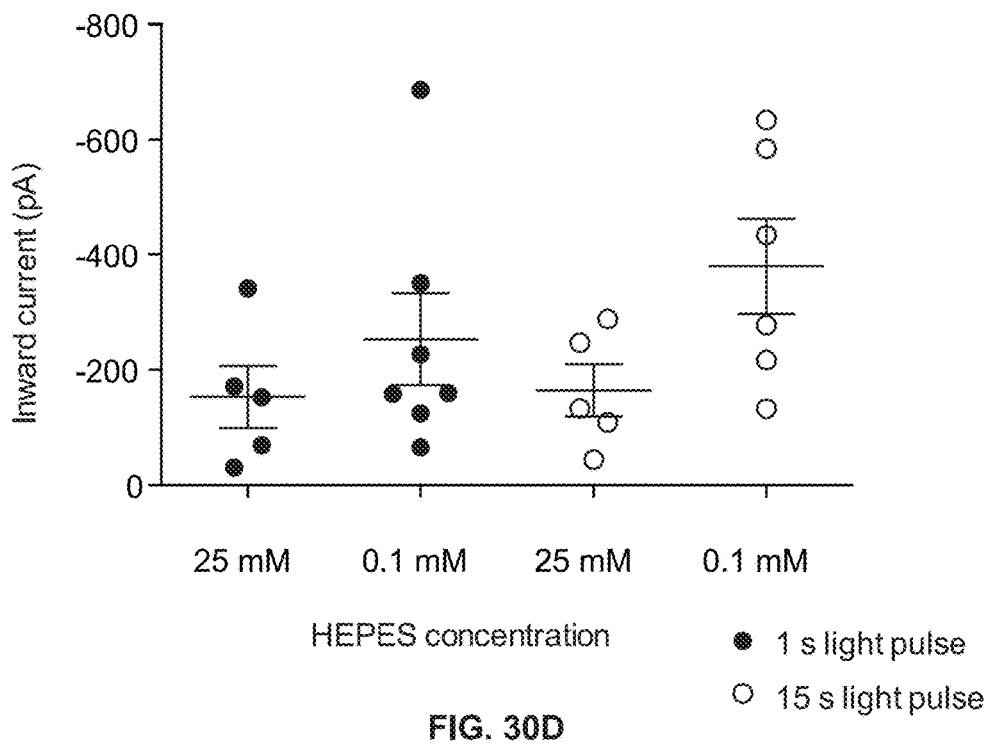
Figure 30E:
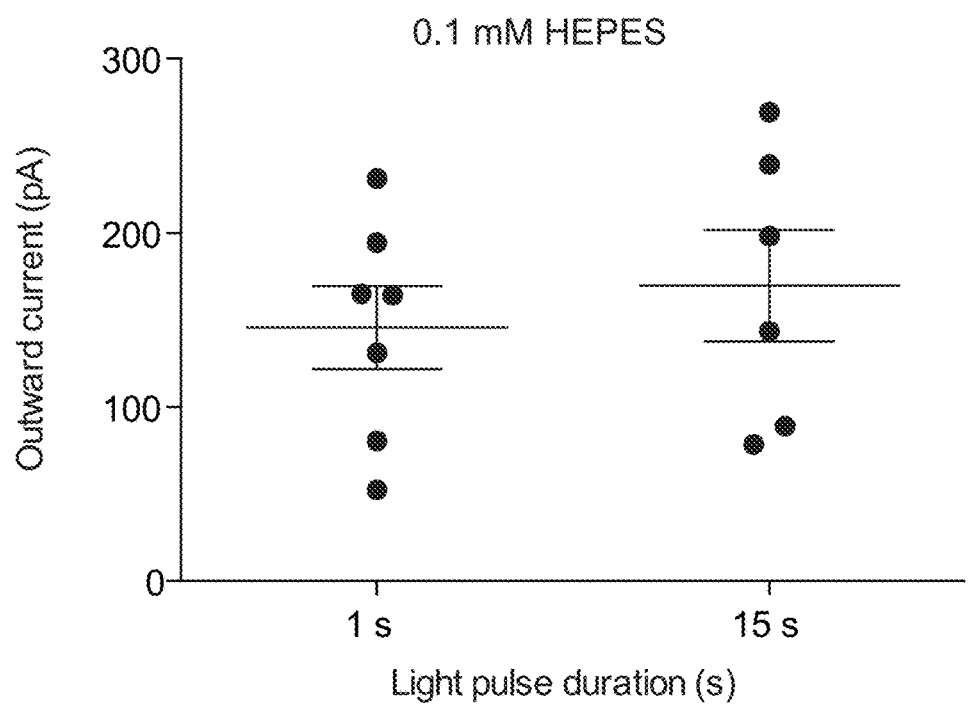
Figure 30F:
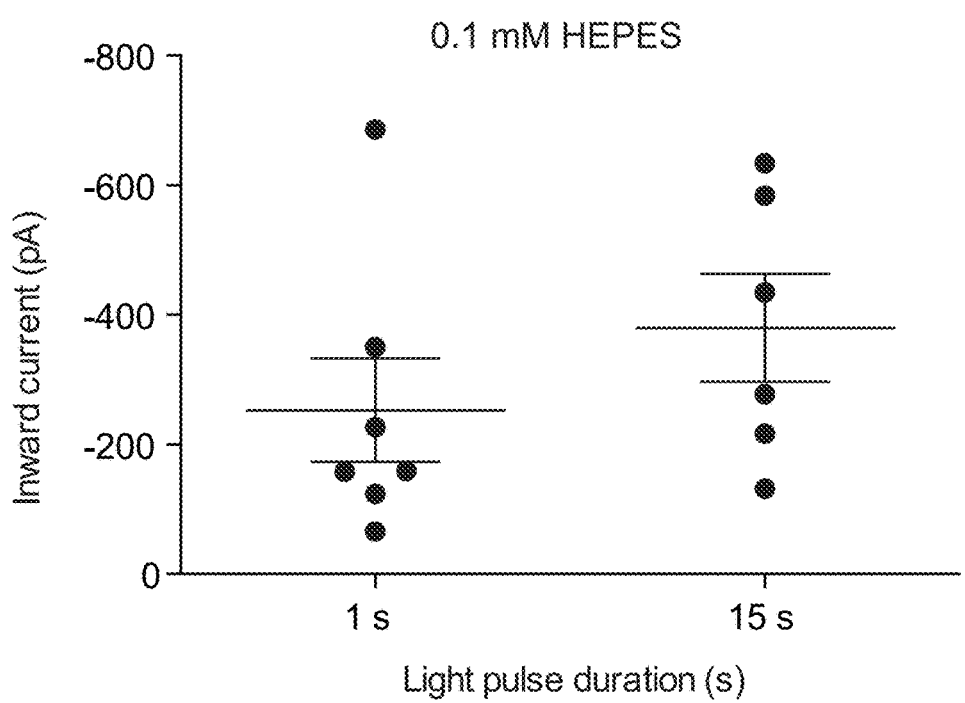

FIGS. 29A and 29B. Champ currents and kinetics in response to light pulses of increasing duration. A Magnitude of outward and inward current components in response to 1 s (n=21), 5 s (n=14) and 15 s (n=10) light pulses. B Off-kinetics of Champ current in response to 1 s (n=18), 5 s (n=9) and 15 s (n=7) light pulses. The off-response is fitted by an exponential with a fast and slow term.

FIGS. 30A-F. Champ currents in low HEPES Tyrode's solution. A Example of an eArch3.0-ASIC2a (Champ) photocurrent in 0.1 mM HEPES, illustrating the rapid decay of the peak current over the duration of the 15 s light pulse. Regions of the trace used for measurement of peak and final currents are indicated. B Ratio of the peak : final current for cells patched in 25 mM HEPES (n=5) and 0.1 mM HEPES (n=6) in response to 15 s light pulses. C Magnitude of inward and outward current components in response to 15 s light pulses in 0.1 mM HEPES (n=6).

D Inward current magnitude in 25 mM and 0.1 mM HEPES during 1 s and 15 s light pulses (n=5-7) under otherwise matched conditions. E & F Outward and inward membrane currents during 1 s and 15 s light pulses in 0.1 mM HEPES.

FIGS. 31A and 31B. Champ potentials in response to light pulses of increasing duration and relationship between Champ-mediated hyperpolarization and depolarization. A Magnitude of membrane hyperpolarization and depolarization in response to 1 s (n=13), 5 s, (n=10) and 15 s (n=4) light pulses. B Linear regression analysis for the relationship between Champ-mediated membrane hyperpolarization and depolarization yields $R^2=0.47$, $p<0.01$ for difference of slope from zero.

The impact of the proximity of the proton pump and ASIC components in generating the characteristic biphasic TCO response was explored. The molecular separation of the two components was systematically increased by interspersing a linker sequence of DNA of increasing length between the two genes: first, a short linker consisting of a 69 base pair trafficking sequence which closely fuses the two proteins (Champ3.0), second, a long (123 base pair) linker sequence that still tethers the two proteins but with a longer intervening peptide chain (Champ2.0), third, a ribosomal p2a skip sequence which cleaves the two proteins during translation (Szymczak-Workman et al. (Cold Spring Harbor Protocols 2012; 2012: 199-204); Prakash et al. (Nat Methods 2012; 9: 1171-1179)). Finally, the neurons were transfected simultaneously using two separate constructs (CamKII-Arch3.0-mCherry and CamKII-ASIC2a-YFP) co-expressing them but without generating a fusion construct. The 4 constructs and a CamKII-eArch3.0-YFP control were tested in a head-to-head comparison under matched experimental conditions (FIG. 32).

Figure 32A:
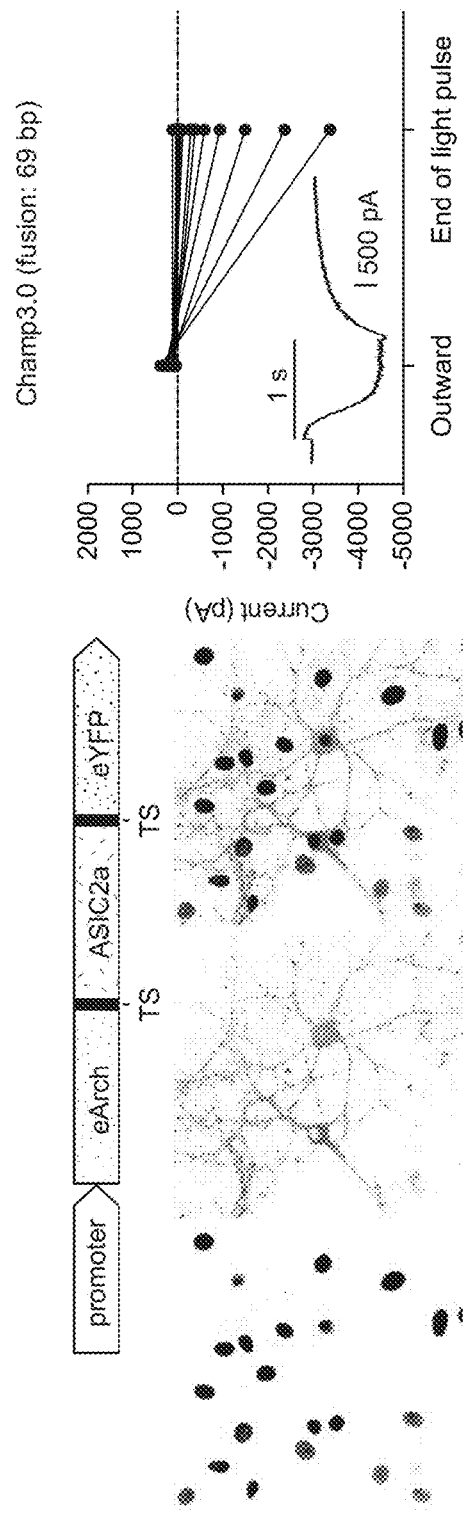
FIGS. 32A-D depict the effects of increasing molecular distance between components in a head-to-head comparison of four Champ constructs.
Figure 32B:
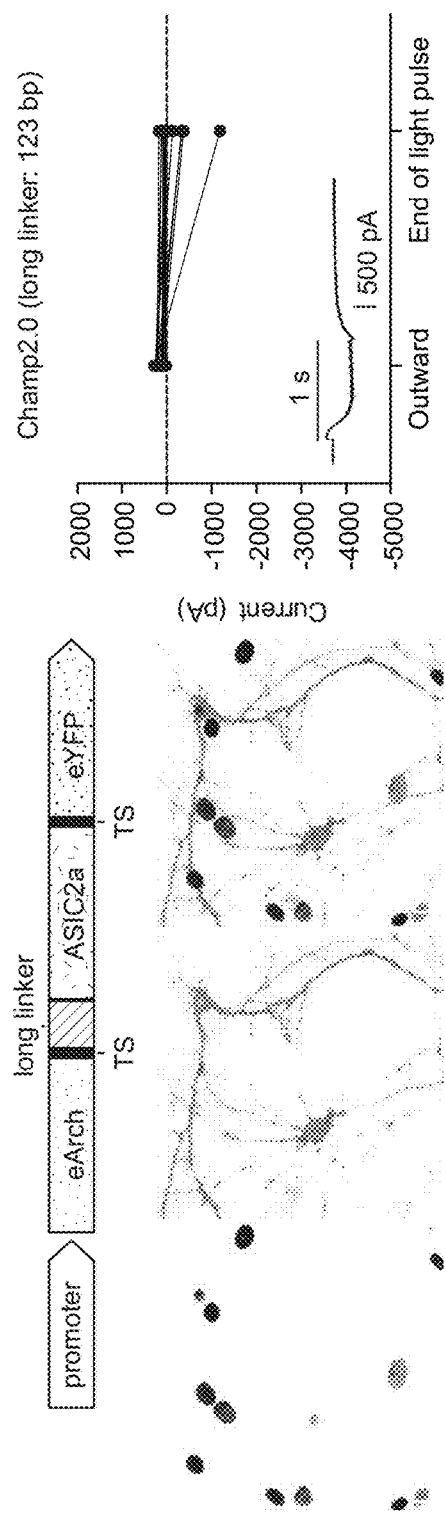
Figure 32C:
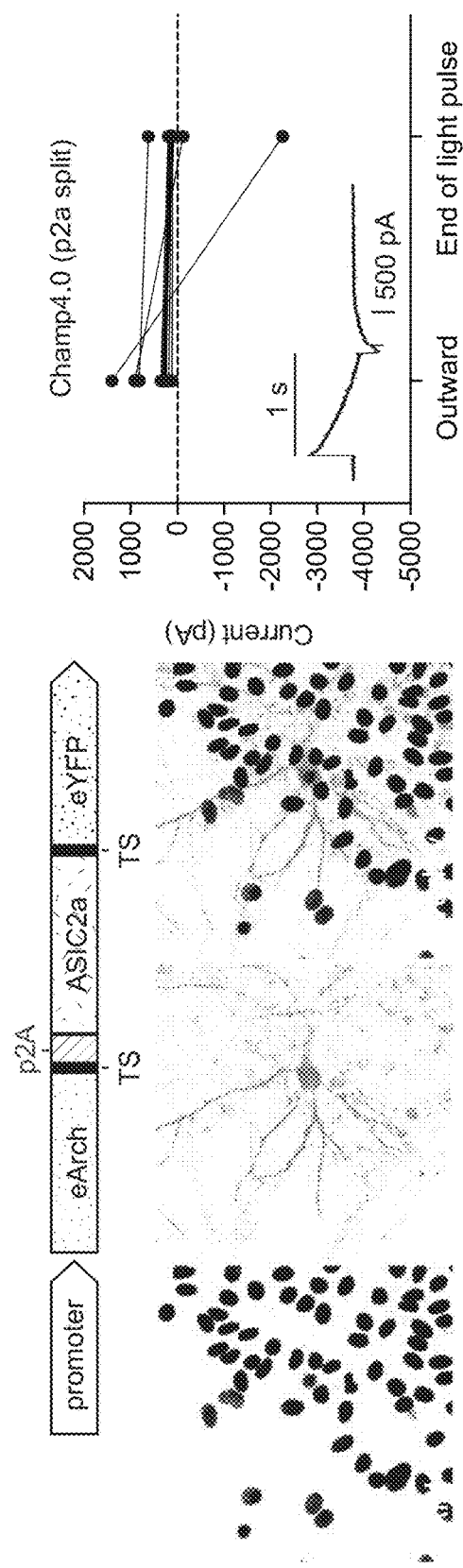
Figure 32D:
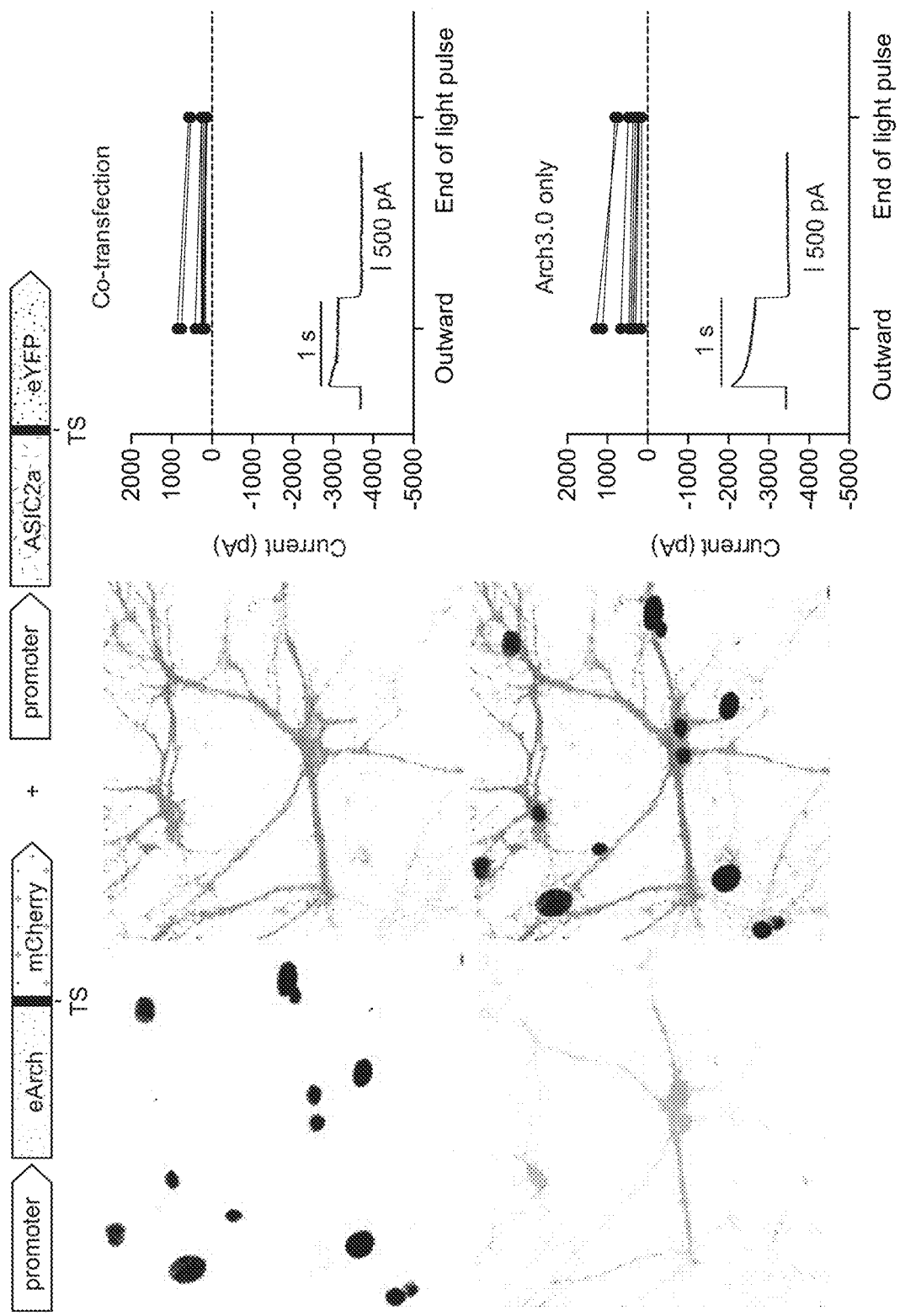
Figure 33A:
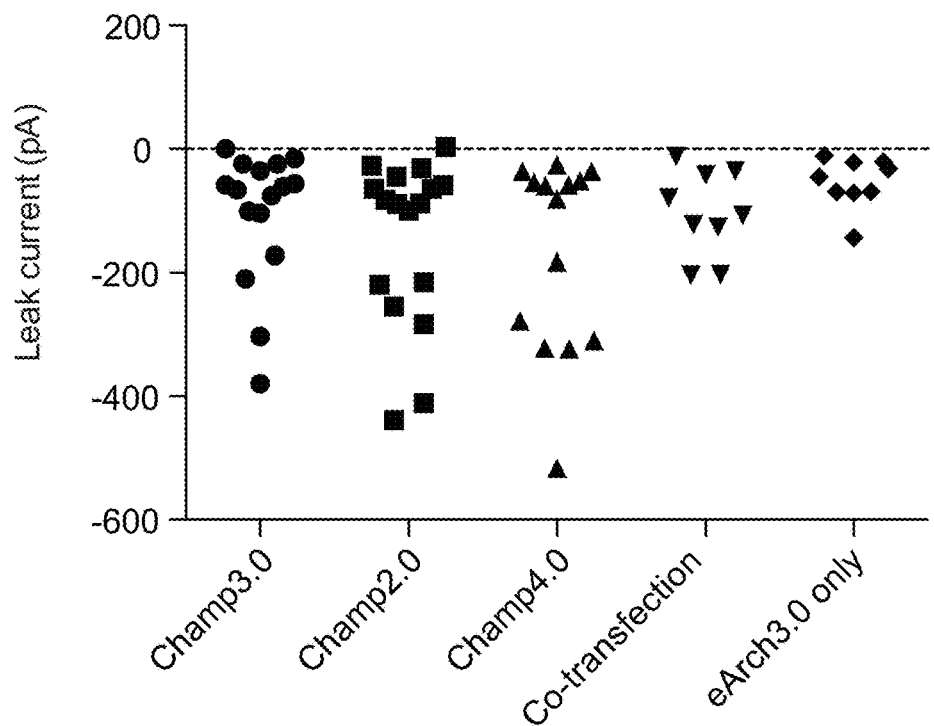
FIGS. 33A-D depict various measures of cell health across 4 different Champ constructs with increasing molecular separation between proton pump and ASIC.
Figure 33B:
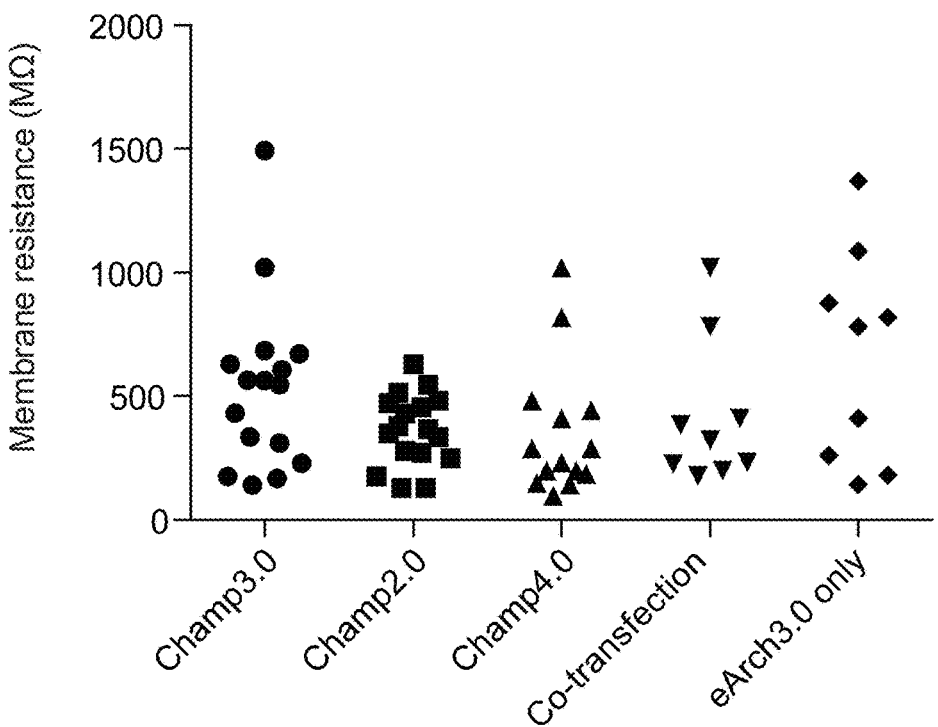
Figure 33C:
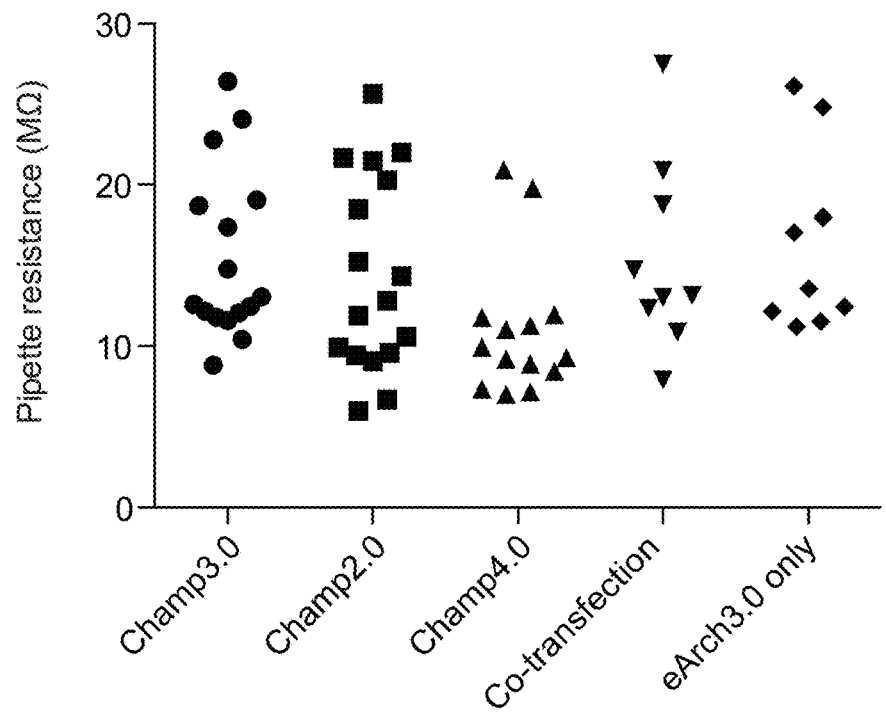
Figure 33D:
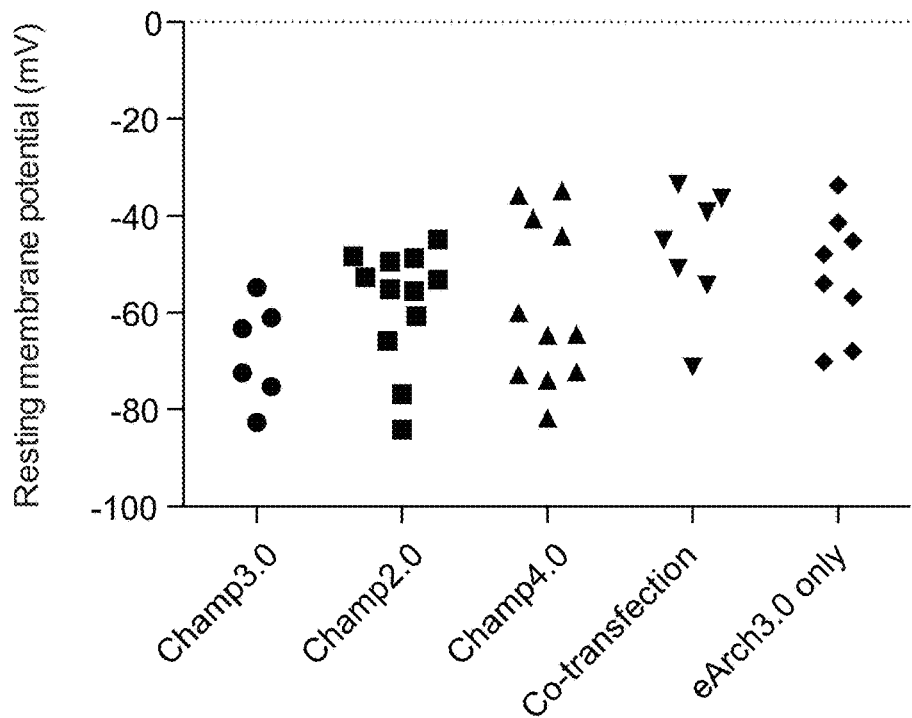

It was found that all four approaches resulted in good YFP expression, indicating successful expression of the ASIC construct. In the co-expression experiment good co-localization of mCherry fluorescence was observed, confirming expression of both constructs within single cells (FIGS. 32A-D). It was found that increasing the molecular separation between the constructs resulted in a lower probability of observing the inward current component of the TCO response, with the short linker sequence (TS) construct (Champ3.0) exhibiting the most reliable and largest inward ASIC-mediated currents at 0.1 mM buffer (mean inward current=−599 pA, mean outward current=150 pA) (FIG. 32A). We occasionally saw large ASIC currents with the separated (p2a split) construct; however these occurred less reliably (FIG. 32D). The co-expressed constructs generated eArch3.0 photocurrents (outward component) only, which were closer in magnitude (mean=377 pA) to the Arch3.0 control (mean=575 pA) than the fusion or p2a split constructs. The observed dependence of TCO function on the physical proximity of the proton pump and ASIC channel highlights the importance of nano-environment ion sensing in the interaction between the two components on the membrane.

FIGS. 32A-D. Head-to-head comparison of four Champ constructs: effect of increasing molecular distance. All electrophysiological recordings were performed in low HEPES (0.1 mM) Tyrode's solution. For each construct: a cartoon illustrates the structure of the two-component construct, confocal images demonstrate fluorescence expression in culture and graphs show the relative magnitude of the peak outward current and the current at the end of the light pulse. A more negative current at the end of the light pulse indicates a larger ASIC component. Insets: representative traces of the current responses to a 1 s pulse of 560 nm light for each two-component construct (timing of light pulse indicated by horizontal line). A Champ3.0: eArch3.0 and ASIC2a are fused by a short linker sequence consisting of a 69 base pair membrane trafficking signal (TS) (n=16). B Champ2.0: eArch3.0 and ASIC2a are fused by a longer (123 base pair) sequence (n=17). C Champ4.0: eArch3.0 and ASIC2a are separated during protein translation by the ribosomal skip sequence, p2A (n=14). D Co-transfection of eArch3.0 and ASIC2a: eArch3.0 is labeled with mCherry and ASIC2a is labeled with YFP to allow identification of both components in a single cell. Electrophysiological characterization of outward and end-of-light pulse currents for the co-transfected construct and an eArch3.0-only control (n=9 and n=9 respectively).

FIGS. 33A-D. Measures of cell health across 4 different Champ constructs with increasing molecular separation between proton pump and ASIC. There were no significant differences in any cell health measures across the 5 groups: Champ3.0, Champ2.0, Champ4.0, co-transfection of eArch3.0 and ASIC2a and eArch3.0 only (one-way ANOVA, F=1.56-2.27, p>0.05, n=9-17) A Leak current B Membrane resistance C Pipette resistance D Resting membrane potential.

REFERENCES

Anastassiou C A, Perin R, Markram H, Koch C. Nat Neurosci 2011; 14: 217-223. Ephaptic coupling of cortical neurons.

Arenkiel B R, Peca J, Davison I G, Feliciano C, Deisseroth K, Augustine G J, Ehlers M D, Feng G. Neuron 2007; 205-218. In vivo light-induced activation of neural circuitry in transgenic mice expressing channelrhodopsin-2.

Askwith C C, Wemmie J A, Price M P, Rokhlina T, Welsh M J. J Biol Chem 2004; 279: 18296-18305. Acid-sensing ion channel 2 (ASIC2) modulates ASIC $H^+$-activated currents in hippocampal neurons.

Babini E, Paukert M, Geisler H S, Grunder S. J Biol Chem 2002; 277: 41597-603. Alternative splicing and interaction with di- and polyvalent cations control the dynamic range of acid-sensing ion channell (ASIC1).

Babinski K, Catarsi S, Biagini G, Seguela P. J Biol Chem 2000; 275: 28519-28525. Mammalian ASIC2a and ASIC3 subunits co-assemble into heteromeric proton-gated channels sensitive to $Gd^{3+}$.

Baburin I, Beyl S, Hering S. Pflügers Archiv 2006; 453.1: 117-123. Automated fast perfusion of *Xenopus* oocytes for drug screening.

Bamann C, Gueta R, Kleinlogel S, Nagel G, Bamberg E. Biochemistry 2010; 49: 267-278. Structural guidance of the photocycle of channelrhodopsin-2 by an interhelical hydrogen bond.

Baron A, Waldmann R, Lazdunski M. J Physiol 2002; 539: 485-494. ASIC-like, proton-activated currents in rat hippocampal neurons.

Bassilana F, Champigny G, Waldmann R, de Weille J R, Heurteaux C, Lazdunski M. J Biol Chem 1997; 272: 28819-28822. The acid-sensitive ionic channel subunit ASIC and the mammalian degenerin MDEG form a heteromultumeric $H^+$-gated $Na^+$ channel with novel properties.

Baylor D A & Nicholls J G. J Physiol 1969; 203: 555-569. Changes in extracellular potassium concentration produced by neuronal activity in the central nervous system of the leech.

Berndt A, Yizhar O, Gunaydin L A, Hegemann P, Deisseroth K. Nat Neurosci 2009; 12: 229-234. Bi-stable neural state switches.

Bevan S, Yeats J. J Physiol 1991; 433: 145-161. Protons activate a cation conductance in a sub-population of rat dorsal root ganglion neurones.

Blanc G, Agarkova I, Grimwood J, Kuo A, Brueggeman A, Dunigan D D, Gurnon J, Ladunga I, Linguist E, Lucas S, Pangilinan J, Proschold T, Salamov A, Schmutz J, Weeks D, Yamada T, Lomsadze A, Borodovsky M, Claverie J M, Grigoriev I V, Van Etten J L. Genome Biology 2012; 13: R39. http://genomebiology.com/2012/15/5/R39

Bolshakov K V, Essin K V, Buldakova S L, Dorofeeva N A, Skatchkov S N, Eaton M J, Tikhonov D B, Magazanik L G. Neuroscience 2002; 110: 723-730. Characterization of acid-sensitive ion channels in freshly isolated rat brain neurons.

Bruun S, Naumann H, Kuhlmann U, Schulz C, Stehfest K, Hegemann P, Hildebrandt P. FEBS Lett 2011; 585: 3998-4001. The chromophore structure of the long-lived intermediate of the C128T channelrhodopsin-2 variant.

Chen C C, England S, Akopian A, Wood J N. Proc Natl Acad Sci USA 1998; 95: 10240-10245. A sensory neuron-specific, proton-gated ion channel.

Chesler M & Kalia K. TINS 1992; 15: 396-402. Modulation of pH by neuronal activity. Chow B Y, Han X, Dobry A S, Qian X, Chuong A S, Li M, Henninger M A, Belfort G M, Lin Y, Monahan P E, Boyden E S. Nature 2010; 463: 98-102. High-performance genetically targetable optical neural silencing by light-driven proton pumps.

Deval E, Gasull X, Noel J, Salinas M, Baron A, Diochot S, Lingueglia E. Pharmacol Ther 2010; 128: 549-558. Acid-sensing ion channels (ASICs): pharmacology and implication in pain.

Ferenczi E, Deisseroth K. Nat Neurosci 2012; 15: 1058-1060. When the electricity (and the lights) go out: transient changes in excitability.

Goldin, A L. 2006. Expression of Ion Channels in *Xenopus* Oocytes. Expression and Analysis of Recombinant Ion Channels: From Structural Studies to Pharmacological Screening.

Gutman M, Nachliel E, Friedman R. Biochim Biophys Acta 2006 1757: 931-41. The mechanism of proton transfer between adjacent sites on the molecular surface.

Gradinaru V, Thompson K R, Deisseroth K. Brain Cell Biol 2008; 36:129-39. eNpHR: a Natronomonas halorhodopsin enhanced for optogenetic applications.

Gradinaru V, Zhang F, Ramakrishnan C, Mattis J, Prakash R, Diester I, Goshen I, Thompson K R, Deisseroth K. Cell 2010; 141: 154-165. Molecular and cellular approaches for diversifying and extending optogenetics.

Gruender S, Chen X. Int J Physiol Pathophysiol Pharmacol 2010; 2: 73-94. Structure, function and pharmacology of acid-sensing ion channels (ASICs): focus on ASIC1a.

Heberle J, Riesle J, Thiedemann G, Oesterhelt D, Dencher N A. Nature 1994; 370: 379-382. Proton migration along the membrane surface and retarded surface to bulk transfer.

Hodgkin A L & Huxley A F. J Physiol 1952; 117, 500-544. A quantitative description of membrane current and its application to conduction and excitation in nerve.

Hodgkin A L & Katz B. J Physiol 1949; 108: 37-77. The effect of sodium ions on the electrical activity of the giant axon of the squid.

Jasti J, Furukawa H, Gonzales E B, Gouaux E. Nature 2007; 449: 316-323. Structure of acid-sensing ion channel 1 at 1.9 A resolution and low pH.

Jordt S E, Tominaga M, Julius D. Proc Natl Acad Sci USA 2000; 97: 8134-8139. Acid potentiation of the capsaicin receptor determined by a key extracellular site.

Katz B, Schmitt O H. J Physiol 1940; 97: 471-488. Electric interaction between two adjacent nerve fibers.

Krishtal O. TINS 2003; 26: 477-483. The ASICs: signaling molecules? modulators?

Krishtal O A, Osipchuk Yu V, Shelest T N, Smirnoff S V. Brain Res 1987; 436: 352-356. Rapid extracellular pH transients related to synaptic transmission in rat hippocampal slices.

Krishtal O A, Pidoplichko V I. Neuroscience 1980; 5: 2325-2327. A receptor for protons in the nerve cell membrane.

Krishtal O A, Pidoplichko V I. Neurosci Lett 1981; 6: 2599-2601. A 'receptor' for protons in small neurons of trigeminal ganglia: possible role in nociception.

Lindemann B. Nature 2001; 413: 219-225. Receptors and transduction in taste.

Liske H, Xiang Q, Anikeeva P, Deisseroth K, Delp S. Optical control of neuronal excitation and inhibition using a single opsin protein. Scientific Reports 2013; 3: 3110.

Mattis J, Tye K M, Ferenczi E A, Ramakrishnan C, O'Shea D J, Prakash R, Gunaydin L A, Hyun M, Fenno L E, Gradinaru V, Yizhar O, Deisseroth K. Nat Methods 2011; 9: 159-72. Principles for applying optogenetic tools derived from direct comparative analysis of microbial opsins.

Nagel G, Szellas T, Huhn W, Kateriya S, Adeishvili N, Berthold P, Ollig D, Hegemann P, Bamberg E. Proc Natl Acad Sci USA 2003; 100: 13940-13945.

Paukert M, Chen X, Polleichtner G, Schindelin H, Grunder S. J Biol Chem 2008; 283: 572-581. Candidate amino acids involved in $H^+$ gating of acid-sensing ion channel 1a.

Poolos N P, Mauk M D, Kocsis J D. J Neurophysiol 1987; 58: 404-416. Activity-evoked increases in extracellular potassium modulate presynaptic excitability in the CA1 region of the hippocampus.

Prakash R, Yizhar O, Grewe B, Ramakrishnan C, Wang N, Goshen I, Packer A M, Peterka D S, Yuste R, Schnitzer M J, Deisseroth K. Nat Methods 2012; 9: 1171-1179. Two-photon optogenetic toolbox for fast inhibition, excitation and bistable modulation.

Raimondo J V, Kay L, Ellender T J, Akerman C J. Nat Neurosci 2012; 15: 1102-4. Optogenetic silencing strategies differ in their effects on inhibitory synaptic transmission.

Ritter E, Piwowarski P, Hegemann P, Barti F J. J Biol Chem 2013; 288: 10451-10458. Light-dark adaptation of channelrhodopsin C128T mutant.

Schoenenberger P, Gerosa D, Oertner T G. PLos One 2009; 4: e8185. Temporal control of immediate early gene induction by light.

Sherwood T W, Lee K G, Gormley M G, Askwith C C. J Neurosci 2011; 31: 9723-9734. Heteromeric acid-sensing ion channels (ASICs) composed of ASIC2b and ASIC1a display novel channel properties and contribute to acidosis-induced neuronal death.

Stehfest K, Hegemann P. Chemphyschem 2010; 11: 1120-1126. Evolution of the channelrhodopsin photocycle model.

Shuba Y M, Dietrich C J, Oermann E, Cleemann L, Morad M. Cell Calcium 2008; 44: 220-229. Local extracellular acidification caused by $Ca^{2+}$-dependent exocytosis in PC12 cells.

Szymczak-Workman A L, Vignali K M, Vignali D A. Cold Spring Harb Protoc 2012; 2012: 199-204. Design and construction of 2A peptide-linked multicistronic vectors.

Torborg C L, Berg A P, Jeffries B W, Bayliss D A, McBain C J. J Neurosci 2006; 26: 7362-7367. TASK-like conductances are present within hippocampal CA1 stratum oriens interneuron subpopulations.

Towne C, Montgomery K L, Iyer S M, Deisseroth K, Delp S L. Optogenetic Control of Targeted Peripheral Axons in Freely Moving Animals. PLoS ONE 2013; 8: e72691

Waldmann R, Champigny G, Bassilana F, Heurteaux C, Lazdunski M. A proton-gated cation channel involved in acid-sensing. Nature 1997; 386: 173-177.

Wang H, Sugiyama Y, Hikima T, Sugano E, Tomita H, Takahashi T, Ishizuka T, Yawo H. Molecular determinants differentiating photocurrent properties of two channelrhodopsins from chlamydomonas. J Biol Chem 2009; 284: 5685-96.

Wang T-M, Holzhausen L C, Kramer R H. Imaging an optogenetic pH sensor reveals that protons mediate lateral inhibition in the retina. Nature Neuroscience 2014; 17: 262-268.

Welch J M, Simon S A, Reinhart P H. Proc Natl Acad Sci USA 2000; 97: 13889-13894. The activation mechanism of rat vanilloid receptor 1 by capsaicin involves the pore domain and differs from the activation by either acid or heat.

Wemmie J A, Taugher R J, Kreple C J. Nat Rev Neurosci 2013; 14: 461-471. Acid sensing ion channels in pain and disease.

Weng J Y, Lin Y C, Lien C C. J Neurosci 2010; 30: 6548-58. Cell type-specific expression of acid-sensing ion channels in hippocampal interneurons.

Xiong Z Q, Stringer J L. J Neurophysiol 2000; 83: 3519-3524. Extracellular pH responses in CA1 and the dentate gyrus during electrical stimulation, seizure discharges, and spreading depression.

Yizhar O, Fenno L E, Davidson T J, Mogri M, Deisseroth K. Neuron 2011; 72: 9-34. Optogenetics in Neural Systems.

Yermolaieva O, Leonard A S, Schnizler M K, Abboud F M, Welsh M J. Proc Natl Acad Sci USA 2004; 101: 6752-6757. Extracellular acidosis increases neuronal cell calcium by activating acid-sensing ion channel 1a.

Yizhar O, Fenno L E, Prigge M, Schneider F, Davidson T J, O'Shea D J, Sohal V S, Goshen I, Finkelstein J, Paz J T, Stehfest K, Fudim R, Ramakrishnan C, Huguenard J R, Hegemann P, Deisseroth K. Nature 2011; 477: 171-178. Neocortical excitation/inhibition balance in information processing and social dysfunction.

Zha X M, Wemmie J A, Green S H, Welsh M J. Proc Natl Acad Sci USA 2006; 103: 16556-16561. Acid-sensing ion channel 1a is a postsynaptic proton receptor that affects the density of dendritic spines.

Zhang F, Vierock J, Yizhar O, Fenno L E, Tsunoda S, Kianianmomeni A, Prigge M, Berndt A, Cushman J, Polle J, Magnuson J, Hegemann P, Deisseroth K. Cell 2011; 147: 1446-1457. The microbial opsin family of optogenetic tools.

Zhang F, Wang L P, Brauner M, Liewald J F, Kay K, Watzke N, Wood P G, Bamberg E, Nagel G, Gottschalk A, Deisseroth K. Nature 2007; 446: 633-639. Multimodal fast optical interrogation of neural circuitry.

Zhang P, Canessa C M. J Gen Physiol 2002; 120: 553-566. Single channel properties of rat acid-sensitive ion channel-1alpha, -2a, and -3 expressed in *Xenopus* oocytes.

Ziemann A E, Schnizler M K, Albert G W, Severson M A, Howard III M A, Welsh M J, Wemmie J A. Nat Neurosci 2008; 11: 816-822. Seizure termination by acidosis depends on ASIC1a.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for modulating the membrane potential of a mammalian cell in response to light, the method comprising exposing the cell to the light, wherein the cell is genetically modified with a nucleic acid comprising a nucleotide sequence encoding a fusion polypeptide comprising:
   a) a light-activated proton pump protein comprising an amino acid sequence having at least 90% homology to one of the amino acid sequences of SEQ ID NOs: 1, 4, 5, and 6; and
   b) an acid-sensitive ion channel, wherein the acid-sensitive ion channel comprises an amino acid sequence having at least 80% homology to the ASIC2a polypeptide amino acid sequence of SEQ ID NO: 19, wherein the nucleotide sequence is operably linked to a promoter, and wherein exposure of the cell to the light activates the light-activated proton pump protein, wherein activation of the light-activated proton pump protein activates the acid-sensitive ion channel and thereby modulates the membrane potential of the cell.

2. The method of claim 1, wherein the acid-sensitive ion channel amino acid sequence has at least 90% homology to the amino acid sequence of SEQ ID NO: 19.

3. The method of claim 1, wherein the light-activated proton pump protein amino acid sequence has at least 95% homology to the amino acid sequence of any one of SEQ ID NOs: 1, 4, 5, and 6, 16, and 62.

4. The method of claim 1, wherein the fusion polypeptide comprises a membrane trafficking signal.

5. The method of claim 4, wherein the membrane trafficking signal comprises the amino acid sequence KSRITSEGEYIPLDQIDINV (SEQ ID NO:37).

6. The method of claim 1, wherein the promoter is a neuron-specific promoter.

7. The method of claim 1, wherein the cell is a neuron.

8. The method of claim 1, wherein the fusion polypeptide comprises an endoplasmic reticulum (ER) export signal.

9. The method of claim 8, wherein the ER export signal comprises the amino acid sequence FCYENEV (SEQ ID NO:47).

10. The method of claim 1, wherein the light-activated proton pump protein amino acid sequence has at least 95% homology to the amino acid sequence of SEQ ID NO:1.

11. The method of claim 1, wherein the light-activated proton pump protein amino acid sequence has at least 95% homology to the amino acid sequence of SEQ ID NO:4.

12. The method of claim 1, wherein the light-activated proton pump protein amino acid sequence has at least 95% homology to the amino acid sequence of SEQ ID NO:5.

13. The method of claim 1, wherein the light-activated proton pump protein amino acid sequence has at least 95% homology to the amino acid sequence of SEQ ID NO:6.

14. The method of claim 1, wherein the acid-sensitive ion channel amino acid sequence has at least 95% homology to the amino acid sequence of SEQ ID NO:19.

15. The method of claim 1, wherein the fusion polypeptide amino acid sequence has at least 95% homology to the amino acid sequence of SEQ ID NO:31.

16. The method of claim 1, wherein the fusion polypeptide amino acid sequence has at least 95% homology to the amino acid sequence of SEQ ID NO:32.

17. The method of claim 1, wherein the fusion polypeptide amino acid sequence has at least 95% homology to the amino acid sequence of SEQ ID NO:33.

18. The method of claim 1, wherein the fusion polypeptide amino acid sequence has at least 95% homology to the amino acid sequence of SEQ ID NO:34.

\* \* \* \* \*

SEQUENCE LISTING

```
<160> NUMBER OF SEQ ID NOS: 64

<210> SEQ ID NO 1
<211> LENGTH: 258
<212> TYPE: PRT
<213> ORGANISM: Halorubrum sodomense

<400> SEQUENCE: 1

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60
```

```
Ala Ala Tyr Leu Ser Met Phe Phe Gly Ile Gly Leu Thr Glu Val Thr
 65                  70                  75                  80

Val Gly Gly Glu Met Leu Asp Ile Tyr Tyr Ala Arg Tyr Ala Asp Trp
                 85                  90                  95

Leu Phe Thr Thr Pro Leu Leu Leu Asp Leu Ala Leu Leu Ala Lys
                100                 105                 110

Val Asp Arg Val Thr Ile Gly Thr Leu Val Gly Val Asp Ala Leu Met
                115                 120                 125

Ile Val Thr Gly Leu Ile Gly Ala Leu Ser His Thr Ala Ile Ala Arg
                130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
                180                 185                 190

Thr Ala Tyr Pro Ile Leu Trp Ile Ile Gly Thr Glu Gly Ala Gly Val
                195                 200                 205

Val Gly Leu Gly Ile Glu Thr Leu Leu Phe Met Val Leu Asp Val Thr
                210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 2
<211> LENGTH: 534
<212> TYPE: PRT
<213> ORGANISM: Artificial sequence
<220> FEATURE:
<223> OTHER INFORMATION: synthetic amino acid sequence

<400> SEQUENCE: 2

Met Asp Pro Ile Ala Leu Gln Ala Gly Tyr Asp Leu Leu Gly Asp Gly
  1               5                  10                  15

Arg Pro Glu Thr Leu Trp Leu Gly Ile Gly Thr Leu Leu Met Leu Ile
                 20                  25                  30

Gly Thr Phe Tyr Phe Leu Val Arg Gly Trp Gly Val Thr Asp Lys Asp
                 35                  40                  45

Ala Arg Glu Tyr Tyr Ala Val Thr Ile Leu Val Pro Gly Ile Ala Ser
 50                  55                  60

Ala Ala Tyr Leu Ser Met Phe Phe Gly Ile Gly Leu Thr Glu Val Thr
 65                  70                  75                  80

Val Gly Gly Glu Met Leu Asp Ile Tyr Tyr Ala Arg Tyr Ala Asp Trp
                 85                  90                  95

Leu Phe Thr Thr Pro Leu Leu Leu Asp Leu Ala Leu Leu Ala Lys
                100                 105                 110

Val Asp Arg Val Thr Ile Gly Thr Leu Val Gly Val Asp Ala Leu Met
                115                 120                 125

Ile Val Thr Gly Leu Ile Gly Ala Leu Ser His Thr Ala Ile Ala Arg
                130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
```

```
            165                 170                 175
Val Ala Ser Thr Phe Asn Thr Leu Thr Ala Leu Val Leu Val Leu Trp
        180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Arg Pro Val Ala Val Ser Lys Ala Ala Ala Lys Ser Arg
            260                 265                 270

Ile Thr Ser Glu Gly Glu Tyr Ile Pro Leu Asp Gln Ile Asp Ile Asn
        275                 280                 285

Val Val Ser Lys Gly Glu Glu Leu Phe Thr Gly Val Val Pro Ile Leu
    290                 295                 300

Val Glu Leu Asp Gly Asp Val Asn Gly His Lys Phe Ser Val Ser Gly
305                 310                 315                 320

Glu Gly Glu Gly Asp Ala Thr Tyr Gly Lys Leu Thr Leu Lys Phe Ile
                325                 330                 335

Cys Thr Thr Gly Lys Leu Pro Val Pro Trp Pro Thr Leu Val Thr Thr
            340                 345                 350

Phe Gly Tyr Gly Leu Gln Cys Phe Ala Arg Tyr Pro Asp His Met Lys
        355                 360                 365

Gln His Asp Phe Phe Lys Ser Ala Met Pro Glu Gly Tyr Val Gln Glu
    370                 375                 380

Arg Thr Ile Phe Phe Lys Asp Asp Gly Asn Tyr Lys Thr Arg Ala Glu
385                 390                 395                 400

Val Lys Phe Glu Gly Asp Thr Leu Val Asn Arg Ile Glu Leu Lys Gly
                405                 410                 415

Ile Asp Phe Lys Glu Asp Gly Asn Ile Leu Gly His Lys Leu Glu Tyr
            420                 425                 430

Asn Tyr Asn Ser His Asn Val Tyr Ile Met Ala Asp Lys Gln Lys Asn
        435                 440                 445

Gly Ile Lys Val Asn Phe Lys Ile Arg His Asn Ile Glu Asp Gly Ser
    450                 455                 460

Val Gln Leu Ala Asp His Tyr Gln Gln Asn Thr Pro Ile Gly Asp Gly
465                 470                 475                 480

Pro Val Leu Leu Pro Asp Asn His Tyr Leu Ser Tyr Gln Ser Ala Leu
                485                 490                 495

Ser Lys Asp Pro Asn Glu Lys Arg Asp His Met Val Leu Leu Glu Phe
            500                 505                 510

Val Thr Ala Ala Gly Ile Thr Leu Gly Met Asp Glu Leu Tyr Lys Phe
        515                 520                 525

Cys Tyr Glu Asn Glu Val
    530
```

<210> SEQ ID NO 3
<211> LENGTH: 248
<212> TYPE: PRT
<213> ORGANISM: Artificial sequence
<220> FEATURE:
<223> OTHER INFORMATION: synthetic amino acid sequence -continued

```
<400> SEQUENCE: 3

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Met Leu Ile
            20                  25                  30

Gly Thr Phe Tyr Phe Ile Val Lys Gly Trp Gly Val Thr Asp Lys Glu
                35                  40                  45

Ala Arg Glu Tyr Tyr Ser Ile Thr Ile Leu Val Pro Gly Ile Ala Ser
            50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
                85                  90                  95

Leu Phe Thr Thr Pro Leu Leu Leu Asp Leu Ala Leu Leu Ala Lys
            100                 105                 110

Val Asp Arg Val Ser Ile Gly Thr Leu Val Gly Val Asp Ala Leu Met
            115                 120                 125

Ile Val Thr Gly Leu Ile Gly Ala Leu Ser His Thr Pro Leu Ala Arg
130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro
                245

<210> SEQ ID NO 4
<211> LENGTH: 223
<212> TYPE: PRT
<213> ORGANISM: Artificial sequence
<220> FEATURE:
<223> OTHER INFORMATION: synthetic amino acid sequence

<400> SEQUENCE: 4

Ala Ser Ser Phe Gly Lys Ala Leu Leu Glu Phe Val Phe Ile Val Phe
1               5                   10                  15

Ala Cys Ile Thr Leu Leu Leu Gly Ile Asn Ala Ala Lys Ser Lys Ala
                20                  25                  30

Ala Ser Arg Val Leu Phe Pro Ala Thr Phe Val Thr Gly Ile Ala Ser
            35                  40                  45

Ile Ala Tyr Phe Ser Met Ala Ser Gly Gly Trp Val Ile Ala Pro
50                  55                  60

Asp Cys Arg Gln Leu Phe Val Ala Arg Tyr Leu Asp Trp Leu Ile Thr
65                  70                  75                  80

Thr Pro Leu Leu Leu Ile Asp Leu Gly Leu Val Ala Gly Val Ser Arg
            85                  90                  95

Trp Asp Ile Met Ala Leu Cys Leu Ser Asp Val Leu Met Ile Ala Thr
```

```
              100                 105                 110
Gly Ala Phe Gly Ser Leu Thr Val Gly Asn Val Lys Trp Val Trp Trp
            115                 120                 125

Phe Phe Gly Met Cys Trp Phe Leu His Ile Ile Phe Ala Leu Gly Lys
            130                 135                 140

Ser Trp Ala Glu Ala Ala Lys Ala Lys Gly Gly Asp Ser Ala Ser Val
145                 150                 155                 160

Tyr Ser Lys Ile Ala Gly Ile Thr Val Ile Thr Trp Phe Cys Tyr Pro
                    165                 170                 175

Val Val Trp Val Phe Ala Glu Gly Phe Gly Asn Phe Ser Val Thr Phe
                180                 185                 190

Glu Val Leu Ile Tyr Gly Val Leu Asp Val Ile Ser Lys Ala Val Phe
            195                 200                 205

Gly Leu Ile Leu Met Ser Gly Ala Ala Thr Gly Tyr Glu Ser Ile
        210                 215                 220

<210> SEQ ID NO 5
<211> LENGTH: 262
<212> TYPE: PRT
<213> ORGANISM: Oxyrrhis marina

<400> SEQUENCE: 5

Met Ala Pro Leu Ala Gln Asp Trp Thr Tyr Ala Glu Trp Ser Ala Val
1               5                   10                  15

Tyr Asn Ala Leu Ser Phe Gly Ile Ala Gly Met Gly Ser Ala Thr Ile
            20                  25                  30

Phe Phe Trp Leu Gln Leu Pro Asn Val Thr Lys Asn Tyr Arg Thr Ala
        35                  40                  45

Leu Thr Ile Thr Gly Ile Val Thr Leu Ile Ala Thr Tyr His Tyr Phe
    50                  55                  60

Arg Ile Phe Asn Ser Trp Val Ala Ala Phe Asn Val Gly Leu Gly Val
65                  70                  75                  80

Asn Gly Ala Tyr Glu Val Thr Val Ser Gly Thr Pro Phe Asn Asp Ala
                85                  90                  95

Tyr Arg Tyr Val Asp Trp Leu Leu Thr Val Pro Leu Leu Leu Val Glu
            100                 105                 110

Leu Ile Leu Val Met Lys Leu Pro Ala Lys Glu Thr Val Cys Leu Ala
        115                 120                 125

Trp Thr Leu Gly Ile Ala Ser Ala Val Met Val Ala Leu Gly Tyr Pro
    130                 135                 140

Gly Glu Ile Gln Asp Asp Leu Ser Val Arg Trp Phe Trp Trp Ala Cys
145                 150                 155                 160

Ala Met Val Pro Phe Val Tyr Val Val Gly Thr Leu Val Val Gly Leu
                165                 170                 175

Gly Ala Ala Thr Ala Lys Gln Pro Glu Gly Val Val Asp Leu Val Ser
            180                 185                 190

Ala Ala Arg Tyr Leu Thr Val Val Ser Trp Leu Thr Tyr Pro Phe Val
        195                 200                 205

Tyr Ile Val Lys Asn Ile Gly Leu Ala Gly Ser Thr Ala Thr Met Tyr
    210                 215                 220

Glu Gln Ile Gly Tyr Ser Ala Ala Asp Val Thr Ala Lys Ala Val Phe
225                 230                 235                 240

Gly Val Leu Ile Trp Ala Ile Ala Asn Ala Lys Ser Arg Leu Glu Glu
                245                 250                 255
```

```
Glu Gly Lys Leu Arg Ala
        260

<210> SEQ ID NO 6
<211> LENGTH: 313
<212> TYPE: PRT
<213> ORGANISM: Leptosphaeria maculans

<400> SEQUENCE: 6

Met Ile Val Asp Gln Phe Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
            35                  40                  45

Asp Ser Gly Ser Lys Thr Leu Trp Val Val Phe Val Leu Met Leu Ile
50                  55                  60

Ala Ser Ala Ala Phe Thr Ala Leu Ser Trp Lys Ile Pro Val Asn Arg
65                  70                  75                  80

Arg Leu Tyr His Val Ile Thr Ile Ile Thr Leu Thr Ala Ala Leu
                85                  90                  95

Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
            115                 120                 125

Tyr Arg Gln Val Tyr Tyr Ala Arg Tyr Ile Asp Trp Ala Ile Thr Thr
        130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
    290                 295                 300

Ile Arg Ile Gly Glu Asp Asp Gly Ala
305                 310

<210> SEQ ID NO 7
<211> LENGTH: 321
<212> TYPE: PRT
<213> ORGANISM: Leptosphaeria maculans

<400> SEQUENCE: 7
```

```
Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Val Phe Val Leu Met Leu Ile
    50                  55                  60

Ala Ser Ala Ala Phe Thr Ala Leu Ser Trp Lys Ile Pro Val Asn Arg
65                  70                  75                  80

Arg Leu Tyr His Val Ile Thr Ile Ile Thr Leu Thr Ala Ala Leu
                85                  90                  95

Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
        115                 120                 125

Tyr Arg Gln Val Tyr Tyr Ala Arg Tyr Ile Asp Trp Ala Ile Thr Thr
    130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
    195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
    275                 280                 285

Val Glu Leu Asn Gly Phe Trp Ala Asn Gly Leu Asn Arg Glu Gly Ala
    290                 295                 300

Ile Arg Ile Gly Glu Asp Asp Gly Ala Arg Pro Val Val Ala Val Ser
305                 310                 315                 320

Lys

<210> SEQ ID NO 8
<211> LENGTH: 310
<212> TYPE: PRT
<213> ORGANISM: Chlamydomonas reinhardtii

<400> SEQUENCE: 8

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45
```

```
Gln Thr Ala Ser Asn Val Leu Gln Trp Leu Ala Ala Gly Phe Ser Ile
         50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Pro
305                 310

<210> SEQ ID NO 9
<211> LENGTH: 310
<212> TYPE: PRT
<213> ORGANISM: Artificial sequence
<220> FEATURE:
<223> OTHER INFORMATION: synthetic amino acid sequence

<400> SEQUENCE: 9

Met Asp Tyr Gly Gly Ala Leu Ser Ala Val Gly Arg Glu Leu Leu Phe
 1               5                  10                  15

Val Thr Asn Pro Val Val Asn Gly Ser Val Leu Val Pro Glu Asp
                 20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
         50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95
```

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 10
<211> LENGTH: 310
<212> TYPE: PRT
<213> ORGANISM: Artificial sequence
<220> FEATURE:
<223> OTHER INFORMATION: synthetic amino acid sequence

<400> SEQUENCE: 10

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
    130                 135                 140

```
Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305             310

<210> SEQ ID NO 11
<211> LENGTH: 349
<212> TYPE: PRT
<213> ORGANISM: Artificial sequence
<220> FEATURE:
<223> OTHER INFORMATION: synthetic amino acid sequence

<400> SEQUENCE: 11

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190
```

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp Ser Glu Gln Ile Asp
            340                 345

<210> SEQ ID NO 12
<211> LENGTH: 344
<212> TYPE: PRT
<213> ORGANISM: Artificial sequence
<220> FEATURE:
<223> OTHER INFORMATION: synthetic amino acid sequence

<400> SEQUENCE: 12

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
            210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 13
<211> LENGTH: 349
<212> TYPE: PRT
<213> ORGANISM: Artificial sequence
<220> FEATURE:
<223> OTHER INFORMATION: synthetic amino acid sequence

<400> SEQUENCE: 13

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
            210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp Ser Glu Gln Ile Asp
            340                 345

<210> SEQ ID NO 14
<211> LENGTH: 349
<212> TYPE: PRT
<213> ORGANISM: Artificial sequence
<220> FEATURE:
<223> OTHER INFORMATION: synthetic amino acid sequence

<400> SEQUENCE: 14

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
            115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
            165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
            210                 215                 220

Met Tyr Thr Tyr Phe His Ala Ala Lys Val Tyr Ile Glu Ala Phe His
225                 230                 235                 240

```
Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                    325                 330                 335

Thr Leu Val Ala Glu Glu Glu Asp Ser Glu Gln Ile Asp
            340                 345

<210> SEQ ID NO 15
<211> LENGTH: 365
<212> TYPE: PRT
<213> ORGANISM: Dunaliella salina

<400> SEQUENCE: 15

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
                20                  25                  30

Glu Arg Arg Pro Pro Ser Glu Arg Asn Thr Pro Tyr Ala Asn Ile Lys
            35                  40                  45

Lys Val Pro Asn Ile Thr Glu Pro Asn Ala Asn Val Gln Leu Asp Gly
    50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
                85                  90                  95

Ser His Gly Thr Asp Arg Glu Gly Glu Ala Ala Val Val Trp Ala Tyr
            100                 105                 110

Ile Val Phe Ala Ile Cys Ile Val Gln Leu Val Tyr Phe Met Phe Ala
            115                 120                 125

Ala Trp Lys Ala Thr Val Gly Trp Glu Glu Val Tyr Val Asn Ile Ile
            130                 135                 140

Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
                165                 170                 175

Ser Ala Trp Leu Leu Ser Cys Pro Val Ile Leu Ile His Leu Ser Asn
            180                 185                 190

Leu Thr Gly Leu Lys Gly Asp Tyr Ser Lys Arg Thr Met Gly Leu Leu
            195                 200                 205

Val Ser Asp Ile Gly Thr Ile Val Phe Gly Thr Ser Ala Ala Leu Ala
            210                 215                 220

Pro Pro Asn His Val Lys Val Ile Leu Phe Thr Ile Gly Leu Leu Tyr
225                 230                 235                 240

Gly Leu Phe Thr Phe Phe Thr Ala Ala Lys Val Tyr Ile Glu Ala Tyr
                245                 250                 255

His Thr Val Pro Lys Gly Gln Cys Arg Asn Leu Val Arg Ala Met Ala
            260                 265                 270
```

Trp Thr Tyr Phe Val Ser Trp Ala Met Phe Pro Ile Leu Phe Ile Leu
            275                 280                 285

Gly Arg Glu Gly Phe Gly His Ile Thr Tyr Phe Gly Ser Ser Ile Gly
        290                 295                 300

His Phe Ile Leu Glu Ile Phe Ser Lys Asn Leu Trp Ser Leu Leu Gly
305                 310                 315                 320

His Gly Leu Arg Tyr Arg Ile Arg Gln His Ile Ile His Gly Asn
                325                 330                 335

Leu Thr Lys Lys Asn Lys Ile Asn Ile Ala Gly Asp Asn Val Glu Val
            340                 345                 350

Glu Glu Tyr Val Asp Ser Asn Asp Lys Asp Ser Asp Val
            355                 360                 365

<210> SEQ ID NO 16
<211> LENGTH: 273
<212> TYPE: PRT
<213> ORGANISM: Natronomonas pharaonis

<400> SEQUENCE: 16

Val Thr Gln Arg Glu Leu Phe Glu Phe Val Leu Asn Asp Pro Leu Leu
1               5                   10                  15

Ala Ser Ser Leu Tyr Ile Asn Ile Ala Leu Ala Gly Leu Ser Ile Leu
            20                  25                  30

Leu Phe Val Phe Met Thr Arg Gly Leu Asp Asp Pro Arg Ala Lys Leu
        35                  40                  45

Ile Ala Val Ser Thr Ile Leu Val Pro Val Val Ser Ile Ala Ser Tyr
50                  55                  60

Thr Gly Leu Ala Ser Gly Leu Thr Ile Ser Val Leu Glu Met Pro Ala
65                  70                  75                  80

Gly His Phe Ala Glu Gly Ser Ser Val Met Leu Gly Gly Glu Glu Val
                85                  90                  95

Asp Gly Val Val Thr Met Trp Gly Arg Tyr Leu Thr Trp Ala Leu Ser
            100                 105                 110

Thr Pro Met Ile Leu Leu Ala Leu Gly Leu Leu Ala Gly Ser Asn Ala
        115                 120                 125

Thr Lys Leu Phe Thr Ala Ile Thr Phe Asp Ile Ala Met Cys Val Thr
        130                 135                 140

Gly Leu Ala Ala Ala Leu Thr Thr Ser Ser His Leu Met Arg Trp Phe
145                 150                 155                 160

Trp Tyr Ala Ile Ser Cys Ala Cys Phe Leu Val Val Leu Tyr Ile Leu
                165                 170                 175

Leu Val Glu Trp Ala Gln Asp Ala Lys Ala Ala Gly Thr Ala Asp Met
            180                 185                 190

Phe Asn Thr Leu Lys Leu Leu Thr Val Val Met Trp Leu Gly Tyr Pro
        195                 200                 205

Ile Val Trp Ala Leu Gly Val Glu Gly Ile Ala Val Leu Pro Val Gly
210                 215                 220

Val Thr Ser Trp Gly Tyr Ser Phe Leu Asp Ile Val Ala Lys Tyr Ile
225                 230                 235                 240

Phe Ala Phe Leu Leu Leu Asn Tyr Leu Thr Ser Asn Glu Ser Val Val
                245                 250                 255

Ser Gly Ser Ile Leu Asp Val Pro Ser Ala Ser Gly Thr Pro Ala Asp
            260                 265                 270

Asp

<210> SEQ ID NO 17
<211> LENGTH: 559
<212> TYPE: PRT
<213> ORGANISM: Artificial sequence
<220> FEATURE:
<223> OTHER INFORMATION: synthetic amino acid sequence

<400> SEQUENCE: 17

```
Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
                20                  25                  30

Leu Leu Ala Ser Ser Leu Tyr Ile Asn Ile Ala Leu Ala Gly Leu Ser
            35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
                100                 105                 110

Glu Val Asp Gly Val Val Thr Met Trp Gly Arg Tyr Leu Thr Trp Ala
            115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
                180                 185                 190

Ile Leu Leu Val Glu Trp Ala Gln Asp Ala Lys Ala Ala Gly Thr Ala
            195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
                260                 265                 270

Val Val Ser Gly Ser Ile Leu Asp Val Pro Ser Ala Ser Gly Thr Pro
            275                 280                 285

Ala Asp Asp Ala Ala Ala Lys Ser Arg Ile Thr Ser Glu Gly Glu Tyr
    290                 295                 300

Ile Pro Leu Asp Gln Ile Asp Ile Asn Val Val Ser Lys Gly Glu Glu
305                 310                 315                 320

Leu Phe Thr Gly Val Val Pro Ile Leu Val Glu Leu Asp Gly Asp Val
                325                 330                 335

Asn Gly His Lys Phe Ser Val Ser Gly Glu Gly Glu Gly Asp Ala Thr
                340                 345                 350

Tyr Gly Lys Leu Thr Leu Lys Phe Ile Cys Thr Thr Gly Lys Leu Pro
            355                 360                 365
```

Val Pro Trp Pro Thr Leu Val Thr Thr Phe Gly Tyr Gly Leu Gln Cys
            370                 375                 380

Phe Ala Arg Tyr Pro Asp His Met Lys Gln His Asp Phe Phe Lys Ser
385                 390                 395                 400

Ala Met Pro Glu Gly Tyr Val Gln Glu Arg Thr Ile Phe Phe Lys Asp
                405                 410                 415

Asp Gly Asn Tyr Lys Thr Arg Ala Glu Val Lys Phe Glu Gly Asp Thr
                420                 425                 430

Leu Val Asn Arg Ile Glu Leu Lys Gly Ile Asp Phe Lys Glu Asp Gly
                435                 440                 445

Asn Ile Leu Gly His Lys Leu Glu Tyr Asn Tyr Asn Ser His Asn Val
            450                 455                 460

Tyr Ile Met Ala Asp Lys Gln Lys Asn Gly Ile Lys Val Asn Phe Lys
465                 470                 475                 480

Ile Arg His Asn Ile Glu Asp Gly Ser Val Gln Leu Ala Asp His Tyr
                485                 490                 495

Gln Gln Asn Thr Pro Ile Gly Asp Gly Pro Val Leu Leu Pro Asp Asn
                500                 505                 510

His Tyr Leu Ser Tyr Gln Ser Ala Leu Ser Lys Asp Pro Asn Glu Lys
            515                 520                 525

Arg Asp His Met Val Leu Leu Glu Phe Val Thr Ala Ala Gly Ile Thr
530                 535                 540

Leu Gly Met Asp Glu Leu Tyr Lys Phe Cys Tyr Glu Asn Glu Val
545                 550                 555

<210> SEQ ID NO 18
<211> LENGTH: 542
<212> TYPE: PRT
<213> ORGANISM: Artificial sequence
<220> FEATURE:
<223> OTHER INFORMATION: synthetic amino acid sequence

<400> SEQUENCE: 18

Met Val Thr Gln Arg Glu Leu Phe Glu Phe Val Leu Asn Asp Pro Leu
1               5                   10                  15

Leu Ala Ser Ser Leu Tyr Ile Asn Ile Ala Leu Ala Gly Leu Ser Ile
                20                  25                  30

Leu Leu Phe Val Phe Met Thr Arg Gly Leu Asp Asp Pro Arg Ala Lys
            35                  40                  45

Leu Ile Ala Val Ser Thr Ile Leu Val Pro Val Ser Ile Ala Ser
            50                  55                  60

Tyr Thr Gly Leu Ala Ser Gly Leu Thr Ile Ser Val Leu Glu Met Pro
65              70                  75                  80

Ala Gly His Phe Ala Glu Gly Ser Ser Val Met Leu Gly Gly Glu Glu
                85                  90                  95

Val Asp Gly Val Val Thr Met Trp Gly Arg Tyr Leu Thr Trp Ala Leu
                100                 105                 110

Ser Thr Pro Met Ile Leu Leu Ala Leu Gly Leu Leu Ala Gly Ser Asn
            115                 120                 125

Ala Thr Lys Leu Phe Thr Ala Ile Thr Phe Asp Ile Ala Met Cys Val
            130                 135                 140

Thr Gly Leu Ala Ala Ala Leu Thr Thr Ser Ser His Leu Met Arg Trp
145                 150                 155                 160

Phe Trp Tyr Ala Ile Ser Cys Ala Cys Phe Leu Val Val Leu Tyr Ile
                165                 170                 175

Leu Leu Val Glu Trp Ala Gln Asp Ala Lys Ala Ala Gly Thr Ala Asp
            180                 185                 190

Met Phe Asn Thr Leu Lys Leu Leu Thr Val Val Met Trp Leu Gly Tyr
            195                 200                 205

Pro Ile Val Trp Ala Leu Gly Val Glu Gly Ile Ala Val Leu Pro Val
        210                 215                 220

Gly Val Thr Ser Trp Gly Tyr Ser Phe Leu Asp Ile Val Ala Lys Tyr
225                 230                 235                 240

Ile Phe Ala Phe Leu Leu Leu Asn Tyr Leu Thr Ser Asn Glu Ser Val
                245                 250                 255

Val Ser Gly Ser Ile Leu Asp Val Pro Ser Ala Ser Gly Thr Pro Ala
            260                 265                 270

Asp Asp Ala Ala Ala Lys Ser Arg Ile Thr Ser Glu Gly Glu Tyr Ile
            275                 280                 285

Pro Leu Asp Gln Ile Asp Ile Asn Val Val Ser Lys Gly Glu Glu Leu
        290                 295                 300

Phe Thr Gly Val Val Pro Ile Leu Val Glu Leu Asp Gly Asp Val Asn
305                 310                 315                 320

Gly His Lys Phe Ser Val Ser Gly Glu Gly Glu Gly Asp Ala Thr Tyr
                325                 330                 335

Gly Lys Leu Thr Leu Lys Phe Ile Cys Thr Thr Gly Lys Leu Pro Val
            340                 345                 350

Pro Trp Pro Thr Leu Val Thr Thr Phe Gly Tyr Gly Leu Gln Cys Phe
        355                 360                 365

Ala Arg Tyr Pro Asp His Met Lys Gln His Asp Phe Phe Lys Ser Ala
        370                 375                 380

Met Pro Glu Gly Tyr Val Gln Glu Arg Thr Ile Phe Phe Lys Asp Asp
385                 390                 395                 400

Gly Asn Tyr Lys Thr Arg Ala Glu Val Lys Phe Glu Gly Asp Thr Leu
                405                 410                 415

Val Asn Arg Ile Glu Leu Lys Gly Ile Asp Phe Lys Glu Asp Gly Asn
            420                 425                 430

Ile Leu Gly His Lys Leu Glu Tyr Asn Tyr Asn Ser His Asn Val Tyr
        435                 440                 445

Ile Met Ala Asp Lys Gln Lys Asn Gly Ile Lys Val Asn Phe Lys Ile
    450                 455                 460

Arg His Asn Ile Glu Asp Gly Ser Val Gln Leu Ala Asp His Tyr Gln
465                 470                 475                 480

Gln Asn Thr Pro Ile Gly Asp Gly Pro Val Leu Leu Pro Asp Asn His
                485                 490                 495

Tyr Leu Ser Tyr Gln Ser Ala Leu Ser Lys Asp Pro Asn Glu Lys Arg
            500                 505                 510

Asp His Met Val Leu Leu Glu Phe Val Thr Ala Ala Gly Ile Thr Leu
        515                 520                 525

Gly Met Asp Glu Leu Tyr Lys Phe Cys Tyr Glu Asn Glu Val
    530                 535                 540

<210> SEQ ID NO 19
<211> LENGTH: 512
<212> TYPE: PRT
<213> ORGANISM: Rattus norvegicus

<400> SEQUENCE: 19

Met Asp Leu Lys Glu Ser Pro Ser Glu Gly Ser Leu Gln Pro Ser Ser

-continued

```
1               5                   10                  15
Ile Gln Ile Phe Ala Asn Thr Ser Thr Leu His Gly Ile Arg His Ile
                20                  25                  30
Phe Val Tyr Gly Pro Leu Thr Ile Arg Arg Val Leu Trp Ala Val Ala
                35                  40                  45
Phe Val Gly Ser Leu Gly Leu Leu Val Glu Ser Ser Glu Arg Val
        50                  55                  60
Ser Tyr Tyr Phe Ser Tyr Gln His Val Thr Lys Val Asp Glu Val Val
65                  70                  75                  80
Ala Gln Ser Leu Val Phe Pro Ala Val Thr Leu Cys Asn Leu Asn Gly
                85                  90                  95
Phe Arg Phe Ser Arg Leu Thr Thr Asn Asp Leu Tyr His Ala Gly Glu
                100                 105                 110
Leu Leu Ala Leu Leu Asp Val Asn Leu Gln Ile Pro Asp Pro His Leu
                115                 120                 125
Ala Asp Pro Thr Val Leu Glu Ala Leu Arg Gln Lys Ala Asn Phe Lys
                130                 135                 140
His Tyr Lys Pro Lys Gln Phe Ser Met Leu Glu Phe Leu His Arg Val
145                 150                 155                 160
Gly His Asp Leu Lys Asp Met Met Leu Tyr Cys Lys Phe Lys Gly Gln
                165                 170                 175
Glu Cys Gly His Gln Asp Phe Thr Thr Val Phe Thr Lys Tyr Gly Lys
                180                 185                 190
Cys Tyr Met Phe Asn Ser Gly Glu Asp Gly Lys Pro Leu Leu Thr Thr
                195                 200                 205
Val Lys Gly Gly Thr Gly Asn Gly Leu Glu Ile Met Leu Asp Ile Gln
                210                 215                 220
Gln Asp Glu Tyr Leu Pro Ile Trp Gly Glu Thr Glu Glu Thr Thr Phe
225                 230                 235                 240
Glu Ala Gly Val Lys Val Gln Ile His Ser Gln Ser Glu Pro Pro Phe
                245                 250                 255
Ile Gln Glu Leu Gly Phe Gly Val Ala Pro Gly Phe Gln Thr Phe Val
                260                 265                 270
Ala Thr Gln Glu Gln Arg Leu Thr Tyr Leu Pro Pro Trp Gly Glu
                275                 280                 285
Cys Arg Ser Ser Glu Met Gly Leu Asp Phe Phe Pro Val Tyr Ser Ile
                290                 295                 300
Thr Ala Cys Arg Ile Asp Cys Glu Thr Arg Tyr Ile Val Glu Asn Cys
305                 310                 315                 320
Asn Cys Arg Met Val His Met Pro Gly Asp Ala Pro Phe Cys Thr Pro
                325                 330                 335
Glu Gln His Lys Glu Cys Ala Glu Pro Ala Leu Gly Leu Leu Ala Glu
                340                 345                 350
Lys Asp Ser Asn Tyr Cys Leu Cys Arg Thr Pro Cys Asn Leu Thr Arg
                355                 360                 365
Tyr Asn Lys Glu Leu Ser Met Val Lys Ile Pro Ser Lys Thr Ser Ala
                370                 375                 380
Lys Tyr Leu Glu Lys Lys Phe Asn Lys Ser Glu Lys Tyr Ile Ser Glu
385                 390                 395                 400
Asn Ile Leu Val Leu Asp Ile Phe Phe Glu Ala Leu Asn Tyr Glu Thr
                405                 410                 415
Ile Glu Gln Lys Lys Ala Tyr Glu Val Ala Ala Leu Leu Gly Asp Ile
                420                 425                 430
```

```
Gly Gly Gln Met Gly Leu Phe Ile Gly Ala Ser Leu Leu Thr Ile Leu
            435                 440                 445

Glu Leu Phe Asp Tyr Ile Tyr Glu Leu Ile Lys Glu Lys Leu Leu Asp
    450                 455                 460

Leu Leu Gly Lys Glu Glu Glu Gly Ser His Asp Glu Asn Met Ser
465                 470                 475                 480

Thr Cys Asp Thr Met Pro Asn His Ser Glu Thr Ile Ser His Thr Val
                485                 490                 495

Asn Val Pro Leu Gln Thr Ala Leu Gly Thr Leu Glu Glu Ile Ala Cys
            500                 505                 510

<210> SEQ ID NO 20
<211> LENGTH: 378
<212> TYPE: PRT
<213> ORGANISM: Helicobacter pylori

<400> SEQUENCE: 20

Met Phe Glu Lys Leu Lys Phe Lys Ile Lys Lys Asp Asp Glu Asp
1               5                   10                  15

Gln Pro Glu Val Asn Leu Asn Ser Glu Ile Tyr Glu Gln Phe Lys Val
            20                  25                  30

Phe Arg Leu Pro Leu Ile Leu Ile Gln Leu Leu Val Leu Leu Gly Thr
        35                  40                  45

Leu Gly Tyr Phe Ala Leu Glu Asn Tyr Ser Leu Met Gln Ala Phe Phe
    50                  55                  60

Gln Thr Thr Tyr Thr Met Thr Ala Thr Gly Phe Gly Ala Leu Asn Glu
65              70                  75                  80

Ser Gln Phe Gly Pro Ile Ser Ile Phe Leu Thr Ser Ile Leu Met Phe
            85                  90                  95

Cys Gly Thr Gly Ile Ile Ala Phe Ser Val Ala Ile Leu Val Ser Val
                100                 105                 110

Val Asn Lys Gly Thr Leu Thr Arg Leu Ile Lys Glu Lys Gly Met Ile
            115                 120                 125

Tyr Lys Ile Ala Arg Leu Lys Asp His Tyr Val Ile Cys Tyr His Asn
    130                 135                 140

Glu Tyr Thr Ile Glu Leu Ser Lys Gln Phe Arg Ser Ala Gln Ile Pro
145                 150                 155                 160

Phe Val Val Val Asp Asn Asp Pro Ser Phe Glu Glu Ala Ile Lys
            165                 170                 175

His Lys Tyr Pro Tyr Tyr Ile Ile Gly Asp Pro His Thr Asn Leu Ala
            180                 185                 190

Met Leu Lys Thr His Leu Ser Ser Ala Arg Gly Val Val Ala Leu Ser
        195                 200                 205

Lys Ile Leu Pro Val Asn Val Ala Leu Met Val Ser Val Arg Leu Phe
    210                 215                 220

Glu Lys Glu Leu Lys Arg Lys Pro Tyr Tyr Ile Ile Ala Ser Ala His
225                 230                 235                 240

Ser Asp Glu Gly Leu Glu Lys Leu Lys Lys Leu Gly Ala Asp Met Val
            245                 250                 255

Val Ser Pro Thr Lys Leu Met Ala Gln Arg Val Ser Ala Met Ala Val
            260                 265                 270

Arg Pro Asp Met Glu Asn Ile Leu Glu Arg Phe Ile Asn Lys Lys Asp
            275                 280                 285

Thr Leu Leu Asp Leu Glu Glu Val Ile Val Pro Lys Thr Ser Trp Leu
```

```
              290                 295                 300
Val Leu Arg Lys Leu Lys Glu Ala His Phe Arg Glu Ile Ala Lys Ala
305                 310                 315                 320

Phe Val Ile Gly Ile Thr Gln Lys Asp Gly Lys Tyr Ile Pro Met Pro
                325                 330                 335

Asp Gly Glu Thr Ile Ile Ala Ser Glu Ser Lys Leu Leu Met Val Gly
                340                 345                 350

Thr Ser Glu Gly Val Ala Thr Cys Lys Gln Leu Ile Thr Ser His Gln
                355                 360                 365

Lys Pro Lys Glu Val Asp Tyr Ile Ser Leu
            370                 375

<210> SEQ ID NO 21
<211> LENGTH: 661
<212> TYPE: PRT
<213> ORGANISM: Homo sapiens

<400> SEQUENCE: 21

Met Asp Leu Gln Gln Ser Thr Thr Ile Thr Ser Leu Glu Lys Trp Cys
1               5                   10                  15

Leu Asp Glu Ser Leu Ser Gly Cys Arg Arg His Tyr Ser Val Lys Lys
                20                  25                  30

Lys Leu Lys Leu Ile Arg Val Leu Gly Leu Phe Met Gly Leu Val Ala
            35                  40                  45

Ile Ser Thr Val Ser Phe Ser Ile Ser Ala Phe Ser Glu Thr Asp Thr
        50                  55                  60

Gln Ser Thr Gly Glu Ala Ser Val Val Ser Gly Pro Arg Val Ala Gln
65                  70                  75                  80

Gly Tyr His Gln Arg Thr Leu Leu Asp Leu Asn Asp Lys Ile Leu Asp
                85                  90                  95

Tyr Thr Pro Gln Pro Pro Leu Ser Lys Glu Gly Glu Ser Glu Asn Ser
                100                 105                 110

Thr Asp His Ala Gln Gly Asp Tyr Pro Lys Asp Ile Phe Ser Leu Glu
            115                 120                 125

Glu Arg Arg Lys Gly Ala Ile Ile Leu His Val Ile Gly Met Ile Tyr
130                 135                 140

Met Phe Ile Ala Leu Ala Ile Val Cys Asp Glu Phe Phe Val Pro Ser
145                 150                 155                 160

Leu Thr Val Ile Thr Glu Lys Leu Gly Ile Ser Asp Asp Val Ala Gly
                165                 170                 175

Ala Thr Phe Met Ala Ala Gly Gly Ser Ala Pro Glu Leu Phe Thr Ser
                180                 185                 190

Leu Ile Gly Val Phe Ile Ala His Ser Asn Val Gly Ile Gly Thr Ile
            195                 200                 205

Val Gly Ser Ala Val Phe Asn Ile Leu Phe Val Ile Gly Met Cys Ala
        210                 215                 220

Leu Phe Ser Arg Glu Ile Leu Asn Leu Thr Trp Trp Pro Leu Phe Arg
225                 230                 235                 240

Asp Val Ser Phe Tyr Ile Val Asp Leu Ile Met Leu Ile Ile Phe Phe
                245                 250                 255

Leu Asp Asn Val Ile Met Trp Trp Glu Ser Leu Leu Leu Leu Thr Ala
                260                 265                 270

Tyr Phe Cys Tyr Val Val Phe Met Lys Phe Asn Val Gln Val Glu Lys
            275                 280                 285
```

```
Trp Val Lys Gln Met Ile Asn Arg Asn Lys Val Val Lys Val Thr Ala
290                 295                 300
Pro Glu Ala Gln Ala Lys Pro Ser Ala Ala Arg Asp Lys Asp Glu Pro
305                 310                 315                 320
Thr Leu Pro Ala Lys Pro Arg Leu Gln Arg Gly Gly Ser Ser Ala Ser
            325                 330                 335
Leu His Asn Ser Leu Met Arg Asn Ser Ile Phe Gln Leu Met Ile His
            340                 345                 350
Thr Leu Asp Pro Leu Ala Glu Glu Leu Gly Ser Tyr Gly Lys Leu Lys
        355                 360                 365
Tyr Tyr Asp Thr Met Thr Glu Glu Gly Arg Phe Arg Glu Lys Ala Ser
370                 375                 380
Ile Leu His Lys Ile Ala Lys Lys Cys His Val Asp Glu Asn Glu
385                 390                 395                 400
Arg Gln Asn Gly Ala Ala Asn His Val Glu Lys Ile Glu Leu Pro Asn
                405                 410                 415
Ser Thr Ser Thr Asp Val Glu Met Thr Pro Ser Ser Asp Ala Ser Glu
            420                 425                 430
Pro Val Gln Asn Gly Asn Leu Ser His Asn Ile Glu Gly Ala Glu Ala
            435                 440                 445
Gln Thr Ala Asp Glu Glu Asp Gln Pro Leu Ser Leu Ala Trp Pro
450                 455                 460
Ser Glu Thr Arg Lys Gln Val Thr Phe Leu Ile Val Phe Pro Ile Val
465                 470                 475                 480
Phe Pro Leu Trp Ile Thr Leu Pro Asp Val Arg Lys Pro Ser Ser Arg
                485                 490                 495
Lys Phe Phe Pro Ile Thr Phe Phe Gly Ser Ile Thr Trp Ile Ala Val
            500                 505                 510
Phe Ser Tyr Leu Met Val Trp Trp Ala His Gln Val Gly Glu Thr Ile
        515                 520                 525
Gly Ile Ser Glu Glu Ile Met Gly Leu Thr Ile Leu Ala Ala Gly Thr
530                 535                 540
Ser Ile Pro Asp Leu Ile Thr Ser Val Ile Val Ala Arg Lys Gly Leu
545                 550                 555                 560
Gly Asp Met Ala Val Ser Ser Val Gly Ser Asn Ile Phe Asp Ile
                565                 570                 575
Thr Val Gly Leu Pro Leu Pro Trp Leu Leu Tyr Thr Val Ile His Arg
            580                 585                 590
Phe Gln Pro Val Ala Val Ser Ser Asn Gly Leu Phe Cys Ala Ile Val
        595                 600                 605
Leu Leu Phe Ile Met Leu Leu Phe Val Ile Leu Ser Ile Ala Leu Cys
610                 615                 620
Lys Trp Arg Met Asn Lys Ile Leu Gly Phe Ile Met Phe Gly Leu Tyr
625                 630                 635                 640
Phe Val Phe Leu Val Val Ser Val Leu Leu Glu Asp Arg Ile Leu Thr
                645                 650                 655
Cys Pro Val Ser Ile
            660

<210> SEQ ID NO 22
<211> LENGTH: 925
<212> TYPE: PRT
<213> ORGANISM: Homo sapiens

<400> SEQUENCE: 22
```

```
Met Ala Trp Leu Arg Leu Gln Pro Leu Thr Ser Ala Phe Leu His Phe
1               5                   10                  15
Gly Leu Val Thr Phe Val Leu Phe Leu Asn Gly Leu Arg Ala Glu Ala
            20                  25                  30
Gly Gly Ser Gly Asp Val Pro Ser Thr Gly Gln Asn Asn Glu Ser Cys
            35                  40                  45
Ser Gly Ser Ser Asp Cys Lys Glu Gly Val Ile Leu Pro Ile Trp Tyr
    50                  55                  60
Pro Glu Asn Pro Ser Leu Gly Asp Lys Ile Ala Arg Val Ile Val Tyr
65                  70                  75                  80
Phe Val Ala Leu Ile Tyr Met Phe Leu Gly Val Ser Ile Ile Ala Asp
                85                  90                  95
Arg Phe Met Ala Ser Ile Glu Val Ile Thr Ser Gln Glu Arg Glu Val
            100                 105                 110
Thr Ile Lys Lys Pro Asn Gly Glu Thr Ser Thr Thr Thr Ile Arg Val
            115                 120                 125
Trp Asn Glu Thr Val Ser Asn Leu Thr Leu Met Ala Leu Gly Ser Ser
    130                 135                 140
Ala Pro Glu Ile Leu Leu Ser Leu Ile Glu Val Cys Gly His Gly Phe
145                 150                 155                 160
Ile Ala Gly Asp Leu Gly Pro Ser Thr Ile Val Gly Ser Ala Ala Phe
                165                 170                 175
Asn Met Phe Ile Ile Ile Gly Ile Cys Val Tyr Val Ile Pro Asp Gly
            180                 185                 190
Glu Thr Arg Lys Ile Lys His Leu Arg Val Phe Phe Ile Thr Ala Ala
            195                 200                 205
Trp Ser Ile Phe Ala Tyr Ile Trp Leu Tyr Met Ile Leu Ala Val Phe
210                 215                 220
Ser Pro Gly Val Val Gln Val Trp Glu Gly Leu Leu Thr Leu Phe Phe
225                 230                 235                 240
Phe Pro Val Cys Val Leu Leu Ala Trp Val Ala Asp Lys Arg Leu Leu
            245                 250                 255
Phe Tyr Lys Tyr Met His Lys Lys Tyr Arg Thr Asp Lys His Arg Gly
            260                 265                 270
Ile Ile Ile Glu Thr Glu Gly Asp His Pro Lys Gly Ile Glu Met Asp
            275                 280                 285
Gly Lys Met Met Asn Ser His Phe Leu Asp Gly Asn Leu Val Pro Leu
    290                 295                 300
Glu Gly Lys Glu Val Asp Glu Ser Arg Arg Glu Met Ile Arg Ile Leu
305                 310                 315                 320
Lys Asp Leu Lys Gln Lys His Pro Glu Lys Asp Leu Asp Gln Leu Val
            325                 330                 335
Glu Met Ala Asn Tyr Tyr Ala Leu Ser His Gln Gln Lys Ser Arg Ala
            340                 345                 350
Phe Tyr Arg Ile Gln Ala Thr Arg Met Met Thr Gly Ala Gly Asn Ile
            355                 360                 365
Leu Lys Lys His Ala Ala Glu Gln Ala Lys Lys Ala Ser Ser Met Ser
    370                 375                 380
Glu Val His Thr Asp Glu Pro Glu Asp Phe Ile Ser Lys Val Phe Phe
385                 390                 395                 400
Asp Pro Cys Ser Tyr Gln Cys Leu Glu Asn Cys Gly Ala Val Leu Leu
            405                 410                 415
```

-continued

```
Thr Val Val Arg Lys Gly Gly Asp Met Ser Lys Thr Met Tyr Val Asp
            420                 425                 430

Tyr Lys Thr Glu Asp Gly Ser Ala Asn Ala Gly Ala Asp Tyr Glu Phe
        435                 440                 445

Thr Glu Gly Thr Val Val Leu Lys Pro Gly Glu Thr Gln Lys Glu Phe
    450                 455                 460

Ser Val Gly Ile Ile Asp Asp Ile Phe Glu Glu Asp Glu His Phe
465                 470                 475                 480

Phe Val Arg Leu Ser Asn Val Arg Ile Glu Glu Gln Pro Glu Glu
                485                 490                 495

Gly Met Pro Pro Ala Ile Phe Asn Ser Leu Pro Leu Pro Arg Ala Val
                500                 505                 510

Leu Ala Ser Pro Cys Val Ala Thr Val Thr Ile Leu Asp Asp His
            515                 520                 525

Ala Gly Ile Phe Thr Phe Glu Cys Asp Thr Ile His Val Ser Glu Ser
            530                 535                 540

Ile Gly Val Met Glu Val Lys Val Leu Arg Thr Ser Gly Ala Arg Gly
545                 550                 555                 560

Thr Val Ile Val Pro Phe Arg Thr Val Glu Gly Thr Ala Lys Gly Gly
                565                 570                 575

Gly Glu Asp Phe Glu Asp Thr Tyr Gly Glu Leu Glu Phe Lys Asn Asp
                580                 585                 590

Glu Thr Val Lys Thr Ile His Ile Lys Val Ile Asp Asp Glu Ala Tyr
            595                 600                 605

Glu Lys Asn Lys Asn Tyr Phe Ile Glu Met Met Gly Pro Arg Met Val
        610                 615                 620

Asp Met Ser Phe Gln Lys Ala Leu Leu Leu Ser Pro Asp Arg Lys Leu
625                 630                 635                 640

Thr Met Glu Glu Glu Ala Lys Arg Ile Ala Glu Met Gly Lys Pro
                645                 650                 655

Val Leu Gly Glu His Pro Lys Leu Glu Val Ile Ile Glu Glu Ser Tyr
                660                 665                 670

Glu Phe Lys Thr Thr Val Asp Lys Leu Ile Lys Lys Thr Asn Leu Ala
            675                 680                 685

Leu Val Val Gly Thr His Ser Trp Arg Asp Gln Phe Met Glu Ala Ile
        690                 695                 700

Thr Val Ser Ala Ala Gly Asp Glu Asp Glu Asp Ser Gly Glu Glu
705                 710                 715                 720

Arg Leu Pro Ser Cys Phe Asp Tyr Val Met His Phe Leu Thr Val Phe
                725                 730                 735

Trp Lys Val Leu Phe Ala Cys Val Pro Pro Thr Glu Tyr Cys His Gly
            740                 745                 750

Trp Ala Cys Phe Ala Val Ser Ile Leu Ile Ile Gly Met Leu Thr Ala
        755                 760                 765

Ile Ile Gly Asp Leu Ala Ser His Phe Gly Cys Thr Ile Gly Leu Lys
770                 775                 780

Asp Ser Val Thr Ala Val Val Phe Val Ala Phe Gly Thr Ser Val Pro
785                 790                 795                 800

Asp Thr Phe Ala Ser Lys Ala Ala Ala Leu Gln Asp Val Tyr Ala Asp
                805                 810                 815

Ala Ser Ile Gly Asn Val Thr Gly Ser Asn Ala Val Asn Val Phe Leu
            820                 825                 830

Gly Ile Gly Leu Ala Trp Ser Val Ala Ala Ile Tyr Trp Ala Leu Gln
```

```
                      835                 840                 845
Gly Gln Glu Phe His Val Ser Ala Gly Thr Leu Ala Phe Ser Val Thr
        850                 855                 860

Leu Phe Thr Ile Phe Ala Phe Val Cys Ile Ser Val Leu Leu Tyr Arg
865                 870                 875                 880

Arg Arg Pro His Leu Gly Gly Glu Leu Gly Gly Pro Arg Gly Cys Lys
                    885                 890                 895

Leu Ala Thr Thr Trp Leu Phe Val Ser Leu Trp Leu Leu Tyr Ile Leu
        900                 905                 910

Phe Ala Thr Leu Glu Ala Tyr Cys Tyr Ile Lys Gly Phe
            915                 920                 925

<210> SEQ ID NO 23
<211> LENGTH: 409
<212> TYPE: PRT
<213> ORGANISM: Moraxella catarrhalis

<400> SEQUENCE: 23

Met Phe Ala Gln Phe Lys Arg Phe Leu Glu Leu Glu Ala Ala Gly Gly
1               5                   10                  15

Ile Val Leu Ala Ala Ala Leu Leu Ala Met Ile Ile Ala Asn Ser
            20                  25                  30

Pro Leu Asp Glu Met Tyr His Ala Phe Ile His Ala Pro Val Val Val
        35                  40                  45

Gln Ile Gly Thr Phe Gln Ile Ala Lys Asp Ala His His Trp Ile Asn
    50                  55                  60

Asp Gly Leu Met Ala Ile Phe Phe Leu Val Gly Leu Glu Leu Lys
65                  70                  75                  80

Arg Glu Ala Leu Ile Gly Glu Leu Ser Asp Val Lys Gln Ile Leu Met
                85                  90                  95

Pro Ala Leu Ala Ala Val Gly Gly Met Ile Met Pro Ala Leu Ile Tyr
            100                 105                 110

Ala Ala Phe Asn Gln Ser Asn Pro Glu Gln Leu Ala Gly Trp Ala Ile
        115                 120                 125

Pro Ala Ala Thr Asp Ile Ala Phe Ala Leu Gly Val Leu Ser Leu Leu
    130                 135                 140

Gly Asn Arg Val Pro Asn Ala Leu Lys Val Phe Leu Val Ser Ile Ala
145                 150                 155                 160

Ile Phe Asp Asp Leu Gly Ala Ile Val Ile Ala Leu Phe Tyr Thr
                165                 170                 175

Ser Asp Leu Ser Leu Ser Ser Leu Ala Val Ala Gly Val Cys Phe Pro
            180                 185                 190

Phe Leu Phe Ile Leu Asn Lys Met Asn Val Val Arg Leu Thr Pro Tyr
        195                 200                 205

Leu Leu Ile Gly Leu Val Met Trp Ala Ala Phe Leu Lys Ser Gly Val
    210                 215                 220

His Ala Thr Leu Ala Gly Val Leu Leu Ala Phe Ile Pro Leu Arg
225                 230                 235                 240

Asn Lys Ser Asp Pro Glu His Ser Pro Leu Glu Glu Leu Glu His Asp
                245                 250                 255

Leu His Asn Thr Val Ala Phe Gly Val Leu Pro Leu Phe Ala Phe Ala
            260                 265                 270

Asn Ala Gly Ile Gly Leu Ala Gly Thr Gly Ile Asp Ser Leu Leu His
        275                 280                 285
```

```
Ser Val Pro Leu Gly Ile Ala Ala Gly Leu Phe Ile Gly Lys Gln Ile
    290                 295                 300
Gly Val Met Thr Ala Val Phe Leu Cys Leu Lys Leu Gly Leu Ala Ser
305                 310                 315                 320
Leu Pro Lys Gly Thr Thr Ile Lys Gln Leu Tyr Gly Val Ser Leu Leu
                325                 330                 335
Cys Gly Ile Gly Phe Thr Met Ser Leu Phe Ile Ser Gly Leu Ala Phe
                340                 345                 350
Gly Asn Thr Pro Lys Asp Phe Asp Pro Arg Leu Gly Ile Ile Leu Gly
                355                 360                 365
Ser Ile Ile Ser Gly Val Ile Gly Tyr Met Ile Leu Arg Gly Asn Ile
    370                 375                 380
Pro Asn Ala Asp His Pro Val Leu Ala Lys Asp Thr Gly Glu Gly Phe
385                 390                 395                 400
Ile Pro Thr Gln His Asp Ala Gln Ala
                405

<210> SEQ ID NO 24
<211> LENGTH: 676
<212> TYPE: PRT
<213> ORGANISM: Homo sapiens

<400> SEQUENCE: 24

Met Ala Ala Ser Ser Pro Pro Arg Ala Glu Arg Lys Arg Trp Gly
1               5                   10                  15
Trp Gly Arg Leu Pro Gly Ala Arg Arg Gly Ser Ala Gly Leu Ala Lys
                20                  25                  30
Lys Cys Pro Phe Ser Leu Glu Leu Ala Glu Gly Gly Pro Ala Gly Gly
            35                  40                  45
Ala Leu Tyr Ala Pro Ile Ala Pro Gly Ala Pro Gly Pro Ala Pro Pro
    50                  55                  60
Ala Ser Pro Ala Ala Pro Ala Ala Pro Pro Val Ala Ser Asp Leu Gly
65                  70                  75                  80
Pro Arg Pro Pro Val Ser Leu Asp Pro Arg Val Ser Ile Tyr Ser Thr
                85                  90                  95
Arg Arg Pro Val Leu Ala Arg Thr His Val Gln Gly Arg Val Tyr Asn
                100                 105                 110
Phe Leu Glu Arg Pro Thr Gly Trp Lys Cys Phe Val Tyr His Phe Ala
            115                 120                 125
Val Phe Leu Ile Val Leu Val Cys Leu Ile Phe Ser Val Leu Ser Thr
    130                 135                 140
Ile Glu Gln Tyr Ala Ala Leu Ala Thr Gly Thr Leu Phe Trp Met Glu
145                 150                 155                 160
Ile Val Leu Val Val Phe Phe Gly Thr Glu Tyr Val Val Arg Leu Trp
                165                 170                 175
Ser Ala Gly Cys Arg Ser Lys Tyr Val Gly Leu Trp Gly Arg Leu Arg
                180                 185                 190
Phe Ala Arg Lys Pro Ile Ser Ile Ile Asp Leu Ile Val Val Val Ala
            195                 200                 205
Ser Met Val Val Leu Cys Val Gly Ser Lys Gly Gln Val Phe Ala Thr
    210                 215                 220
Ser Ala Ile Arg Gly Ile Arg Phe Leu Gln Ile Leu Arg Met Leu His
225                 230                 235                 240
Val Asp Arg Gln Gly Gly Thr Trp Arg Leu Leu Gly Ser Val Val Phe
                245                 250                 255
```

-continued

Ile His Arg Gln Glu Leu Ile Thr Thr Leu Tyr Ile Gly Phe Leu Gly
             260                 265                 270

Leu Ile Phe Ser Ser Tyr Phe Val Tyr Leu Ala Glu Lys Asp Ala Val
             275                 280             285

Asn Glu Ser Gly Arg Val Glu Phe Gly Ser Tyr Ala Asp Ala Leu Trp
         290                 295                 300

Trp Gly Val Val Thr Val Thr Thr Ile Gly Tyr Gly Asp Lys Val Pro
305                 310                 315                 320

Gln Thr Trp Val Gly Lys Thr Ile Ala Ser Cys Phe Ser Val Phe Ala
                 325                 330                 335

Ile Ser Phe Phe Ala Leu Pro Ala Gly Ile Leu Gly Ser Gly Phe Ala
             340                 345                 350

Leu Lys Val Gln Gln Lys Gln Arg Gln Lys His Phe Asn Arg Gln Ile
             355                 360                 365

Pro Ala Ala Ala Ser Leu Ile Gln Thr Ala Trp Arg Cys Tyr Ala Ala
         370                 375                 380

Glu Asn Pro Asp Ser Ser Thr Trp Lys Ile Tyr Ile Arg Lys Ala Pro
385                 390                 395                 400

Arg Ser His Thr Leu Leu Ser Pro Ser Pro Lys Pro Lys Lys Ser Val
                 405                 410                 415

Val Val Lys Lys Lys Lys Phe Lys Leu Asp Lys Asp Asn Gly Val Thr
             420                 425                 430

Pro Gly Glu Lys Met Leu Thr Val Pro His Ile Thr Cys Asp Pro Pro
         435                 440                 445

Glu Glu Arg Arg Leu Asp His Phe Ser Val Asp Gly Tyr Asp Ser Ser
450                 455                 460

Val Arg Lys Ser Pro Thr Leu Leu Glu Val Ser Met Pro His Phe Met
465                 470                 475                 480

Arg Thr Asn Ser Phe Ala Glu Asp Leu Asp Leu Glu Gly Glu Thr Leu
             485                 490                 495

Leu Thr Pro Ile Thr His Ile Ser Gln Leu Arg Glu His His Arg Ala
             500                 505                 510

Thr Ile Lys Val Ile Arg Arg Met Gln Tyr Phe Val Ala Lys Lys Lys
             515                 520                 525

Phe Gln Gln Ala Arg Lys Pro Tyr Asp Val Arg Asp Val Ile Glu Gln
         530                 535                 540

Tyr Ser Gln Gly His Leu Asn Leu Met Val Arg Ile Lys Glu Leu Gln
545                 550                 555                 560

Arg Arg Leu Asp Gln Ser Ile Gly Lys Pro Ser Leu Phe Ile Ser Val
                 565                 570                 575

Ser Glu Lys Ser Lys Asp Arg Gly Ser Asn Thr Ile Gly Ala Arg Leu
             580                 585                 590

Asn Arg Val Glu Asp Lys Val Thr Gln Leu Asp Gln Arg Leu Ala Leu
             595                 600                 605

Ile Thr Asp Met Leu His Gln Leu Leu Ser Leu His Gly Gly Ser Thr
         610                 615                 620

Pro Gly Ser Gly Gly Pro Pro Arg Glu Gly Gly Ala His Ile Thr Gln
625                 630                 635                 640

Pro Cys Gly Ser Gly Gly Ser Val Asp Pro Glu Leu Phe Leu Pro Ser
                 645                 650                 655

Asn Thr Leu Pro Thr Tyr Glu Gln Leu Thr Val Pro Arg Arg Gly Pro
             660                 665                 670

Asp Glu Gly Ser
        675

<210> SEQ ID NO 25
<211> LENGTH: 1159
<212> TYPE: PRT
<213> ORGANISM: Homo sapiens

<400> SEQUENCE: 25

Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45

Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Glu Arg Lys Val Glu Ile
                85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
        115                 120                 125

Phe Glu Val Val Met Glu Lys Asp Met Val Gly Ser Pro Ala His Asp
    130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Gly Ala Gly Gly Ala Gly Ala Pro Gly
            180                 185                 190

Ala Val Val Val Asp Val Asp Leu Thr Pro Ala Ala Pro Ser Ser Glu
        195                 200                 205

Ser Leu Ala Leu Asp Glu Val Thr Ala Met Asp Asn His Val Ala Gly
    210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Ala Ser Ser Ala Asp Asp Ile
        275                 280                 285

Glu Ala Met Arg Ala Gly Val Leu Pro Pro Pro Arg His Ala Ser
    290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
        355                 360                 365

-continued

```
Asn Val Thr Glu Lys Val Thr Gln Val Leu Ser Leu Gly Ala Asp Val
    370                 375                 380
Leu Pro Glu Tyr Lys Leu Gln Ala Pro Arg Ile His Arg Trp Thr Ile
385                 390                 395                 400
Leu His Tyr Ser Pro Phe Lys Ala Val Trp Asp Trp Leu Ile Leu Leu
                405                 410                 415
Leu Val Ile Tyr Thr Ala Val Phe Thr Pro Tyr Ser Ala Ala Phe Leu
            420                 425                 430
Leu Lys Glu Thr Glu Glu Gly Pro Pro Ala Thr Glu Cys Gly Tyr Ala
        435                 440                 445
Cys Gln Pro Leu Ala Val Val Asp Leu Ile Val Asp Ile Met Phe Ile
    450                 455                 460
Val Asp Ile Leu Ile Asn Phe Arg Thr Thr Tyr Val Asn Ala Asn Glu
465                 470                 475                 480
Glu Val Val Ser His Pro Gly Arg Ile Ala Val His Tyr Phe Lys Gly
                485                 490                 495
Trp Phe Leu Ile Asp Met Val Ala Ala Ile Pro Phe Asp Leu Leu Ile
            500                 505                 510
Phe Gly Ser Gly Ser Glu Glu Leu Ile Gly Leu Leu Lys Thr Ala Arg
        515                 520                 525
Leu Leu Arg Leu Val Arg Val Ala Arg Lys Leu Asp Arg Tyr Ser Glu
    530                 535                 540
Tyr Gly Ala Ala Val Leu Phe Leu Leu Met Cys Thr Phe Ala Leu Ile
545                 550                 555                 560
Ala His Trp Leu Ala Cys Ile Trp Tyr Ala Ile Gly Asn Met Glu Gln
                565                 570                 575
Pro His Met Asp Ser Arg Ile Gly Trp Leu His Asn Leu Gly Asp Gln
            580                 585                 590
Ile Gly Lys Pro Tyr Asn Ser Ser Gly Leu Gly Gly Pro Ser Ile Lys
        595                 600                 605
Asp Lys Tyr Val Thr Ala Leu Tyr Phe Thr Phe Ser Ser Leu Thr Ser
    610                 615                 620
Val Gly Phe Gly Asn Val Ser Pro Asn Thr Asn Ser Glu Lys Ile Phe
625                 630                 635                 640
Ser Ile Cys Val Met Leu Ile Gly Ser Leu Met Tyr Ala Ser Ile Phe
                645                 650                 655
Gly Asn Val Ser Ala Ile Ile Gln Arg Leu Tyr Ser Gly Thr Ala Arg
            660                 665                 670
Tyr His Thr Gln Met Leu Arg Val Arg Glu Phe Ile Arg Phe His Gln
        675                 680                 685
Ile Pro Asn Pro Leu Arg Gln Arg Leu Glu Glu Tyr Phe Gln His Ala
    690                 695                 700
Trp Ser Tyr Thr Asn Gly Ile Asp Met Asn Ala Val Leu Lys Gly Phe
705                 710                 715                 720
Pro Glu Cys Leu Gln Ala Asp Ile Cys Leu His Leu Asn Arg Ser Leu
                725                 730                 735
Leu Gln His Cys Lys Pro Phe Arg Gly Ala Thr Lys Gly Cys Leu Arg
            740                 745                 750
Ala Leu Ala Met Lys Phe Lys Thr Thr His Ala Pro Pro Gly Asp Thr
        755                 760                 765
Leu Val His Ala Gly Asp Leu Leu Thr Ala Leu Tyr Phe Ile Ser Arg
    770                 775                 780
```

```
Gly Ser Ile Glu Ile Leu Arg Gly Asp Val Val Ala Ile Leu Gly
785                 790                 795                 800

Lys Asn Asp Ile Phe Gly Glu Pro Leu Asn Leu Tyr Ala Arg Pro Gly
                805                 810                 815

Lys Ser Asn Gly Asp Val Arg Ala Leu Thr Tyr Cys Asp Leu His Lys
                820                 825                 830

Ile His Arg Asp Asp Leu Leu Glu Val Leu Asp Met Tyr Pro Glu Phe
            835                 840                 845

Ser Asp His Phe Trp Ser Ser Leu Glu Ile Thr Phe Asn Leu Arg Asp
    850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
                885                 890                 895

Lys Asp Thr Glu Gln Pro Gly Glu Val Ser Ala Leu Gly Pro Gly Arg
                900                 905                 910

Ala Gly Ala Gly Pro Ser Ser Arg Gly Arg Pro Gly Pro Trp Gly
            915                 920                 925

Glu Ser Pro Ser Ser Gly Pro Ser Pro Glu Ser Ser Asp Glu
930                 935                 940

Gly Pro Gly Arg Ser Ser Pro Leu Arg Leu Val Pro Phe Ser Ser
945                 950                 955                 960

Pro Arg Pro Pro Gly Glu Pro Pro Gly Gly Pro Leu Met Glu Asp
                965                 970                 975

Cys Glu Lys Ser Ser Asp Thr Cys Asn Pro Leu Ser Gly Ala Phe Ser
                980                 985                 990

Gly Val Ser Asn Ile Phe Ser Phe Trp Gly Asp Ser Arg Gly Arg Gln
                995                 1000                1005

Tyr Gln Glu Leu Pro Arg Cys Pro Ala Pro Thr Pro Ser Leu Leu
    1010                1015                1020

Asn Ile Pro Leu Ser Ser Pro Gly Arg Arg Pro Arg Gly Asp Val
    1025                1030                1035

Glu Ser Arg Leu Asp Ala Leu Gln Arg Gln Leu Asn Arg Leu Glu
    1040                1045                1050

Thr Arg Leu Ser Ala Asp Met Ala Thr Val Leu Gln Leu Leu Gln
    1055                1060                1065

Arg Gln Met Thr Leu Val Pro Pro Ala Tyr Ser Ala Val Thr Thr
    1070                1075                1080

Pro Gly Pro Gly Pro Thr Ser Thr Ser Pro Leu Leu Pro Val Ser
    1085                1090                1095

Pro Leu Pro Thr Leu Thr Leu Asp Ser Leu Ser Gln Val Ser Gln
    1100                1105                1110

Phe Met Ala Cys Glu Glu Leu Pro Pro Gly Ala Pro Glu Leu Pro
    1115                1120                1125

Gln Glu Gly Pro Thr Arg Arg Leu Ser Leu Pro Gly Gln Leu Gly
    1130                1135                1140

Ala Leu Thr Ser Gln Pro Leu His Arg His Gly Ser Asp Pro Gly
    1145                1150                1155

Ser

<210> SEQ ID NO 26
<211> LENGTH: 427
<212> TYPE: PRT
<213> ORGANISM: Homo sapiens
```

```
<400> SEQUENCE: 26

Met Gly Ser Val Arg Thr Asn Arg Tyr Ser Ile Val Ser Glu Glu
1               5                   10                  15

Asp Gly Met Lys Leu Ala Thr Met Ala Val Ala Asn Gly Phe Gly Asn
            20                  25                  30

Gly Lys Ser Lys Val His Thr Arg Gln Gln Cys Arg Ser Arg Phe Val
            35                  40                  45

Lys Lys Asp Gly His Cys Asn Val Gln Phe Ile Asn Val Gly Glu Lys
50                  55                  60

Gly Gln Arg Tyr Leu Ala Asp Ile Phe Thr Thr Cys Val Asp Ile Arg
65                  70                  75                  80

Trp Arg Trp Met Leu Val Ile Phe Cys Leu Ala Phe Val Leu Ser Trp
                85                  90                  95

Leu Phe Phe Gly Cys Val Phe Trp Leu Ile Ala Leu Leu His Gly Asp
                100                 105                 110

Leu Asp Ala Ser Lys Glu Gly Lys Ala Cys Val Ser Glu Val Asn Ser
                115                 120                 125

Phe Thr Ala Ala Phe Leu Phe Ser Ile Glu Thr Gln Thr Thr Ile Gly
130                 135                 140

Tyr Gly Phe Arg Cys Val Thr Asp Glu Cys Pro Ile Ala Val Phe Met
145                 150                 155                 160

Val Val Phe Gln Ser Ile Val Gly Cys Ile Ile Asp Ala Phe Ile Ile
                165                 170                 175

Gly Ala Val Met Ala Lys Met Ala Lys Pro Lys Lys Arg Asn Glu Thr
                180                 185                 190

Leu Val Phe Ser His Asn Ala Val Ile Ala Met Arg Asp Gly Lys Leu
                195                 200                 205

Cys Leu Met Trp Arg Val Gly Asn Leu Arg Lys Ser His Leu Val Glu
210                 215                 220

Ala His Val Arg Ala Gln Leu Leu Lys Ser Arg Ile Thr Ser Glu Gly
225                 230                 235                 240

Glu Tyr Ile Pro Leu Asp Gln Ile Asp Ile Asn Val Gly Phe Asp Ser
                245                 250                 255

Gly Ile Asp Arg Ile Phe Leu Val Ser Pro Ile Thr Ile Val His Glu
                260                 265                 270

Ile Asp Glu Asp Ser Pro Leu Tyr Asp Leu Ser Lys Gln Asp Ile Asp
                275                 280                 285

Asn Ala Asp Phe Glu Ile Val Val Ile Leu Glu Gly Met Val Glu Ala
                290                 295                 300

Thr Ala Met Thr Thr Gln Cys Arg Ser Ser Tyr Leu Ala Asn Glu Ile
305                 310                 315                 320

Leu Trp Gly His Arg Tyr Glu Pro Val Leu Phe Glu Glu Lys His Tyr
                325                 330                 335

Tyr Lys Val Asp Tyr Ser Arg Phe His Lys Thr Tyr Glu Val Pro Asn
                340                 345                 350

Thr Pro Leu Cys Ser Ala Arg Asp Leu Ala Glu Lys Lys Tyr Ile Leu
                355                 360                 365

Ser Asn Ala Asn Ser Phe Cys Tyr Glu Asn Glu Val Ala Leu Thr Ser
                370                 375                 380

Lys Glu Glu Asp Ser Glu Asn Gly Val Pro Glu Ser Thr Ser Thr
385                 390                 395                 400

Asp Thr Pro Pro Asp Ile Asp Leu His Asn Gln Ala Ser Val Pro Leu
```

```
                        405                 410                 415
Glu Pro Arg Pro Leu Arg Arg Glu Ser Glu Ile
            420                 425

<210> SEQ ID NO 27
<211> LENGTH: 215
<212> TYPE: PRT
<213> ORGANISM: Homo sapiens

<400> SEQUENCE: 27

Met Leu Ser Tyr Gly Glu Arg Leu Gly Ser Pro Ala Val Ser Pro Leu
1               5                   10                  15

Pro Val Arg Gly Gly His Val Met Arg Gly Thr Ala Phe Ala Tyr Val
            20                  25                  30

Pro Ser Pro Gln Val Leu His Arg Ile Pro Gly Thr Ser Ala Tyr Ala
        35                  40                  45

Phe Pro Ser Leu Gly Pro Val Ala Leu Ala Glu His Thr Cys Pro Cys
    50                  55                  60

Gly Glu Val Leu Glu Arg His Glu Pro Leu Pro Ala Lys Leu Ala Leu
65                  70                  75                  80

Glu Glu Glu Gln Lys Pro Glu Ser Arg Leu Val Pro Lys Leu Arg Gln
                85                  90                  95

Ala Gly Ala Met Leu Leu Lys Val Pro Leu Met Leu Thr Phe Leu Tyr
            100                 105                 110

Leu Phe Val Cys Ser Leu Asp Met Leu Ser Ser Ala Phe Gln Leu Ala
        115                 120                 125

Gly Gly Lys Val Ala Gly Asp Ile Phe Lys Asp Asn Ala Ile Leu Ser
    130                 135                 140

Asn Pro Val Ala Gly Leu Val Val Gly Ile Leu Val Thr Val Leu Val
145                 150                 155                 160

Gln Ser Ser Ser Thr Ser Thr Ser Ile Ile Val Ser Met Val Ser Ser
                165                 170                 175

Gly Leu Leu Glu Val Ser Ser Ala Ile Pro Ile Ile Met Gly Ser Asn
            180                 185                 190

Ile Gly Thr Ser Val Thr Asn Thr Ile Val Ala Leu Met Gln Ala Gly
        195                 200                 205

Asp Arg Thr Asp Phe Arg Arg
    210                 215

<210> SEQ ID NO 28
<211> LENGTH: 311
<212> TYPE: PRT
<213> ORGANISM: Homo sapiens

<400> SEQUENCE: 28

Val Ile Val Leu Gly Leu Tyr Ile Tyr Val Thr Tyr Lys Lys Pro Asp
1               5                   10                  15

Val Asn Trp Gly Ser Ser Thr Gln Ala Leu Thr Tyr Leu Asn Ala Leu
            20                  25                  30

Gln His Ser Ile Arg Leu Ser Gly Val Glu Asp His Val Lys Asn Phe
        35                  40                  45

Arg Pro Gln Cys Leu Val Met Thr Gly Ala Pro Asn Ser Arg Pro Ala
    50                  55                  60

Leu Leu His Leu Val His Asp Phe Thr Lys Asn Val Gly Leu Met Ile
65                  70                  75                  80

Cys Gly His Val His Met Gly Pro Arg Arg Gln Ala Met Lys Glu Met
```

```
                    85                  90                  95
Ser Ile Asp Gln Ala Lys Tyr Gln Arg Trp Leu Ile Lys Asn Lys Met
                100                 105                 110

Lys Ala Phe Tyr Ala Pro Val His Ala Asp Leu Arg Glu Gly Ala
            115                 120                 125

Gln Tyr Leu Met Gln Ala Ala Gly Leu Gly Arg Met Lys Pro Asn Thr
        130                 135                 140

Leu Val Leu Gly Phe Lys Lys Asp Trp Leu Gln Ala Asp Met Arg Asp
145                 150                 155                 160

Val Asp Met Tyr Ile Asn Leu Phe His Asp Ala Phe Asp Ile Gln Tyr
                165                 170                 175

Gly Val Val Val Ile Arg Leu Lys Glu Gly Leu Asp Ile Ser His Leu
            180                 185                 190

Gln Gly Gln Glu Glu Leu Leu Ser Ser Gln Lys Ser Pro Gly Thr
        195                 200                 205

Lys Asp Val Val Ser Val Glu Tyr Ser Lys Lys Ser Asp Leu Asp
210                 215                 220

Thr Ser Lys Pro Leu Ser Glu Lys Pro Ile Thr His Lys Glu Ser Lys
225                 230                 235                 240

Gly Pro Ile Val Pro Leu Asn Val Ala Asp Gln Lys Leu Leu Glu Ala
                245                 250                 255

Ser Thr Gln Phe Gln Lys Lys Gln Gly Lys Asn Thr Ile Asp Val Trp
            260                 265                 270

Trp Leu Phe Asp Asp Gly Gly Leu Thr Leu Leu Ile Pro Tyr Leu Leu
        275                 280                 285

Thr Thr Lys Lys Lys Trp Lys Asp Cys Lys Ile Arg Val Phe Ile Gly
290                 295                 300

Gly Lys Ile Asn Arg Ile Asp
305                 310

<210> SEQ ID NO 29
<211> LENGTH: 353
<212> TYPE: PRT
<213> ORGANISM: Artificial sequence
<220> FEATURE:
<223> OTHER INFORMATION: synthetic amino acid sequence

<400> SEQUENCE: 29

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
```

```
                130             135             140
Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
                180                 185                 190

Val Ser Asp Ile Gly Thr Ile Val Trp Gly Thr Thr Ala Ala Leu Ser
                195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Val Tyr Gly Ser Thr Val Gly His
                275                 280                 285

Thr Ile Ile Asp Leu Met Ser Lys Asn Cys Trp Gly Leu Leu Gly His
                290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val Ser Glu Gln Ile
                340                 345                 350

Asp

<210> SEQ ID NO 30
<211> LENGTH: 350
<212> TYPE: PRT
<213> ORGANISM: Artificial sequence
<220> FEATURE:
<223> OTHER INFORMATION: synthetic amino acid sequence

<400> SEQUENCE: 30

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
                35                  40                  45

Glu Arg Met Leu Phe Gln Thr Ser Tyr Thr Leu Glu Asn Asn Gly Ser
50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Thr Phe Ala Leu Ser Val Ala Cys Leu Gly Tyr Ala Tyr
                100                 105                 110

Gln Ala Trp Arg Ala Thr Cys Gly Trp Glu Glu Val Tyr Val Ala Leu
                115                 120                 125

Ile Glu Met Met Lys Ser Ile Ile Glu Ala Phe His Glu Phe Asp Ser
130                 135                 140
```

```
Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
            165                 170                 175

Asn Leu Thr Gly Leu Lys Asp Asp Tyr Ser Lys Arg Thr Met Gly Leu
        180                 185                 190

Leu Val Ser Asp Val Gly Cys Ile Val Trp Gly Ala Thr Ser Ala Met
    195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Pro Tyr Gly Ser Ala Ile Gly
        275                 280                 285

His Ser Ile Leu Asp Leu Ile Ala Lys Asn Met Trp Gly Val Leu Gly
    290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 31
<211> LENGTH: 1061
<212> TYPE: PRT
<213> ORGANISM: Artificial sequence
<220> FEATURE:
<223> OTHER INFORMATION: synthetic amino acid sequence

<400> SEQUENCE: 31

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160
```

```
Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Lys Ser Arg Ile Thr Ser Glu Gly Glu Tyr Ile Pro Leu Asp
            260                 265                 270

Gln Ile Asp Ile Asn Val Gly Ala Pro Gly Ser Gly Ala Thr Asn Phe
        275                 280                 285

Ser Leu Leu Lys Gln Ala Gly Asp Val Glu Glu Asn Pro Met Asp Leu
    290                 295                 300

Lys Glu Ser Pro Ser Glu Gly Ser Leu Gln Pro Ser Ser Ile Gln Ile
305                 310                 315                 320

Phe Ala Asn Thr Ser Thr Leu His Gly Ile Arg His Ile Phe Val Tyr
                325                 330                 335

Gly Pro Leu Thr Ile Arg Arg Val Leu Trp Ala Val Ala Phe Val Gly
            340                 345                 350

Ser Leu Gly Leu Leu Leu Val Glu Ser Ser Glu Arg Val Ser Tyr Tyr
        355                 360                 365

Phe Ser Tyr Gln His Val Thr Lys Val Asp Glu Val Val Ala Gln Ser
    370                 375                 380

Leu Val Phe Pro Ala Val Thr Leu Cys Asn Leu Asn Gly Phe Arg Phe
385                 390                 395                 400

Ser Arg Leu Thr Thr Asn Asp Leu Tyr His Ala Gly Glu Leu Leu Ala
                405                 410                 415

Leu Leu Asp Val Asn Leu Gln Ile Pro Asp Pro His Leu Ala Asp Pro
            420                 425                 430

Thr Val Leu Glu Ala Leu Arg Gln Lys Ala Asn Phe Lys His Tyr Lys
        435                 440                 445

Pro Lys Gln Phe Ser Met Leu Glu Phe Leu His Arg Val Gly His Asp
    450                 455                 460

Leu Lys Asp Met Met Leu Tyr Cys Lys Phe Lys Gly Gln Glu Cys Gly
465                 470                 475                 480

His Gln Asp Phe Thr Thr Val Phe Thr Lys Tyr Gly Lys Cys Tyr Met
                485                 490                 495

Phe Asn Ser Gly Glu Asp Gly Lys Pro Leu Leu Thr Thr Val Lys Gly
            500                 505                 510

Gly Thr Gly Asn Gly Leu Glu Ile Met Leu Asp Ile Gln Gln Asp Glu
        515                 520                 525

Tyr Leu Pro Ile Trp Gly Glu Thr Glu Thr Thr Phe Glu Ala Gly
    530                 535                 540

Val Lys Val Gln Ile His Ser Gln Ser Glu Pro Pro Phe Ile Gln Glu
545                 550                 555                 560

Leu Gly Phe Gly Val Ala Pro Gly Phe Gln Thr Phe Val Ala Thr Gln
                565                 570                 575
```

```
Glu Gln Arg Leu Thr Tyr Leu Pro Pro Pro Trp Gly Glu Cys Arg Ser
                580                 585                 590

Ser Glu Met Gly Leu Asp Phe Phe Pro Val Tyr Ser Ile Thr Ala Cys
        595                 600                 605

Arg Ile Asp Cys Glu Thr Arg Tyr Ile Val Glu Asn Cys Asn Cys Arg
    610                 615                 620

Met Val His Met Pro Gly Asp Ala Pro Phe Cys Thr Pro Glu Gln His
625                 630                 635                 640

Lys Glu Cys Ala Glu Pro Ala Leu Gly Leu Leu Ala Glu Lys Asp Ser
                645                 650                 655

Asn Tyr Cys Leu Cys Arg Thr Pro Cys Asn Leu Thr Arg Tyr Asn Lys
            660                 665                 670

Glu Leu Ser Met Val Lys Ile Pro Ser Lys Thr Ser Ala Lys Tyr Leu
        675                 680                 685

Glu Lys Lys Phe Asn Lys Ser Glu Lys Tyr Ile Ser Glu Asn Ile Leu
    690                 695                 700

Val Leu Asp Ile Phe Phe Glu Ala Leu Asn Tyr Glu Thr Ile Glu Gln
705                 710                 715                 720

Lys Lys Ala Tyr Glu Val Ala Ala Leu Leu Gly Asp Ile Gly Gly Gln
                725                 730                 735

Met Gly Leu Phe Ile Gly Ala Ser Leu Leu Thr Ile Leu Glu Leu Phe
            740                 745                 750

Asp Tyr Ile Tyr Glu Leu Ile Lys Glu Lys Leu Leu Asp Leu Leu Gly
        755                 760                 765

Lys Glu Glu Glu Gly Ser His Asp Glu Asn Met Ser Thr Cys Asp
    770                 775                 780

Thr Met Pro Asn His Ser Glu Thr Ile Ser His Thr Val Asn Val Pro
785                 790                 795                 800

Leu Gln Thr Ala Leu Gly Thr Leu Glu Glu Ile Ala Cys Ala Ala Ala
                805                 810                 815

Val Ser Lys Gly Glu Glu Leu Phe Thr Gly Val Val Pro Ile Leu Val
            820                 825                 830

Glu Leu Asp Gly Asp Val Asn Gly His Lys Phe Ser Val Ser Gly Glu
        835                 840                 845

Gly Glu Gly Asp Ala Thr Tyr Gly Lys Leu Thr Leu Lys Phe Ile Cys
    850                 855                 860

Thr Thr Gly Lys Leu Pro Val Pro Trp Pro Thr Leu Val Thr Thr Phe
865                 870                 875                 880

Gly Tyr Gly Leu Gln Cys Phe Ala Arg Tyr Pro Asp His Met Lys Gln
                885                 890                 895

His Asp Phe Phe Lys Ser Ala Met Pro Glu Gly Tyr Val Gln Glu Arg
            900                 905                 910

Thr Ile Phe Phe Lys Asp Asp Gly Asn Tyr Lys Thr Arg Ala Glu Val
        915                 920                 925

Lys Phe Glu Gly Asp Thr Leu Val Asn Arg Ile Glu Leu Lys Gly Ile
    930                 935                 940

Asp Phe Arg Glu Asp Gly Asn Ile Leu Gly His Lys Leu Glu Tyr Asn
945                 950                 955                 960

Tyr Asn Ser His Asn Val Tyr Ile Met Ala Asp Lys Gln Lys Asn Gly
                965                 970                 975

Ile Lys Val Asn Phe Lys Ile Arg His Asn Ile Glu Asp Gly Ser Val
            980                 985                 990

Gln Leu Ala Asp His Tyr Gln Gln Asn Thr Pro Ile Gly Asp Gly Pro
```

```
              995              1000             1005
Val Leu Leu Pro Asp Asn His Tyr Leu Ser Tyr Gln Ser Ala Leu
       1010             1015             1020

Ser Lys Asp Pro Asn Glu Lys Arg Asp His Met Val Leu Leu Glu
   1025              1030            1035

Phe Val Thr Ala Ala Gly Ile Thr Leu Gly Met Asp Glu Leu Tyr
       1040             1045            1050

Lys Phe Cys Tyr Glu Asn Glu Val
   1055             1060

<210> SEQ ID NO 32
<211> LENGTH: 1081
<212> TYPE: PRT
<213> ORGANISM: Artificial sequence
<220> FEATURE:
<223> OTHER INFORMATION: synthetic amino acid sequence

<400> SEQUENCE: 32

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Met Leu Ile
           20                  25                  30

Gly Thr Phe Tyr Phe Leu Val Arg Gly Trp Gly Val Thr Asp Lys Asp
       35                  40                  45

Ala Arg Glu Tyr Tyr Ala Val Thr Ile Leu Val Pro Gly Ile Ala Ser
   50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
               85                  90                  95

Leu Phe Thr Thr Pro Leu Leu Leu Asp Leu Ala Leu Leu Ala Lys
           100                 105                 110

Val Asp Arg Val Thr Ile Gly Thr Leu Val Gly Val Asp Ala Leu Met
       115                 120                 125

Ile Val Thr Gly Leu Ile Gly Ala Leu Ser His Thr Ala Ile Ala Arg
   130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
               165                 170                 175

Val Ala Ser Thr Phe Asn Thr Leu Thr Ala Leu Val Leu Val Leu Trp
           180                 185                 190

Thr Ala Tyr Pro Ile Leu Trp Ile Ile Gly Thr Glu Gly Ala Gly Val
       195                 200                 205

Val Gly Leu Gly Ile Glu Thr Leu Leu Phe Met Val Leu Asp Val Thr
   210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
               245                 250                 255

Ala Asp Lys Ser Arg Ile Thr Ser Glu Gly Glu Tyr Ile Pro Leu Asp
           260                 265                 270

Gln Ile Asp Ile Asn Val Gly Ala Pro Gly Ser Gly Ala Thr Asn Phe
       275                 280                 285

Ser Leu Leu Lys Gln Ala Gly Asp Val Glu Glu Asn Pro Met Asp Leu
```

```
                290                 295                 300
Lys Glu Ser Pro Ser Glu Gly Ser Leu Gln Pro Ser Ser Ile Gln Ile
305                 310                 315                 320

Phe Ala Asn Thr Ser Thr Leu His Gly Ile Arg His Ile Phe Val Tyr
                325                 330                 335

Gly Pro Leu Thr Ile Arg Arg Val Leu Trp Ala Val Ala Phe Val Gly
                340                 345                 350

Ser Leu Gly Leu Leu Val Glu Ser Ser Glu Arg Val Ser Tyr Tyr
                355                 360                 365

Phe Ser Tyr Gln His Val Thr Lys Val Asp Glu Val Val Ala Gln Ser
370                 375                 380

Leu Val Phe Pro Ala Val Thr Leu Cys Asn Leu Asn Gly Phe Arg Phe
385                 390                 395                 400

Ser Arg Leu Thr Thr Asn Asp Leu Tyr His Ala Gly Glu Leu Leu Ala
                405                 410                 415

Leu Leu Asp Val Asn Leu Gln Ile Pro Asp Pro His Leu Ala Asp Pro
                420                 425                 430

Thr Val Leu Glu Ala Leu Arg Gln Lys Ala Asn Phe Lys His Tyr Lys
                435                 440                 445

Pro Lys Gln Phe Ser Met Leu Glu Phe Leu His Arg Val Gly His Asp
                450                 455                 460

Leu Lys Asp Met Met Leu Tyr Cys Lys Phe Lys Gly Gln Glu Cys Gly
465                 470                 475                 480

His Gln Asp Phe Thr Thr Val Phe Thr Lys Tyr Gly Lys Cys Tyr Met
                485                 490                 495

Phe Asn Ser Gly Glu Asp Gly Lys Pro Leu Leu Thr Thr Val Lys Gly
                500                 505                 510

Gly Thr Gly Asn Gly Leu Glu Ile Met Leu Asp Ile Gln Gln Asp Glu
                515                 520                 525

Tyr Leu Pro Ile Trp Gly Glu Thr Glu Thr Thr Phe Glu Ala Gly
                530                 535                 540

Val Lys Val Gln Ile His Ser Gln Ser Glu Pro Pro Phe Ile Gln Glu
545                 550                 555                 560

Leu Gly Phe Gly Val Ala Pro Gly Phe Gln Thr Phe Val Ala Thr Gln
                565                 570                 575

Glu Gln Arg Leu Thr Tyr Leu Pro Pro Pro Trp Gly Glu Cys Arg Ser
                580                 585                 590

Ser Glu Met Gly Leu Asp Phe Phe Pro Val Tyr Ser Ile Thr Ala Cys
                595                 600                 605

Arg Ile Asp Cys Glu Thr Arg Tyr Ile Val Glu Asn Cys Asn Cys Arg
610                 615                 620

Met Val His Met Pro Gly Asp Ala Pro Phe Cys Thr Pro Glu Gln His
625                 630                 635                 640

Lys Glu Cys Ala Glu Pro Ala Leu Gly Leu Leu Ala Glu Lys Asp Ser
                645                 650                 655

Asn Tyr Cys Leu Cys Arg Thr Pro Cys Asn Leu Thr Arg Tyr Asn Lys
                660                 665                 670

Glu Leu Ser Met Val Lys Ile Pro Ser Lys Thr Ser Ala Lys Tyr Leu
                675                 680                 685

Glu Lys Lys Phe Asn Lys Ser Glu Lys Tyr Ile Ser Glu Asn Ile Leu
                690                 695                 700

Val Leu Asp Ile Phe Phe Glu Ala Leu Asn Tyr Glu Thr Ile Glu Gln
705                 710                 715                 720
```

Lys Lys Ala Tyr Glu Val Ala Ala Leu Leu Gly Asp Ile Gly Gly Gln
                725                 730                 735

Met Gly Leu Phe Ile Gly Ala Ser Leu Leu Thr Ile Leu Glu Leu Phe
            740                 745                 750

Asp Tyr Ile Tyr Glu Leu Ile Lys Glu Lys Leu Leu Asp Leu Leu Gly
            755                 760                 765

Lys Glu Glu Glu Gly Ser His Asp Glu Asn Met Ser Thr Cys Asp
    770                 775                 780

Thr Met Pro Asn His Ser Glu Thr Ile Ser His Thr Val Asn Val Pro
785                 790                 795                 800

Leu Gln Thr Ala Leu Gly Thr Leu Glu Glu Ile Ala Cys Ala Ala Ala
                805                 810                 815

Lys Ser Arg Ile Thr Ser Glu Gly Glu Tyr Ile Pro Leu Asp Gln Ile
                820                 825                 830

Asp Ile Asn Val Val Ser Lys Gly Glu Glu Leu Phe Thr Gly Val Val
                835                 840                 845

Pro Ile Leu Val Glu Leu Asp Gly Asp Val Asn Gly His Lys Phe Ser
    850                 855                 860

Val Ser Gly Glu Gly Glu Gly Asp Ala Thr Tyr Gly Lys Leu Thr Leu
865                 870                 875                 880

Lys Phe Ile Cys Thr Thr Gly Lys Leu Pro Val Pro Trp Pro Thr Leu
                885                 890                 895

Val Thr Thr Phe Gly Tyr Gly Leu Gln Cys Phe Ala Arg Tyr Pro Asp
                900                 905                 910

His Met Lys Gln His Asp Phe Phe Lys Ser Ala Met Pro Glu Gly Tyr
                915                 920                 925

Val Gln Glu Arg Thr Ile Phe Phe Lys Asp Asp Gly Asn Tyr Lys Thr
                930                 935                 940

Arg Ala Glu Val Lys Phe Glu Gly Asp Thr Leu Val Asn Arg Ile Glu
945                 950                 955                 960

Leu Lys Gly Ile Asp Phe Arg Glu Asp Gly Asn Ile Leu Gly His Lys
                965                 970                 975

Leu Glu Tyr Asn Tyr Asn Ser His Asn Val Tyr Ile Met Ala Asp Lys
            980                 985                 990

Gln Lys Asn Gly Ile Lys Val Asn Phe Lys Ile Arg His Asn Ile Glu
        995                 1000                1005

Asp Gly Ser Val Gln Leu Ala Asp His Tyr Gln Gln Asn Thr Pro
    1010                1015                1020

Ile Gly Asp Gly Pro Val Leu Leu Pro Asp Asn His Tyr Leu Ser
    1025                1030                1035

Tyr Gln Ser Ala Leu Ser Lys Asp Pro Asn Glu Lys Arg Asp His
    1040                1045                1050

Met Val Leu Leu Glu Phe Val Thr Ala Ala Gly Ile Thr Leu Gly
    1055                1060                1065

Met Asp Glu Leu Tyr Lys Phe Cys Tyr Glu Asn Glu Val
    1070                1075                1080

<210> SEQ ID NO 33
<211> LENGTH: 1061
<212> TYPE: PRT
<213> ORGANISM: Artificial sequence
<220> FEATURE:
<223> OTHER INFORMATION: synthetic amino acid sequence

<400> SEQUENCE: 33

```
Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65              70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
                100                 105                 110

Val Asp Arg Val Thr Ile Gly Thr Leu Val Gly Val Asp Ala Leu Met
    115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Lys Ser Arg Ile Thr Ser Glu Gly Tyr Ile Pro Leu Asp
            260                 265                 270

Gln Ile Asp Ile Asn Val Gly Ala Pro Met Asp Leu Lys Glu Ser Pro
    275                 280                 285

Ser Glu Gly Ser Leu Gln Pro Ser Ser Ile Gln Ile Phe Ala Asn Thr
    290                 295                 300

Ser Thr Leu His Gly Ile Arg His Ile Phe Val Tyr Gly Pro Leu Thr
305                 310                 315                 320

Ile Arg Arg Val Leu Trp Ala Val Ala Phe Val Gly Ser Leu Gly Leu
                325                 330                 335

Leu Leu Val Glu Ser Ser Glu Arg Val Ser Tyr Tyr Phe Ser Tyr Gln
                340                 345                 350

His Val Thr Lys Val Asp Glu Val Ala Gln Ser Leu Val Phe Pro
            355                 360                 365

Ala Val Thr Leu Cys Asn Leu Asn Gly Phe Arg Phe Ser Arg Leu Thr
            370                 375                 380

Thr Asn Asp Leu Tyr His Ala Gly Glu Leu Leu Ala Leu Leu Asp Val
385                 390                 395                 400

Asn Leu Gln Ile Pro Asp Pro His Leu Ala Asp Pro Thr Val Leu Glu
                405                 410                 415
```

```
Ala Leu Arg Gln Lys Ala Asn Phe Lys His Tyr Lys Pro Lys Gln Phe
                420                 425                 430

Ser Met Leu Glu Phe Leu His Arg Val Gly His Asp Leu Lys Asp Met
            435                 440                 445

Met Leu Tyr Cys Lys Phe Lys Gly Gln Glu Cys Gly His Gln Asp Phe
        450                 455                 460

Thr Thr Val Phe Thr Lys Tyr Gly Lys Cys Tyr Met Phe Asn Ser Gly
465                 470                 475                 480

Glu Asp Gly Lys Pro Leu Leu Thr Thr Val Lys Gly Thr Gly Asn
                485                 490                 495

Gly Leu Glu Ile Met Leu Asp Ile Gln Gln Asp Glu Tyr Leu Pro Ile
            500                 505                 510

Trp Gly Glu Thr Glu Thr Thr Phe Glu Ala Gly Val Lys Val Gln
            515                 520                 525

Ile His Ser Gln Ser Glu Pro Pro Phe Ile Gln Glu Leu Gly Phe Gly
        530                 535                 540

Val Ala Pro Gly Phe Gln Thr Phe Val Ala Thr Gln Glu Gln Arg Leu
545                 550                 555                 560

Thr Tyr Leu Pro Pro Pro Trp Gly Glu Cys Arg Ser Ser Glu Met Gly
                565                 570                 575

Leu Asp Phe Phe Pro Val Tyr Ser Ile Thr Ala Cys Arg Ile Asp Cys
            580                 585                 590

Glu Thr Arg Tyr Ile Val Glu Asn Cys Asn Cys Arg Met Val His Met
        595                 600                 605

Pro Gly Asp Ala Pro Phe Cys Thr Pro Glu Gln His Lys Glu Cys Ala
610                 615                 620

Glu Pro Ala Leu Gly Leu Leu Ala Glu Lys Asp Ser Asn Tyr Cys Leu
625                 630                 635                 640

Cys Arg Thr Pro Cys Asn Leu Thr Arg Tyr Asn Lys Glu Leu Ser Met
                645                 650                 655

Val Lys Ile Pro Ser Lys Thr Ser Ala Lys Tyr Leu Glu Lys Lys Phe
            660                 665                 670

Asn Lys Ser Glu Lys Tyr Ile Ser Glu Asn Ile Leu Val Leu Asp Ile
        675                 680                 685

Phe Phe Glu Ala Leu Asn Tyr Glu Thr Ile Glu Gln Lys Lys Ala Tyr
690                 695                 700

Glu Val Ala Ala Leu Leu Gly Asp Ile Gly Gly Gln Met Gly Leu Phe
705                 710                 715                 720

Ile Gly Ala Ser Leu Leu Thr Ile Leu Glu Leu Phe Asp Tyr Ile Tyr
                725                 730                 735

Glu Leu Ile Lys Glu Lys Leu Leu Asp Leu Leu Gly Lys Glu Glu Glu
            740                 745                 750

Glu Gly Ser His Asp Glu Asn Met Ser Thr Cys Asp Thr Met Pro Asn
        755                 760                 765

His Ser Glu Thr Ile Ser His Thr Val Asn Val Pro Leu Gln Thr Ala
770                 775                 780

Leu Gly Thr Leu Glu Glu Ile Ala Cys Ala Ala Lys Ser Arg Ile
785                 790                 795                 800

Thr Ser Glu Gly Glu Tyr Ile Pro Leu Asp Gln Ile Asp Ile Asn Val
                805                 810                 815

Val Ser Lys Gly Glu Glu Leu Phe Thr Gly Val Val Pro Ile Leu Val
            820                 825                 830

Glu Leu Asp Gly Asp Val Asn Gly His Lys Phe Ser Val Ser Gly Glu
```

```
                835                 840                 845
Gly Glu Gly Asp Ala Thr Tyr Gly Lys Leu Thr Leu Lys Phe Ile Cys
    850                 855                 860
Thr Thr Gly Lys Leu Pro Val Pro Trp Pro Thr Leu Val Thr Thr Phe
865                 870                 875                 880
Gly Tyr Gly Leu Gln Cys Phe Ala Arg Tyr Pro Asp His Met Lys Gln
                885                 890                 895
His Asp Phe Phe Lys Ser Ala Met Pro Glu Gly Tyr Val Gln Glu Arg
            900                 905                 910
Thr Ile Phe Phe Lys Asp Asp Gly Asn Tyr Lys Thr Arg Ala Glu Val
            915                 920                 925
Lys Phe Glu Gly Asp Thr Leu Val Asn Arg Ile Glu Leu Lys Gly Ile
        930                 935                 940
Asp Phe Arg Glu Asp Gly Asn Ile Leu Gly His Lys Leu Glu Tyr Asn
945                 950                 955                 960
Tyr Asn Ser His Asn Val Tyr Ile Met Ala Asp Lys Gln Lys Asn Gly
                965                 970                 975
Ile Lys Val Asn Phe Lys Ile Arg His Asn Ile Glu Asp Gly Ser Val
            980                 985                 990
Gln Leu Ala Asp His Tyr Gln Gln Asn Thr Pro Ile Gly Asp Gly Pro
        995                 1000                1005
Val Leu Leu Pro Asp Asn His Tyr Leu Ser Tyr Gln Ser Ala Leu
    1010                1015                1020
Ser Lys Asp Pro Asn Glu Lys Arg Asp His Met Val Leu Leu Glu
    1025                1030                1035
Phe Val Thr Ala Ala Gly Ile Thr Leu Gly Met Asp Glu Leu Tyr
    1040                1045                1050
Lys Phe Cys Tyr Glu Asn Glu Val
    1055                1060

<210> SEQ ID NO 34
<211> LENGTH: 1083
<212> TYPE: PRT
<213> ORGANISM: Artificial sequence
<220> FEATURE:
<223> OTHER INFORMATION: synthetic amino acid sequence

<400> SEQUENCE: 34

Met Asp Pro Ile Ala Leu Gln Ala Gly Tyr Asp Leu Leu Gly Asp Gly
1               5                   10                  15
Arg Pro Glu Thr Leu Trp Leu Gly Ile Gly Thr Leu Leu Met Leu Ile
                20                  25                  30
Gly Thr Phe Tyr Phe Leu Val Arg Gly Trp Gly Val Thr Asp Lys Asp
            35                  40                  45
Ala Arg Glu Tyr Tyr Ala Val Thr Ile Leu Val Pro Gly Ile Ala Ser
        50                  55                  60
Ala Ala Tyr Leu Ser Met Phe Phe Gly Ile Gly Leu Thr Glu Val Thr
65                  70                  75                  80
Val Gly Gly Glu Met Leu Asp Ile Tyr Tyr Ala Arg Tyr Ala Asp Trp
                85                  90                  95
Leu Phe Thr Thr Pro Leu Leu Leu Asp Leu Ala Leu Leu Ala Lys
                100                 105                 110
Val Asp Arg Val Thr Ile Gly Thr Leu Val Gly Val Asp Ala Leu Met
            115                 120                 125
Ile Val Thr Gly Leu Ile Gly Ala Leu Ser His Thr Ala Ile Ala Arg
```

```
            130                 135                 140
Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
                195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Lys Ser Arg Ile Thr Ser Glu Gly Glu Tyr Ile Pro Leu Asp
            260                 265                 270

Gln Ile Asp Ile Asn Val Gly Ala Pro Gly Ser Gly Ala Thr Asn Phe
        275                 280                 285

Ser Leu Leu Lys Gln Ala Gly Asp Val Glu Glu Asn Pro Gly Pro Met
    290                 295                 300

Asp Leu Lys Glu Ser Pro Ser Glu Gly Ser Leu Gln Pro Ser Ser Ile
305                 310                 315                 320

Gln Ile Phe Ala Asn Thr Ser Thr Leu His Gly Ile Arg His Ile Phe
                325                 330                 335

Val Tyr Gly Pro Leu Thr Ile Arg Arg Val Leu Trp Ala Val Ala Phe
            340                 345                 350

Val Gly Ser Leu Gly Leu Leu Leu Val Glu Ser Ser Glu Arg Val Ser
                355                 360                 365

Tyr Tyr Phe Ser Tyr Gln His Val Thr Lys Val Asp Glu Val Val Ala
        370                 375                 380

Gln Ser Leu Val Phe Pro Ala Val Thr Leu Cys Asn Leu Asn Gly Phe
385                 390                 395                 400

Arg Phe Ser Arg Leu Thr Thr Asn Asp Leu Tyr His Ala Gly Glu Leu
                405                 410                 415

Leu Ala Leu Leu Asp Val Asn Leu Gln Ile Pro Asp Pro His Leu Ala
            420                 425                 430

Asp Pro Thr Val Leu Glu Ala Leu Arg Gln Lys Ala Asn Phe Lys His
                435                 440                 445

Tyr Lys Pro Lys Gln Phe Ser Met Leu Glu Phe Leu His Arg Val Gly
        450                 455                 460

His Asp Leu Lys Asp Met Met Leu Tyr Cys Lys Phe Lys Gly Gln Glu
465                 470                 475                 480

Cys Gly His Gln Asp Phe Thr Thr Val Phe Thr Lys Tyr Gly Lys Cys
                485                 490                 495

Tyr Met Phe Asn Ser Gly Glu Asp Gly Lys Pro Leu Leu Thr Thr Val
            500                 505                 510

Lys Gly Gly Thr Gly Asn Gly Leu Glu Ile Met Leu Asp Ile Gln Gln
                515                 520                 525

Asp Glu Tyr Leu Pro Ile Trp Gly Glu Thr Glu Glu Thr Thr Phe Glu
        530                 535                 540

Ala Gly Val Lys Val Gln Ile His Ser Gln Ser Glu Pro Pro Phe Ile
545                 550                 555                 560
```

```
Gln Glu Leu Gly Phe Gly Val Ala Pro Gly Phe Gln Thr Phe Val Ala
                565                 570                 575

Thr Gln Glu Gln Arg Leu Thr Tyr Leu Pro Pro Trp Gly Glu Cys
            580                 585                 590

Arg Ser Ser Glu Met Gly Leu Asp Phe Phe Pro Val Tyr Ser Ile Thr
            595                 600                 605

Ala Cys Arg Ile Asp Cys Glu Thr Arg Tyr Ile Val Glu Asn Cys Asn
        610                 615                 620

Cys Arg Met Val His Met Pro Gly Asp Ala Pro Phe Cys Thr Pro Glu
625                 630                 635                 640

Gln His Lys Glu Cys Ala Glu Pro Ala Leu Gly Leu Leu Ala Glu Lys
                645                 650                 655

Asp Ser Asn Tyr Cys Leu Cys Arg Thr Pro Cys Asn Leu Thr Arg Tyr
            660                 665                 670

Asn Lys Glu Leu Ser Met Val Lys Ile Pro Ser Lys Thr Ser Ala Lys
            675                 680                 685

Tyr Leu Glu Lys Lys Phe Asn Lys Ser Glu Lys Tyr Ile Ser Glu Asn
        690                 695                 700

Ile Leu Val Leu Asp Ile Phe Phe Glu Ala Leu Asn Tyr Glu Thr Ile
705                 710                 715                 720

Glu Gln Lys Lys Ala Tyr Glu Val Ala Ala Leu Leu Gly Asp Ile Gly
                725                 730                 735

Gly Gln Met Gly Leu Phe Ile Gly Ala Ser Leu Leu Thr Ile Leu Glu
            740                 745                 750

Leu Phe Asp Tyr Ile Tyr Glu Leu Ile Lys Glu Lys Leu Leu Asp Leu
            755                 760                 765

Leu Gly Lys Glu Glu Glu Gly Ser His Asp Glu Asn Met Ser Thr
        770                 775                 780

Cys Asp Thr Met Pro Asn His Ser Glu Thr Ile Ser His Thr Val Asn
785                 790                 795                 800

Val Pro Leu Gln Thr Ala Leu Gly Thr Leu Glu Ile Ala Cys Ala
                805                 810                 815

Ala Ala Lys Ser Arg Ile Thr Ser Glu Gly Tyr Ile Pro Leu Asp
            820                 825                 830

Gln Ile Asp Ile Asn Val Val Ser Lys Gly Glu Glu Leu Phe Thr Gly
        835                 840                 845

Val Val Pro Ile Leu Val Glu Leu Asp Gly Asp Val Asn Gly His Lys
850                 855                 860

Phe Ser Val Ser Gly Glu Gly Glu Gly Asp Ala Thr Tyr Gly Lys Leu
865                 870                 875                 880

Thr Leu Lys Phe Ile Cys Thr Thr Gly Lys Leu Pro Val Pro Trp Pro
            885                 890                 895

Thr Leu Val Thr Thr Phe Gly Tyr Gly Leu Gln Cys Phe Ala Arg Tyr
            900                 905                 910

Pro Asp His Met Lys Gln His Asp Phe Phe Lys Ser Ala Met Pro Glu
        915                 920                 925

Gly Tyr Val Gln Glu Arg Thr Ile Phe Phe Lys Asp Asp Gly Asn Tyr
        930                 935                 940

Lys Thr Arg Ala Glu Val Lys Phe Glu Gly Asp Thr Leu Val Asn Arg
945                 950                 955                 960

Ile Glu Leu Lys Gly Ile Asp Phe Arg Glu Asp Gly Asn Ile Leu Gly
                965                 970                 975
```

His Lys Leu Glu Tyr Asn Tyr Asn Ser His Asn Val Tyr Ile Met Ala
                980                 985                 990
Asp Lys Gln Lys Asn Gly Ile Lys Val Asn Phe Lys Ile Arg His Asn
            995                 1000                1005
Ile Glu Asp Gly Ser Val Gln Leu Ala Asp His Tyr Gln Gln Asn
    1010                1015                1020
Thr Pro Ile Gly Asp Gly Pro Val Leu Leu Pro Asp Asn His Tyr
    1025                1030                1035
Leu Ser Tyr Gln Ser Ala Leu Ser Lys Asp Pro Asn Glu Lys Arg
    1040                1045                1050
Asp His Met Val Leu Leu Glu Phe Val Thr Ala Ala Gly Ile Thr
    1055                1060                1065
Leu Gly Met Asp Glu Leu Tyr Lys Phe Cys Tyr Glu Asn Glu Val
    1070                1075                1080

<210> SEQ ID NO 35
<211> LENGTH: 3171
<212> TYPE: PRT
<213> ORGANISM: Artificial sequence
<220> FEATURE:
<223> OTHER INFORMATION: synthetic amino acid sequence

<400> SEQUENCE: 35

Ala Thr Gly Gly Ala Cys Cys Cys Ala Thr Cys Gly Cys Thr Cys
1               5                   10                  15
Thr Gly Cys Ala Gly Gly Cys Thr Gly Gly Thr Thr Ala Cys Gly Ala
                20                  25                  30
Cys Cys Thr Gly Cys Thr Gly Gly Thr Gly Ala Cys Gly Gly Cys
            35                  40                  45
Ala Gly Ala Cys Cys Thr Gly Ala Ala Ala Cys Thr Cys Thr Gly Thr
50                  55                  60
Gly Gly Cys Thr Gly Gly Gly Cys Ala Thr Cys Gly Gly Cys Ala Cys
65                  70                  75                  80
Thr Cys Thr Gly Cys Thr Gly Ala Thr Gly Cys Thr Gly Ala Thr Thr
                85                  90                  95
Gly Gly Ala Ala Cys Cys Thr Cys Thr Ala Cys Thr Thr Thr Cys
            100                 105                 110
Thr Gly Gly Thr Cys Cys Gly Cys Gly Gly Ala Thr Gly Gly Gly
            115                 120                 125
Ala Gly Thr Cys Ala Cys Cys Gly Ala Thr Ala Ala Gly Gly Ala Thr
            130                 135                 140
Gly Cys Cys Cys Gly Gly Gly Ala Ala Thr Ala Thr Ala Cys Gly
145                 150                 155                 160
Cys Thr Gly Thr Gly Ala Cys Thr Ala Thr Cys Cys Thr Gly Gly Thr
                165                 170                 175
Gly Cys Cys Cys Gly Gly Ala Ala Thr Cys Gly Cys Ala Thr Cys Cys
                180                 185                 190
Gly Cys Cys Gly Cys Ala Thr Ala Thr Cys Thr Cys Thr Ala
            195                 200                 205
Thr Gly Thr Thr Cys Thr Thr Thr Gly Gly Thr Ala Thr Cys Gly Gly
            210                 215                 220
Gly Cys Thr Thr Ala Cys Thr Gly Ala Gly Gly Thr Gly Ala Cys Cys
225                 230                 235                 240
Gly Thr Cys Gly Gly Gly Gly Gly Cys Gly Ala Ala Ala Thr Gly Thr
                245                 250                 255

-continued

```
Thr Gly Gly Ala Thr Ala Thr Cys Thr Ala Thr Thr Ala Thr Gly Cys
            260                 265                 270

Cys Ala Gly Gly Thr Ala Cys Gly Cys Cys Gly Ala Cys Thr Gly Gly
        275                 280                 285

Cys Thr Gly Thr Thr Thr Ala Cys Cys Ala Cys Cys Cys Cys Ala Cys
    290                 295                 300

Thr Thr Cys Thr Gly Cys Thr Gly Cys Thr Gly Gly Ala Thr Cys Thr
305                 310                 315                 320

Gly Gly Cys Cys Cys Thr Thr Cys Thr Cys Gly Cys Thr Ala Ala Gly
                325                 330                 335

Gly Thr Gly Gly Ala Thr Cys Gly Gly Gly Thr Gly Ala Cys Cys Ala
            340                 345                 350

Thr Cys Gly Gly Cys Ala Cys Cys Cys Thr Gly Gly Thr Gly Gly Gly
        355                 360                 365

Thr Gly Thr Gly Gly Ala Cys Gly Cys Cys Cys Thr Gly Ala Thr Gly
    370                 375                 380

Ala Thr Cys Gly Thr Cys Ala Cys Thr Gly Gly Cys Cys Thr Cys Ala
385                 390                 395                 400

Thr Cys Gly Gly Ala Gly Cys Cys Thr Thr Gly Ala Gly Cys Cys Ala
                405                 410                 415

Cys Ala Cys Gly Gly Cys Cys Ala Thr Ala Gly Cys Cys Ala Gly Ala
            420                 425                 430

Thr Ala Cys Ala Gly Thr Thr Gly Gly Thr Gly Gly Thr Thr Gly Thr
        435                 440                 445

Thr Cys Thr Cys Thr Ala Cys Ala Ala Thr Thr Thr Gly Cys Ala Thr
    450                 455                 460

Gly Ala Thr Ala Gly Thr Gly Gly Thr Gly Cys Thr Cys Thr Ala Thr
465                 470                 475                 480

Thr Thr Thr Cys Thr Gly Gly Cys Thr Ala Cys Ala Thr Cys Cys Cys
                485                 490                 495

Thr Gly Cys Gly Ala Thr Cys Thr Gly Cys Thr Gly Cys Ala Ala Ala
            500                 505                 510

Gly Gly Ala Gly Cys Gly Gly Gly Gly Cys Cys Cys Gly Ala Gly
        515                 520                 525

Gly Thr Gly Gly Cys Ala Thr Cys Thr Ala Cys Cys Thr Thr Thr Ala
    530                 535                 540

Ala Cys Ala Cys Cys Cys Thr Gly Ala Cys Ala Gly Cys Thr Cys Thr
545                 550                 555                 560

Gly Gly Thr Cys Thr Thr Gly Gly Thr Gly Cys Thr Gly Thr Gly Gly
                565                 570                 575

Ala Cys Cys Gly Cys Thr Thr Ala Cys Cys Cys Thr Ala Thr Cys Cys
            580                 585                 590

Thr Gly Thr Gly Gly Ala Thr Cys Ala Thr Ala Gly Gly Cys Ala Cys
        595                 600                 605

Thr Gly Ala Gly Gly Gly Cys Gly Cys Thr Gly Gly Cys Gly Thr Gly
    610                 615                 620

Gly Thr Gly Gly Gly Cys Cys Thr Gly Gly Gly Cys Ala Thr Cys Gly
625                 630                 635                 640

Ala Ala Ala Cys Thr Cys Thr Gly Cys Thr Gly Thr Thr Thr Ala Thr
                645                 650                 655

Gly Gly Thr Gly Thr Thr Gly Gly Ala Cys Gly Thr Gly Ala Cys Thr
            660                 665                 670

Gly Cys Cys Ala Ala Gly Gly Thr Cys Gly Gly Cys Thr Thr Thr Gly
```

-continued

```
        675                 680                 685

Gly Cys Thr Thr Thr Ala Thr Cys Cys Thr Gly Thr Thr Gly Ala Gly
    690                 695                 700

Ala Thr Cys Cys Cys Gly Gly Gly Cys Thr Ala Thr Thr Cys Thr Gly
705                 710                 715                 720

Gly Gly Cys Gly Ala Cys Ala Cys Cys Gly Ala Gly Gly Cys Ala Cys
                725                 730                 735

Cys Ala Gly Ala Ala Cys Cys Cys Ala Gly Thr Gly Cys Cys Gly Gly
            740                 745                 750
Thr Gly Cys Cys Gly Ala Thr Gly Thr Cys Ala Gly Thr Gly Cys Cys
        755                 760                 765

Gly Cys Cys Gly Ala Cys Ala Ala Gly Ala Gly Cys Ala Gly Gly Ala
    770                 775                 780

Thr Cys Ala Cys Cys Ala Gly Cys Gly Ala Gly Gly Gly Cys Gly Ala
785                 790                 795                 800

Gly Thr Ala Cys Ala Thr Cys Cys Cys Cys Cys Thr Gly Gly Ala Cys
                805                 810                 815

Cys Ala Gly Ala Thr Cys Gly Ala Cys Ala Thr Cys Ala Ala Cys Gly
            820                 825                 830

Thr Gly Gly Gly Cys Gly Cys Gly Cys Cys Cys Gly Gly Cys Thr Cys
        835                 840                 845

Cys Gly Gly Ala Gly Cys Cys Ala Cys Gly Ala Ala Cys Thr Thr Cys
    850                 855                 860

Thr Cys Thr Cys Thr Gly Thr Thr Ala Ala Ala Gly Cys Ala Ala Gly
865                 870                 875                 880
Cys Ala Gly Gly Ala Gly Ala Cys Gly Thr Gly Gly Ala Ala Gly Ala
                885                 890                 895

Ala Ala Ala Cys Cys Cys Cys Gly Gly Thr Cys Cys Cys Ala Thr Gly
            900                 905                 910
Gly Ala Cys Cys Thr Gly Ala Ala Gly Gly Ala Gly Thr Cys Ala Cys
        915                 920                 925

Cys Ala Ala Gly Cys Gly Ala Gly Gly Gly Ala Thr Cys Ala Cys Thr
    930                 935                 940
Gly Cys Ala Gly Cys Cys Ala Thr Cys Ala Ala Gly Cys Ala Thr Thr
945                 950                 955                 960

Cys Ala Gly Ala Thr Thr Thr Thr Cys Gly Cys Thr Ala Ala Thr Ala
                965                 970                 975

Cys Ala Ala Gly Cys Ala Cys Ala Cys Thr Gly Cys Ala Cys Gly Gly
            980                 985                 990
Cys Ala Thr Cys Cys Gly Gly Cys  Ala Thr Ala Thr Cys  Thr Thr Cys
        995                 1000                1005

Gly Thr  Gly Thr Ala Cys Gly  Gly Cys Cys Cys Ala  Cys Thr Gly
    1010                 1015                 1020

Ala Cys  Cys Ala Thr Thr Cys  Gly Gly Ala Gly Ala  Gly Thr Cys
    1025                 1030                 1035

Cys Thr  Gly Thr Gly Gly Gly  Cys Ala Gly Thr Gly  Gly Cys Cys
    1040                 1045                 1050

Thr Thr  Thr Gly Thr Cys Gly  Gly Ala Ala Gly Cys  Cys Thr Gly
    1055                 1060                 1065

Gly Gly  Ala Cys Thr Gly Cys  Thr Gly Cys Thr Gly  Gly Thr Gly
    1070                 1075                 1080

Gly Ala  Gly Ala Gly Cys Thr  Cys Cys Gly Ala Ala  Ala Gly Ala
    1085                 1090                 1095
```

```
Gly Thr Cys Ala Gly Thr Thr Ala Cys Thr Ala Thr Thr Thr Cys
    1100                1105                1110

Thr Cys Ala Thr Ala Thr Cys Ala Gly Cys Ala Cys Gly Thr Gly
    1115                1120                1125

Ala Cys Thr Ala Ala Gly Gly Thr Gly Gly Ala Cys Gly Ala Gly
    1130                1135                1140

Gly Thr Gly Gly Thr Cys Gly Cys Thr Cys Ala Gly Thr Cys Cys
    1145                1150                1155

Cys Thr Gly Gly Thr Gly Thr Thr Thr Cys Cys Cys Gly Cys Ala
    1160                1165                1170

Gly Thr Cys Ala Cys Cys Cys Thr Gly Thr Gly Cys Ala Ala Cys
    1175                1180                1185

Cys Thr Gly Ala Ala Thr Gly Gly Gly Thr Thr Cys Ala Gly Gly
    1190                1195                1200

Thr Thr Thr Thr Cys Thr Cys Gly Cys Cys Thr Gly Ala Cys Cys
    1205                1210                1215

Ala Cys Ala Ala Ala Cys Gly Ala Cys Cys Thr Gly Thr Ala Cys
    1220                1225                1230

Cys Ala Cys Gly Cys Cys Gly Gly Ala Gly Ala Gly Cys Thr Gly
    1235                1240                1245

Cys Thr Gly Gly Cys Thr Cys Thr Gly Cys Thr Gly Gly Ala Thr
    1250                1255                1260

Gly Thr Gly Ala Ala Thr Cys Thr Gly Cys Ala Gly Ala Thr Cys
    1265                1270                1275

Cys Cys Ala Gly Ala Cys Cys Cys Cys Cys Ala Thr Cys Thr Gly
    1280                1285                1290

Gly Cys Cys Gly Ala Thr Cys Cys Ala Ala Cys Cys Gly Thr Gly
    1295                1300                1305

Cys Thr Gly Gly Ala Ala Gly Cys Ala Cys Thr Gly Ala Gly Gly
    1310                1315                1320

Cys Ala Gly Ala Ala Gly Gly Cys Cys Ala Ala Cys Thr Thr Cys
    1325                1330                1335

Ala Ala Ala Cys Ala Cys Thr Ala Cys Ala Ala Gly Cys Cys Cys
    1340                1345                1350

Ala Ala Ala Cys Ala Gly Thr Thr Cys Ala Gly Cys Ala Thr Gly
    1355                1360                1365

Cys Thr Gly Gly Ala Gly Thr Thr Thr Cys Thr Gly Cys Ala Cys
    1370                1375                1380

Cys Gly Cys Gly Thr Gly Gly Gly Ala Cys Ala Thr Gly Ala Cys
    1385                1390                1395

Cys Thr Gly Ala Ala Ala Gly Ala Thr Ala Thr Gly Ala Thr Gly
    1400                1405                1410

Cys Thr Gly Thr Ala Thr Thr Gly Cys Ala Ala Gly Thr Thr Cys
    1415                1420                1425

Ala Ala Ala Gly Gly Cys Cys Ala Gly Gly Ala Gly Thr Gly Thr
    1430                1435                1440

Gly Gly Gly Cys Ala Thr Cys Ala Gly Gly Ala Cys Thr Thr Cys
    1445                1450                1455

Ala Cys Thr Ala Cys Cys Gly Thr Gly Thr Thr Thr Ala Cys Ala
    1460                1465                1470

Ala Ala Gly Thr Ala Cys Gly Gly Cys Ala Ala Ala Thr Gly Thr
    1475                1480                1485
```

-continued

Thr Ala Cys Ala Thr Gly Thr Thr Cys Ala Ala Cys Thr Cys Cys
            1490            1495            1500

Gly Gly Gly Gly Ala Ala Gly Ala Thr Gly Gly Ala Ala Ala Ala
            1505            1510            1515

Cys Cys Thr Cys Thr Gly Cys Thr Gly Ala Cys Ala Ala Cys Thr
            1520            1525            1530

Gly Thr Gly Ala Ala Gly Gly Gly Cys Gly Gly Ala Cys Ala
            1535            1540            1545

Gly Gly Gly Ala Ala Thr Gly Gly Ala Cys Thr Gly Gly Ala Gly
            1550            1555            1560

Ala Thr Cys Ala Thr Gly Cys Thr Gly Gly Ala Cys Ala Thr Thr
            1565            1570            1575

Cys Ala Gly Cys Ala Gly Gly Ala Thr Gly Ala Gly Thr Ala Cys
            1580            1585            1590

Cys Thr Gly Cys Cys Ala Ala Thr Cys Thr Gly Gly Gly Gly Ala
            1595            1600            1605

Gly Ala Ala Ala Cys Thr Gly Ala Gly Gly Ala Ala Ala Cys Cys
            1610            1615            1620

Ala Cys Ala Thr Thr Cys Gly Ala Gly Gly Cys Cys Gly Gly Cys
            1625            1630            1635

Gly Thr Gly Ala Ala Gly Gly Thr Cys Cys Ala Gly Ala Thr Cys
            1640            1645            1650

Cys Ala Cys Thr Cys Ala Cys Ala Gly Ala Gly Cys Gly Ala Gly
            1655            1660            1665

Cys Cys Cys Cys Cys Thr Thr Thr Cys Ala Thr Thr Cys Ala Gly
            1670            1675            1680

Gly Ala Ala Cys Thr Gly Gly Ala Thr Thr Gly Gly Ala
            1685            1690            1695

Gly Thr Gly Gly Cys Ala Cys Cys Ala Gly Gly Ala Thr Thr Cys
            1700            1705            1710

Cys Ala Gly Ala Cys Ala Thr Thr Thr Gly Thr Cys Gly Cys Thr
            1715            1720            1725

Ala Cys Thr Cys Ala Gly Gly Ala Gly Cys Ala Gly Cys Gly Cys
            1730            1735            1740

Cys Thr Gly Ala Cys Cys Thr Ala Thr Cys Thr Gly Cys Cys Ala
            1745            1750            1755

Cys Cys Cys Cys Cys Thr Thr Gly Gly Gly Gly Cys Gly Ala Gly
            1760            1765            1770

Thr Gly Cys Cys Gly Ala Thr Cys Thr Ala Gly Thr Gly Ala Ala
            1775            1780            1785

Ala Thr Gly Gly Gly Gly Cys Thr Gly Gly Ala Cys Thr Thr Cys
            1790            1795            1800

Thr Thr Thr Cys Cys Thr Gly Thr Gly Thr Ala Cys Thr Cys Thr
            1805            1810            1815

Ala Thr Cys Ala Cys Cys Gly Cys Cys Thr Gly Cys Cys Gly Ala
            1820            1825            1830

Ala Thr Thr Gly Ala Thr Thr Gly Thr Gly Ala Gly Ala Cys Ala
            1835            1840            1845

Cys Gly Gly Thr Ala Thr Ala Thr Cys Gly Thr Gly Gly Ala Ala
            1850            1855            1860

Ala Ala Cys Thr Gly Cys Ala Ala Thr Thr Gly Thr Ala Gly Gly
            1865            1870            1875

Ala Thr Gly Gly Thr Cys Cys Ala Cys Ala Thr Gly Cys Cys Thr

-continued

```
    1880                1885                1890

Gly Gly  Cys Gly Ala Cys Gly  Cys Cys Cys Cys Ala  Thr Thr Cys
    1895                1900                1905

Thr Gly  Cys Ala Cys Thr Cys  Cys Cys Gly Ala Ala  Cys Ala Gly
    1910                1915                1920

Cys Ala  Thr Ala Ala Ala Gly  Ala Gly Thr Gly Thr  Gly Cys Thr
    1925                1930                1935

Gly Ala  Ala Cys Cys Thr Gly  Cys Ala Cys Thr Gly  Gly Gly Gly
    1940                1945                1950

Cys Thr  Gly Cys Thr Gly Gly  Cys Thr Gly Ala Gly  Ala Ala Gly
    1955                1960                1965

Gly Ala  Thr Ala Gly Thr Ala  Ala Cys Thr Ala Cys  Thr Gly Cys
    1970                1975                1980

Cys Thr  Gly Thr Gly Thr Ala  Gly Ala Ala Cys Ala  Cys Cys Cys
    1985                1990                1995

Thr Gly  Thr Ala Ala Cys Cys  Thr Gly Ala Cys Thr  Ala Gly Gly
    2000                2005                2010

Thr Ala  Thr Ala Ala Thr Ala  Ala Gly Gly Ala Ala  Cys Thr Gly
    2015                2020                2025

Ala Gly  Cys Ala Thr Gly Gly  Thr Gly Ala Ala Gly  Ala Thr Cys
    2030                2035                2040

Cys Cys  Thr Thr Cys Cys Ala  Ala Ala Ala Cys Ala  Thr Cys Thr
    2045                2050                2055

Gly Cys  Ala Ala Ala Gly Thr  Ala Cys Cys Thr Gly  Gly Ala Gly
    2060                2065                2070

Ala Ala  Gly Ala Ala Gly Thr  Thr Cys Ala Ala Cys  Ala Ala Gly
    2075                2080                2085

Thr Cys  Thr Gly Ala Gly Ala  Ala Gly Thr Ala Cys  Ala Thr Cys
    2090                2095                2100

Ala Gly  Thr Gly Ala Ala Ala  Ala Cys Ala Thr Thr  Cys Thr Gly
    2105                2110                2115

Gly Thr  Gly Cys Thr Gly Gly  Ala Cys Ala Thr Cys  Thr Thr Cys
    2120                2125                2130

Thr Thr  Thr Gly Ala Ala Gly  Cys Thr Cys Thr Gly  Ala Ala Thr
    2135                2140                2145

Thr Ala  Cys Gly Ala Gly Ala  Cys Cys Ala Thr Thr  Gly Ala Ala
    2150                2155                2160

Cys Ala  Gly Ala Ala Gly Ala  Ala Ala Gly Cys Ala  Thr Ala Thr
    2165                2170                2175

Gly Ala  Gly Gly Thr Gly Gly  Cys Cys Gly Cys Thr  Cys Thr Gly
    2180                2185                2190

Cys Thr  Gly Gly Gly Gly Gly  Ala Thr Ala Thr Thr  Gly Gly Ala
    2195                2200                2205

Gly Gly  Cys Cys Ala Gly Ala  Thr Gly Gly Gly Ala  Cys Thr Gly
    2210                2215                2220

Thr Thr  Cys Ala Thr Cys Gly  Gly Cys Gly Cys Cys  Ala Gly Cys
    2225                2230                2235

Cys Thr  Gly Cys Thr Gly Ala  Cys Ala Ala Thr Thr  Cys Thr Gly
    2240                2245                2250

Gly Ala  Gly Cys Thr Gly Thr  Thr Thr Gly Ala Cys  Thr Ala Cys
    2255                2260                2265

Ala Thr  Cys Thr Ala Thr Gly  Ala Gly Cys Thr Gly  Ala Thr Thr
    2270                2275                2280
```

```
Ala Ala Gly Gly Ala Ala Ala Ala Cys Thr Gly Cys Thr Gly
    2285            2290            2295

Gly Ala Thr Cys Thr Gly Cys Thr Gly Gly Gly Ala Ala Gly
    2300            2305            2310

Gly Ala Gly Gly Ala Ala Gly Ala Gly Gly Ala Ala Gly Gly Ala
    2315            2320            2325

Thr Cys Ala Cys Ala Cys Gly Ala Cys Gly Ala Ala Ala Cys
    2330            2335            2340

Ala Thr Gly Ala Gly Cys Ala Cys Thr Gly Cys Gly Ala Thr
    2345            2350            2355

Ala Cys Cys Ala Thr Gly Cys Cys Thr Ala Ala Thr Cys Ala Cys
    2360            2365            2370

Ala Gly Cys Gly Ala Gly Ala Cys Cys Ala Thr Cys Thr Cys Cys
    2375            2380            2385

Cys Ala Thr Ala Cys Ala Gly Thr Gly Ala Ala Thr Gly Thr Cys
    2390            2395            2400

Cys Cys Ala Cys Thr Gly Cys Ala Gly Ala Cys Thr Gly Cys Ala
    2405            2410            2415

Cys Thr Gly Gly Gly Cys Ala Cys Cys Cys Thr Gly Gly Ala Gly
    2420            2425            2430

Gly Ala Ala Ala Thr Thr Gly Cys Cys Thr Gly Thr Gly Cys Gly
    2435            2440            2445

Gly Cys Cys Gly Cys Cys Gly Thr Gly Ala Gly Cys Ala Ala Gly
    2450            2455            2460

Gly Gly Cys Gly Ala Gly Gly Ala Gly Cys Thr Gly Thr Thr Cys
    2465            2470            2475

Ala Cys Cys Gly Gly Gly Gly Thr Gly Gly Thr Gly Cys Cys Cys
    2480            2485            2490

Ala Thr Cys Cys Thr Gly Gly Thr Cys Gly Ala Gly Cys Thr Gly
    2495            2500            2505

Gly Ala Cys Gly Gly Cys Gly Ala Cys Gly Thr Ala Ala Ala Cys
    2510            2515            2520

Gly Gly Cys Cys Ala Cys Ala Ala Gly Thr Thr Cys Ala Gly Cys
    2525            2530            2535

Gly Thr Gly Thr Cys Cys Gly Cys Gly Ala Gly Gly Gly Cys
    2540            2545            2550

Gly Ala Gly Gly Gly Cys Gly Ala Thr Gly Cys Cys Ala Cys Cys
    2555            2560            2565

Thr Ala Cys Gly Gly Cys Ala Ala Gly Cys Thr Gly Ala Cys Cys
    2570            2575            2580

Cys Thr Gly Ala Ala Gly Thr Thr Cys Ala Thr Cys Thr Gly Cys
    2585            2590            2595

Ala Cys Cys Ala Cys Cys Gly Gly Cys Ala Ala Gly Cys Thr Gly
    2600            2605            2610

Cys Cys Cys Gly Thr Gly Cys Cys Cys Thr Gly Gly Cys Cys Cys
    2615            2620            2625

Ala Cys Cys Cys Thr Cys Gly Thr Gly Ala Cys Cys Ala Cys Cys
    2630            2635            2640

Thr Thr Cys Gly Gly Cys Thr Ala Cys Gly Gly Cys Cys Thr Gly
    2645            2650            2655

Cys Ala Gly Thr Gly Cys Thr Thr Cys Gly Cys Cys Cys Gly Cys
    2660            2665            2670
```

```
Thr Ala Cys Cys Cys Cys Gly Ala Cys Ala Cys Ala Thr Gly
    2675            2680            2685

Ala Ala Gly Cys Ala Gly Cys Ala Cys Gly Ala Cys Thr Thr Cys
    2690            2695            2700

Thr Thr Cys Ala Ala Gly Cys Cys Gly Cys Cys Ala Thr Gly
    2705            2710            2715

Cys Cys Cys Gly Ala Ala Gly Gly Cys Thr Ala Cys Gly Thr Cys
    2720            2725            2730

Cys Ala Gly Gly Ala Gly Cys Gly Cys Ala Cys Cys Ala Thr Cys
    2735            2740            2745

Thr Thr Cys Thr Thr Cys Ala Ala Gly Gly Ala Cys Gly Ala Cys
    2750            2755            2760

Gly Gly Cys Ala Ala Cys Thr Ala Cys Ala Ala Gly Ala Cys Cys
    2765            2770            2775

Cys Gly Cys Gly Cys Cys Gly Ala Gly Gly Thr Gly Ala Ala Gly
    2780            2785            2790

Thr Thr Cys Gly Ala Gly Gly Cys Gly Ala Cys Ala Cys Cys
    2795            2800            2805

Cys Thr Gly Gly Thr Gly Ala Ala Cys Cys Gly Cys Ala Thr Cys
    2810            2815            2820

Gly Ala Gly Cys Thr Gly Ala Ala Gly Gly Cys Ala Thr Cys
    2825            2830            2835

Gly Ala Cys Thr Thr Cys Ala Ala Gly Gly Ala Gly Gly Ala Cys
    2840            2845            2850

Gly Gly Cys Ala Ala Cys Ala Thr Cys Cys Thr Gly Gly Gly Gly
    2855            2860            2865

Cys Ala Cys Ala Ala Gly Cys Thr Gly Gly Ala Gly Thr Ala Cys
    2870            2875            2880

Ala Ala Cys Thr Ala Cys Ala Ala Cys Ala Gly Cys Cys Ala Cys
    2885            2890            2895

Ala Ala Cys Gly Thr Cys Thr Ala Thr Ala Thr Cys Ala Thr Gly
    2900            2905            2910

Gly Cys Cys Gly Ala Cys Ala Ala Gly Cys Ala Gly Ala Ala Gly
    2915            2920            2925

Ala Ala Cys Gly Gly Cys Ala Thr Cys Ala Ala Gly Gly Thr Gly
    2930            2935            2940

Ala Ala Cys Thr Thr Cys Ala Ala Gly Ala Thr Cys Cys Gly Cys
    2945            2950            2955

Cys Ala Cys Ala Ala Cys Ala Thr Cys Gly Ala Gly Gly Ala Cys
    2960            2965            2970

Gly Gly Cys Ala Gly Cys Gly Thr Gly Cys Ala Gly Cys Thr Cys
    2975            2980            2985

Gly Cys Cys Gly Ala Cys Cys Ala Cys Thr Ala Cys Cys Ala Gly
    2990            2995            3000

Cys Ala Gly Ala Ala Cys Ala Cys Cys Cys Cys Ala Thr Cys
    3005            3010            3015

Gly Gly Cys Gly Ala Cys Gly Cys Cys Cys Cys Gly Thr Gly
    3020            3025            3030

Cys Thr Gly Cys Thr Gly Cys Cys Cys Gly Ala Cys Ala Ala Cys
    3035            3040            3045

Cys Ala Cys Thr Ala Cys Cys Thr Gly Ala Gly Cys Thr Ala Cys
    3050            3055            3060

Cys Ala Gly Thr Cys Cys Gly Cys Cys Cys Thr Gly Ala Gly Cys
```

```
            3065                3070                3075
Ala Ala  Ala Gly Ala Cys  Cys Cys Ala Ala Cys  Gly Ala Gly
            3080                3085                3090

Ala Ala  Gly Cys Gly Cys  Gly Ala Thr Cys Ala  Cys Ala Thr Gly
            3095                3100                3105

Gly Thr  Cys Cys Thr Gly  Cys Thr Gly Gly Ala  Gly Thr Thr Cys
            3110                3115                3120

Gly Thr  Gly Ala Cys Cys  Gly Cys Cys Gly Cys  Cys Gly Gly Gly
            3125                3130                3135

Ala Thr  Cys Ala Cys Thr  Cys Thr Cys Gly Gly  Cys Ala Thr Gly
            3140                3145                3150

Gly Ala  Cys Gly Ala Gly  Cys Thr Gly Thr Ala  Cys Ala Ala Gly
            3155                3160                3165

Thr Ala  Ala
            3170

<210> SEQ ID NO 36
<211> LENGTH: 3252
<212> TYPE: PRT
<213> ORGANISM: Artificial sequence
<220> FEATURE:
<223> OTHER INFORMATION: synthetic amino acid sequence

<400> SEQUENCE: 36

Ala Thr Gly Gly Ala Cys Cys Cys Cys Ala Thr Cys Gly Cys Thr Cys
1               5                   10                  15

Thr Gly Cys Ala Gly Gly Cys Thr Gly Gly Thr Thr Ala Cys Gly Ala
            20                  25                  30

Cys Cys Thr Gly Cys Thr Gly Gly Thr Gly Ala Cys Gly Gly Cys
        35                  40                  45

Ala Gly Ala Cys Cys Thr Gly Ala Ala Ala Cys Thr Cys Thr Gly Thr
    50                  55                  60

Gly Gly Cys Thr Gly Gly Gly Cys Ala Thr Cys Gly Gly Cys Ala Cys
65                  70                  75                  80

Thr Cys Thr Gly Cys Thr Gly Ala Thr Gly Cys Thr Gly Ala Thr Thr
            85                  90                  95

Gly Gly Ala Ala Cys Cys Thr Thr Cys Thr Ala Cys Thr Thr Thr Cys
            100                 105                 110

Thr Gly Gly Thr Cys Cys Gly Cys Gly Gly Ala Thr Gly Gly Gly Gly
            115                 120                 125

Ala Gly Thr Cys Ala Cys Cys Gly Ala Thr Ala Ala Gly Gly Ala Thr
    130                 135                 140

Gly Cys Cys Cys Gly Gly Gly Ala Ala Thr Thr Ala Thr Ala Cys Gly
145                 150                 155                 160

Cys Thr Gly Thr Gly Ala Cys Thr Ala Thr Cys Cys Thr Gly Gly Thr
            165                 170                 175

Gly Cys Cys Cys Gly Gly Ala Ala Thr Cys Gly Cys Ala Thr Cys Cys
            180                 185                 190

Gly Cys Cys Gly Cys Ala Thr Ala Thr Cys Thr Gly Thr Cys Thr Ala
        195                 200                 205

Thr Gly Thr Thr Cys Thr Thr Thr Gly Gly Thr Ala Cys Gly Gly
    210                 215                 220

Gly Cys Thr Thr Ala Cys Thr Gly Ala Gly Gly Thr Gly Ala Cys Cys
225                 230                 235                 240

Gly Thr Cys Gly Gly Gly Gly Gly Cys Gly Ala Ala Ala Thr Gly Thr
```

-continued

```
                245                 250                 255

Thr Gly Gly Ala Thr Ala Thr Cys Thr Ala Thr Thr Ala Thr Gly Cys
            260                 265                 270

Cys Ala Gly Gly Thr Ala Cys Gly Cys Cys Gly Ala Cys Thr Gly Gly
        275                 280                 285

Cys Thr Gly Thr Thr Thr Ala Cys Cys Ala Cys Cys Cys Cys Ala Cys
    290                 295                 300

Thr Thr Cys Thr Gly Cys Thr Gly Cys Thr Gly Gly Ala Thr Cys Thr
305                 310                 315                 320
Gly Gly Cys Cys Cys Thr Thr Cys Thr Cys Gly Cys Thr Ala Ala Gly
                325                 330                 335

Gly Thr Gly Gly Ala Thr Cys Gly Gly Gly Thr Gly Ala Cys Cys Ala
            340                 345                 350

Thr Cys Gly Gly Cys Ala Cys Cys Cys Thr Gly Gly Thr Gly Gly Gly
        355                 360                 365

Thr Gly Thr Gly Gly Ala Cys Gly Cys Cys Cys Thr Gly Ala Thr Gly
    370                 375                 380
Ala Thr Cys Gly Thr Cys Ala Cys Thr Gly Gly Cys Cys Thr Cys Ala
385                 390                 395                 400
Thr Cys Gly Gly Ala Gly Cys Cys Thr Thr Gly Ala Gly Cys Cys Ala
                405                 410                 415

Cys Ala Cys Gly Gly Cys Cys Ala Thr Ala Gly Cys Cys Ala Gly Ala
            420                 425                 430

Thr Ala Cys Ala Gly Thr Thr Gly Gly Thr Gly Gly Thr Thr Gly Thr
        435                 440                 445

Thr Cys Thr Cys Thr Ala Cys Ala Ala Thr Thr Thr Gly Cys Ala Thr
    450                 455                 460

Gly Ala Thr Ala Gly Thr Gly Gly Thr Gly Cys Thr Cys Thr Ala Thr
465                 470                 475                 480

Thr Thr Thr Cys Thr Gly Gly Cys Thr Ala Cys Ala Thr Cys Cys Cys
                485                 490                 495

Thr Gly Cys Gly Ala Thr Cys Thr Gly Cys Thr Gly Cys Ala Ala Ala
            500                 505                 510

Gly Gly Ala Gly Cys Gly Gly Gly Gly Cys Cys Cys Cys Gly Ala Gly
        515                 520                 525

Gly Thr Gly Gly Cys Ala Thr Cys Thr Ala Cys Cys Thr Thr Thr Ala
    530                 535                 540

Ala Cys Ala Cys Cys Cys Thr Gly Ala Cys Ala Gly Cys Thr Cys Thr
545                 550                 555                 560

Gly Gly Thr Cys Thr Thr Gly Gly Thr Gly Cys Thr Gly Thr Gly Gly
                565                 570                 575

Ala Cys Cys Gly Cys Thr Thr Ala Cys Cys Cys Thr Ala Thr Cys Cys
            580                 585                 590

Thr Gly Thr Gly Gly Ala Thr Cys Ala Thr Ala Gly Gly Cys Ala Cys
        595                 600                 605

Thr Gly Ala Gly Gly Gly Cys Gly Cys Thr Gly Gly Cys Gly Thr Gly
    610                 615                 620

Gly Thr Gly Gly Gly Cys Cys Thr Gly Gly Gly Cys Ala Thr Cys Gly
625                 630                 635                 640

Ala Ala Ala Cys Thr Cys Thr Gly Cys Thr Gly Thr Thr Thr Ala Thr
                645                 650                 655

Gly Gly Thr Gly Thr Thr Gly Gly Ala Cys Gly Thr Gly Ala Cys Thr
            660                 665                 670
```

Gly Cys Cys Ala Ala Gly Gly Thr Cys Gly Gly Cys Thr Thr Thr Gly
675 680 685

Gly Cys Thr Thr Thr Ala Thr Cys Cys Thr Gly Thr Thr Gly Ala Gly
690 695 700

Ala Thr Cys Cys Cys Gly Gly Gly Cys Thr Ala Thr Thr Cys Thr Gly
705 710 715 720

Gly Gly Cys Gly Ala Cys Ala Cys Cys Gly Ala Gly Gly Cys Ala Cys
725 730 735

Cys Ala Gly Ala Ala Cys Cys Cys Ala Gly Thr Gly Cys Cys Gly Gly
740 745 750

Thr Gly Cys Cys Gly Ala Thr Gly Thr Cys Ala Gly Thr Gly Cys Cys
755 760 765

Gly Cys Cys Gly Ala Cys Ala Ala Gly Ala Gly Cys Ala Gly Gly Ala
770 775 780

Thr Cys Ala Cys Cys Ala Gly Cys Gly Ala Gly Gly Gly Cys Gly Ala
785 790 795 800

Gly Thr Ala Cys Ala Thr Cys Cys Cys Cys Cys Thr Gly Gly Ala Cys
805 810 815

Cys Ala Gly Ala Thr Cys Gly Ala Cys Ala Thr Cys Ala Ala Cys Gly
820 825 830

Thr Gly Gly Gly Cys Gly Cys Gly Cys Cys Cys Gly Gly Cys Thr Cys
835 840 845

Cys Gly Gly Ala Gly Cys Cys Ala Cys Gly Ala Ala Cys Thr Thr Cys
850 855 860

Thr Cys Thr Cys Thr Gly Thr Thr Ala Ala Ala Gly Cys Ala Ala Gly
865 870 875 880

Cys Ala Gly Gly Ala Gly Ala Cys Gly Thr Gly Gly Ala Ala Gly Ala
885 890 895

Ala Ala Ala Cys Cys Cys Cys Gly Gly Thr Cys Cys Cys Ala Thr Gly
900 905 910

Gly Ala Cys Cys Thr Gly Ala Ala Gly Gly Ala Gly Thr Cys Ala Cys
915 920 925

Cys Ala Ala Gly Cys Gly Ala Gly Gly Gly Ala Thr Cys Ala Cys Thr
930 935 940

Gly Cys Ala Gly Cys Cys Ala Thr Cys Ala Ala Gly Cys Ala Thr Thr
945 950 955 960

Cys Ala Gly Ala Thr Thr Thr Thr Cys Gly Cys Thr Ala Ala Thr Ala
965 970 975

Cys Ala Ala Gly Cys Ala Cys Ala Cys Thr Gly Cys Ala Cys Gly Gly
980 985 990

Cys Ala Thr Cys Cys Gly Gly Cys Ala Thr Ala Thr Cys Thr Thr Cys
995 1000 1005

Gly Thr Gly Thr Ala Cys Gly Gly Cys Cys Cys Ala Cys Thr Gly
1010 1015 1020

Ala Cys Cys Ala Thr Thr Cys Gly Gly Ala Gly Ala Gly Thr Cys
1025 1030 1035

Cys Thr Gly Thr Gly Gly Gly Cys Ala Gly Thr Gly Gly Cys Cys
1040 1045 1050

Thr Thr Thr Gly Thr Cys Gly Gly Ala Ala Gly Cys Cys Thr Gly
1055 1060 1065

Gly Gly Ala Cys Thr Gly Cys Thr Gly Cys Thr Gly Gly Thr Gly
1070 1075 1080

Gly Ala Gly Ala Gly Cys Thr Cys Cys Gly Ala Ala   Ala Gly Ala
    1085                1090                1095

Gly Thr Cys Ala Gly Thr Thr Ala Cys Thr Ala Thr   Thr Thr Cys
    1100                1105                1110

Thr Cys Ala Thr Ala Thr Cys Ala Gly Cys Ala Cys   Gly Thr Gly
    1115                1120                1125

Ala Cys Thr Ala Ala Gly Gly Thr Gly Gly Ala Cys   Gly Ala Gly
    1130                1135                1140

Gly Thr Gly Gly Thr Cys Gly Cys Thr Cys Ala Gly   Thr Cys Cys
    1145                1150                1155

Cys Thr Gly Gly Thr Gly Thr Thr Thr Cys Cys Cys   Gly Cys Ala
    1160                1165                1170

Gly Thr Cys Ala Cys Cys Cys Thr Gly Thr Gly Cys   Ala Ala Cys
    1175                1180                1185

Cys Thr Gly Ala Ala Thr Gly Gly Thr Thr Cys Ala   Gly Gly
    1190                1195                1200

Thr Thr Thr Thr Cys Thr Cys Gly Cys Cys Thr Gly   Ala Cys Cys
    1205                1210                1215

Ala Cys Ala Ala Ala Cys Gly Ala Cys Cys Thr Gly   Thr Ala Cys
    1220                1225                1230

Cys Ala Cys Gly Cys Cys Gly Gly Ala Gly Ala Gly   Cys Thr Gly
    1235                1240                1245

Cys Thr Gly Gly Cys Thr Cys Thr Gly Cys Thr Gly   Gly Ala Thr
    1250                1255                1260

Gly Thr Gly Ala Ala Thr Cys Thr Gly Cys Ala Gly   Ala Thr Cys
    1265                1270                1275

Cys Cys Ala Gly Ala Cys Cys Cys Cys Ala Thr   Cys Thr Gly
    1280                1285                1290

Gly Cys Cys Gly Ala Thr Cys Cys Ala Ala Cys Cys   Gly Thr Gly
    1295                1300                1305

Cys Thr Gly Gly Ala Ala Gly Cys Ala Cys Thr Gly   Ala Gly Gly
    1310                1315                1320

Cys Ala Gly Ala Ala Gly Gly Cys Cys Ala Ala Cys   Thr Thr Cys
    1325                1330                1335

Ala Ala Ala Cys Ala Cys Thr Ala Cys Ala Ala Gly   Cys Cys Cys
    1340                1345                1350

Ala Ala Ala Cys Ala Gly Thr Thr Cys Ala Gly Cys   Ala Thr Gly
    1355                1360                1365

Cys Thr Gly Gly Ala Gly Thr Thr Cys Thr Gly Cys   Ala Cys
    1370                1375                1380

Cys Gly Cys Gly Thr Gly Gly Ala Cys Ala Thr Gly   Ala Cys
    1385                1390                1395

Cys Thr Gly Ala Ala Ala Gly Ala Thr Ala Thr Gly   Ala Thr Gly
    1400                1405                1410

Cys Thr Gly Thr Ala Thr Thr Gly Cys Ala Ala Gly   Thr Thr Cys
    1415                1420                1425

Ala Ala Ala Gly Gly Cys Cys Ala Gly Gly Ala Gly   Thr Gly Thr
    1430                1435                1440

Gly Gly Gly Cys Ala Thr Cys Ala Gly Gly Ala Cys   Thr Thr Cys
    1445                1450                1455

Ala Cys Thr Ala Cys Cys Gly Thr Gly Thr Thr Ala   Cys Ala
    1460                1465                1470

Ala Ala Gly Thr Ala Cys Gly Gly Cys Ala Ala Ala   Thr Gly Thr

-continued

```
               1475                1480                1485

Thr Ala Cys Ala Thr Gly Thr Cys Ala Ala Cys Thr Cys Cys
        1490                1495                1500

Gly Gly Gly Gly Ala Ala Gly Ala Thr Gly Gly Ala Ala Ala
        1505                1510                1515

Cys Cys Thr Cys Thr Gly Cys Thr Gly Ala Cys Ala Ala Cys Thr
        1520                1525                1530

Gly Thr Gly Ala Ala Gly Gly Gly Cys Gly Gly Ala Cys Ala
        1535                1540                1545

Gly Gly Gly Ala Ala Thr Gly Gly Ala Cys Thr Gly Gly Ala Gly
        1550                1555                1560

Ala Thr Cys Ala Thr Gly Cys Thr Gly Gly Ala Cys Ala Thr Thr
        1565                1570                1575

Cys Ala Gly Cys Ala Gly Gly Ala Thr Gly Ala Gly Thr Ala Cys
        1580                1585                1590

Cys Thr Gly Cys Cys Ala Ala Thr Cys Thr Gly Gly Gly Gly Ala
        1595                1600                1605

Gly Ala Ala Ala Cys Thr Gly Ala Gly Gly Ala Ala Ala Cys Cys
        1610                1615                1620

Ala Cys Ala Thr Thr Cys Gly Ala Gly Gly Cys Cys Gly Gly Cys
        1625                1630                1635

Gly Thr Gly Ala Ala Gly Gly Thr Cys Cys Ala Gly Ala Thr Cys
        1640                1645                1650

Cys Ala Cys Thr Cys Ala Cys Ala Gly Ala Gly Cys Gly Ala Gly
        1655                1660                1665

Cys Cys Cys Cys Cys Thr Thr Thr Cys Ala Thr Thr Cys Ala Gly
        1670                1675                1680

Gly Ala Ala Cys Thr Gly Gly Gly Ala Thr Thr Thr Gly Gly Ala
        1685                1690                1695

Gly Thr Gly Gly Cys Ala Cys Ala Gly Gly Ala Thr Thr Cys
        1700                1705                1710

Cys Ala Gly Ala Cys Ala Thr Thr Thr Gly Thr Cys Gly Cys Thr
        1715                1720                1725

Ala Cys Thr Cys Ala Gly Gly Ala Gly Cys Ala Gly Cys Gly Cys
        1730                1735                1740

Cys Thr Gly Ala Cys Cys Thr Ala Thr Cys Thr Gly Cys Cys Ala
        1745                1750                1755

Cys Cys Cys Cys Cys Thr Thr Gly Gly Gly Gly Cys Gly Ala Gly
        1760                1765                1770

Thr Gly Cys Cys Gly Ala Thr Cys Thr Ala Gly Thr Gly Ala Ala
        1775                1780                1785

Ala Thr Gly Gly Gly Gly Cys Thr Gly Gly Ala Cys Thr Thr Cys
        1790                1795                1800

Thr Thr Thr Cys Cys Thr Gly Thr Gly Thr Ala Cys Thr Cys Thr
        1805                1810                1815

Ala Thr Cys Ala Cys Cys Gly Cys Cys Thr Gly Cys Cys Gly Ala
        1820                1825                1830

Ala Thr Thr Gly Ala Thr Thr Gly Thr Gly Ala Gly Ala Cys Ala
        1835                1840                1845

Cys Gly Gly Thr Ala Thr Ala Thr Cys Gly Thr Gly Gly Ala Ala
        1850                1855                1860

Ala Ala Cys Thr Gly Cys Ala Ala Thr Thr Gly Thr Ala Gly Gly
        1865                1870                1875
```

-continued

```
Ala Thr Gly Gly Thr Cys Cys Ala Cys Ala Gly Cys Cys Thr
        1880            1885            1890

Gly Gly Cys Gly Ala Cys Gly Cys Cys Cys Ala Thr Thr Cys
        1895            1900            1905

Thr Gly Cys Ala Cys Thr Cys Cys Cys Gly Ala Ala Cys Ala Gly
        1910            1915            1920

Cys Ala Thr Ala Ala Ala Gly Ala Gly Thr Gly Thr Gly Cys Thr
        1925            1930            1935

Gly Ala Ala Cys Cys Thr Gly Cys Ala Cys Thr Gly Gly Gly
        1940            1945            1950

Cys Thr Gly Cys Thr Gly Gly Cys Thr Gly Ala Gly Ala Ala Gly
        1955            1960            1965

Gly Ala Thr Ala Gly Thr Ala Ala Cys Thr Ala Cys Thr Gly Cys
        1970            1975            1980

Cys Thr Gly Thr Gly Thr Ala Gly Ala Ala Cys Ala Cys Cys Cys
        1985            1990            1995

Thr Gly Thr Ala Ala Cys Cys Thr Gly Ala Cys Thr Ala Gly Gly
        2000            2005            2010

Thr Ala Thr Ala Ala Thr Ala Ala Gly Gly Ala Ala Cys Thr Gly
        2015            2020            2025

Ala Gly Cys Ala Thr Gly Gly Thr Gly Ala Ala Gly Ala Thr Cys
        2030            2035            2040

Cys Cys Thr Thr Cys Cys Ala Ala Ala Cys Ala Thr Cys Thr
        2045            2050            2055

Gly Cys Ala Ala Ala Gly Thr Ala Cys Cys Thr Gly Gly Ala Gly
        2060            2065            2070

Ala Ala Gly Ala Ala Gly Thr Thr Cys Ala Ala Cys Ala Ala Gly
        2075            2080            2085

Thr Cys Thr Gly Ala Gly Ala Ala Gly Thr Ala Cys Ala Thr Cys
        2090            2095            2100

Ala Gly Thr Gly Ala Ala Ala Ala Cys Ala Thr Thr Cys Thr Gly
        2105            2110            2115

Gly Thr Gly Cys Thr Gly Gly Ala Cys Ala Thr Cys Thr Thr Cys
        2120            2125            2130

Thr Thr Thr Gly Ala Ala Gly Cys Thr Cys Thr Gly Ala Ala Thr
        2135            2140            2145

Thr Ala Cys Gly Ala Gly Ala Cys Cys Ala Thr Gly Ala Ala
        2150            2155            2160

Cys Ala Gly Ala Ala Gly Ala Ala Gly Cys Ala Thr Ala Thr
        2165            2170            2175

Gly Ala Gly Gly Thr Gly Gly Cys Cys Gly Cys Thr Cys Thr Gly
        2180            2185            2190

Cys Thr Gly Gly Gly Gly Ala Thr Ala Thr Gly Gly Ala
        2195            2200            2205

Gly Gly Cys Cys Ala Gly Ala Thr Gly Gly Ala Cys Thr Gly
        2210            2215            2220

Thr Thr Cys Ala Thr Cys Gly Gly Cys Gly Cys Ala Gly Cys
        2225            2230            2235

Cys Thr Gly Cys Thr Gly Ala Cys Ala Ala Thr Thr Cys Thr Gly
        2240            2245            2250

Gly Ala Gly Cys Thr Gly Thr Thr Thr Gly Ala Cys Thr Ala Cys
        2255            2260            2265
```

-continued

```
Ala Thr Cys Thr Ala Thr Gly Ala Gly Cys Thr Gly Ala Thr Thr
    2270                2275                2280

Ala Ala Gly Gly Ala Ala Ala Ala Ala Cys Thr Gly Cys Thr Gly
    2285                2290                2295

Gly Ala Thr Cys Thr Gly Cys Thr Gly Gly Gly Gly Ala Ala Gly
    2300                2305                2310

Gly Ala Gly Gly Ala Ala Gly Ala Gly Gly Ala Ala Gly Gly Ala
    2315                2320                2325

Thr Cys Ala Cys Ala Cys Gly Ala Cys Gly Ala Ala Ala Ala Cys
    2330                2335                2340

Ala Thr Gly Ala Gly Cys Ala Cys Thr Thr Gly Cys Gly Ala Thr
    2345                2350                2355

Ala Cys Cys Ala Thr Gly Cys Cys Thr Ala Ala Thr Cys Ala Cys
    2360                2365                2370

Ala Gly Cys Gly Ala Gly Ala Cys Cys Ala Thr Cys Thr Cys Cys
    2375                2380                2385

Cys Ala Thr Ala Cys Ala Gly Thr Gly Ala Ala Thr Gly Thr Cys
    2390                2395                2400

Cys Cys Ala Cys Thr Gly Cys Ala Gly Ala Cys Thr Gly Cys Ala
    2405                2410                2415

Cys Thr Gly Gly Gly Cys Ala Cys Cys Cys Thr Gly Gly Ala Gly
    2420                2425                2430

Gly Ala Ala Ala Thr Thr Gly Cys Cys Thr Gly Thr Gly Cys Gly
    2435                2440                2445

Gly Cys Cys Gly Cys Cys Ala Ala Gly Ala Gly Cys Ala Gly Gly
    2450                2455                2460

Ala Thr Cys Ala Cys Cys Ala Gly Cys Gly Ala Gly Gly Gly Cys
    2465                2470                2475

Gly Ala Gly Thr Ala Cys Ala Thr Cys Cys Cys Cys Cys Thr Gly
    2480                2485                2490

Gly Ala Cys Cys Ala Gly Ala Thr Cys Gly Ala Cys Ala Thr Cys
    2495                2500                2505

Ala Ala Cys Gly Thr Gly Gly Thr Gly Ala Gly Cys Ala Ala Gly
    2510                2515                2520

Gly Gly Cys Gly Ala Gly Gly Ala Gly Cys Thr Gly Thr Thr Cys
    2525                2530                2535

Ala Cys Cys Gly Gly Gly Gly Thr Gly Gly Thr Gly Cys Cys Cys
    2540                2545                2550

Ala Thr Cys Cys Thr Gly Gly Thr Cys Gly Ala Gly Cys Thr Gly
    2555                2560                2565

Gly Ala Cys Gly Gly Cys Gly Ala Cys Gly Thr Ala Ala Ala Cys
    2570                2575                2580

Gly Gly Cys Cys Ala Cys Ala Ala Gly Thr Thr Cys Ala Gly Cys
    2585                2590                2595

Gly Thr Gly Thr Cys Cys Gly Gly Cys Gly Ala Gly Gly Gly Cys
    2600                2605                2610

Gly Ala Gly Gly Gly Cys Gly Ala Thr Gly Cys Cys Ala Cys Cys
    2615                2620                2625

Thr Ala Cys Gly Gly Cys Ala Ala Gly Cys Thr Gly Ala Cys Cys
    2630                2635                2640

Cys Thr Gly Ala Ala Gly Thr Thr Cys Ala Thr Cys Thr Gly Cys
    2645                2650                2655

Ala Cys Cys Ala Cys Cys Gly Gly Cys Ala Ala Gly Cys Thr Gly
```

```
    2660                2665                2670

Cys Cys  Cys Gly Thr Gly Cys  Cys Cys Thr Gly Gly  Cys Cys Cys
    2675                2680                2685

Ala Cys  Cys Cys Thr Cys Gly  Thr Gly Ala Cys Cys  Ala Cys Cys
    2690                2695                2700

Thr Thr  Cys Gly Gly Cys Thr  Ala Cys Gly Gly Cys  Cys Thr Gly
    2705                2710                2715

Cys Ala  Gly Thr Gly Cys Thr  Thr Cys Gly Cys Cys  Cys Gly Cys
    2720                2725                2730

Thr Ala  Cys Cys Cys Cys Gly  Ala Cys Cys Ala Cys  Ala Thr Gly
    2735                2740                2745

Ala Ala  Gly Cys Ala Gly Cys  Ala Cys Gly Ala Cys  Thr Thr Cys
    2750                2755                2760

Thr Thr  Cys Ala Ala Gly Thr  Cys Cys Gly Cys Cys  Ala Thr Gly
    2765                2770                2775

Cys Cys  Cys Gly Ala Ala Gly  Gly Cys Thr Ala Cys  Gly Thr Cys
    2780                2785                2790

Cys Ala  Gly Gly Ala Gly Cys  Gly Cys Ala Cys Cys  Ala Thr Cys
    2795                2800                2805

Thr Thr  Cys Thr Thr Cys Ala  Ala Gly Gly Ala Cys  Gly Ala Cys
    2810                2815                2820

Gly Gly  Cys Ala Ala Cys Thr  Ala Cys Ala Ala Gly  Ala Cys Cys
    2825                2830                2835

Cys Gly  Cys Gly Cys Cys Gly  Ala Gly Gly Thr Gly  Ala Ala Gly
    2840                2845                2850

Thr Thr  Cys Gly Ala Gly Gly  Gly Cys Gly Ala Cys  Ala Cys Cys
    2855                2860                2865

Cys Thr  Gly Gly Thr Gly Ala  Ala Cys Cys Gly Cys  Ala Thr Cys
    2870                2875                2880

Gly Ala  Gly Cys Thr Gly Ala  Ala Gly Gly Gly Cys  Ala Thr Cys
    2885                2890                2895

Gly Ala  Cys Thr Thr Cys Ala  Gly Gly Gly Ala Gly  Gly Ala Cys
    2900                2905                2910

Gly Gly  Cys Ala Ala Cys Ala  Thr Cys Cys Thr Gly  Gly Gly Gly
    2915                2920                2925

Cys Ala  Cys Ala Ala Gly Cys  Thr Gly Gly Ala Gly  Thr Ala Cys
    2930                2935                2940

Ala Ala  Cys Thr Ala Cys Ala  Ala Cys Ala Gly Cys  Cys Ala Cys
    2945                2950                2955

Ala Ala  Cys Gly Thr Cys Thr  Ala Thr Ala Thr Cys  Ala Thr Gly
    2960                2965                2970

Gly Cys  Cys Gly Ala Cys Ala  Ala Gly Cys Ala Gly  Ala Ala Gly
    2975                2980                2985

Ala Ala  Cys Gly Gly Cys Ala  Thr Cys Ala Ala Gly  Gly Thr Gly
    2990                2995                3000

Ala Ala  Cys Thr Thr Cys Ala  Ala Gly Ala Thr Cys  Cys Gly Cys
    3005                3010                3015

Cys Ala  Cys Ala Ala Cys Ala  Thr Cys Gly Ala Gly  Gly Ala Cys
    3020                3025                3030

Gly Gly  Cys Ala Gly Cys Gly  Thr Gly Cys Ala Gly  Cys Thr Cys
    3035                3040                3045

Gly Cys  Cys Gly Ala Cys Cys  Ala Cys Thr Ala Cys  Cys Ala Gly
    3050                3055                3060
```

Cys Ala Gly Ala Ala Cys Ala Cys Cys Cys Cys Ala Thr Cys
3065                3070                3075

Gly Gly Cys Gly Ala Cys Gly Gly Cys Cys Cys Gly Thr Gly
3080                3085                3090

Cys Thr Gly Cys Thr Gly Cys Cys Cys Gly Ala Cys Ala Ala Cys
3095                3100                3105

Cys Ala Cys Thr Ala Cys Thr Gly Ala Gly Cys Thr Ala Cys
3110                3115                3120

Cys Ala Gly Thr Cys Cys Gly Cys Cys Cys Thr Gly Ala Gly Cys
3125                3130                3135

Ala Ala Ala Gly Ala Cys Cys Cys Cys Ala Ala Cys Gly Ala Gly
3140                3145                3150

Ala Ala Gly Cys Gly Cys Gly Ala Thr Cys Ala Cys Ala Thr Gly
3155                3160                3165

Gly Thr Cys Cys Thr Gly Cys Thr Gly Gly Ala Gly Thr Thr Cys
3170                3175                3180

Gly Thr Gly Ala Cys Cys Gly Cys Cys Gly Cys Cys Gly Gly Gly
3185                3190                3195

Ala Thr Cys Ala Cys Thr Cys Thr Cys Gly Gly Cys Ala Thr Gly
3200                3205                3210

Gly Ala Cys Gly Ala Gly Cys Thr Gly Thr Ala Cys Ala Ala Gly
3215                3220                3225

Thr Thr Cys Thr Gly Cys Thr Ala Cys Gly Ala Gly Ala Ala Cys
3230                3235                3240

Gly Ala Gly Gly Thr Gly Thr Ala Ala
3245                3250

<210> SEQ ID NO 37
<211> LENGTH: 20
<212> TYPE: PRT
<213> ORGANISM: Homo sapiens

<400> SEQUENCE: 37

Lys Ser Arg Ile Thr Ser Glu Gly Glu Tyr Ile Pro Leu Asp Gln Ile
1               5                   10                  15

Asp Ile Asn Val
            20

<210> SEQ ID NO 38
<211> LENGTH: 26
<212> TYPE: PRT
<213> ORGANISM: Homo sapiens

<400> SEQUENCE: 38

Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25

<210> SEQ ID NO 39
<211> LENGTH: 27
<212> TYPE: PRT
<213> ORGANISM: Homo sapiens

<400> SEQUENCE: 39

Met Ala Gly His Ser Asn Ser Met Ala Leu Phe Ser Phe Ser Leu Leu
1               5                   10                  15

Trp Leu Cys Ser Gly Val Leu Gly Thr Glu Phe
            20                  25

<210> SEQ ID NO 40
<211> LENGTH: 23
<212> TYPE: PRT
<213> ORGANISM: Homo sapiens

<400> SEQUENCE: 40

Met Gly Leu Arg Ala Leu Met Leu Trp Leu Leu Ala Ala Ala Gly Leu
1               5                   10                  15

Val Arg Glu Ser Leu Gln Gly
            20

<210> SEQ ID NO 41
<211> LENGTH: 18
<212> TYPE: PRT
<213> ORGANISM: Homo sapiens

<400> SEQUENCE: 41

Met Arg Gly Thr Pro Leu Leu Leu Val Val Ser Leu Phe Ser Leu Leu
1               5                   10                  15

Gln Asp

<210> SEQ ID NO 42
<211> LENGTH: 5
<212> TYPE: PRT
<213> ORGANISM: Artificial sequence
<220> FEATURE:
<223> OTHER INFORMATION: synthetic amino acid sequence
<220> FEATURE:
<221> NAME/KEY: MISC_FEATURE
<222> LOCATION: (2)..(3)
<223> OTHER INFORMATION: X may be any amino acid

<400> SEQUENCE: 42

Val Xaa Xaa Ser Leu
1               5

<210> SEQ ID NO 43
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 43

Val Lys Glu Ser Leu
1               5

<210> SEQ ID NO 44
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 44

Val Leu Gly Ser Leu
1               5

<210> SEQ ID NO 45
<211> LENGTH: 16
<212> TYPE: PRT
<213> ORGANISM: Artificial sequence
<220> FEATURE:

<223> OTHER INFORMATION: synthetic amino acid sequence

<400> SEQUENCE: 45

Asn Ala Asn Ser Phe Cys Tyr Glu Asn Glu Val Ala Leu Thr Ser Lys
1               5                   10                  15

<210> SEQ ID NO 46
<211> LENGTH: 6
<212> TYPE: PRT
<213> ORGANISM: Artificial sequence
<220> FEATURE:
<223> OTHER INFORMATION: synthetic amino acid sequence
<220> FEATURE:
<221> NAME/KEY: MISC_FEATURE
<222> LOCATION: (2)..(2)
<223> OTHER INFORMATION: X may be any amino acid

<400> SEQUENCE: 46

Phe Xaa Tyr Glu Asn Glu
1               5

<210> SEQ ID NO 47
<211> LENGTH: 7
<212> TYPE: PRT
<213> ORGANISM: Artificial sequence
<220> FEATURE:
<223> OTHER INFORMATION: synthetic amino acid sequence

<400> SEQUENCE: 47

Phe Cys Tyr Glu Asn Glu Val
1               5

<210> SEQ ID NO 48
<211> LENGTH: 18
<212> TYPE: PRT
<213> ORGANISM: Artificial sequence
<220> FEATURE:
<223> OTHER INFORMATION: synthetic amino acid sequence

<400> SEQUENCE: 48

Met Thr Glu Thr Leu Pro Pro Val Thr Glu Ser Ala Val Ala Leu Gln
1               5                   10                  15

Ala Glu

<210> SEQ ID NO 49
<211> LENGTH: 19
<212> TYPE: PRT
<213> ORGANISM: Artificial sequence
<220> FEATURE:
<223> OTHER INFORMATION: synthetic amino acid sequence

<400> SEQUENCE: 49

Ala Thr Asn Phe Ser Leu Leu Lys Gln Ala Gly Asp Val Glu Glu Asn
1               5                   10                  15

Pro Gly Pro

<210> SEQ ID NO 50
<211> LENGTH: 18
<212> TYPE: PRT
<213> ORGANISM: Artificial sequence
<220> FEATURE:
<223> OTHER INFORMATION: synthetic amino acid sequence

<400> SEQUENCE: 50

Glu Gly Arg Gly Ser Leu Leu Thr Cys Gly Asp Val Glu Glu Asn Pro
1               5                   10                  15

Gly Pro

<210> SEQ ID NO 51
<211> LENGTH: 20
<212> TYPE: PRT
<213> ORGANISM: Artificial sequence
<220> FEATURE:
<223> OTHER INFORMATION: synthetic amino acid sequence

<400> SEQUENCE: 51

Gln Cys Thr Asn Tyr Ala Leu Leu Lys Leu Ala Gly Asp Val Glu Ser
1               5                   10                  15

Asn Pro Gly Pro
            20

<210> SEQ ID NO 52
<211> LENGTH: 22
<212> TYPE: PRT
<213> ORGANISM: Artificial sequence
<220> FEATURE:
<223> OTHER INFORMATION: synthetic amino acid sequence

<400> SEQUENCE: 52

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 53
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 53

Gly Ser Gly Gly Ser
1               5

<210> SEQ ID NO 54
<211> LENGTH: 4
<212> TYPE: PRT
<213> ORGANISM: Artificial sequence
<220> FEATURE:
<223> OTHER INFORMATION: synthetic amino acid sequence

<400> SEQUENCE: 54

Gly Gly Gly Ser
1

<210> SEQ ID NO 55
<211> LENGTH: 4
<212> TYPE: PRT
<213> ORGANISM: Artificial sequence
<220> FEATURE:
<223> OTHER INFORMATION: synthetic amino acid sequence

<400> SEQUENCE: 55

Gly Gly Ser Gly
1

<210> SEQ ID NO 56
<211> LENGTH: 5
<212> TYPE: PRT
<213> ORGANISM: Artificial sequence

```
<220> FEATURE:
<223> OTHER INFORMATION: synthetic amino acid sequence

<400> SEQUENCE: 56

Gly Gly Ser Gly Gly
1               5

<210> SEQ ID NO 57
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 57

Gly Ser Gly Ser Gly
1               5

<210> SEQ ID NO 58
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 58

Gly Ser Gly Gly Gly
1               5

<210> SEQ ID NO 59
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 59

Gly Gly Gly Ser Gly
1               5

<210> SEQ ID NO 60
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 60

Gly Ser Ser Ser Gly
1               5

<210> SEQ ID NO 61
<211> LENGTH: 22
<212> TYPE: PRT
<213> ORGANISM: Artificial sequence
<220> FEATURE:
<223> OTHER INFORMATION: synthetic amino acid sequence

<400> SEQUENCE: 61

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 62
<211> LENGTH: 314
```

```
<212> TYPE: PRT
<213> ORGANISM: Coccomyxa subellipsoidea

<400> SEQUENCE: 62

Met Ala Val His Gln Ile Gly Glu Gly Gly Leu Val Met Tyr Trp Val
1               5                   10                  15

Thr Phe Gly Leu Met Ala Phe Ser Ala Leu Ala Phe Ala Val Met Thr
            20                  25                  30

Phe Thr Arg Pro Leu Asn Lys Arg Ser His Gly Tyr Ile Thr Leu Ala
        35                  40                  45

Ile Val Thr Ile Ala Ala Ile Ala Tyr Tyr Ala Met Ala Ala Ser Gly
    50                  55                  60

Gly Lys Ala Leu Val Ser Asn Pro Asp Gly Asn Leu Arg Asp Ile Tyr
65                  70                  75                  80

Tyr Ala Arg Tyr Ile Asp Trp Phe Phe Thr Thr Pro Leu Leu Leu Leu
                85                  90                  95

Asp Ile Ile Leu Leu Thr Gly Ile Pro Ile Gly Val Thr Leu Trp Ile
            100                 105                 110

Val Leu Ala Asp Val Ala Met Ile Met Leu Gly Leu Phe Gly Ala Leu
        115                 120                 125

Ser Thr Asn Ser Tyr Arg Trp Gly Tyr Tyr Gly Val Ser Cys Ala Phe
    130                 135                 140

Phe Phe Val Val Leu Trp Gly Leu Phe Phe Pro Gly Ala Lys Gly Ala
145                 150                 155                 160

Arg Ala Arg Gly Gly Gln Val Pro Gly Leu Tyr Phe Gly Leu Ala Gly
                165                 170                 175

Tyr Leu Ala Leu Leu Trp Phe Gly Tyr Pro Ile Val Trp Gly Leu Ala
            180                 185                 190

Glu Gly Ser Asp Tyr Ile Ser Val Thr Ala Glu Ala Ser Tyr Ala
        195                 200                 205

Gly Leu Asp Ile Ala Ala Lys Val Val Phe Gly Trp Ala Val Met Leu
    210                 215                 220

Ser His Pro Leu Ile Ala Arg Asn Gln Thr Asp Gly Ser Leu Leu Ile
225                 230                 235                 240

Asn Ser Thr Asn Asp Pro Phe Val Ala Ser Thr Thr His Ile Pro Glu
                245                 250                 255

Arg Gln Gly Gly Ile Phe Gly Gly Leu Met Gly Lys Lys Arg Gly Ala
            260                 265                 270

Gly Thr Pro Leu Ala Thr Asn Glu Gly Val Pro Arg Lys Ala Ala Pro
        275                 280                 285

Thr Ala Ala Thr Thr Thr Ala Gly Asn Pro Thr Ala Ala Glu Val
    290                 295                 300

Arg Thr Pro Arg Glu Leu Met Ala Arg Leu
305                 310

<210> SEQ ID NO 63
<211> LENGTH: 3171
<212> TYPE: DNA
<213> ORGANISM: Artificial Sequence
<220> FEATURE:
<223> OTHER INFORMATION: Synthetic Sequence

<400> SEQUENCE: 63
atggacccca tcgctctgca ggctggttac gacctgctgg gtgacggcag acctgaaact    60
ctgtggctgg gcatcggcac tctgctgatg ctgattggaa ccttctactt tctggtccgc   120
```

```
ggatggggag tcaccgataa ggatgcccgg gaatattacg ctgtgactat cctggtgccc    180
ggaatcgcat ccgccgcata tctgtctatg ttctttggta tcgggcttac tgaggtgacc    240 gtcggggggcg aaatgttgga tatctattat gccaggtacg ccgactggct gtttaccacc    300
ccacttctgc tgctggatct ggcccttctc gctaaggtgg atcgggtgac catcggcacc    360
ctggtgggtg tggacgccct gatgatcgtc actggcctca tcggagcctt gagccacacg    420
gccatagcca gatacagttg gtggttgttc tctacaattt gcatgatagt ggtgctctat    480
tttctggcta catccctgcg atctgctgca aaggagcggg gccccgaggt ggcatctacc    540
tttaacaccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacaccg aggcaccaga acccagtgcc ggtgccgatg tcagtgccgc cgacaagagc    780
aggatcacca gcgagggcga gtacatcccc ctggaccaga tcgacatcaa cgtgggcgcg    840
cccggctccg gagccacgaa cttctctctg ttaaagcaag caggagacgt ggaagaaaac    900
cccggtccca tggacctgaa ggagtcacca agcgagggat cactgcagcc atcaagcatt    960
cagattttcg ctaatacaag cacactgcac ggcatccggc atatcttcgt gtacggccca   1020
ctgaccattc ggagagtcct gtgggcagtg gcctttgtcg aagcctggga actgctgctg   1080
gtggagagct ccgaaagagt cagttactat ttctcatatc agcacgtgac taaggtggac   1140
gaggtggtcg ctcagtccct ggtgtttccc gcagtcaccc tgtgcaacct gaatgggttc   1200
aggttttctc gcctgaccac aaacgacctg taccacgccg gagagctgct ggctctgctg   1260
gatgtgaatc tgcagatccc agaccccat ctggccgatc caaccgtgct ggaagcactg   1320
aggcagaagg ccaacttcaa acactacaag cccaaacagt tcagcatgct ggagtttctg   1380
caccgcgtgg acatgacctg aaagatatg atgctgtatt gcaagttcaa aggccaggag   1440
tgtgggcatc aggacttcac taccgtgttt acaaagtacg gcaaatgtta catgttcaac   1500
tccggggaag atggaaaacc tctgctgaca actgtgaagg gcgggacagg gaatggactg   1560
gagatcatgc tggacattca gcaggatgag tacctgccaa tctggggaga aactgaggaa   1620
accacattcg aggccggcgt gaaggtccag atccactcac agagcgagcc ccctttcatt   1680
caggaactgg gatttggagt ggcaccagga ttccagacat ttgtcgctac tcaggagcag   1740
cgcctgacct atctgccacc cccttggggc gagtgccgat ctagtgaaat ggggctggac   1800
ttctttcctg tgtactctat caccgcctgc cgaattgatt gtgagacacg gtatatcgtg   1860
gaaaactgca attgtaggat ggtccacatg cctggcgacg ccccattctg cactcccgaa   1920
cagcataaag agtgtgctga acctgcactg gggctgctgg ctgagaagga tagtaactac   1980
tgcctgtgta gaacaccctg taacctgact aggtataata aggaactgag catggtgaag   2040
atcccttcca aaacatctgc aaagtacctg gagaagaagt tcaacaagtc tgagaagtac   2100
atcagtgaaa acattctggt gctggacatc ttctttgaag ctctgaatta cgagaccatt   2160
gaacagaaga aagcatatga ggtggccgct ctgctggggg atattggagg ccagatggga   2220
ctgttcatcg gcgccagcct gctgacaatt ctggagctgt tgactacat ctatgagctg   2280 attaaggaaa aactgctgga tctgctgggg aaggaggaag aggaaggatc acacgacgaa   2340
aacatgagca cttgcgatac catgcctaat cacagcgaga ccatctccca tacagtgaat   2400
gtcccactgc agactgcact gggcaccctg gaggaaattg cctgtgcggc cgccgtgagc   2460
aagggcgagg agctgttcac cggggtggtg cccatcctgg tcgagctgga cggcgacgta   2520
```

```
aacggccaca agttcagcgt gtccggcgag ggcgagggcg atgccaccta cggcaagctg   2580
accctgaagt tcatctgcac caccggcaag ctgcccgtgc cctggccac cctcgtgacc    2640 accttcggct acggcctgca gtgcttcgcc cgctaccccg accacatgaa gcagcacgac   2700
ttcttcaagt ccgccatgcc cgaaggctac gtccaggagc gcaccatctt cttcaaggac   2760
gacggcaact acaagacccg cgccgaggtg aagttcgagg gcgacaccct ggtgaaccgc   2820
atcgagctga agggcatcga cttcaaggag gacggcaaca tcctggggca caagctggag   2880
tacaactaca acagccacaa cgtctatatc atggccgaca agcagaagaa cggcatcaag   2940
gtgaacttca gatccgcca caacatcgag gacggcagcg tgcagctcgc cgaccactac    3000
cagcagaaca cccccatcgg cgacggcccc gtgctgctgc ccgacaacca ctacctgagc   3060
taccagtccg ccctgagcaa agaccccaac gagaagcgcg atcacatggt cctgctggag   3120
ttcgtgaccg ccgccgggat cactctcggc atggacgagc tgtacaagta a            3171

<210> SEQ ID NO 64
<211> LENGTH: 3252
<212> TYPE: DNA
<213> ORGANISM: Artificial Sequence
<220> FEATURE:
<223> OTHER INFORMATION: Synthetic Sequence

<400> SEQUENCE: 64
atggacccca tcgctctgca ggctggttac gacctgctgg gtgacggcag acctgaaact     60
ctgtggctgg gcatcggcac tctgctgatg ctgattggaa ccttctactt tctggtccgc    120
ggatggggag tcaccgataa ggatgcccgg gaatattacg ctgtgactat cctggtgccc    180
ggaatcgcat ccgccgcata tctgtctatg ttctttggta tcgggcttac tgaggtgacc    240 gtcggggcg aaatgttgga tatctattat gccaggtacg ccgactggct gtttaccacc     300
ccacttctgc tgctggatct ggcccttctc gctaaggtgg atcgggtgac catcggcacc    360
ctggtgggtg tggacgccct gatgatcgtc actggcctca tcggagcctt gagccacacg   420
gccatagcca gatacagttg gtggttgttc tctacaatttt gcatgatagt ggtgctctat   480
tttctggcta catccctgcg atctgctgca aaggagcggg gccccgaggt ggcatctacc    540
tttaacaccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacaccg aggcaccaga acccagtgcc ggtgccgatg tcagtgccgc cgacaagagc    780
aggatcacca gcgagggcga gtacatcccc ctggaccaga tcgacatcaa cgtgggcgcg    840
cccggctccg gagccacgaa cttctctctg ttaaagcaag caggagacgt ggaagaaaac    900
cccggtccca tggacctgaa ggagtcacca agcgagggat cactgcagcc atcaagcatt    960
cagattttcg ctaatacaag cacactgcac ggcatccggc atatcttcgt gtacggccca   1020
ctgaccattc ggagagtcct gtgggcagtg gcctttgtcg aagcctggg actgctgctg    1080 gtggagagct ccgaaagagt cagttactat ttctcatatc agcacgtgac taaggtggac   1140
gaggtggtcg ctcagtccct ggtgtttccc gcagtcaccc tgtgcaacct gaatgggttc   1200
aggttttctc gcctgaccac aaacgacctg taccacgccg gagagctgct ggctctgctg   1260
gatgtgaatc tgcagatccc agaccccat ctggccgatc caaccgtgct ggaagcactg   1320
aggcagaagg ccaacttcaa acactacaag cccaaacagt tcagcatgct ggagtttctg   1380
```

-continued

```
caccgcgtgg gacatgacct gaaagatatg atgctgtatt gcaagttcaa aggccaggag    1440
tgtgggcatc aggacttcac taccgtgttt acaaagtacg gcaaatgtta catgttcaac    1500
tccggggaag atggaaaacc tctgctgaca actgtgaagg gcgggacagg gaatggactg    1560
gagatcatgc tggacattca gcaggatgag tacctgccaa tctggggaga aactgaggaa    1620
accacattcg aggccggcgt gaaggtccag atccactcac agagcgagcc cccttcatt     1680 caggaactgg gatttggagt ggcaccagga ttccagacat ttgtcgctac tcaggagcag    1740
cgcctgacct atctgccacc cccttgggc gagtgccgat ctagtgaaat ggggctggac     1800
ttctttcctg tgtactctat caccgcctgc cgaattgatt gtgagacacg gtatatcgtg    1860
gaaaactgca attgtaggat ggtccacatg cctggcgacg ccccattctg cactcccgaa    1920
cagcataaag agtgtgctga acctgcactg gggctgctgg ctgagaagga tagtaactac    1980
tgcctgtgta gaacaccctg taacctgact aggtataata aggaactgag catggtgaag    2040
atcccttcca aaacatctgc aaagtacctg gagaagaagt tcaacaagtc tgagaagtac    2100
atcagtgaaa acattctggt gctggacatc ttctttgaag ctctgaatta cgagaccatt    2160
gaacagaaga aagcatatga ggtggccgct ctgctggggg atattggagg ccagatggga    2220
ctgttcatcg gcgccagcct gctgacaatt ctggagctgt ttgactacat ctatgagctg    2280
attaaggaaa aactgctgga tctgctgggg aaggaggaag aggaaggatc acacgacgaa    2340
aacatgagca cttgcgatac catgcctaat cacagcgaga ccatctccca tacagtgaat    2400
gtcccactgc agactgcact gggcaccctg gaggaaattg cctgtgcggc cgccaagagc    2460
aggatcacca gcgagggcga gtacatcccc ctggaccaga tcgacatcaa cgtggtgagc    2520
aagggcgagg agctgttcac cggggtggtg cccatcctgg tcgagctgga cggcgacgta    2580
aacggccaca gttcagcgt gtccggcgag ggcgagggcg atgccaccta cggcaagctg     2640
accctgaagt tcatctgcac caccggcaag ctgcccgtgc cctggcccac cctcgtgacc    2700
accttcggct acggcctgca gtgcttcgcc cgctacccg accacatgaa gcagcacgac     2760
ttcttcaagt ccgccatgcc cgaaggctac gtccaggagc gcaccatctt cttcaaggac    2820
gacggcaact acaagacccg cgccgaggtg aagttcgagg gcgacaccct ggtgaaccgc    2880
atcgagctga agggcatcga cttcagggag gacggcaaca tcctggggca aagctggag     2940 tacaactaca acagccacaa cgtctatatc atggccgaca gcagaagaa cggcatcaag     3000 gtgaacttca agatccgcca caacatcgag gacggcagcg tgcagctcgc cgaccactac    3060
cagcagaaca ccccccatcgg cgacggcccc gtgctgctgc ccgacaacca ctacctgagc    3120
taccagtccg ccctgagcaa agacccccaac gagaagcgcg atcacatggt cctgctggag   3180
ttcgtgaccg ccgccgggat cactctcggc atggacgagc tgtacaagtt ctgctacgag    3240
aacgaggtgt aa                                                         3252
```